(12) United States Patent
Aylsworth et al.

(10) Patent No.: US 7,393,534 B2
(45) Date of Patent: Jul. 1, 2008

(54) COMPOSITIONS AND METHODS FOR IMMUNOTHERAPY OF CANCER AND INFECTIOUS DISEASES

(75) Inventors: Charles Aylsworth, Holt, MI (US); Siu-Cheong Ho, East Lansing, MI (US); David Juckett, East Lansing, MI (US); John W. Judge, Holt, MI (US); Igor V. Zlatkin, Lansing, MI (US); Tatiana Zlatkin, Lansing, MI (US)

(73) Assignee: Barros Research Institute, Holt, MI (US)

( * ) Notice: Subject to any disclaimer, the term of this patent is extended or adjusted under 35 U.S.C. 154(b) by 0 days.

(21) Appl. No.: 10/892,659

(22) Filed: Jul. 15, 2004

(65) Prior Publication Data

US 2005/0169935 A1   Aug. 4, 2005

Related U.S. Application Data

(60) Provisional application No. 60/487,336, filed on Jul. 15, 2003.

(51) Int. Cl.
*A61K 38/00* (2006.01)
*A61K 39/00* (2006.01)

(52) U.S. Cl. .......................... 424/185.1; 514/2
(58) Field of Classification Search ................. 435/69.7; 424/185.1; 514/2
See application file for complete search history.

(56) References Cited

U.S. PATENT DOCUMENTS

| | | | |
|---|---|---|---|
| 4,444,887 A | 4/1984 | Hoffmann | |
| 4,716,111 A | 12/1987 | Osband et al. | |
| 4,816,397 A | 3/1989 | Boss et al. | |
| 4,816,567 A | 3/1989 | Cabilly et al. | |
| 4,980,286 A | 12/1990 | Morgan et al. | |
| 5,122,464 A | 6/1992 | Wilson et al. | |
| 5,223,409 A | 6/1993 | Ladner et al. | |
| 5,225,539 A | 7/1993 | Winter | |
| 5,403,484 A | 4/1995 | Ladner et al. | |
| 5,427,908 A | 6/1995 | Dower et al. | |
| 5,436,146 A | 7/1995 | Shenk et al. | |
| 5,516,637 A | 5/1996 | Huang et al. | |
| 5,530,101 A | 6/1996 | Queen et al. | |
| 5,565,332 A | 10/1996 | Hoogenboom et al. | |
| 5,571,698 A | 11/1996 | Ladner et al. | |
| 5,580,717 A | 12/1996 | Dower et al. | |
| 5,585,089 A | 12/1996 | Queen et al. | |
| 5,658,727 A | 8/1997 | Barbas et al. | |
| 5,698,426 A | 12/1997 | Huse | |
| 5,733,743 A | 3/1998 | Johnson et al. | |
| 5,750,753 A | 5/1998 | Kimae et al. | |
| 5,766,886 A | 6/1998 | Studnicka et al. | |
| 5,780,225 A | 7/1998 | Wigler et al. | |
| 5,792,644 A | 8/1998 | Vermeulen et al. | |
| 5,807,715 A | 9/1998 | Morrison et al. | |
| 5,821,047 A | 10/1998 | Garrard et al. | |
| 5,969,108 A | 10/1999 | McCafferty et al. | |
| 6,001,363 A | 12/1999 | Tomley et al. | |
| 6,008,342 A | 12/1999 | Binger et al. | |
| 6,100,241 A | 8/2000 | Kok et al. | |
| 6,331,415 B1 | 11/2001 | Lind | |
| 6,407,213 B1 | 6/2002 | Carter et al. | |
| 6,451,984 B1 | 9/2002 | Lillehoj et al. | |
| 6,528,485 B1 | 3/2003 | Veronese et al. | |

FOREIGN PATENT DOCUMENTS

| | | |
|---|---|---|
| EP | 239400 A2 | 9/1987 |
| EP | 519596 A1 | 12/1992 |
| EP | 592106 A1 | 4/1994 |
| WO | WO 86/05807 A1 | 6/1987 |
| WO | WO 89/01036 A1 | 2/1989 |
| WO | WO 90/02809 A1 | 3/1990 |
| WO | WO 91/10737 A1 | 7/1991 |
| WO | WO 91/10741 A1 | 7/1991 |
| WO | WO 92/04461 | 3/1992 |
| WO | WO 92/06180 A1 | 4/1992 |
| WO | WO 91/01134 A1 | 10/1992 |

(Continued)

OTHER PUBLICATIONS

Aliberti et al. (2003), "*Molecular mimicry of a CCR5 binding-clomain in the microbial activation of dendritic cells*", Nature Immunology 4(5): 485-490.

(Continued)

*Primary Examiner*—Karen Cochrane Carlson
*Assistant Examiner*—Marsha Tsay
(74) *Attorney, Agent, or Firm*—Wolf, Greenfield & Sacks, P.C.

(57) ABSTRACT

The present invention provides compositions and methods for the prevention and treatment of primary and metastatic neoplastic diseases and infectious diseases, for stimulating an immune response in a subject, and for use as an alternative to interleukin-12 (IL-12) treatment. In particular, the present invention provides Apicomplexa-related proteins (ARPs) that have immune stimulatory activity and thus have uses in the treatment and prevention of cancer and infectious diseases and in immune modulation. Compositions comprising an ARP are provided. Methods of use of an ARP for the prevention and/or treatment of cancer and/or infectious diseases, for use as an alternative to interleukin-12 (IL-12) treatment, and for eliciting an immune response in a subject, are also provided.

13 Claims, 38 Drawing Sheets

FOREIGN PATENT DOCUMENTS

| WO | WO 92/18619 A1 | 10/1992 |
|---|---|---|
| WO | WO 92/20316 A2 | 11/1992 |
| WO | WO 92/22324 A1 | 12/1992 |
| WO | WO 92/22635 A1 | 12/1992 |
| WO | WO 93/14188 A1 | 7/1993 |
| WO | WO 93/15199 A1 | 8/1993 |
| WO | WO 93/15200 A1 | 8/1993 |
| WO | WO 93/20221 A1 | 10/1993 |
| WO | WO 94/08598 A1 | 4/1994 |
| WO | WO 94/12649 A2 | 6/1994 |
| WO | WO 93/17105 A1 | 12/1994 |
| WO | WO 95/15982 A2 | 6/1995 |
| WO | WO 95/20401 A1 | 8/1995 |
| WO | WO 96/33735 A1 | 10/1996 |
| WO | WO 96/34096 A1 | 10/1996 |
| WO | WO 97/13844 A1 | 4/1997 |
| WO | WO 98/24893 A2 | 6/1998 |
| WO | WO 98/46645 A2 | 10/1998 |
| WO | WO 93/11236 A1 | 3/1999 |
| WO | WO 98/16654 A1 | 6/1999 |
| WO | WO 91/09967 A1 | 7/1999 |
| WO | WO 92/01047 A1 | 10/1999 |
| WO | WO 98/50433 A2 | 5/2001 |
| WO | WO 01/77137 A1 | 10/2001 |
| WO | WO 2004/020630 | 3/2004 |

OTHER PUBLICATIONS

Allen & Fetterer, (2002), "*Recent Advances in Biology and Immunobiology of Eimeria Species and in Diagnosis and Control of Infection with These occidian Parasites of Poultry*" Clin. Microbiol. Rev. 15:58-65.

Almeida and Gazzinelli, "*Proinflammatory activity of glycosylphosphatidylinositol anchors derived from Trypanosoma cruzi: structural and functional analyses*" J Leukoc Biol. 70(4):467-77 (2001).

Altschul et al., "*Gapped BLAST and PSI-BLAST: a new generation of protein database search programs*"Nucleic Acids Res, 25(17):3389-3402, 1997.

Ames et al., "*Conversion of murine Fabs isolated from a combinatoria phage display library to full length immunoglobulins*" 1995, J. Immunol. Methods 184:177-186.

Ausubel et al., (eds.), "*Informatics For Molecular Biologists*" Current Protocols in Molecular Biology, Ch. 19 John Wiley & Sons, NY (2002).

Baca et al., "*Antibody Humanization Using Monovalent Phage Display*" J. Biol. Chem. 272(16):10678-84 (1997).

Bebbington and Hentschel, *The use of vectors based on gene amplification for the expression of cloned genes in mammalian cells*vol. 3. (Academic Press, New York, 1987) pp. 163-189.

Better et al., "*Escherichia coli Secretion of an Active Chimeric Antibody Fragment*" 1988, Science 240:1041-1043.

Beverley, Cell, "*Hijacking the Cell: Parasites in the Driver's Seat*" 1996 87:787-789.

Bitter et al., "*Expression and Secretion Vectors For Yeast*", 1987, Methods in Enzymol. 153:516-544.

Blackman & Bannister, (2001), "*Apical organelles of Apicomplexa: biology and isolation by subcellular fractionation*" Mol. Biochem. Parasitol. 117:11-25.

Boesen et al., "*Circumvention of chemotherapy-induced myelosuppression by transfer of the mdr1 gene*" 1994, Biotherapy 6:291-302.

Bout et al. "*Lung Gene Therapy: In Vivo Adenovirus-Mediated Gene Transfer to Rhesus Monkey Airway Epithelium*"(1994, Human Gene Therapy 5:3-10.

Brightbill et al., "*Host Defense Mechanisms Triggered by Microbial Lipoproteins Through Toll-Like Receptors*" Science 285(5428):732-6 (1999).

Brinkman et al., "*Phage display of disulfide-stabilized Fv fragments*" 1995, J. Immunol. Methods 182:41-50.

Buckheit et al., "*Efficacy, Pharmacokinetics, and in Vivo Antiviral Activity of UC781, a Highly Potent, Orally Bioavailable Non-nucleoside Reverse Transcriptase Inhibitor of HIV Type 1*" AIDS Res. Hum. Retroviruses 1997, 13:9 pp. 789-796.

Burton et al., "*Human Antibodies from Combinatorial Libraries*" 1994, Advances in Immunology 57:191-280.

Cabilly et al. "*Generation of antibody activity from immunoglobulin polypeptide chains produced in Escherichia coli*" Proc Natl Acad Sci U S A. 81(11):3273-7 (1984).

Caldas et al., "*Design and sythesis of germline-based hemi-humanized single-chain Fv against the CD18 surface antigen*" Protein Eng. 13(5):353-60 (2000).

Campos et al., "*Activation of Toll-Like Receptor-2 by Glycosylphosphatidylinositol Anchors from a Protrozoan Parasite[1]*" The J. Immunol. 2001, 167:416-423.

Carpenter, et al., "*Antiretroviral Therapy for HIV infection in 1998*" JAMA 280(1): 78-86 (1998).

Chomczynsky, P., and N. Sacchi., "*Single-Step Method RNA Isolation by Acid Guanidinium Thiocyanate-Phenol-Chloroform Extraction*" 1987. Anal. Biochem. 162:156-159.

Chothia et al., 1998, "*Structural Determinants in the Sequences of Immunoglobulin Variable Domain*" J. Mol. Biol. 278: 457-479.

Chou, P. and Fasman, G., "*Prediction of Protein Conformation*" 1974, Biochemistry vol. 13: No. 2 222.

Cline, "*Perspectives For Gene Therapy: Inserting New Genetic Information Into Mammalian Cells By Physical Techniques And Viral Vectors*" 1985, Pharmac. Ther. 29:69-92.

Clowes et al., "*Long-Term Biological Response of Injured Rat Carotid Artery Seeded with Smooth Muscle Cells Expressing Retrovirally Introduced Human Genes*"1994, J. Clin. Invest. 93:644-651.

Cockett et al., "High Level Expression Of Tissue Ibnhibitor Of Metalloproteinases In Chinese Hamster Ovary Cells Using Glutamine Synthetase Gene Amplification", Jul. 1990, Bio/Technology 8: pp. 662-667.

Cotten et al., 1993, "*Receptor-Mediated Transport of DNA into Eukaryotic Cells*" Meth. Enzymol. 217:618-644.

Colberre-Garapin et al., "*A New Dominant Hybrid Selective Marker for Higher Eukaryotic Cells*", 1981, J. Mol. Biol. 150:1-14.

Couto et al., Designing Human Consensus Antibodies with Minimal Positional Templates[1] Cancer Res. 55 (23 Supp):5973s-5977s (Dec. 1, 1995).

Couto et al., "*Anti-BA46 Monoclonal Antibody Mc3: Humanization Using a Novel Positional Concensus and in Vivo and in Vitro Characterization*" CancerRes. 55(8):1717-22 (Apr. 15, 1995).

Crouse et al., "*Expression and Amplification of Engineered Mouse Dihydrofolate Reductase Minigenes*" (Feb. 1983), Mol. Cell. Biol. vol. 3, No. 2, pp. 257-266.

Davies et al "*Isolation of DNA from Plants*" (Methods in Molecular Biology vol. 28: Protocols for nucleic acid analysis by non-radioactive probes, Isaac, P.G. (ed) pp. 9-15, Humana Press Inc., Totowa N.J, USA (date?)).

Dracopoli et al. (eds), Chapters 12 and 13, Current Protocols in Human Genetics, John Wiley & Sons, NY (1994).

Engstrom, A., "*The Arrangement Of The Protein Molecules In Nuclear-Polyhedrosis Inclusions*"1974, Biochem. Exp. Biol. 11:7-13.

Faber et al., "*Eimeria Infections in Cows in the Periparturient Phase, And Their Calves: Oocyst Excretion and Levels of Specific Serum and Colostrum Antibodies*", (2002), Vet. Parasitol. 104:1-17.

Foecking et al., "*Powerful and Versatile Enhancer-Promoter Unit for Mammalian Expression Vectors*" 1986, Gene 45:101-105.

Gillies et al., "*High-level Expression of Chimeric Antibodies Using Adapted Cdna Variable Region Cassettes*", 1989, J. Immunol. Methods 125:191-202.

Goldspiel et al., "*Human Gene Therapy*", Jul. 1993, Clinical Pharmacy 12:488-505.

Greenspan & Bona, "*Idiotypes: structure and immunogenicity[1]*" Mar. 1993, FASEB J. 7(5):437-444.

Grossman and Wilson, "*Retroviruses: delivery vehicle to the liver*", 1993, Curr. Opin. in Genetics and Devel. 3:110-114.

Gulick, R.M. et al., "*Treatment With Indinavir, Zidovudine, and Lamivudine in Adults With Human Immunodeficiency Virus Infection and Prior Antiretroviral Therapy*" N. Engl. J. Med. Sep. 11, 1997, 337:734-739.

Hammer, S.M. et al., *A Controlled Trial of Two Nucleoside Analogues plus Indinavir in Persons With Human Immunodeficiency Virus Infectio and CD4 Cell Counts of 200 Per Cubic Millimeter or Less* N. Engl. J. Med. Sep. 11, 1997, 337:725-733.

Hammerling et al., *"Production of hybridomas in the rodent system"* in: Monoclonal Antibodies and T Cell Hybridomas 563 681 (Elsevier, N.Y., 1981).

Hollingshead et al., "In vivo drug screening applications of HIV-infected cells cultivated within hollow fibers in two physiologic compartments of mice", Antiviral Res. 1995, 28:265-279.

Hopp and Woods, *"Prediction of protein antigenic determinants from amino acid sequences"*, Jun. 1981, Proc. Natl. Acad. Sci. U.S.A. 78:6, 3824-3828.

Hutchinson, C. et al., *"Mutagenesis at a Specific Position in a DNA Sequence"*, Feb. 25, 1978, J. Biol. Chem 253:18, 6551-6560.

Inouye & Inouye, *"Up-promoter mutations in the lpp gene of Escherichia coli"*, 1985, Nucleic Acids Res. 13:9, 3101-3109.

Jenkins et al. *"Eimeria acervulina: DNA Cloning and Characterization of Recombinant Sporozoite and Merozoite Antigens"* (1988), Exp. Parasitol. 66:96-107.

Joliot et al., *"Antennapedia homeobox peptide regulates neural morphogenesis"*, Mar. 1, 1991, Proc. Natl. Acad. Sci. USA 88:1864-1868.

Kettleborough et al., *"Isolation of tumor cell-specific single-chain Fv from immunized mice using phage-antibody libraries and the reconstruction of whole antibodies from these antibody fragments"*, 1994, Eur. J. Immunol. 24:952-958.

Kiem et al., *"Retrovirus-Mediated Gene Transduction Into Canine Peripheral Blood Repopulating Cells"*, Mar. 15, 1994, Blood 83:6, 1467-1473.

Kohler, *"Immunoglobulin chain loss in hubridoma lines"* Apr. 1980, Proc. Natl. Acad. Sci. USA 77:4 2-2199 Apr. 1980.

Koller and Smithies, *"Inactivating the $\beta_2$-microglobulin locus in mouse embryonic stem cells by homologus recombination"* Nov. 1989, Proc. Natl. Acad. Sci. USA 86:8932-8935.

Kozarsky and Wilson, *"Gene Therapy: Adenovirus Vectors"* 1993, Current Opinion in Genetics and Development 3:499-503).

Kutmeier et al., *"An Acetylated (Nuclease-Free) Bovine Serum Albumin in a PCR Buffer Inhibits Amplification"*, 1994, BioTechniques 17:2, 242-246.

Laemmli, U.K. *"Cleavage of Structural Proteins during the Assembly of the Head of Bacteriophage T4"*, (Aug. 15, 1970), Nature 227, 680-685.

Laurent et al., *"The Immunodominant Eimeria acervulina sporozoite antigen previously described as p160/p240 is a 19-kilodalton antigen present in several Eimeria species"* (1994), Mol. Bioch. Parasitol. 63:79-86.

Lillehoj et al., *"A Recombinant Eimeria Protein Inducing Interferon-γ-Production: Comparison of Different Gene Expression Systems and Immunization Strategies for Vaccination Against Coccidiosi"*, (2000), Avian Diseases 44:379-389.

Loeffler and Behr, *"Gene Transfer into Primary and Established Mammalian Cell Lines with Lipopolyamine-Coated DNA"* 1993, Meth. Enzymol. 217:599-618.

Logan & Shenk, *"Andenovirus tripartite leader sequence enhances translation of mRNAs late after infection"* Jun. 1984, Proc. Natl. Acad. Sci. USA, vol. 81:3655-3659.

Magez et al., *"The Glycosyl-Inositol-Phosphate and Dimyristoylglycerol Moieties of the Glycosylphosphatidylinositol Anchor of the Trypanosome Variant-Specific Surface Glycoprotein Are Distinct Macrophage-Activating Factors[1.]"* The Journal of Immunology. 15;160(4):1949-56 (1998).

Marchler-Bauer et al., *"CDD:a database of conserved domain alignments with links to domain three-dimensional structure"* (2002) Nucleic Acids Research vol. 30, No. 1, pp. 281-283.

Marchler-Bauer et al., *"CDD: a curated Entrez database of conserved domain alignments"* (2003) Nucleic Acids Reserch vol. 31, No. 1, pp. 383-387.

Martin et al , *"Molecular analysis of instability in flower pigmentation of Antirrhinum majus, following isolation of the pallida locus by transposon tagging"* (EMBO J 4:1625-1630 (1985)).

Mastrangeli et al., *"Diversity of Airway Epithelial Cell Targets for In Vivo Recombinant Adenovirus-medicated Gene Transfer"*, Jan. 1993, J. Clin. Invest. 91:225-234.

TIBTECH Biotechnology *"Gene Therapy—proceeding from laboratory to clinic"*, 11(5):155-215, May 1993.

Merrifield, *"Solid Phase Peptide Synthesis. I. The Synthesis of a Tetrapeptide"*, Journal of The American Chemical Society, vol. 14, Jul. 20, 1964 pp. 2149-2154.

Miller et al., *"Use of Retroviral Vectors for Gene Transfer and Expression"*, 1993, Meth. Enzymol. 217:581-599.

Min et al., Adjuvant effects of IL-1βIL -2, IL-8, IL-15, IFN-α, IFN-γTGF-β4 and lymphotactin on DNA vaccination against *Elmeria acervulina* (2001), Vaccine 20:267-274.

Morea et al., *"Antibody Modeling: Implications for Engineering and Design"*, Methods 20(3):267-79 (2000).

Morgan and Anderson, *"Human Gene Therapy"* 1993, Ann. Rev. Biochem. 62:191-217.

Morrison, *"Transfectomas Provide Novel Chimeric Antibodies"*, 1985, Science 229:1202-1207.

Mossman, *"Rapid Colorimetric Assay for Cellular Growth and Survival: Application to Proliferation and Cytotoxicity Assays"*, T. J. Immunol. Methods 65:55-63 (1983).

Mulligan & Berg, *"Selection for animal cells that express the Escherichia coli gene coding for xanthine-guanine phosphoribosyltransferase"* 1981, Proc. Natl. Acad. Sci. USA 78:2072-2076.

Mulligan, *"The Basic Science of Gene Therapy"*, 1993, Science 260:926-932.

Mullinax et al., *"Expression of a Heterodimeric Fab Antibody Protein in One Cloning Step"*, 1992, BioTechniques 12(6):864-869.

Nissinoff, *"American Association of Immunologists Presidential Address Idotypes: Concepts And Applications"* 1991, J. Immunol. 147(8):2429-2438.

O'Hare et al., *"Transformation of mouse fibroblasts to methotrexate resistance by a recombinant plasmid expressing a prokaryotic dihydrofolate reductase"* 1981, Proc. Natl. Acad. Sci. USA 78: No. 3, 1527-1531.

Oi et al., 1986, BioTechniques vol. 4, No. 3,:214-211.

Padlan, *"A Possible Procedure For Reducing The Immunogenicity Of Antibody Variable Domains While Preserving Their Ligand-Binding Properties"* 1991, Molecular Immunology vol. 28(4/5):489-498.

Pedersen et al., *"Comparison of Surface Accessible Residues in Human and Murine Immunoglobulin Fv Domains"*, J. Mol. Biol. 235(3):959-73 (1994).

Persic et al., *"An integrated vector system for the eukaryotic expression of anibodies or their fragments after selection from phage display libraries"*, 1997, Gene 187:9-18.

Pittelkow and Scott, *"New Techniques for the In Vitro Culture of Human Skin Keratinocytes and Perpectives on Their Use for Grafting of Patients With Extensive Burns"*, Mayo Clinic Proc. 1986, 61:771-777.

Proudfoot, *"Transcriptional interference and termination between duplicated α-globin gene constructs suggests a novel mechanism for gene regulation"* 1986, Nature 322:52.

Quenelle et al., *Evaluation of anti-AIDS drugs in conventional mice implated with a permeable membrane device containing human T cells infected with HIV*, Antiviral Res. 1997, 35:123-129.

Rheinwald, *"Serial Cultivation of Normal Human Epidermal Keratinocytes"* Meth. Cell Bio. 1980, 21A:229-254.

Riechmann et al., *"Reshaping human antibodies for therapy"*, 1988, Nature 332:323.

Roguska et al., *"Humanization of murine monoclonal antibodies through variable domain resurfacing"* 1994, PNAS 91:969-973.

Roguska et al., *"A comparison of two murine monoclonal antibodies humanize by CDR-grafting and variable domain resurfacing"*, Protein Eng. 9(10):895-904 (1996).

Ropert and Gazzinelli, *"Signaling of immune system cells by glycosylphosphatidylinositol (GPI) anchor and related structures derived from parasitic protozoa"*, Curr Opin Microbiol. 3(4):395-403 (2000).

Rose, (1987), *Eimeria, Isopora, and Cryptosporidium*, in: Immune Responses in Parasitic Infections: Immunology, Immunopathology, and Immuneoprophylaxis (ed. E.J.L. Soulsby) pp. 275-311.

Rosenfeld et al., "*Adenovirus-Mediated Transfer of a Recombinant α1-Antitrypsin Gene to the Lung Epithelium in Vivo*", 1991, Science 252:431-434.

Rosenfeld et al., "*In Vivo Transfer of the Human Cystic Fibrosis Transmembrane Conductance Regulator Gene to the Airway Epithelium*" 1992, Cell 68:143-155.

Ryley et al., "*Methods in coccidiosis research: separation of oocysts from faeces*", Parasitology, 73:311-362(1976).

Salmons and Gunzberg, "*Targeting of Retroviral Vectors for Gene Therapy*" 1993, Human Gene Therapy 4:129-141.

Sandhu JS, "*A rapid procedure for the humanization of monoclonal antibodies*" Gene 150(2):409-10 (1994).

Santerre et al., "*Expression of prokaryotic genees for hygromycin B and G418 as dominant-selection markers in mouse L cells*", 1984, Gene 30:147-156.

Sawai et al., "*Direct Production of the Fab Fragment Derived From the Sperm Immobilizing Antibody Using Polymerase Chain Reaction and CDNa Expression Vectors*", 1995, AJRI 34:26-34.

Scopes, Protein Purification, "*Principles of Affinity Chromatography*", Principles and Practice, 3rd Ed., Springer (1994) pp. 187-237.

Shilo and Weinberg, "*DNA sequences homologous to vertebrate oncogenes are conserved in Drosophila melanogaster*", 1981, Proc. Natl. Acad. Sci. U.S.A. vol. 78, No. 11, 6789-6792.

Sigma Chemical MTT "*Tissue Culture Media and Reagents*", (M5655) product application note Biochemicals and Reagents, 2000-2001.

Song, et al., "*A DNA vaccine encoding a conserved Eimeria protein induces protective immunity against live Eimeria acervulina challenge*" (2001), Vaccine 19:243-252.

Stemple and Anderson, "*Isolation of a Stem Cell for Neurons and Glia from the Mammalian Neural Crest*" Cell 1992, 71:973-985.

Studnicka et al., "*Human-engineered monoclonal antibodies retain full specific binding activity by preserving non-CDR complementarity-modulating residues*", 1994, Protein Engineering 7(6):805-814.

Tan et al., ""*Superhumanized*" Antibodies: Reduction of Immunogenic Potential by Complementarity-Determining Region Grafting with Human Germline Sequences: Application to an Anti-CD28[1]" J. Immunol. 169:1119-25(2002).

Tijssen, *Techniques in Biochemistry and Molecular Biology-Hybridization with Nucleic Probes*, "Overview of principles of hybridization and the strategy of nucleic acid assays" (1993).

Tolstoshev, 1993, "*Gene Therapy, Concepts, Current Trials And Future Directions*",Ann. Rev. Pharmacol. Toxicol. 32:573-596.

Tomley, "*Techniques for Isolation and Characterization of Apical Organelles from Eimeria tenella Sporozoites*", Methods: A Companion to Methods in Enzymology 13:171-176 (1997).

Van Heeke & Schuster, "*Expression of Human Asparagine Sythetase in Escherichia coli*", 1989, J. Biol. Chem. 24:5503-5509.

Walsh et al., 1993, "*Gene Therapy for Human Hemoglobinopathies*" Proc. Soc. Exp. Biol. Med. 204:289-300.

Wang et al., 1995, "*A packaging cell line for propagation of recombinant adenovirus vectors containing two lethal gene-region deletions*" Gene Therapy 2:775-783.

Wang, "*Instability, stabilization, and formulation of liquid protein pharmaceuticals*" International J. of Pharmaceutics, 185:129-188 (1999).

Wigler et al., "*Transformation of mammalian cells with an amplifiable dominate-acting gene*" 1980, Natl. Acad. Sci. USA vol. 77, No. 6:3567-3570.

Wu and Wu, "Receptor-mediated in Vitro Gene Transformation by a Soluble DNA Carrier System", Apr. 5, 1987, J. Biol. Chem. vol. 262, No. 10:4429-4432.

Wu and Wu, "*Delivery Systems For Gene Therapy*", 1991, Biotherapy 3:87-95.

Zambrano-Villa et al., "*How protozoan parasites evade the immune response*", Trends Parasitol. 18(6):272-8 (2002).

Zijlstra et al., "*Germ-line transmission of a disrupted $β_2$—microglobulin gene produced by homologous recombination in embryonic stem cells*", Nov. 23, 1989, Nature 342:435-438.

Xu et al., "*In Vivo Anti-Hiv Activity of (+)-Calanolide A In The Hollow Fiber Mouse Model*", Bioorg. Med. Chem. Lett. 1999, 9:133-138.

Wang et al., "*A Phosphatidylinositol 3,4,5-Trisphosphate Analogue with Low Serum Protein-Binding Affinity*", Biororganic & NMedicinal Chemistry 9 (2001) 133-139.

Aliprantis et al., "*Cell Activation and Apoptosis by Bacterial Lipoproteins Through Toll-like Receptor-2*", Jul. 30, 1999, Science Vo. 285, pp. 736-739.

Stacey et al., "*Isolation of DNA from Plants*", Methods in Molecular Biology, vol. 28, pp. 9-15.

Ajioka, J. W. et al., 1998, "Gene Discovery by EST Sequencing in *Toxoplama gondii* Reveals Sequences Restricted to the Apicomplexa," Genome Research.

Aliberti, J. & Sher, A., 2002, "Role of G-protein-coupled signaling in the induction and regulation of dendritic cell function by *Toxoplasma gondii*," Microbes and Infection 4: 991-997.

Aliprantis A. et al., 1999, "Cell Activation and Apoptosis by Bacterial Lipoproteins Through Toll-like Receptor-2," Science, 285:736-739.

Ashley S. & Wells S., 1988, "Tumors of the Small Intestine," Seminars in Oncology, 15(2):116-128.

Bennett, L. et al., 1951, "Effect of Ultracentrifugal Fractions of Small Intestinal Tissue upon Transplanted Lymphosarcoma," Proc. Society of Experimental Biology, 700-701.

Billiau, A., 1996, "Interferon- γ Biology and Role in Pathogenesis," Advanced in Immunology, 62: 61-130.

Brake, D.A., 2002, "Vaccinology for control of apicomplexan parasites: a simplified language of immune programming and its use in vaccine design," Int J Parasitol. 23(5): 509-15.

Cairns, J., 1975, "Mutation selection and the natural history of cancer," Nature, 255:197-200.

Calman, K. 1974, "Why are small bowel tumors rare? An experimental model," Gut, 15:552-554.

Chan P. et al., 1975, "Small bowel extracts in the inhibition of tumour growth," Gut, 16: 50-52.

Fong, L. & Engleman, E. G., 2000, "Dedritic Cells in Cancer Immunotherapy," Annu Rev Immunol. 18:245-273.

Gately, M. et al., 1993, "Administration of recombinant IL-12 to normal mice enhances cytolytic lymphocyte activity and induces production of IFN-γ in vivo," Intl Immuno, 6(1): 157-167.

Hayday A. et al., 2001, "Intraepithelial lymphocytes: exploring the Third Way in Immunology," Nature Immunology, 2(11): 997-1003.

Horvath-Arcidiacono J. et al., 1996, "IL-12 administered in vivo to young and aged mice. Discrepancy between the effects on tumor growth in vivo and cytotoxic T lymphocyte generation ex vivo: dependence on IFN-γ," Intl Immuno. 8(5): 661-673.

Lightdale, C. et al., 1982, "Small Intestine," Cancer Epidemiology and Prevention, 692-702.

Lingeman C. et al. 1972, "Comparative Study of Intestinal Adenocarcinomas of Animals and Man," Nat'l Cancer Inst. 48(2): 325-340.

Maldonado-Lopez, R. & Moser M., 2001, "Dedritic cell subsets and the regulation of Th1/Th2 responses," Immunology, vol. 0: 1-8.

Moulton, J. (ed.), 1990, "Tumors in Domestic Animals," Univ Cal. Press, 403, 435.

Neutra, M. et al., 2001, "Collaboration of epithelial cells with organized mucosal lymphoid tissues," Nature Immunology, 2(11): 1004-1009.

Okamura H. et al., 1995, "Cloning of a new cytokine that induces IFN-γ production in T cells," Nature 378: 88-91.

Pardoll, D. M., 2002, "Spinning Molecular Immunology into Successful Immunotherapy," Nature, 2:227-238.

PCT International Search Report, PCT/US2004/023113, dated Jul. 1, 2005.

Pollak, Y, et al., 2003, "The EAE-associated behavioral syndrome: II. Modulation by anti-inflammatory treatments," J Neuroimmunology, 137: 100-108.

Reis e Sousa, C. et al., 1997, "In Vivo Microbial Stimulation Induces Rapid CD40 Ligand-independent Production of Interleukin 12 by Dendritic Cells and their Redistribution to T Cell Areas," J Exp. Med., 186(11): 1819-1829.

Stern A. et al., 1996, "Interleukin-12 an Integral Cytokine in the Immune Response," Life Sciences, 58(8): 639-654.

Tatusova, T. & Madden T.L., 1999, "BLAST 2 Sequences, a new tool for comparing protein and nucleotide sequences," FEMS Microbiology Letters 174: 247-250.

Van der Auwera, P., 1989, Ex Vivo Study of Serum Bacterial Titers and Killing Rates of Daptomycin (LY 146032) Combined or Not Combined with Amikacin Compared with Those of Vancomycin.

Yarovinsky, F. et al., 2005, "TLR 11 Activation of Dedritic Cells by a Protozoan Profilin-Like Protein," Science, 308: 1626-1629.

```
                       Probable N terminus
                              ↓
EtU3:     SSFCFLFQI  IFYLVCKMG   EADTQAWDTS  VREWLVDTGR  VFAGGVASIA
3-1E:     ARVFIVCSFF VFPYSVKMGE  EADTQAWDTS  VKEWLVDTGK  VYAGGIASIA
bov:                             EWLVDTGK    VFAGGVASIA
50-mer:                                                  IASIA EtU3:     DGCRLFGA██████████████████YQIEVP  QEDGTSISVD  CDEAETLRQA
3-1E:     DGCRLFGA██████████████████YQIEVL  QEDGSSTQED  CDEAETLRQA
bov:      DG RMFGA██████████████████YQIESV  QEDNGTVQ                QA
50-mer:   DGCRMFGAST DSGGDPYAEL VQ--TGYQIEVL QEDGSSTQED  CDEAE EtU3:     VVDGRAPNGV YIGGTKYKLA EVKRDFTFND QNYDVAILGK NKGGGFLIKT
3-1E:     IVDGRAPNGV YIGGIKYKLA EVKRDFTYND QNYDVAILGK NKGGGFLIKT
bov:      IV    APDGV YIGGVK                                GGGFLIKT EtU3:     PNENVVIALY DEEKEQNKAD ALTTALNFAE YLHQSGF
3-1E:     PNDNVVIALY DEEKEQNKAD ALTTALAFAE YLYQGGF
bov:      PNENIAIALY DEEKEQNKAD ALTTALNFAD FLYQ
```

Note: A weakly conserved region is shown in highlight. Gaps in the bovine sequence indicate no data. Hyphens indicate display shifts for alignment purposes.

Figure 4

DNA SEQUENCE OF THE CLONE EtU3

```
TCCAGTTTTTGCTTTCTTTTCCAAATTATTTTCTATTTAGTTTGCAAAATG
GGAGAAGCAGACACCCAGGCCTGGGACACTTCGGTCCGCGAGTGGCTGGTT
GACACCGGCAGGGTCTTCGCCGGCGGCGTTGCTAGCATAGCCGACGGCTGC
CGGCTCTTCGGAGCAGCAGTGGAGGGCGAGGGCAACGCCTGGGAAGAACTC
GTCAAGACCAACTACCAAATTGAAGTCCCCCAGGAAGACGGAACCTCTATT
TCAGTGGATTGCGACGAGGCGGAGACTCTGCGGCAGGCGGTGGTGGACGGC
CGCGCGCCCAACGGCGTCTACATCGGCGGCACCAAGTACAAGCTCGCCGAA
GTCAAAGGGACTTCACCTTCAACGACCAAAACTATGATGTGGCGATTCTG
GGAAAAAACAAAGGCGGAGGGTTTTTGATTAAAACTCCAAACGAAATGTT
GTTATAGCTTTGTATGATGAAGAAAAGAACAAAACAAAGCTGATGCTCTC
ACAACAGCTCTTAACTTCGCGGAGTACCTTCACCAGTCCGGCTTCTAA
```

Figure 7(A)

Figure 9
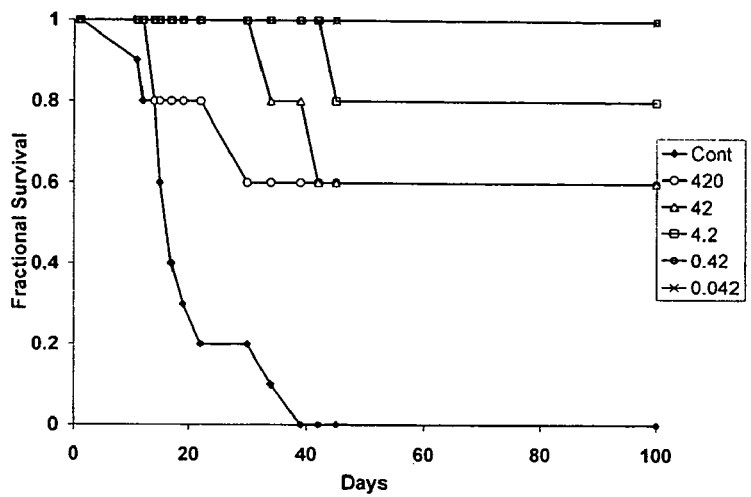
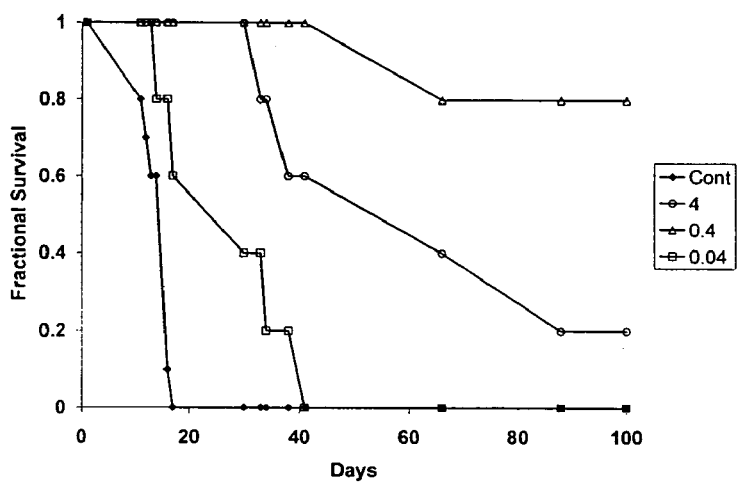
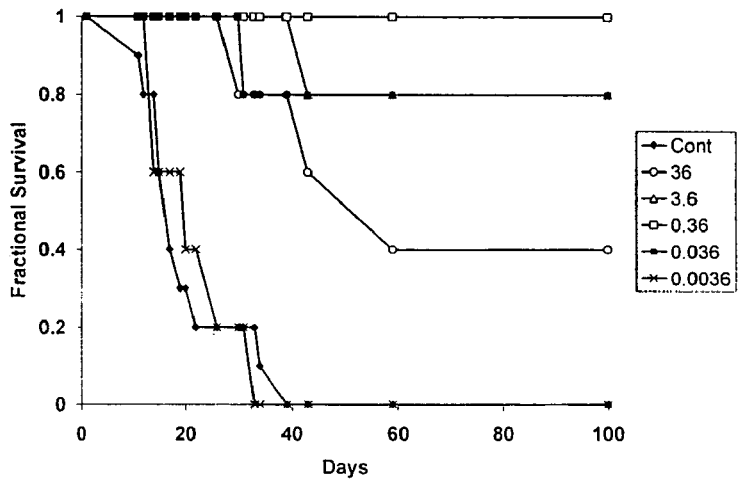

Figure 17

DC & Anti-timor Activity of E. tenella Crude Membrane Preparation

```
                    1                                                        50
   C parvum    .......... .......... ......LKM ......S.EW DDMVKEWLID
 E acervulin   .....ARVFI VCSFF..VFP YS.....VKM GEEAD.TQAW DTSVKEWLVD
   E tenella   RQCAGIRPSS FCFLFQIIFY LV.....CKM G.EAD.TQAW DTSVREWLVD
   N caninum   .......... .......... .........M ......S.DW DPVVKEWLVD
  N caninum2   .......... .......... .........M ......S.DW DPVVKEWLVD
 P falciparu   .......... .......... .......... .......... ..........
    P yoelii   .......... .......... .........M .EE..YS..W ENFLNDKLLA
  S neurona    ..FFFFRDSS SS.VLPSH.L GV.....TIM AEEQAGTEEW DTLCQDWLPG
   T gondii1   .......... .......... .......... .......... ..........
   T gondii2   ...FPPRSSA TSYRILFRFF RGLFPFFSKM ......S.DW DPVVKEWLVD
   T gondii3   ...FPPRSSA TSYRILFRFF RGLFPFFSKM ......S.DW DPVVKEWLVD
   IDENTITY    .......... .......... .........M .EE......W .......L..
 SIMILARITY    .......... .......... .........M GEE...S..W D..VKEWLVD 51                                                       100
   C parvum    TGSVCAGGLC SI.DG...AF Y..AASADQG ....D.AWKT LVREDHEENV
 E acervulin   TGKVYAGGIA SIADGCR.LF ...GAAIDNG E...D.AWSQ LVKTGYQIEV
   E tenella   TGRVFAGGVA SIADGCR.LF ...GAAVE.G EGN...AWEE LVKTNYQIEV
   N caninum   TGYCCAGGIA NAEDG..VVF ...AAAADDD ....D.GWSK LYKEDHEED.
  N caninum2   TGYCCAGGIA NAEDG..VVF ...AAAADDD ....D.GWSK LYKEDHEED.
 P falciparu   ....SGAGLA SEEDG..VV. YACVAQGEES DPNFDK.WSL FYKEDYDIEV
    P yoelii   TNQVSAAGLA SEEDG..VV. YECVATPDEN NPDFDK.WSL FYKEDYDIEI
  S neurona    TGYCSAGGLC SAEDG..VI. Y.AAAS...N SH...KGWAV LYRDDHEQDE
   T gondii1   ....SGAGLA SEEDG..VV. YACVAQGEES DPNFDK.WSL FYKEDYDIEV
   T gondii2   TGYCCAGGIA NAEDG..VVF ...AAAADDD ....D.GWSK LYKDDHEEDT
   T gondii3   TGYCCAGGIA NAEDG..VVF ...AAAADDD ....D.GWSK LYKDDHEEDT
   IDENTITY    T......G.. ...DG..V.F Y...A..... ....D..W.. ..........
 SIMILARITY    TG...AGG.A ..EDG..VVF Y...A..D.. ....D.GW... ..K..H..D.

101                                                      150
   C parvum    .IQSDGVSEA AEL..INDQT TLCQAISEG. KAPNGVWVGG NKYKIIRVEK
 E acervulin   .LQEDGSSTQ ED..C.DEAE TLRQAIVDG. RAPNGVYIGG IKYKLAEVKR
   E tenella   .PQEDGTSIS VD..C.DEAE TLRQAVVDG. RAPNGVYIGG TKYKLAEVKR
   N caninum   TIGEDGNVNG K.V.TVNEAS TIKAAVDDGS .APNGVWIGG QKYKVVRPEK
  N caninum2   TIGEDGNVNG K.V.TVNEAS TIKAAVDDGS .APNGVWIGG QKYKVVRPEK
 P falciparu   ..EDE.NGTK TT.KTINEGQ TILVVFNEGY .APDGVWLGG TKYQFINIER
    P yoelii   ..EDE.NGNK TT.KTITEGQ TILTMFNEGY .APDGIWLGG TKYQFINMEK
  S neurona    .LGEDGNPIG K.V.TINEGS TIKKAMEEGS .APNGVWIGG VKYKVVRPEK
   T gondii1   ..EDE.NGTK TT.KTINEGQ TILVVFNEGY .APDGVWLGG TKYQFINIER
   T gondii2   .IGEDGNACG K.V.SINEAS TIKAAVDDGS .APNGVWIGG QKYKVVRPEK
   T gondii3   .IGEDGNACG K.V.SINEAS TIKAAVDDGS .APNGVWIGG QKYKVVRPEK
   IDENTITY    T....G.... .......... T......G. .AP.G...GG .KY.......
 SIMILARITY    T...DG.... ..V..I.EA. T......EG. .AP.GVWIGG .KYK.V..ER 151                                                      200
   C parvum    DFQQNDATV. HV.T.FCNRP Q.GGCFLVDT Q.NGTVVVAV YDESKDQSSG
 E acervulin   DFTYNDQ.NY DVA.IL.GK. NKGGGFLIKT .PNDNVVIAL YDEEKEQNKA
   E tenella   DFTFNDQ.NY DVA.IL.GK. NKGGGFLIKT .PNENVVIAL YDEEKEQNKA
   N caninum   GFEYNDCT.F DI.T.MCARS .KGGAHLIKT .PNGSIVIAL YDEENEQDKG
  N caninum2   GFEYNDCT.F DI.T.MCARS .KGGAHLIKT .PNGSIVIAL YDEEKEQDKG
 P falciparu   DLEF.EGYNF DVAT..CAKL .KGGLHLVK. VPGGNILVVL YDEEKEQDRG
    P yoelii   GLEY.EGYSF DVAT..CAKL .KGGMHIIK. VGGGHILIVL YDEEKEQDRG
  S neurona    NVEYN.GIMY D..TVMCARP .KGGAHLIKT .PKGTIIVAV YDEEKEQSAG
   T gondii1   DLEF.EGYNF DVAT..CAKL .KGGLHLVK. VPGGNILVVL YDEEKEQDRG
   T gondii2   GFEYNDCT.F DI.T.MCARS .KGGAHLIKT .PNGSIVIAL YDEEKEQDKG
   T gondii3   GFEYNDCT.F DI.T.MCARS .KGGAHLIKT .PNGSIVIAL YDEEKEQDKG
   IDENTITY    ....N..... ..AT..C... .KGG.....T .......... YDEE..Q...
 SIMILARITY    ....ND...F DVATI.CAKS .KGG.HLIKT VP.G.IVIAL YDEEKEQ..G
```

Figure 19

```
                201                      223
C parvum     NCKKLLCN..  ............  ...
E acervulin  DALTTALAFA  ..EYLYQGGF    ...
E tenella    DALTTALNFA  ..EYLYQGGF    ...
N caninum    NSMTSALAFA  ..EYLHQSGY    ...
N caninum2   NSRTSALAFA  ..EYLHQSGY    ...
P falciparu  NSKIAALTFA  K.ELAESSQ.    ...
P yoelii     NSKNAALAFS  K.ELAESTDA    GAA
S neurona    NSRTCALAFA  HH.LNFLGC.    ...
T gondii1    NSKIAALTFA  K.ELAESSQ.    ...
T gondii2    NSRTSALAFA  ..EYLHQSGY    ...
T gondii3    NSRTSALAFA  ..EYLHQSGY    ...
IDENTITY     ........F.  ..E.......    ...
SIMILARITY   N....AL.FA  K.EYL...S.Y   ...
```

Figure 19 Cont.

DNA sequences of E1 and U3 clones

```
      1                                                        50
E1 ATGGGTGAAG AGGCTGATAC TCAGGCCTGG GACACTTCGG TCCGCGAGTG
U3    ATGGGAG AAGCAGACAC CCAGGCCTGG GACACTTCGG TCCGCGAGTG 51                                                       100
E1 GCTGGTTGAC ACCGGCAGGG TCTTCGCCGG CGGCGTTGCT AGCATAGCCG
U3 GCTGGTTGAC ACCGGCAGGG TCTTCGCCGG CGGCGTTGCT AGCATAGCCG 101                                                       150
E1 ACGGCTGCCG GCTCTTCGGA GCAGCAGTGG AGGGCGAGGG CAACGCCTGG
U3 ACGGCTGCCG GCTCTTCGGA GCAGCAGTGG AGGGCGAGGG CAACGCCTGG 151                                                       200
E1 GAAGAACTCG TCAAGACCAA CTACCAAATT GAAGTCCCCC AGGAAGACGG
U3 GAAGAACTCG TCAAGACCAA CTACCAAATT GAAGTCCCCC AGGAAGACGG 201                                                       250
E1 AACCTCTATT TCAGTGGATT GCGACGAGGC GGAGACTCTG CGGCAGGCGG
U3 AACCTCTATT TCAGTGGATT GCGACGAGGC GGAGACTCTG CGGCAGGCGG 251                                                       300
E1 TGGTGGACGG CCGCGCGCCC AACGGCGTCT ACATCGGCGG CACCAAGTAC
U3 TGGTGGACGG CCGCGCGCCC AACGGCGTCT ACATCGGCGG CACCAAGTAC 301                                                       350
E1 AAGCTCGCCG AAGTCAAAAG GGACTTCACC TTCAACGACC AAAACTATGA
U3 AAGCTCGCCG AAGTCAAAAG GGACTTCACC TTCAACGACC AAAACTATGA 351                                                       400
E1 TGTGGCGATT CTGGGAAAAA ACAAAGGCGG AGGGTTTTTG ATTAAAACTC
U3 TGTGGCGATT CTGGGAAAAA ACAAAGGCGG AGGGTTTTTG ATTAAAACTC 401                                                       450
E1 CAAACGAAAA TGTTGTTATA GCTTTGTATG ATGAAGAAAA AGAACAAAAC
U3 CAAACGAAAA TGTTGTTATA GCTTTGTATG ATGAAGAAAA AGAACAAAAC 451                                                       500
E1 AAAGCTGATG CTCTCACAAC AGCTCTTAAC TTCGCTGAGT ACCTGTACCA
U3 AAAGCTGATG CTCTCACAAC AGCTCTTAAC TTCGCGGAGT ACCTTCACCA 501        513
E1 GGGCGGCTTC TAA
U3 GTCCGGCTTC TAA
```

FIG. 20

Protein Sequences of E1 and U3 clones

```
          1                                              40
E1    MGEEADTQAW  DTSVREWLVD  TGRVFAGGVA  SIADGCRLFG
U3     MGEADTQAW  DTSVREWLVD  TGRVFAGGVA  SIADGCRLFG 41                                             80
E1    AAVEGEGNAW  EELVKTNYQI  EVPQEDGTSI  SVDCDEAETL
U3    AAVEGEGNAW  EELVKTNYQI  EVPQEDGTSI  SVDCDEAETL 80                                            120
E1    ROAVVDGRAP  NGVYIGGTKY  KLAEVKRDFT  FNDQNYDVAI
U3    ROAVVDGRAP  NGVYIGGTKY  KLAEVKRDFT  FNDQNYDVAI 121                                           160
E1    LGKNKGGGFL  IKTPNENVVI  ALYDEEKEQN  KADALTTALN
U3    LGKNKGGGFL  IKTPNENVVI  ALYDEEKEQN  KADALTTALN 161      170
E1    FAEYLYQGGF
U3    FAEYLHQSGF
```

Figure 20 Cont.

```
                        SEQUENCE LISTING

<160> NUMBER OF SEQ ID NOS: 30

<210> SEQ ID NO 1
<211> LENGTH: 169
<212> TYPE: PRT
<213> ORGANISM: Eimeria tenella

<400> SEQUENCE: 1

Met Gly Glu Ala Asp Thr Gln Ala Trp Asp Thr Ser Val Arg Glu Trp
1               5                   10                  15

Leu Val Asp Thr Gly Arg Val Phe Ala Gly Gly Val Ala Ser Ile Ala
            20                  25                  30

Asp Gly Cys Arg Leu Phe Gly Ala Ala Val Glu Gly Glu Gly Asn Ala
        35                  40                  45

Trp Glu Glu Leu Val Lys Thr Asn Tyr Gln Ile Glu Val Pro Gln Glu
    50                  55                  60

Asp Gly Thr Ser Ile Ser Val Asp Cys Asp Glu Ala Glu Thr Leu Arg
65                  70                  75                  80

Gln Ala Val Val Asp Gly Arg Ala Pro Asn Gly Val Tyr Ile Gly Gly
                85                  90                  95

Thr Lys Tyr Lys Leu Ala Glu Val Lys Arg Asp Phe Thr Phe Asn Asp
            100                 105                 110

Gln Asn Tyr Asp Val Ala Ile Leu Gly Lys Asn Lys Gly Gly Gly Phe
        115                 120                 125

Leu Ile Lys Thr Pro Asn Glu Asn Val Val Ile Ala Leu Tyr Asp Glu
    130                 135                 140

Glu Lys Glu Gln Asn Lys Ala Asp Ala Leu Thr Thr Ala Leu Asn Phe
145                 150                 155                 160

Ala Glu Tyr Leu His Gln Ser Gly Phe
                165

<210> SEQ ID NO 2
<211> LENGTH: 170
<212> TYPE: PRT
<213> ORGANISM: Eimeria acervulina

<400> SEQUENCE: 2

Met Gly Glu Glu Ala Asp Thr Gln Ala Trp Asp Thr Ser Val Lys Glu
1               5                   10                  15
```

Trp Leu Val Asp Thr Gly Lys Val Tyr Ala Gly Gly Ile Ala Ser Ile
            20                  25                  30

Ala Asp Gly Cys Arg Leu Phe Gly Ala Ala Ile Asp Asn Gly Glu Asp
        35                  40                  45

Ala Trp Ser Gln Leu Val Lys Thr Gly Tyr Gln Ile Glu Val Leu Gln
    50                  55                  60

Glu Asp Gly Ser Ser Thr Gln Glu Asp Cys Asp Glu Ala Glu Thr Leu
65                  70                  75                  80

Arg Gln Ala Ile Val Asp Gly Arg Ala Pro Asn Gly Val Tyr Ile Gly
                85                  90                  95

Gly Ile Lys Tyr Lys Leu Ala Glu Val Lys Arg Asp Phe Thr Tyr Asn
            100                 105                 110

Asp Gln Asn Tyr Asp Val Ala Ile Leu Gly Lys Asn Lys Gly Gly
        115                 120                 125

Phe Leu Ile Lys Thr Pro Asn Asp Asn Val Val Ile Ala Leu Tyr Asp
    130                 135                 140

Glu Glu Lys Glu Gln Asn Lys Ala Asp Ala Leu Thr Thr Ala Leu Ala
145                 150                 155                 160

Phe Ala Glu Tyr Leu Tyr Gln Gly Gly Phe
                165                 170

<210> SEQ ID NO 3
<211> LENGTH: 20
<212> TYPE: PRT
<213> ORGANISM: Eimeria tenella

<400> SEQUENCE: 3

Glu Trp Leu Val Asp Thr Gly Lys Val Phe Ala Gly Gly Val Ala Ser
1               5                   10                  15

Ile Ala Asp Gly
            20

<210> SEQ ID NO 4
<211> LENGTH: 31
<212> TYPE: PRT
<213> ORGANISM: Eimeria tenella

<400> SEQUENCE: 4

Arg Met Phe Gly Ala Ser Thr Asp Ser Gly Gly Asp Pro Asn Ala Glu
1               5                   10                  15

Leu Val Lys Ala Gly Tyr Gln Ile Glu Ser Val Gln Glu Asp Asn
            20                  25                  30

<210> SEQ ID NO 5
<211> LENGTH: 4
<212> TYPE: PRT
<213> ORGANISM: Eimeria tenella

<400> SEQUENCE: 5

Gln Ala Ile Val
1

<210> SEQ ID NO 6
<211> LENGTH: 11
<212> TYPE: PRT
<213> ORGANISM: Eimeria tenella

<400> SEQUENCE: 6

Ala Pro Asp Gly Val Tyr Ile Gly Gly Val Lys
1               5                   10

<210> SEQ ID NO 7
<211> LENGTH: 42
<212> TYPE: PRT
<213> ORGANISM: Eimeria tenella

<400> SEQUENCE: 7

Gly Gly Gly Phe Leu Ile Lys Thr Pro Asn Glu Asn Ile Ala Ile Ala
1               5                   10                  15

Leu Tyr Asp Glu Glu Lys Glu Gln Asn Lys Ala Asp Ala Leu Thr Thr
            20                  25                  30

Ala Leu Asn Phe Ala Asp Phe Leu Tyr Gln
        35                  40

<210> SEQ ID NO 8
<211> LENGTH: 152
<212> TYPE: PRT
<213> ORGANISM: Plasmodium falciparum

<400> SEQUENCE: 8

Leu Leu Ala Thr Asn Gln Val Ser Gly Ala Gly Leu Ala Ser Glu Glu
1               5                   10                  15

Asp Gly Val Val Tyr Ala Cys Val Ala Gln Gly Glu Glu Ser Asp Pro
            20                  25                  30

Asn Phe Asp Lys Trp Ser Leu Phe Tyr Lys Glu Asp Tyr Asp Ile Glu
        35                  40                  45

Val Glu Asp Glu Asn Gly Thr Lys Thr Thr Lys Thr Ile Asn Glu Gly
    50                  55                  60

Gln Thr Ile Leu Val Val Phe Asn Glu Gly Tyr Ala Pro Asp Gly Val
65                  70                  75                  80

Trp Leu Gly Gly Thr Lys Tyr Gln Phe Ile Asn Ile Glu Arg Asp Leu
                85                  90                  95

Glu Phe Glu Gly Tyr Asn Phe Asp Val Ala Thr Cys Ala Lys Leu Lys
            100                 105                 110

Gly Gly Leu His Leu Val Lys Val Pro Gly Gly Asn Ile Leu Val Val
        115                 120                 125

Leu Tyr Asp Glu Glu Lys Glu Gln Asp Arg Gly Asn Ser Lys Ile Ala
    130                 135                 140

Ala Leu Thr Phe Ala Lys Glu Leu
145                 150

<210> SEQ ID NO 9
<211> LENGTH: 152
<212> TYPE: PRT
<213> ORGANISM: Plasmodium falciparum

<400> SEQUENCE: 9

Leu Leu Ala Thr Asn Gln Val Ser Gly Ala Gly Leu Ala Ser Glu Glu
1               5                   10                  15

Asp Gly Val Val Tyr Ala Cys Val Ala Gln Gly Glu Glu Ser Asp Pro
            20                  25                  30

Asn Phe Asp Lys Trp Ser Leu Phe Tyr Lys Glu Asp Tyr Asp Ile Glu
        35                  40                  45

Val Glu Asp Glu Asn Gly Thr Lys Thr Thr Lys Thr Ile Asn Glu Gly
    50                  55                  60

Gln Thr Ile Leu Val Val Phe Asn Glu Gly Tyr Ala Pro Asp Gly Val
65                  70                  75                  80

```
Trp Leu Gly Gly Thr Lys Tyr Gln Phe Ile Asn Ile Glu Arg Asp Leu
                85                  90                  95

Glu Phe Glu Gly Tyr Asn Phe Asp Val Ala Thr Cys Ala Lys Leu Lys
            100                 105                 110

Gly Gly Leu His Leu Val Lys Val Pro Gly Gly Asn Ile Leu Val Val
            115                 120                 125

Leu Tyr Asp Glu Glu Lys Glu Gln Asp Arg Gly Asn Ser Lys Ile Ala
130                 135                 140

Ala Leu Thr Phe Ala Lys Glu Leu
145                 150

<210> SEQ ID NO 10
<211> LENGTH: 116
<212> TYPE: PRT
<213> ORGANISM: Plasmodium falciparum

<400> SEQUENCE: 10

Cys Val Ala Gln Gly Glu Glu Ser Asp Pro Asn Phe Asp Lys Trp Ser
1               5                   10                  15

Leu Phe Tyr Lys Glu Asp Tyr Asp Ile Glu Val Glu Asp Glu Asn Gly
            20                  25                  30

Thr Lys Thr Thr Lys Thr Ile Asn Glu Gly Gln Thr Ile Leu Val Val
        35                  40                  45

Phe Asn Glu Gly Tyr Ala Pro Asp Gly Val Trp Leu Gly Gly Thr Lys
    50                  55                  60

Tyr Gln Phe Ile Asn Ile Glu Arg Asp Leu Glu Phe Glu Gly Tyr Asn
65                  70                  75                  80

Phe Asp Val Ala Thr Cys Ala Lys Leu Lys Gly Gly Leu His Leu Val
                85                  90                  95

Lys Val Pro Gly Gly Asn Ile Leu Val Val Leu Tyr Asp Glu Glu Lys
            100                 105                 110

Glu Gln Asp Arg
            115

<210> SEQ ID NO 11
<211> LENGTH: 131
<212> TYPE: PRT
<213> ORGANISM: Hevea brasiliensis

<400> SEQUENCE: 11

Met Ser Trp Gln Thr Tyr Val Asp Asp His Leu Met Cys Asp Ile Asp
1               5                   10                  15

Gly His Arg Leu Thr Ala Ala Ala Ile Ile Gly His Asp Gly Ser Val
            20                  25                  30

Trp Ala Gln Ser Ser Ser Phe Pro Gln Phe Lys Ser Asp Glu Val Ala
        35                  40                  45

Ala Val Met Lys Asp Phe Asp Glu Pro Gly Ser Leu Ala Pro Thr Gly
    50                  55                  60

Leu His Leu Gly Gly Thr Lys Tyr Met Val Ile Gln Gly Glu Pro Gly
65                  70                  75                  80

Ala Val Ile Arg Gly Lys Lys Gly Ser Gly Gly Ile Thr Val Lys Arg
                85                  90                  95

Thr Gly Gln Ala Leu Ile Ile Gly Ile Tyr Asp Glu Pro Leu Thr Pro
            100                 105                 110

Gly Gln Cys Asn Met Ile Val Glu Arg Leu Gly Asp Tyr Leu Leu Asp
            115                 120                 125
```

```
Gln Gly Leu
    130

<210> SEQ ID NO 12
<211> LENGTH: 130
<212> TYPE: PRT
<213> ORGANISM: Arabidopsis thaliana
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (72)..(72)
<223> OTHER INFORMATION: Xaa can be any naturally occurring amino acid
<220> FEATURE:
<221> NAME/KEY: misc_feature
<222> LOCATION: (109)..(109)
<223> OTHER INFORMATION: Xaa can be any naturally occurring amino acid

<400> SEQUENCE: 12

Ser Trp Gln Ser Tyr Val Asp Asp His Leu Xaa Cys Asp Val Glu Gly
1               5                   10                  15

Asn His Leu Thr Ala Ala Ala Ile Leu Gly Gln Asp Gly Ser Val Trp
            20                  25                  30

Ala Gln Ser Ala Lys Phe Pro Gln Leu Lys Pro Gln Glu Ile Asp Gly
        35                  40                  45

Ile Lys Lys Asp Phe Glu Glu Pro Gly Phe Leu Ala Pro Thr Gly Leu
    50                  55                  60

Phe Leu Gly Gly Glu Lys Tyr Xaa Val Ile Gln Gly Glu Gln Gly Ala
65                  70                  75                  80

Val Ile Arg Gly Lys Lys Gly Pro Gly Val Thr Ile Lys Lys Thr
                85                  90                  95

Asn Gln Ala Leu Val Phe Gly Phe Tyr Asp Glu Pro Xaa Thr Gly Gly
            100                 105                 110

Gln Cys Asn Leu Val Val Glu Arg Leu Gly Asp Tyr Leu Ile Glu Ser
        115                 120                 125

Glu Leu
    130

<210> SEQ ID NO 13
<211> LENGTH: 133
<212> TYPE: PRT
<213> ORGANISM: Betula pendula

<400> SEQUENCE: 13

Met Ser Trp Gln Thr Tyr Val Asp Glu His Leu Met Cys Asp Ile Asp
1               5                   10                  15

Gly Gln Gly Glu Glu Leu Ala Ala Ser Ala Ile Val Gly His Asp Gly
            20                  25                  30

Ser Val Trp Ala Gln Ser Ser Phe Pro Gln Phe Lys Pro Gln Glu
        35                  40                  45

Ile Thr Gly Ile Met Lys Asp Phe Glu Glu Pro Gly His Leu Ala Pro
    50                  55                  60

Thr Gly Leu His Leu Gly Gly Ile Lys Tyr Met Val Ile Gln Gly Glu
65                  70                  75                  80

Ala Gly Ala Val Ile Arg Gly Lys Lys Gly Ser Gly Gly Ile Thr Ile
                85                  90                  95

Lys Lys Thr Gly Gln Ala Leu Val Phe Gly Ile Tyr Glu Glu Pro Val
            100                 105                 110
```

```
Thr Pro Gly Gln Cys Asn Met Val Val Glu Arg Leu Gly Asp Tyr Leu
        115                 120                 125
Ile Asp Gln Gly Leu
    130

<210> SEQ ID NO 14
<211> LENGTH: 131
<212> TYPE: PRT
<213> ORGANISM: Arabidopsis thaliana

<400> SEQUENCE: 14

Met Ser Trp Gln Ser Tyr Val Asp Asp His Leu Met Cys Asp Val Glu
1               5                   10                  15
Gly Asn His Leu Thr Ala Ala Ala Ile Leu Gly Gln Asp Gly Ser Val
                20                  25                  30
Trp Ala Gln Ser Ala Lys Phe Pro Gln Leu Lys Pro Gln Glu Ile Asp
            35                  40                  45
Gly Ile Lys Lys Asp Phe Glu Glu Pro Gly Phe Leu Ala Pro Thr Gly
        50                  55                  60
Leu Phe Leu Gly Gly Glu Lys Tyr Met Val Ile Gln Gly Glu Gln Gly
65                  70                  75                  80
Ala Val Ile Arg Gly Lys Lys Gly Pro Gly Gly Val Thr Ile Lys Lys
                85                  90                  95
Thr Asn Gln Ala Leu Val Phe Gly Phe Tyr Asp Glu Pro Met Thr Gly
            100                 105                 110
Gly Gln Cys Asn Leu Val Val Glu Arg Leu Gly Asp Tyr Leu Ile Glu
        115                 120                 125
Ser Glu Leu
    130

<210> SEQ ID NO 15
<211> LENGTH: 999
<212> TYPE: DNA
<213> ORGANISM: Eimeria acervulina

<400> SEQUENCE: 15
tgtttctctt cattgtttgt agtttctttg tatttcctta ctcagttaaa atgggtgaag    60
aggctgatac tcaggcgtgg gatacctcag tgaaggaatg gctcgtggat acggggaagg   120
tatacgccgg cggcattgct agcattgcag atgggtgccg cctgtttggc gctgcaatag   180
acaatgggga ggatgcgtgg agtcagttgg tgaagacagg atatcagatt gaagtgcttc   240
aagaggacgg ctcttcaact caagaggact gcgatgaagc ggaaaccctg cggcaagcaa   300
ttgttgacgg ccgtgcccca aacggtgttt atattggagg agttaaatat aaactcgcag   360
aagttaaacg tgatttcacc tataacgacc agaactacga cgtggcgatt tggggaaga   420
acaagggtgg cggtttcctg attaagactc cgaacgacaa tgtggtgatt gctctttatg   480
acgaggagaa ggagcagaac aaagcagatg cgctgacaac ggcacttgcc ttcgctgagt   540
acctgtacca gggcggcttc taattgatct ccagtgcaca accacttgat gagaaggaaa   600
aacctttcat aacaacgact ccccccagt gttaccacac agggagaaga gagacgcaca   660
acttctctac aaatagcgga cagcgtattg cacaccctga cctttgttta ttgaagaggg   720
tgtaggggga ggagcatcag caggcagcag ctttgggcgg tctggacagt cgccatgga   780
gggagagctg tgtagacact cgagagcagc agcagcagca cggttaagtg gcagacgcag   840
agacgccttt gttgtacaac ttctctctca cccgcgtttg ttgtagagag gagtatttat   900
```

| | |
|---|---:|
| tatgaatgca tatccagcaa acaacgaggc aaacagcggg tgcttactgc cgtgcaaatg | 960 |
| atacgcacac caccaaccat ttaataagtg cttttctta | 999 |

<210> SEQ ID NO 16
<211> LENGTH: 977
<212> TYPE: DNA
<213> ORGANISM: Eimeria acervulina

<400> SEQUENCE: 16

| | |
|---|---:|
| cgtttctttg tatttcctta ctcagttaaa atgggtgaag aggctgatac tcaggcgtgg | 60 |
| gatacctcag tgaaggaatg gctcgtggat acggggaagt atacgccgg cggcattgct | 120 |
| agcattgcag atgggtgccg cctgtttggc gctgcaatag acaatgggga ggatgcgtgg | 180 |
| agtcagttgg tgaagacagg atatcagatt gaagtgcttc aagaggacgg ctcttcaact | 240 |
| caagaggact gcgatgaagc ggaaaccctg cggcaagcaa ttgttgacgg ccgtgcccca | 300 |
| aacggtgttt atattggagg aattaaatat aaactcgcag aagttaaacg tgatttcacc | 360 |
| tataacgacc agaactacga cgtggcgatt tggggaaga acaagggtgg cggtttcctg | 420 |
| attaagactc cgaacgacaa tgtggtgatt gctctttatg acgaggagaa agagcagaac | 480 |
| aaagcagatg cgctgacaac ggcacttgcc ttcgctgagt acctgtacca gggcggcttc | 540 |
| taattgatct ccagtgcaca accacttgat gagaaggaaa aacctttcat aacaacaact | 600 |
| tcccccagtg ttgccacaca gggagaagag agacgcacaa cttctctaca aatagcggac | 660 |
| agcgtattgc acaccctgac ctttgtttat tgaagagggt gtaggggag gagcatcagc | 720 |
| aggcagcagc tttgggcggt ctggacagtt cgccatggag ggagagctgt gtagacactc | 780 |
| gagagcagca gcagcagcac ggttaagtgg cagacgcaga gacgcctttg ttgtacaact | 840 |
| tctctctcac ccgcgtttgt tgtagagagg agtatttatt atgaatgcat atccagcaaa | 900 |
| caacgaggca aacagcgggt gcttactgcc gtgcaaatga tacgcacacc accaaccatt | 960 |
| taataagtgc ttttctt | 977 |

<210> SEQ ID NO 17
<211> LENGTH: 1074
<212> TYPE: DNA
<213> ORGANISM: Eimeria acervulina

<400> SEQUENCE: 17

| | |
|---|---:|
| ggcacgagtc ttcattgttt gtagtttctt tgtatttcct tactcagtta aaatgggtga | 60 |
| agaggctgat actcaggcgt gggatacctc agtgaaggaa tggctcgtgg atacggggaa | 120 |
| ggtatacgcc ggcggcattg ctagcattgc agatgggtgc cgcctgtttg gcgctgcaat | 180 |
| agacaatggg gaggatgcgt ggagtcagtt ggtgaagaca ggatatcaga ttgaagtgct | 240 |
| tcaagaggac ggctcttcaa ctcaagagga ctgcgatgaa gcggaaaccc tgcggcaagc | 300 |
| aattgttgac ggccgtgccc caaacggtgt ttatattgga ggaattaaat ataaactcgc | 360 |
| agaagttaaa cgtgatttca cctataacga ccagaactac gacgtggcga ttttggggaa | 420 |
| gaacaagggt ggcggtttcc tgattaagac tccgaacgac aatgtggtga ttgctcttta | 480 |
| tgacgaggag aaagagcaga acaaagcaga tgcgctgaca acggcacttg ccttcgctga | 540 |
| gtacctgtac cagggcggct tctaattgat ctccagtgca caaccacttg atgagaagga | 600 |
| aaaacctttc ataacaacaa cttcccccag tgttgccaca cagggagaag agagacgcac | 660 |
| aacttctcta caaatagcgg acagcgtatt gcacaccctg acctttgttt attgaagagg | 720 |
| gtgtaggggg aggagcatca gcaggcagca gctttgggcg gtctggacag ttcgccatgg | 780 |

```
agggagagct gtgtagacac tcgagagcag cagcagcagc acggttaagt ggcagacgca      840
gagacgcctt tgttgtacaa cttctctctc acccgcgttt gttgtagaga ggagtattta      900
ttatgaatgc atatccagca aacaacgagg caaacagcgg gtgcttactg ccgtgcaaat      960
gatacgcaca ccaccaacca tttaataagt gctttcttta atatggcttg acgctcccag     1020
cgaaaaaaaa aaaaaaaaaa aaaaaaaaaa aaaaaaaaaa aaaaaaaaaa aaaa           1074

<210> SEQ ID NO 18
<211> LENGTH: 460
<212> TYPE: DNA
<213> ORGANISM: Eimeria acervulina
<220> FEATURE:
<221> NAME/KEY: misc_feature
<222> LOCATION: (240)..(241)
<223> OTHER INFORMATION: n is a, c, g, or t

<400> SEQUENCE: 18
tgttgacggc cgtgccccaa acggtgttta tattggagga gttaaatata aactcgcaga       60
agttgtaagt ttccttcata ctctagaaga atagcgcttg ctcatccatg gtgtcgtgca      120
gtgggatgca atcgccacgc ggggctgtac agacacctca aagttgaatg gtagtaataa      180
tagtcatgtt cttcatgatg atggaataag tgaataatta gggtgttttg tgacggcgtn      240
ntcgcttttt tgtcattttc gtcgtttctc ttttgtttat ttcggccga tgatgcagaa       300 acgtgatttc acctataacg accagaacta cgacgtggcg attttgggga agaacaaggg      360
tggcggtttc ctgattaaga ctccgaacga caatgtggtg attgctcttt atgacgagga      420
gaaggagcag aacaaagcag atgcgctgac aacgcaccc                             460

<210> SEQ ID NO 19
<211> LENGTH: 529
<212> TYPE: DNA
<213> ORGANISM: Eimeria tenella
<220> FEATURE:
<221> NAME/KEY: misc_feature
<222> LOCATION: (406)..(406)
<223> OTHER INFORMATION: n is a, c, g, or t

<400> SEQUENCE: 19
ttattttcta tttagtttgc aaaatgggag aagcagacac ccagcctggg acacttcggt       60
ccgcgagtgg ctggttgaca ccggcagggt cttcgccggc ggcgttgcta gcatagccga      120
cggctgccgg ctcttcggag cagcagtgga gggcgagggc aacgcctggg aagaactcgt      180
caagaccaac taccaaattg aagtcccca ggaagacgga acctccattt cagtggattg      240
cgacgaggcc gagactctgc ggcaggcggt ggtggacggc cgcgcgccca acggcgtcta      300
catcggcggc accaagtaca agctcgccga agtcaaaagg gacttcacct tcaacgacca      360
aaactatgat gtggcgattc tgggaaaaaa caaaggcgga gggttnttga ttaaaactcc      420
aaacgaaaat gttgttatag ctttgtatga tgaagaaaaa gaacataaca aagctgatgc      480
tctcacaaca gctcttaact tcgcggagta tctgtaccaa ggaagcttc                  529

<210> SEQ ID NO 20
<211> LENGTH: 558
<212> TYPE: DNA
<213> ORGANISM: Eimeria tenella

<400> SEQUENCE: 20
tccagttttt gctttctttt ccaaattatt ttctatttag tttgcaaaat gggagaagca       60
```

-continued

```
gacacccagg cctgggacac ttcggtccgc gagtggctgg ttgacaccgg cagggtcttc    120
gccggcggcg ttgctagcat agccgacggc tgccggctct tcggagcagc agtggagggc    180
gagggcaacg cctgggaaga actcgtcaag accaactacc aaattgaagt cccccaggaa    240
gacggaacct ctatttcagt ggattgcgac gaggcggaga ctctgcggca ggcggtggtg    300 gacgccgcg cgcccaacgg cgtctacatc ggcggcacca agtacaagct cgccgaagtc     360
aaaagggact tcaccttcaa cgaccaaaac tatgatgtgg cgattctggg aaaaaacaaa    420
ggcggagggt ttttgattaa aactccaaac gaaaatgttg ttatagcttt gtatgatgaa    480
gaaaaagaac aaaacaaagc tgatgctctc acaacagctc ttaacttcgc ggagtacctt    540
caccagtccg gcttctaa                                                  558
```

<210> SEQ ID NO 21
<211> LENGTH: 529
<212> TYPE: DNA
<213> ORGANISM: Eimeria tenella
<220> FEATURE:
<221> NAME/KEY: misc_feature
<222> LOCATION: (406)..(406)
<223> OTHER INFORMATION: n is a, c, g, or t

<400> SEQUENCE: 21

```
ttatttcta tttagtttgc aaaatgggag aagcagacac ccagcctggg acacttcggt     60
ccgcgagtgg ctggttgaca ccggcagggt cttcgccggc ggcgttgcta gcatagccga    120
cggctgccgg ctcttcggag cagcagtgga gggcagggc aacgcctggg aagaactcgt    180
caagaccaac taccaaattg aagtccccca ggaagacgga acctccattt cagtggattg    240
cgacgaggcc gagactctgc ggcaggcggt ggtggacgcc gcgcgcccca acggcgtcta    300
catcggcggc accaagtaca agctcgccga agtcaaaagg gacttcacct tcaacgacca    360
aaactatgat gtggcgattc tgggaaaaaa caaaggcgga gggttnttga ttaaaactcc    420
aaacgaaaat gttgttatag ctttgtatga tgaagaaaaa gaacataaca aagctgatgc    480
tctcacaaca gctcttaact tcgcggagta tctgtaccaa ggaagcttc                529
```

<210> SEQ ID NO 22
<211> LENGTH: 529
<212> TYPE: DNA
<213> ORGANISM: Toxoplasma gondii
<220> FEATURE:
<221> NAME/KEY: misc_feature
<222> LOCATION: (483)..(483)
<223> OTHER INFORMATION: n is a, c, g, or t

<400> SEQUENCE: 22

```
ttttcgcttc tttcgcggct tgtttccatt cttttccaag atgtccgact gggaccctgt     60
tgtcaaggag tggcttgttg acacaggcta ctgctgcgca ggcggcatcg ccaacgcgga    120
ggacggtgtt gtgttcgccg cggcggctga tgatgatgac ggatggtcca agctgtacaa    180
ggatgatcat gaggaggaca ctatcggaga ggatggcaac gcgtgcggca aggtgtcgat    240
caacgaggcc tccacgatca aagctgcagt tgacgatggc agtgccccta acggtgtttg    300
gattggcggc cagaagtaca aggttgtccg acctgagaaa ggattcgagt acaacgactg    360 cacctttcgac atcaccatgt gtgcacggtc caagggtggc gcgcacttga tcaagacccc    420
gaatggctct atcgtcattg ccctttacga tgaggaagaa gaacaggaca agggaaacag    480
cangacttcg gcattggcct ttgccgagta tcttcaccag tctgggtac                529
```

-continued

<210> SEQ ID NO 23
<211> LENGTH: 509
<212> TYPE: DNA
<213> ORGANISM: Toxoplasma gondii

<400> SEQUENCE: 23

```
tgtttccatt cttttccaag atgtccgact gggaccctgt tgtcaaggag tggcttgttg      60
acacaggcta ctgctgcgca ggcggcatcg ccaacgcgga ggacggtgtt gtgttcgccg     120
cggcggctga tgatgatgac ggatggtcca agctgtacaa ggatgatcat gaggaggaca     180
ctatcggaga ggatggcaac gcgtgcggca aggtgtcgat caacgaggcc tccacgatca     240
aagctgcagt tgacgatggc agtgccccta acggtgtttg gattggcggc cagaagtaca     300
aggttgtccg acctgagaaa ggattcgagt acaacgactg caccttcgac atcaccatgt     360
gtgcacggtc caagggtggc gcgcacttga tcaagacccc gaatggctct atcgtcattg     420
ccctttacga tgaggagaag gaacaggaca agggaaacag caggacttcg gcattggcct     480
ttgccgagta tcttcaccag tctgggtac                                      509
```

<210> SEQ ID NO 24
<211> LENGTH: 549
<212> TYPE: DNA
<213> ORGANISM: Cryptosporidium parvum

<400> SEQUENCE: 24

```
ctcaatcaga acttatatta ttttatcttt tactccgcta tttttatatt ttacttaatt      60
aattaaagat gtctgaatgg gatgatatgg tcaaagaatg gttaattgac accggtagtg     120
tatgtgctgg tggtctttgt tcaatagatg gtgcattcta tgctgcttct gctgatcaag     180
gtgatgcctg gaagactctt gttagagaag atcatgaaga gaatgttatt caatctgacg     240
gagtttcaga ggctgctgaa ttaattaatg atcaaactac actatgccaa gcaatctccg     300
aaggtaaggc accaaacggc gtttgggtcg gaggaaacaa atataagatt atccgtgtag     360
agaaggactt ccagcaaaac gatgctaccg ttcatgttac attttgtaac agacctcaag     420
gtggatgttt tttagttgat actcaaaacg gtactgttgt tgttgcagtt tacgacgaat     480
ccaaggatca atcatcaggt aattgcaaga agttgctctg caactagccg agtacctcgt     540
atctcaggg                                                            549
```

<210> SEQ ID NO 25
<211> LENGTH: 487
<212> TYPE: DNA
<213> ORGANISM: Plasmodium falciparum

<400> SEQUENCE: 25

```
ggcagaagaa tattcatggg acagttattt aaatgatcgc cttttagcaa ccaatcaagt      60
ttcaggagct ggattagctt cggaagaaga tggagttgtc tatgcttgtg tagctcaggg     120
tgaagagagt gacccaaatt ttgataaatg gtcacttttt tataaagaag attatgatat     180
tgaagttgaa gatgaaaatg gtactaaaac taccaaaacg ataaatgaag gacaaacgat     240
cctggtcgtt tttaatgaag gatatgctcc tgatggagtt tggttaggtg gtactaaata     300
tcaatttata aatattgaaa gagatttaga atttgaaggt tataattttg atgtagctac     360
ttgtgctaaa ttaaaaggtg gtcttcactt ggtgaaagtt ccaggaggaa atatattagt     420
tgtattatat gatgaagaaa aagagcaaga cagaggaaat tccaaaatcg ctgccttgac     480
ttttgca                                                              487
```

<210> SEQ ID NO 26
<211> LENGTH: 114
<212> TYPE: PRT
<213> ORGANISM: Artificial Sequence
<220> FEATURE:
<223> OTHER INFORMATION: Artificial protein for antibody generation

<400> SEQUENCE: 26

```
Glu Trp Leu Val Asp Thr Gly Lys Val Phe Ala Gly Gly Val Ala Ser
1               5                   10                  15

Ile Ala Asp Gly Arg Met Phe Gly Ala Ser Thr Asp Ser Gly Asx Asp
            20                  25                  30

Pro Asn Ala Glu Leu Val Gln Tyr Asn Ala Gly Tyr Gln Ile Glu Ser
        35                  40                  45

Val Gln Glu Asp Asn Gly Thr Val Gln Gln Ala Ile Val Ala Pro Asp
    50                  55                  60

Gly Val Tyr Ile Gly Gly Val Lys Gly Gly Phe Leu Ile Lys Thr
65                  70                  75                  80

Pro Asn Glu Asn Ile Ala Ile Ala Leu Tyr Asp Glu Glu Lys Glu Gln
                85                  90                  95

Asn Lys Ala Asp Ala Leu Thr Thr Ala Leu Asn Phe Ala Asp Phe Leu
            100                 105                 110

Tyr Gln
```

<210> SEQ ID NO 27
<211> LENGTH: 513
<212> TYPE: DNA
<213> ORGANISM: Eimeria tenella

<400> SEQUENCE: 27

```
atgggtgaag aggctgatac tcaggcctgg gacacttcgg tccgcgagtg gctggttgac      60
accggcaggg tcttcgccgg cggcgttgct agcatagccg acggctgccg gctcttcgga     120
gcagcagtgg agggcgaggg caacgcctgg gaagaactcg tcaagaccaa ctaccaaatt     180
gaagtccccc aggaagacgg aacctctatt tcagtggatt gcgacgaggc ggagactctg     240
cggcaggcgg tggtggacgg ccgcgcgccc aacggcgtct acatcggcgg caccaagtac     300
aagctcgccg aagtcaaaag ggacttcacc ttcaacgacc aaaactatga tgtggcgatt     360
ctgggaaaaa acaaaggcgg agggttttg attaaaactc caaacgaaaa tgttgttata     420
gctttgtatg atgaagaaaa agaacaaaac aaagctgatg ctctcacaac agctcttaac     480
ttcgctgagt acctgtacca gggcggcttc taa                                  513
```

<210> SEQ ID NO 28
<211> LENGTH: 169
<212> TYPE: PRT
<213> ORGANISM: Eimeria tenella

<400> SEQUENCE: 28

```
Met Gly Glu Glu Ala Asp Thr Gln Ala Trp Asp Thr Ser Val Arg Glu
1               5                   10                  15

Trp Leu Val Asp Thr Gly Arg Val Phe Ala Gly Gly Val Ala Ser Ile
            20                  25                  30

Ala Asp Gly Cys Arg Leu Phe Gly Ala Ala Val Glu Gly Glu Gly Asn
        35                  40                  45

Ala Trp Glu Glu Leu Val Lys Thr Asn Tyr Gln Ile Glu Val Pro Gln
    50                  55                  60
```

```
Glu Asp Gly Thr Ser Ile Ser Val Asp Cys Asp Ala Glu Thr Leu
65                  70                  75                  80

Arg Ala Val Val Asp Gly Arg Ala Pro Asn Gly Val Tyr Ile Gly Gly
                85                  90                  95

Thr Lys Tyr Lys Leu Ala Glu Val Lys Arg Asp Phe Thr Phe Asn Asp
            100                 105                 110

Gln Asn Tyr Asp Val Ala Ile Leu Gly Lys Asn Lys Gly Gly Gly Phe
        115                 120                 125

Leu Ile Lys Thr Pro Asn Glu Asn Val Val Ile Ala Leu Tyr Asp Glu
    130                 135                 140

Glu Lys Glu Gln Asn Lys Ala Asp Ala Leu Thr Thr Ala Leu Asn Phe
145                 150                 155                 160

Ala Glu Tyr Leu Tyr Gln Gly Gly Phe
                165
```

```
<210> SEQ ID NO 29
<211> LENGTH: 19
<212> TYPE: PRT
<213> ORGANISM: Eimeria tenella

<400> SEQUENCE: 29

Thr Pro Asn Glu Asn Ile Ala Ile Ala Leu Tyr Asp Glu Glu Lys Glu
1               5                   10                  15

Gln Asn Lys
```

```
<210> SEQ ID NO 30
<211> LENGTH: 168
<212> TYPE: PRT
<213> ORGANISM: Eimeria tenella

<400> SEQUENCE: 30

Gly Glu Glu Ala Asp Thr Gln Ala Trp Asp Thr Ser Val Arg Glu Trp
1               5                   10                  15

Leu Val Asp Thr Gly Arg Val Phe Ala Gly Gly Val Ala Ser Ile Ala
                20                  25                  30

Asp Gly Cys Arg Leu Phe Gly Ala Ala Val Glu Gly Glu Gly Asn Ala
            35                  40                  45

Trp Glu Glu Leu Val Lys Thr Asn Tyr Gln Ile Glu Val Pro Gln Glu
50                  55                  60

Asp Gly Thr Ser Ile Ser Val Asp Cys Asp Glu Ala Glu Thr Leu Arg
65                  70                  75                  80

Ala Val Val Asp Gly Arg Ala Pro Asn Gly Val Tyr Ile Gly Gly Thr
                85                  90                  95

Lys Tyr Lys Leu Ala Glu Val Lys Arg Asp Phe Thr Phe Asn Asp Gln
            100                 105                 110

Asn Tyr Asp Val Ala Ile Leu Gly Lys Asn Lys Gly Gly Gly Phe Leu
        115                 120                 125

Ile Lys Thr Pro Asn Glu Asn Val Val Ile Ala Leu Tyr Asp Glu Glu
    130                 135                 140

Lys Glu Gln Asn Lys Ala Asp Ala Leu Thr Thr Ala Leu Asn Phe Ala
145                 150                 155                 160

Glu Tyr Leu Tyr Gln Gly Gly Phe
                165
```

COMPOSITIONS AND METHODS FOR IMMUNOTHERAPY OF CANCER AND INFECTIOUS DISEASES

RELATED APPLICATIONS

This application claims the priority of U.S. application Ser. No. 60/487,336 filed on Jul. 15, 2003.

The present invention relates to compositions and methods for stimulating an immune response and the prevention and treatment of primary and metastatic neoplastic diseases and infectious diseases. More particularly, the present invention relates to compositions comprising Apicomplexa-related proteins (ARPs), a fragment, a derivative, a homolog or an analog thereof, and their uses in immune stimulation, cancer and infectious disease prevention and treatment.

BACKGROUND OF INVENTION

Based on the National Cancer Institute's Surveillance, Epidemiology, and End Results (SEER) database and the population data from the Bureau of the Census, in 2000, 1.22 million new cases of invasive cancer (619,700 men, 600,400 women) were diagnosed and 552,200 people died from cancer in the United States. See Braunwald et al., HARRISON'S PRINCIPLES OF INTERNAL MEDICINE, 15$^{th}$ ed., McGraw-Hill (2001), at pp 491. Cancer is still the second leading cause of death behind heart disease in the United States. Id. Much resource and effort are invested in seeking effective ways to prevent and treat cancer.

Small Intestine Tumors

As pervasive as cancer is, tumors of the small intestine are a rare event (see, e.g., Juckett & Rosenberg, (1988) Mech. Ageing Dev. 43: 239-257). Over the years, preliminary experiments have reported attempts to determine the cause of this natural tumor-free environment. However, the results were inconclusive and the work was not pursued vigorously.

The small intestine's profound resistance to cancer can be demonstrated by the low number of small intestine cancer deaths compared to other gastro-intestinal cancers. The fractional ratio of small intestine cancers compared to all others is only 0.0071. Parkin et al. eds (1997) Cancer Incidence in Five Continents, Vol. V (IARC Scientific Publications No. 143) Lyon, IARC. This is approximately the same for all the years Publications No. 143) Lyon, IARC. This is approximately the same for all the years examined and for all the various cohorts. Id. Incidence of small intestine tumors also follows the same trend as mortality (Parkin et al., eds., (1997), Cancer Incidence in Five Continents, Vol. VII (IARC Scientific Publications No. 143) Lyon, IARC). The low incidence rate is almost universally true for the human species, for all genetic pools, and over long periods of time. It also appears to be true for almost all other mammalian species (with the possible exception of two varieties of sheep). See Lingeman et al., (1972), J. of the National Cancer Institute 48: 325-346.

Additional observations, regarding the unusual nature of the small intestine, come from studies on radiation-induced illness (primarily from Nagasaki and Hiroshima) and in genetic diseases of the intestine. Large doses of high-energy radiation cause death by the destruction of the cells of the bone marrow and the epithelial cells lining the small intestine, both of which are easily damaged or destroyed by radiation. In bomb survivors that received a non-lethal dose of radiation, there is a much higher than normal incidence of cancers of the bone marrow at later times, but there is no increased incidence of cancers of the small intestine. See Shimizu et al. (1991), J. Radiat. Res. Supplement, 212-230.

In Familial Polyposis Coli, a genetic disease, it is known that patients have a predisposition to large intestine cancers. However, the potential for cancers of the small intestine is very low even in those individuals where the polyposis appears in the entire gastrointestinal tract. See Lightdale et al., (1982), Small Intestine, in: Cancer epidemiology and Prevention (eds, Schottenfield et al.,) W.B Saunders Co.

Finally, and most significantly, the spread of metastases from cancers arising in other sites to the small intestine is very rare. This suggests that whatever mechanism protecting the small intestine from local cancers also operates to block the occurrence of most other cancers as well.

The very low incidence of cancers in, or of, the small intestine is a robust fact of nature, and cries for explanation. The facts described above have been known for a long time. They have astonished many scientists and stimulated them to speculate on its causes. The low incidence of small intestine tumors cannot be attributed to the relative size of the organs of the digestive tract, since in humans the small intestine constitutes 90% of the length of the tract, and 98% of the absorptive surface area (Gabos et al., (1993) International J. of Epidemiology 22: 198-206). This is also true for other animals as well. The low incidence cannot be attributed to a low cell turnover rate, as it is in neural cells and muscle cells, since the epithelium of the small intestine crypts have the fastest turnover rates of all organs of the body. Potten and Loeffler (1990, Development 110: 1001-1020) have commented, "Since there are about $7.5 \times 10^5$ crypts in the ileum of the mouse there must be between $3 \times 10^6$ and $1.2 \times 10^7$ stem cells in the ileum. Thus, there are between $10^9$ and $10^{10}$ stem cell divisions in the mouse small intestine in its 3-year life span. With a spontaneous mutation rate of approximately 1 in $10^6$, about $10^3$ or $10^4$ spontaneous mutations would be expected, i.e. about 1-10 per day. It is therefore surprising that the small intestine rarely develops cancer. It must be very well protected by ill-understood mechanisms."

Ashley and Wells (1988, Seminars in Oncology 15: 116-128) listed various speculations regarding the protected status of the small intestine. They include: a) protection from exposure to noxious substances by the liquidity and rapid transit of its contents; b) the alkalinity of the interior lumen of the small intestine; c) the high concentrations of secretory immunoglobulins; d) the low bacterial concentration; and e) the presence of hydroxylases which may inactivate potential carcinogens. Another mechanism was proposed by Cairns (1975, Nature 255: 197-200). This involves the physical movement of epithelial cells, which begin as stem cells at the bottom of the crypt, move along the surface of the crypt and then the villus, and are finally shed into the lumen. This might prevent the accumulation of variant (abnormal) stem cells which may eventually be further mutated into transformed cells (cancer). None of these speculations have been proven.

In a paper by Bennett et al. (1951, Proceedings of Society for Experimental Biology 78: 790-791, referred as "Bennett" herein after), it was suggested that the small intestine contained a chemical inhibitory to tumor growth. Cells of the small intestine of mice were extracted and separated into 3 fractions—the pellet arising from a low speed centrifugation of the raw material (fraction 4), a pellet arising from a high speed centrifugation (fraction 90), and its supernatant (supernatant). Lymphosarcoma cells were incubated with each fraction for a specified time and both were inoculated into mice. The results were that few animals developed tumors using fraction 90, but a larger number of animals developed a tumor and died using the cells incubated with the supernatant and fraction 4. Similar extracts from liver, spleen and muscles failed to show any tumor inhibition. Bennett concluded that the tests confirmed their hypothesis. Bennett also showed in further tests that the supernatant activity was due to contamination with components of fraction 90 (containing microsomes), and could be eliminated by more careful preparation. Thus the supernatant was not active by itself. Bennett also stated that they have eliminated proteolytic enzymes as the probable cause of the activity.

In the mid 1970's, another group examined small intestine extracts (Chan et al., 1975, J. of the British Society of Gastroenterology 16: 50-52, referred as "Chan" herein after) and came to a different explanation of Bennett's result. Chan concluded that the in vitro incubation of tumor cells with small intestine extracts resulted in killing the cells prior to inoculation into animals; that the extracts kill normal cells as well as tumor cells; and that the activity was predominantly in the microsomal fraction and not in the supernatant. They suggested that the enzymatic activity of the epithelium was responsible for the observations.

In a paper by Calman (1974, Gut 15: 552-554), the antitumor effect in the small intestine was shown to require the presence of an intact immune system. Thymectomy and radiation was shown to allow tumors to be transplanted to the small intestine. In animals that received the same treatment, but with their immune system reconstituted with thymus grafts, tumors would again no longer grow in the small intestine. In both groups, tumors could be transplanted successfully to the stomach. Thus, the protective effect of the small intestine appeared to be related to an enhancement of the local immune system. However, the search for factor(s) that controlled the local immune system was not performed.

Protozoa and Immune Responses of their Hosts

Parasites have evolved multiple evasion strategies allowing them to survive in their primary host and to complete their life cycle through a series of stages that usually involve passage through the environment and often through secondary hosts. These strategies include antigen shedding, antigen shifting, living intracellularly for long periods, manipulating host cell biochemistry, infecting multiple organs, and encystment (see, e.g., Beverley, (1996), Cell 87: 787-789; Zambrano-Villa et al., (2002), Trends in Parasitol. 18: 272-278). Such mechanisms have been fine-tuned through evolutionary pressures to help the protozoan avoid the immune response of the host. In many cases, protozoans are so specialized in these avoidance mechanisms that they can only complete their life cycle in one host species or genera.

Apicomplexa are spore-forming single-celled parasites of animals and include species that cause various disease, such as malaria, coccidiosis, redwater disease, corridor disease, east coast fever and binary fever. Four major classes within the phylum Apicomplexa are: Coccidia (genera include, e.g., *Besnoitia, Caryospora, Cryptosporidium, Eimeria, Frenkelia, Hammondia, Hepatozoon, Isospora, Lankesterella, Neospora, Sarcocystis*, and *Toxoplasma*); Gregarinia (genera include, e.g., *Gregarina, Monocystis, Ophriocystis*, and *Pseudomonocystis*); Haemosporida or haemosporidians (genera include, e.g., *Haemoproteus, Hepatocystis*, and *Plasmodium*); and Piroplasmida or Piroplasmids (genera include, e.g., *Babesia, Cytauxzoon*, and *Theileria*). Seven species that infect humans have been identified (*Plasmodium, Babesia, Cryptosporidium, Isospora, Cyclospora, Sarcocystis, Toxoplasma*).

A defining characteristic of the Apicomplexa is a group of organelles found at one end—called the apical end—of the organism. This "apical complex" includes secretory organelles known as micronemes and rhoptries, polar rings composed of microtubules, and in some species a conoid which lies within the polar rings. At some point during their life cycle, members of the Apicomplexa either invade or attach to host cells. The apical organelles play a role in these host-parasite interactions.

A few *Eimeria* species are known to cause severe morbidity and occasionally mortality in certain animals. In particular, *E. tenella, E. acervulina*, and *E. maxima* are a problem in the chicken industry. The stress and crowded conditions exacerbate *Eimeria* infections and cause massive diarrhea and death. A similar problem can occur in the cattle industry, where crowding among calves can lead to severe disease. Usually, adult animals are immune to *Eimeria* but a low, asymptomatic infection is endemic in most vertebrates. Upon first exposure, a brief humoral immune response has been documented in animals (Faber et al., (2002), Vet. Parasitol. 104: 1-17; Allen & Fetterer, (2002), Clin. Microbiol. Rev. 15: 58-65; Rose, (1987), *Eimeria, Isopora*, and *Cryptosporidium*, in: Immune Responses in Parasitic Infections: Immunology, Immunopathology, and Immuneoprophylaxis (ed. E. J. L. Soulsby) pp 275-230), but this is replaced by a localized cellular immune response that appears to provide lasting protection throughout a host's life. The exact mechanism of this protection is not fully known and why low levels of the organism survive without undergoing the explosive growth of its life cycle remains a mystery.

Aliberti et al. (2003, Nature Immunology 4(5): 485-490) showed a purified protein, C-18, which is an isoform of *Toxoplasma gondii* cyclophilin (which does not contain a profilin domain), can stimulate production of interleukin-12 (IL-12) from dendritic cells (DCs). However, recombinant *T. gondii* C-18 showed reduced IL-12 stimulatory activity relative to the crude *T. gondii* tachyzoite extract (STAg).

The 19 kD Sporozoite Antigen

Vaccination against *Eimeria* has been the subject of substantial research in the animal husbandry of poultry, and to a lesser extent, cattle. Chemical prophylaxes are standard treatment in the poultry industry, but resistant strains of *Eimeria* are beginning to be a problem. The development of vaccines is considered an alternative approach and has focused on the use of surface antigens from the sporozoite stage, which is the stage that invades the epithelial layer of the small intestine (see e.g., Allen & Fetterer, (2002), Clin. Microbiol. Rev. 15: 58-65; Blackman & Bannister, (2001), Mol. Biochem. Parasitol. 117: 11-25; Min et al., (2001), Vaccine 20: 267-274). Merozoite surface antigens are also of interest because this protozoan stage is released after the first round of multiplication and infects neighboring cells. During this process an effective immune response could limit the expansion of the infection.

One of the surface molecules, eventually examined for use as a vaccine, was isolated several times from cDNA expression libraries of *E. acervulina*. It was originally identified by Jenkins et al. (1988, Exp. Parasitol. 66: 96-107) as a low-abundance surface protein (clone cSZ-1) detected by rabbit antibodies made to acervulina membranes. Sera from infected chickens, however did not react with it. They identified two bands in Western blots at 240 and 160 kD and showed that the β-galactosidase fusion protein, made in *E. coli*, could activate T-cell division. Another group (Laurent et al., (1994), Mol. Bioch. Parasitol. 63: 79-86) subsequently reported that a 19 kD surface protein, referred to as IP, was conserved across three poultry *Eimeria* species, shared the same cDNA sequence as the cSZ-1 clone of Jenkins et al., and suggested that iodination may have given the anomalously high molecular weights in the previous work. The nucleotide sequence of their clone was submitted to GenBank under the name of '19 kD sporozoite antigen ' (Accession Z26584). Most recently, Lillehoj et al. (2000, Avian Diseases 44: 379-389) isolated a slightly longer protein reading frame from a cDNA clone (3-1E) that reacted with rabbit antiserum to *E. acervulina* merozoites (Accession Z26584). The translation included 17 additional amino acids at the N terminus, but the remainder of the molecule was virtually identical. They demonstrated that the 3-1 E protein activated cell mediated immunity by showing in vitro IFNγ production from spleen cell isolated from chickens doubly challenged with *E. acervulina* and then exposed to the protein. They also showed that the protein can be used as a modestly effective vaccine to prevent coccidiosis from *Eimeria*. This group continues to explore this potential using the nucleotide sequence as a DNA vaccine (Song, et al., (2001), Vaccine 19: 234-252; Min, et al., (2001), Vaccine 20: 267-274). As the sole agent, the DNA vaccine generated only partial protection from challenge. Addition of plasmids carrying various chicken cytokine genes offered some improvement, but still did not reduce oocyst production by more than two-fold.

Citation or discussion of a reference herein shall not be construed as an admission that such is prior art to the present invention.

SUMMARY OF INVENTION

As used herein, the term "isolated" means that the referenced material is removed from its native environment, e.g., a cell. Thus, an isolated biological material can be free of some or all cellular components, i.e., components of the cells in which the native material is occurs naturally (e.g., cytoplasmic or membrane component). In the case of nucleic acid molecules, an isolated nucleic acid includes a PCR product, an isolated mRNA, a cDNA, or a restriction fragment. In another embodiment, an isolated nucleic acid is preferably excised from the chromosome in which it may be found, and more preferably is no longer joined or proximal to non-coding regions (but may be joined to its native regulatory regions or portions thereof), or to other genes, located upstream or downstream of the gene contained by the isolated nucleic acid molecule when found in the chromosome. In yet another embodiment, the isolated nucleic acid lacks one or more introns. Isolated nucleic acid molecules include sequences inserted into plasmids, cosmids, artificial chromosomes, and the like, i.e., when it forms part of a chimeric recombinant nucleic acid construct. Thus, in a specific embodiment, a recombinant nucleic acid is an isolated nucleic acid. An isolated protein may be associated with other proteins or nucleic acids, or both, with which it associates in the cell, or with cellular membranes if it is a membrane-associated protein. An isolated organelle, cell, or tissue is removed from the anatomical site in which it is found in an organism. An isolated material may be, but need not be, purified.

The term "purified" in reference to a protein or a nucleic acid, refers to the separation of the desired substance from contaminants to a degree sufficient to allow the practioner to use the purified substance for the desired purpose. Preferably this means at least one order of magnitude of purification is achieved, more preferably two or three orders of magnitude, most preferably four or five orders of magnitude of purification of the starting material or of the natural material. In specific embodiments, a purified ARP is at least 60%, at least 80%, or at least 90% of total protein or nucleic acid, as the case may be, by weight. In a specific embodiment, a purified ARP is purified to homogeneity as assayed by, e.g., sodium dodecyl sulfate polyacrylamide gel electrophoresis, or agarose gel electrophoresis.

The present invention provides a method of treating or preventing a disease in an animal, where the method comprises administering to the animal a pharmaceutically effective amount of a pharmaceutical composition which provides a protein to the animal, where the protein has at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 98% or at least 99% identity to the sequence of SEQ ID NO:1, SEQ ID NO:2, SEQ ID NO:28 or SEQ ID NO:30 as determined by a BLAST 2.0 algorithm set to default parameters, and where the protein possesses immunostimulatory activity. The present invention further provides a pharmaceutical composition which provides the protein to an animal as a protein, a nucleic acid encoding the protein or a cell transfected with a nucleic acid encoding the protein.

The present invention provides a method of treating or preventing cancer in an animal comprising administering to the animal a pharmaceutical composition which provides the protein to the animal as: (a) an isolated protein comprising SEQ ID NO:1; (b) an isolated protein comprising SEQ ID NO:2; (c) an isolated protein comprising SEQ ID NO:28; (d) an isolated protein comprising SEQ ID NO:30; (e) an isolated protein comprising SEQ ID NO: 3, 4, 5, 6 and 7; (f) an isolated nucleic acid comprising a nucleotide sequence encoding any of (a)-(e), above; or (f) a cell transformed with a nucleic acid comprising a nucleotide sequence encoding any of (a)-(e) above, the nucleotide sequence being operably linked to a promoter.

The present invention provides a method of treating or preventing cancer where a pharmaceutical composition provides a protein to an animal as: (a) an isolated protein that is the product of a process comprising the steps of: (1) producing a cell extract of *Eimeria* infected tissue or cells; (2) centrifuging the cell extract to produce a supernatant; (3) fractionating the supernatant by ammonium sulfate to precipitate proteins to a pellet, and resuspending the pellet into a solution; (4) applying the solution to a HIC column; (5) eluting material bound to the HIC column to produce eluted material; (6) dialyzing the eluted material to produce a sample for loading on a DEAE column; (7) applying the sample to a DEAE column; (8) eluting material bound to the DEAE column with buffer to produce an eluted fraction and concentrating the eluted fraction; (9) applying the concentrated eluted fraction to a size exclusion column; (10) collecting and pooling fractions eluted from the size exclusion column; (11) applying the pooled fractions to a HIC column to remove calcium binding proteins; (12) applying eluted fractions from the HIC column to a HPLC HIC column and collecting active fractions, wherein said active fractions have the ability to stimulate interleukin-12 release from dendritic cells, said dendritic cells having been isolated from a mammal within 10 hours of assaying said ability; (13) dialyzing the active fractions; and (14) applying the dialyzed active fractions to a HPLC DEAE column and collecting one or more active fractions, wherein said active fractions have the ability to stimulate interleukin-12 release from dendritic cells, said dendritic cells having been isolated from a mammal within 10 hours of assaying said ability; (b) a recombinately expressed protein; (c) an isolated nucleic acid comprising a nucleotide sequence encoding (a) above; or (d) a cell transformed with a nucleic acid comprising a nucleotide sequence encoding (a) above, said nucleotide sequence being operably linked to a promoter.

The present invention provides a method of treating or preventing cancer comprising a pharmaceutical composition which is an isolated protein that is the product of a process comprising the steps of: (a) producing a homogenate of a purified Apicomplexan organism or a cell infected with an Apicomplexan organism; (b) centrifuging the homogenate to obtain a pellet; (c) treating the pellet with a solution comprising a phospholipase; (d) centrifuging the solution to obtain a supernatant; (e) applying the supernatant to a reverse phase HPLC column; and (f) eluting bound protein from the reverse phase HPLC column, to produce eluted protein, wherein said protein has the activity to stimulate interleukin-12 release from dendritic cells, said dendritic cells having been isolated from a mammal within 10 hours of assaying said activity.

The present invention provides a method of treating or preventing cancer in an animal comprising administering to the animal a pharmaceutical composition which provides the protein to the animal as: (a) an isolated protein comprising SEQ ID NO: 3, 4, 6 or 7; (b) an isolated protein comprising a variant of any one of SEQ ID NO:1, SEQ ID NO:2, SEQ ID NO:28 or SEQ ID NO:30, wherein said variant has only conservative amino acid substitutions relative to SEQ ID NO:1, SEQ ID NO:2, SEQ ID NO:28 or SEQ ID NO:30, respectively; (c) an isolated protein comprising a variant of SEQ ID NO: 3, 4, 6 or 7, wherein said variant has only conservative amino acid substitutions relative to SEQ ID NO: 3, 4, 6 or 7, respectively; (d) an isolated protein comprising a PROF (profilin) domain; (e) an isolated Apicomplexan protein comprising an amino acid sequence encoded by a nucleic acid consisting of a nucleotide sequence hybridizable to SEQ ID NO:15, 16, 17, 18, 19, 20 or 27, or a complement of any of the foregoing SEQ ID NOs, under conditions of low stringency; (f) an isolated Apicomplexan protein comprising an amino acid sequence encoded by a nucleic acid consisting of a nucleotide sequence hybridizable to SEQ ID NO:15, 16, 17, 18, 19, 20 or 27, or a complement of any of the foregoing SEQ ID NOs, under conditions of high stringency; (g) an isolated nucleic acid comprising a nucleotide sequence encoding any of (a)-(f), above; (h) a cell transformed with a nucleic acid comprising a nucleotide sequence encoding any of (a)-(f) above, said nucleotide sequence being operably linked to a promoter; and wherein said pharmaceutical composition has the ability to stimulate interleukin-12 release from dendritic cells, said dendritic cells having been isolated from a mammal within 10 hours of assaying said ability.

The present invention provides a method of treating or preventing infectious disease in an animal comprising administering to the animal a pharmaceutical composition which provides the protein to the animal as: (a) an isolated protein comprising SEQ ID NO: 1; (b) an isolated protein comprising SEQ ID NO:2; (c) an isolated protein comprising SEQ ID NO:28; (d) an isolated protein comprising SEQ ID NO:30; (e) an isolated protein comprising SEQ ID NO: 3, 4, 5, 6 and 7; (f) an isolated nucleic acid comprising a nucleotide sequence encoding any of (a)-(e), above; or (f) a cell transformed with a nucleic acid comprising a nucleotide sequence encoding any of (a)-(e) above, the nucleotide sequence being operably linked to a promoter.

The present invention provides a method of treating or preventing infectious disease where a pharmaceutical composition provides a protein to an animal as: (a) an isolated protein that is the product of a process comprising the steps of: (1) producing a cell extract of *Eimeria* infected tissue or cells; (2) centrifuging the cell extract to produce a supernatant; (3) fractionating the supernatant by ammonium sulfate to precipitate proteins to a pellet, and resuspending the pellet into a solution; (4) applying the solution to a HIC column; (5) eluting material bound to the HIC column to produce eluted material; (6) dialyzing the eluted material to produce a sample for loading on a DEAE column; (7) applying the sample to a DEAE column; (8) eluting material bound to the DEAE column with buffer to produce an eluted fraction and concentrating the eluted fraction; (9) applying the concentrated eluted fraction to a size exclusion column; (10) collecting and pooling fractions eluted from the size exclusion column; (11) applying the pooled fractions to a HIC column to remove calcium binding proteins; (12) applying eluted fractions from the HIC column to a HPLC HIC column and collecting active fractions, wherein said active fractions have the ability to stimulate interleukin-12 release from dendritic cells, said dendritic cells having been isolated from a mammal within 10 hours of assaying said ability; (13) dialyzing the active fractions; and (14) applying the dialyzed active fractions to a HPLC DEAE column and collecting one or more active fractions, wherein said active fractions have the ability to stimulate interleukin-12 release from dendritic cells, said dendritic cells having been isolated from a mammal within 10 hours of assaying said ability; (b) a recombinately expressed protein; (c) an isolated nucleic acid comprising a nucleotide sequence encoding (a) above; or (d) a cell transformed with a nucleic acid comprising a nucleotide sequence encoding (a) above, said nucleotide sequence being operably linked to a promoter.

The present invention provides a method of treating or preventing infectious disease comprising a pharmaceutical composition which is an isolated protein that is the product of a process comprising the steps of: (a) producing a homogenate of a purified Apicomplexan organism or a cell infected with an Apicomplexan organism; (b) centrifuging the homogenate to obtain a pellet; (c) treating the pellet with a solution comprising a phospholipase; (d) centrifuging the solution to obtain a supernatant; (e) applying the supernatant to a reverse phase HPLC column; and (f) eluting bound protein from the reverse phase HPLC column, to produce eluted protein, wherein said protein has the activity to stimulate interleukin-12 release from dendritic cells, said dendritic cells having been isolated from a mammal within 10 hours of assaying said activity.

The present invention provides a method of treating or preventing infectious disease in an animal comprising administering to the animal a pharmaceutical composition which provides the protein to the animal as: (a) an isolated protein comprising SEQ ID NO: 3, 4, 6 or 7; (b) an isolated protein comprising a variant of any one of SEQ ID NO:1, SEQ ID NO:2, SEQ ID NO:28 or SEQ ID NO:30, wherein said variant has only conservative amino acid substitutions relative to SEQ ID NO:1, SEQ ID NO:2, SEQ ID NO:28 or SEQ ID NO:30, respectively; (c) an isolated protein comprising a variant of SEQ ID NO: 3, 4, 6 or 7, wherein said variant has only conservative amino acid substitutions relative to SEQ ID NO: 3, 4, 6 or 7, respectively; (d) an isolated protein comprising a PROF (profilin) domain; (e) an isolated Apicomplexan protein comprising an amino acid sequence encoded by a nucleic acid consisting of a nucleotide sequence hybridizable to SEQ ID NO:15, 16, 17, 18, 19, 20 or 27, or a complement of any of the foregoing SEQ ID NOs, under conditions of low stringency; (f) an isolated Apicomplexan protein comprising an amino acid sequence encoded by a nucleic acid consisting of a nucleotide sequence hybridizable to SEQ ID NO:15, 16, 17, 18, 19, 20 or 27, or a complement of any of the foregoing SEQ ID NOs, under conditions of high stringency; (g) an isolated nucleic acid comprising a nucleotide sequence encoding any of (a)-(f), above; (h) a cell transformed with a nucleic acid comprising a nucleotide sequence encoding any of (a)-(f) above, said nucleotide sequence being operably linked to a promoter; and wherein said pharmaceutical composition has the ability to stimulate interleukin-12 release from dendritic cells, said dendritic cells having been isolated from a mammal within 10 hours of assaying said ability.

The present invention provides a method of treating or preventing cancer comprising administering to a subject in whom such treatment or prevention is desired therapeutically or prophylactically effective amount of a substance selected from the group consisting of (a) an isolated protein comprising SEQ ID NO:1 (ARP of *E. tenella*); (b) an isolated protein comprising SEQ ID NO:2 (ARP of *E. acervulina*); (c) an isolated protein comprising SEQ ID NO: 3, 4, 5, 6 and 7 (partial amino acid sequence of bovine *Eimeria* spp. ARP; (d) an isolated protein comprising SEQ ID NO:28 (ARP of clone E1); (e) an isolated protein comprising SEQ ID NO:30 (ARP of clone E1 drug product). SEQ ID NOs: 3-7 are not necessarily contiguous, there may be intervening or adjacent sequences to each fragment. Preferably, a protein comprises SEQ ID NOs:3, 4, 5, 6 and 7 in an order of SEQ ID NO:3 to SEQ ID NO:7 from the N terminus to the C terminus); (f) an isolated protein that is a product of process comprising the steps of: (1) producing a cell extract of *Eimeria* infected tissue or cells; (2) centrifuging the cell extract to produce a supernatant; (3) fractionating the supernatant by ammonium sulfate to precipitate proteins to a pellet, and resuspending the pellet into a solution; (4) applying the solution to a hydrophobic interaction column (hereinafter "HIC"); (5) eluting material bound to the HIC column to produce eluted material; (6) dialyzing the eluted material to produce a sample for loading on a diethylaminoethyl (hereinafter "DEAE") column; (7) applying the sample to a DEAE column; (8) eluting material bound to the DEAE column with buffer to produce an eluted fraction and concentrating the eluted fraction; (9) applying the concentrated eluted fraction to a size exclusion column; (10) collecting and pooling fractions eluted from the size exclusion column; (11) applying the pooled fractions to a HIC column to remove calcium-binding proteins; (12) applying eluted fractions from the HIC column to a high performance liquid chromatography (hereinafter "HPLC") HIC column and collecting active (immunostimulatory) fractions, wherein said active fractions have the ability to stimulate interleukin-12 release from dendritic cells, said dendritic cells having been isolated from a mammal within 10 hours of assaying said ability (or as assayed by one or more assays described in Section 5.6 and Section 12, infra); (13) dialyzing the active fractions; and (14) applying the dialyzed active fractions to a HPLC DEAE column and collecting one or more active (immunostimulatory) fractions, wherein said active fractions have the ability to stimulate interleukin-12 release from dendritic cells, said dendritic cells having been isolated from a mammal within 10 hours of assaying said ability (or as assayed by one or more assays described in Section 5.6 and Section 12, infra); (g) an isolated protein that is the product of a process comprising the steps of: (1) producing a homogenate of a purified Apicomplexan organism or a cell infected with an Apicomplexan organism; (2) centrifuging the homogenate to obtain a pellet; (3) treating the pellet with a solution comprising a phospholipase; (4) centrifuging the solution to obtain a supernatant; (5) applying the supernatant to a reverse phase HPLC column; and (6) eluting bound protein from the reverse phase HPLC column, to produce eluted protein, wherein said protein has the ability (immunostimulatory ability) to stimulate interleukin-12 release from dendritic cells, said dendritic cells having been isolated from a mammal within 10 hours of assaying said ability (or as assayed by one or more assays described in Section 5.6 and Section 12, infra); (f) an isolated nucleic acid comprising a nucleotide sequence encoding any of (a)-(g), above; and (h) a cell transformed with a nucleic acid comprising a nucleotide sequence encoding any of (a)-(g) above, said nucleotide sequence being operably linked to a promoter.

The present invention also provides a method of treating or preventing cancer comprising administering to a subject in whom such treatment or prevention is desired a therapeutically or prophylactically effective amount of a substance selected from the group consisting of: (a) an isolated protein comprising SEQ ID NO:3, 4, 6 or 7; (b) an isolated protein comprising a variant of SEQ ID NO:1, SEQ ID NO:2, SEQ ID NO:28 or SEQ ID NO:30 wherein said variant has only conservative amino acid substitutions relative to SEQ ID NO:1, SEQ ID NO:2, SEQ ID NO:28 or SEQ ID NO:30 respectively; (c) an isolated protein comprising a variant of SEQ ID NO:3, 4, 6 or 7, wherein said variant has only conservative amino acid substitutes relative to SEQ ID NO:3, 4, 6 or 7, respectively; (d) an isolated protein that has at least 25%, at least 30%, at least 35%, at least 40%, at least 45%, at least 50%, at least 55%, at least 60%, at least 65%, at least 70%, at least 75%, or at least 80% identity to the sequence of SEQ ID NO:1, SEQ ID NO:2, SEQ ID NO:28 or SEQ ID NO:30 as determined by a BLAST 2.0 algorithm set to default parameters; (e) an isolated protein comprising a PROF (profiling) domain; (f) an isolated Apicomplexan protein comprising an amino acid sequence encoded by a nucleic acid consisting of a nucleotide sequence hybridizable to SEQ ID NO:15, 16, 17, 18, 19, 20 or 27, or a complement of any of the foregoing SEQ ID NOs, under conditions of low stringency; (g) an isolated nucleic acid comprising a nucleotide sequence encoding any of (a)-(f) above; (h) a cell transformed with a nucleic acid comprising a nucleotide sequence encoding any of (a)-(f) above, said nucleotide sequence being operably linked to a promoter; and wherein said substance has immune stimulatory ability, e.g., has the ability to stimulate interleukin-12 release from dendritic cells, said dendritic cells having been isolated from a mammal within 10 hours of assaying said ability.

The present invention also provides a method of treating or preventing an infectious disease, wherein said infectious disease is not caused by infection with a human immunodeficiency virus (HIV) or an *Eimeria* organism, comprising administering to a subject in whom such treatment or prevention is desired a therapeutically or prophylactically effective amount of a substance selected from the group consisting of: (a) an isolated protein comprising SEQ ID NO:1 (ARP of *E. tenella*); (b) an isolated protein comprising SEQ ID NO:2 (ARP of *E. acervulina*); (c) an isolated protein comprising SEQ ID NO:28 (ARP of E1 clone); (d) an isolated protein comprising SEQ ID NO:30 (ARP of E1 clone drug product); (e) an isolated protein comprising SEQ ID NO: 3, 4, 5, 6 and 7 (partial amino acid sequence of bovine *Eimeria* spp. ARP); (f) an isolated protein that is a product of process comprising the steps of: (1) producing a cell extract of *Eimeria* infected tissue or cells; (2) centrifuging the cell extract to produce a supernatant; (3) fractionating the supernatant by ammonium sulfate to precipitate proteins to a pellet, and resuspending the pellet into a solution; (4) applying the solution to a HIC column; (5) eluting material bound to the HIC column to produce eluted material; (6) dialyzing the eluted material to produce a sample for loading on a DEAE column; (7) applying the sample to a DEAE column; (8) eluting material bound to the DEAE column with buffer to produce an eluted fraction and concentrating the eluted fraction; (9) applying the concentrated eluted fraction to a size exclusion column; (10) collecting and pooling fractions eluted from the size exclusion column; (11) applying the pooled fractions to a HIC column to remove calcium-binding proteins; (12) applying eluted fractions from the HIC column to a HPLC HIC column and collecting active (immunostimulatory) fractions, wherein said active fractions have the ability to stimulate interleukin-12 release from dendritic cells, said dendritic cells having been isolated from a mammal within 10 hours of assaying said ability (or as assayed by one or more assays described in Section 5.6 and Section 12, infra); (13) dialyzing the active fractions; and (14) applying the dialyzed active fractions to a HPLC DEAE column and collecting one or more active (immunostimulatory) fractions, wherein said active fractions have the ability to stimulate interleukin-12 release from dendritic cells, said dendritic cells having been isolated from a mammal within 10 hours of assaying said ability (or as assayed by one or more assays described in Section 5.6 and Section 12, infra); (g) an isolated protein that is the product of a process comprising the steps of: (1) producing a homogenate of a purified Apicomplexan organism or a cell infected with an Apicomplexan organism; (2) centrifuging the homogenate to obtain a pellet; (3) treating the pellet with a solution comprising phospholipase; (4) centrifuging the solution to obtain a supernatant; (5) applying the supernatant to a reverse phase HPLC column; and (6) eluting bound protein from the reverse phase HPLC column, to produce eluted protein, wherein said protein has the ability (immunostimulatory ability) to stimulate interleukin-12 release from dendritic cells, said dendritic cells having been isolated from a mammal within 10 hours of assaying said ability (or as assayed by one or more assays described in Section 5.6 and Section 12, infra); (h) an isolated nucleic acid encoding any of (a)-(g), above; and (i) a cell transformed with a nucleic acid comprising a nucleotide sequence encoding any of (a)-(g) above, said nucleotide sequence being operably linked to a promoter.

The present invention provides a method of treating or preventing an infectious disease, wherein said infectious disease is not caused by infection with a human immunodeficiency virus (HIV) or an Apicomplexan organism, comprising administering to a subject in whom such treatment or prevention is desired a therapeutically or prophylactically effective amount of a substance selected from the group consisting of: (a) an isolated protein comprising SEQ ID NO:3, 4, 6 or 7; (b) an isolated protein comprising a variant of SEQ ID NO:1 or SEQ ID NO:2, wherein said variant has only conservative amino acid substitutions relative to SEQ ID NO:1, SEQ ID NO:2, SEQ ID NO:28 or SEQ ID NO:30 respectively; (c) an isolated protein comprising a variant of SEQ ID NO:3, 4, 6 or 7, wherein said variant has only conservative amino acid substitutes relative to SEQ ID NO:3, 4, 6 or 7, respectively; (d) an isolated protein that has at least 25%, at least 30%, at least 35%, at least 40%, at least 45%, at least 50%, at least 55%, at least 60%, at least 65%, at least 70%, at least 75%, or at least 80% identity to the sequence of SEQ ID NO:1 or SEQ ID NO:2, SEQ ID NO:28 or SEQ ID NO:30 as determined by a BLAST 2.0 algorithm set to default parameters; (e) an isolated protein comprising a PROF (profilin) domain; (f) an isolated Apicomplexan protein comprising an amino acid sequence encoded by a nucleic acid consisting of a nucleotide sequence hybridizable to SEQ ID NO:15, 16, 17, 18, 19, 20 or 27, or a complement of any of the foregoing SEQ ID NOs, under conditions of low stringency; (g) an isolated nucleic acid comprising a nucleotide sequence encoding any of (a)-(f) above; (h) a cell transformed with a nucleic acid comprising a nucleotide sequence encoding any of (a)-(f) above, said nucleotide sequence being operably linked to a promoter; and wherein said substance has immune stimulatory ability, e.g., has the ability to stimulate interleukin-12 release from dendritic cells, said dendritic cells having been isolated from a mammal within 10 hours of assaying said ability.

The present invention also provides a method of stimulating an immune response comprising administering to a subject, with the proviso that said subject is not an avian species and is not infected with a human immunodeficiency virus (HIV), an effective amount of a substance selected from the group consisting of: (a) an isolated protein comprising SEQ ID NO:1 (ARP of *E. tenella*); (b) an isolated protein comprising SEQ ID NO:2 (ARP of *E. acervulina*); (c) and isolated protein comprising SEQ ID NO:28 (ARP of E1 clone); (d) an isolated protein comprising SEQ ID NO:30 (ARP of E1 clone drug product); (e) an isolated protein comprising SEQ ID NO: 3, 4, 5, 6 and 7 (partial amino acid sequence of bovine *Eimeria* spp. ARP); (f) an isolated protein that is a product of process comprising the steps of: (1) producing a cell extract of *Eimeria* infected tissue or cells; (2) centrifuging the cell extract to produce a supernatant; (3) fractionating the supernatant by ammonium sulfate to precipitate proteins to a pellet, and resuspending the pellet into a solution; (4) applying the solution to a HIC column; (5) eluting material bound to the HIC column to produce eluted material; (6) dialyzing the eluted material to produce a sample for loading on a DEAE column; (7) applying the sample to a DEAE column; (8) eluting material bound to the DEAE column with buffer to produce an eluted fraction and concentrating the eluted fraction; (9) applying the concentrated eluted fraction to a size exclusion column; (10) collecting and pooling fractions eluted from the size exclusion column; (11) applying the pooled fractions to a HIC column to remove calcium-binding proteins; (12) applying eluted fractions from the HIC column to a HPLC HIC column and collecting active (immunostimulatory) fractions, wherein said active fractions have the ability to stimulate interleukin-12 release from dendritic cells, said dendritic cells having been isolated from a mammal within 10 hours of assaying said ability (or as assayed by one or more assays described in Section 5.6 and Section 12, infra); (13) dialyzing the active fractions; and (14) applying the dialyzed active (immunostimulatory) fractions to a HPLC DEAE column and collecting one or more active fractions, wherein said active fractions have the ability to stimulate interleukin-12 release from dendritic cells, said dendritic cells having been isolated from a mammal within 10 hours of assaying said ability (or as assayed by one or more assays described in Section 5.6 and Section 12, infra); (g) an isolated protein that is the product of a process comprising the steps of: (1) producing a homogenate of a purified Apicomplexan organism or a cell infected with an Apicomplexan organism; (2) centrifuging the homogenate to obtain a pellet; (3) treating the pellet with a solution comprising a phospholipase; (4) centrifuging the solution to obtain a supernatant; (5) applying the supernatant to a reverse phase HPLC column; and (6) eluting bound protein from the reverse phase HPLC column, to produce eluted protein, wherein said protein has the ability (immunostimulatory ability) to stimulate interleukin-12 release from dendritic cells, said dendritic cells having been isolated from a mammal within 10 hours of assaying said ability (or as assayed by one or more assays described in Section 5.6 and Section 12, infra); (h) an isolated nucleic acid comprising a nucleotide sequence encoding any of (a)-(f), above; and (i) a cell transformed with a nucleic acid comprising a nucleotide sequence encoding any of (a)-(f) above, said nucleotide sequence being operably linked to a promoter.

The present invention provides a method of stimulating an immune response comprising administering to a subject, with the proviso that said subject is not infected with a human immunodeficiency virus (HIV), an effective amount of a substance selected from the group consisting of: (a) an isolated protein comprising SEQ ID NO: 3, 4, 5, 6 and 7; (b) an isolated protein that is a product of a process comprising the steps of: (1) producing a cell extract of *Eimeria* infected tissue or cells, wherein said *Eimeria* do not naturally infect an avian species; (2) centrifuging the cell extract to produce a supernatant; (3) fractionating the supernatant by ammonium sulfate to precipitate proteins to a pellet, and resuspending the pellet into a solution; (4) applying the solution to a HIC column; (5) eluting material bound to the HIC column to produce eluted material; (6) dialyzing the eluted material to produce a sample for loading on a DEAF column; (7) applying the sample to a DEAE column; (8) eluting material bound to the DEAE column with buffer to produce an eluted fraction and concentrating the eluted fraction; (9) applying the concentrated eluted fraction to a size exclusion column; (10) collecting and pooling fractions eluted from the size exclusion column; (11) applying the pooled fractions to a HIC column to remove calcium-binding proteins; (12) applying eluted fractions from the HIC column to a HPLC HIC column and collecting active (immunostimulatory) fractions, wherein said active fractions have the ability to stimulate interleukin-12 release from dendritic cells, said dendritic cells having been isolated from a mammal within 10 hours of assaying said ability (or as assayed by one or more assays described in Section 5.6 and Section 12, infra); (13) dialyzing the active fractions; and (14) applying the dialyzed active fractions to a HPLC DEAF column and collecting one or more active (immunostimulatory) fractions, wherein said active fractions have the ability to stimulate interleukin-12 release from dendritic cells, said dendritic cells having been isolated from a mammal within 10 hours of assaying said ability (or as assayed by one or more assays described in Section 5.6 and Section 12, infra); (c) an isolated protein that is the product of a process comprising the steps of: (1) producing a homogenate of a purified Apicomplexan organism or a cell infected with an Apicomplexan organism; (2) centrifuging the homogenate to obtain a pellet; (3) treating the pellet with a solution comprising a phospholipase; (4) centrifuging the solution to obtain a supernatant; (5) applying the supernatant to a reverse phase HPLC column; and (6) eluting bound protein from the reverse phase HPLC column, to produce eluted protein, wherein said protein has the ability (immunostimulatory ability) to stimulate interleukin-12 release from dendritic cells, said dendritic cells having been isolated from a mammal within 10 hours of assaying said ability (or as assayed by one or more assays described in Section 5.6 and Section 12, infra); (d) an isolated nucleic acid comprising a nucleotide sequence encoding any of (a)-(c), above; and (e) a cell transformed with a nucleic acid comprising a nucleotide sequence encoding any of (a)-(c) above, said nucleotide sequence being operably linked to a promoter.

The present invention also provides a method of stimulating an immune response comprising administering to a subject, with the proviso that said subject is not an avian species and is not infected with a human immunodeficiency virus (HIV), an effective amount of a substance selected from the group consisting of: (a) an isolated protein comprising SEQ ID NO:3, 4, 6 or 7; (b) an isolated protein comprising a variant of SEQ ID NO:1, SEQ ID NO:2, SEQ ID NO:28 or SEQ ID NO:30, wherein said variant has only conservative amino acid substitutions relative to SEQ ID NO:1, SEQ ID NO:2, SEQ ID NO:28 or SEQ ID NO:30, respectively; (c) an isolated protein comprising a variant of SEQ ID NO:3, 4, 6 or 7, wherein said variant has only conservative amino acid substitutes relative to SEQ ID NO:3, 4, 6 or 7, respectively; (d) an isolated protein that has at least 25%, at least 30%, at least 35%, at least 40%, at least 45%, at least 50%, at least 55%, at least 60%, at least 65%, at least 70%, at least 75%, or at least 80% identity to the sequence of SEQ ID NO:1, SEQ ID NO:2, SEQ ID NO:28 or SEQ ID NO:30, as determined by a BLAST 2.0 algorithm set to default parameters; (e) an isolated protein comprising a PROF (profilin) domain; (f) an isolated Apicomplexan protein comprising an amino acid sequence encoded by a nucleic acid consisting of a nucleotide sequence hybridizable to SEQ ID NO:15, 16, 17, 18, 19, 20 or 27, or a complement of any of the foregoing SEQ ID NOs, under conditions of low stringency; (g) an isolated nucleic acid comprising a nucleotide sequence encoding any of (a)-(f) above; (h) a cell transformed with a nucleic acid comprising a nucleotide sequence encoding any of (a)-(f) above, said nucleotide sequence being operably linked to a promoter; and wherein said substance has immune stimulatory ability, e.g., has the ability to stimulate interleukin-12 release from dendritic cells, said dendritic cells having been isolated from a mammal within 10 hours of assaying said ability.

The present invention provides a method of elevating systemic level of interleukin-12 (IL-12) in a subject, wherein the subject is not infected with a human immunodeficiency virus (HIV), comprising administering to said subject in whom such elevation of IL-12 level is desired an effective amount of a substance selected from the group consisting of: (a) an isolated protein comprising SEQ ID NO:1; (b) an isolated protein comprising SEQ ID NO:2; (c) an isolated protein comprising SEQ ID NO:28; (d) and isolated protein comprising SEQ ID NO:30; (e) an isolated protein comprising SEQ ID NO: 3, 4, 5, 6 and 7; (f) an isolated protein that is a product of process comprising the steps of: (1) producing a cell extract of *Eimeria* infected tissue or cells; (2) centrifuging the cell extract to produce a supernatant; (3) fractionating the supernatant by ammonium sulfate to precipitate proteins to a pellet, and resuspending the pellet into a solution; (4) applying the solution to a HIC column; (5) eluting material bound to the HIC column to produce eluted material; (6) dialyzing the eluted material to produce a sample for loading on a DEAE column; (7) applying the sample to a DEAE column; (8) eluting material bound to the DEAE column with buffer to produce an eluted fraction and concentrating the eluted fraction; (9) applying the concentrated eluted fraction to a size exclusion column; (10) collecting and pooling fractions eluted from the size exclusion column; (11) applying the pooled fractions to a HIC column to remove calcium-binding proteins; (12) applying eluted fractions from the HIC column to a HPLC HIC column and collecting active (immunostimulatory) fractions, wherein said active fractions have the ability to stimulate interleukin-12 release from dendritic cells, said dendritic cells having been isolated from a mammal within 10 hours of assaying said ability (or as assayed by one or more assays described in Section 5.6 and Section 12, infra); (13) dialyzing the active fractions; and (14) applying the dialyzed active fractions to a HPLC DEAE column and collecting one or more active (immunostimulatory) fractions, wherein said active fractions have the ability to stimulate interleukin-12 release from dendritic cells, said dendritic cells having been isolated from a mammal within 10 hours of assaying said ability (or as assayed by one or more assays described in Section 5.6 and Section 12, infra); (g) an isolated protein that is the product of a process comprising the steps of: (1) producing a homogenate of a purified Apicomplexan organism or a cell infected with an Apicomplexan organism; (2) centrifuging the homogenate to obtain a pellet; (3) treating the pellet with a solution comprising a phospholipase; (4) centrifuging the solution to obtain a supernatant; (5) applying the supernatant to a reverse phase HPLC column; and (6) eluting bound protein from the reverse phase HPLC column, to produce eluted protein, wherein said protein has the ability (immunostimulatory ability) to stimulate interleukin-12 release from dendritic cells, said dendritic cells having been isolated from a mammal within 10 hours of assaying said ability (or as assayed by one or more assays described in Section 5.6 and Section 12, infra); (h) an isolated nucleic acid comprising a nucleotide sequence encoding any of (a)-(g), above; and (i) a cell transformed with a nucleic acid comprising a nucleotide sequence encoding any of (a)-(g) above, said nucleotide sequence being operably linked to a promoter.

The present invention also provides a method of elevating systemic level of interleukin-12 (IL-12) in a subject, wherein the subject is not infected with a human immunodeficiency virus (HIV), comprising administering to said subject in whom such elevation of IL-12 level is desired an effective amount of a substance selected from the group consisting of: (a) an isolated protein comprising SEQ ID NO:3, 4, 6 or 7; (b) an isolated protein comprising a variant of SEQ ID NO:1, SEQ ID NO:2, SEQ ID NO:28 or SEQ ID NO:30, wherein said variant has only conservative amino acid substitutions relative to SEQ ID NO:1, SEQ ID NO:2, SEQ ID NO:28 or SEQ ID NO:30, respectively; (c) an isolated protein comprising a variant of SEQ ID NO:3, 4, 6 or 7, wherein said variant has only conservative amino acid substitutes relative to SEQ ID NO:3, 4, 6 or 7, respectively; (d) an isolated protein that has at least 25%, at least 30%, at least 35%, at least 40%, at least 45%, at least 50%, at least 55%, at least 60%, at least 65%, at least 70%, at least 75%, or at least 80% identity to the sequence of SEQ ID NO:1, SEQ ID NO:2, SEQ ID NO:28 or SEQ ID NO:30, as determined by a BLAST 2.0 algorithm set to default parameters; (e) an isolated protein comprising a PROF (profilin) domain; (f) an isolated Apicomplexan protein comprising an amino acid sequence encoded by a nucleic acid consisting of a nucleotide sequence hybridizable to SEQ ID NO:15, 16, 17, 18, 19, 20 or 27, or a complement of any of the foregoing SEQ ID NOs, under conditions of low stringency; (g) an isolated nucleic acid comprising a nucleotide sequence encoding any of (a)-(f) above; (h) a cell transformed with a nucleic acid comprising a nucleotide sequence encoding any of (a)-(f) above, said nucleotide sequence being operably linked to a promoter; and wherein said substance has immune stimulatory ability, e.g., has the ability to stimulate interleukin-12 release from dendritic cells, said dendritic cells having been isolated from a mammal within 10 hours of assaying said ability.

The present invention also provides a method of extracting ARP proteins expressed in recombinant cells comprising (a) producing an extract of said host cell; (b) centrifuging the host cell extract to produce a supernatant; (c) fractionate the supernatant by ammonium sulfate to precipitate proteins; (d) centrifuging the precipitate to obtain a pellet; (e) resuspending the pellet into a solution; (f) applying the solution to a low pressure hydrophobic interaction column; (g) collecting active fractions eluted from the low pressure hydrophobic interaction column, wherein said active fractions have the ability to stimulate interleukin-12 release from dendritic cells, said dendritic cells having been isolated from a mammal within 10 hours of assaying said ability; (h) dialyzing the eluted active fractions from the low pressure hydrophobic interaction column; (i) applying the dialyzed active fractions to a low pressure DEAE column; 0) collecting one or more active fractions eluted from the low pressure DEAE column, wherein said active fractions have the ability to stimulate interleukin-12 release from dendritic cells, said dendritic cells having been isolated from a mammal within 10 hours of assaying said ability; (k) applying the active fractions eluted from the low pressure DEAE column to a size exclusion column; and (l) eluting the active fractions from the size exclusion column, wherein said active fractions have the ability to stimulate interleukin-12 release from dendritic cells, said dendritic cells having been isolated from a mammal within 10 hours of assaying said ability.

The present invention also provides a method of treating or preventing cancer comprising administering to a subject in whom such treatment or prevention is desired a therapeutically or prophylactically effective amount of a purified Apicomplexan organism or a protein-containing membrane fraction of a purified Apicomplexan organism.

The present invention also provides a method of treating or preventing an infectious disease, wherein said infectious disease is not caused by infection with an human immunodeficiency virus (HIV) or an *Eimeria* organism, comprising administering to a subject in whom such treatment or prevention is desired a therapeutically or prophylactically effective amount of a purified Apicomplexan organism or a protein-containing membrane fraction of a purified Apicomplexan organism.

The present invention further provides a method of stimulating an immune response comprising administering to a subject, with the proviso that said subject is not infected with human immunodeficiency virus (HIV) and is not an avian species, a therapeutically or prophylactically effective amount of a purified Apicomplexan organism or a protein-containing membrane fraction of a purified Apicomplexan organism.

The present invention provides a purified polypeptide selected from the group consisting of: (a) a purified polypeptide which comprises SEQ ID NO: 3, 4, 6, or 7; (b) a purified polypeptide which comprises SEQ ID NOs: 3, 4, 5, 6, and 7; (c) a purified polypeptide which comprises an amino acid sequence which has at least 90%, at least 91%, at least 92%, at least 93%, at least 94%, or at least 95% identity to SEQ ID NO: 29 as determined by a BLAST 2.0 algorithm set to default parameters; and (d) a purified polypeptide which comprises a variant of an amino acid sequence comprising SEQ ID NO: 3, 4, 5, 6 and 7, wherein said variant has only conservative amino acid substitutions relative to SEQ ID NO:3, 4, 5, 6 and 7, respectively. The present invention also provides a pharmaceutical composition comprising a therapeutically effective amount of the polypeptide and a pharmaceutically acceptable carrier.

The present invention also provides a method of isolating a polypeptide comprising the steps of: (a) producing a cell extract of *Eimeria* infected tissue or cells; (b) centrifuging the cell extract to produce a supernatant; (c) fractionating the supernatant by ammonium sulfate to precipitate proteins to a pellet, and resuspending the pellet into a solution; (d) applying the solution to a HIC column; (e) eluting material bound to the HIC column to produce eluted material; (f) dialyzing the eluted material to produce a sample for loading on a DEAE column; (g) applying the sample to a DEAE column; (h) eluting material bound to the DEAE column with buffer to produce an eluted fraction and concentrating the eluted fraction; (i) applying the concentrated eluted fraction to a size exclusion column; (j) collecting and pooling fractions eluted from the size exclusion column; (k) applying the pooled fractions to a HIC column to remove calcium-binding proteins; (l) applying eluted fractions from the HIC column to a HPLC HIC column and collecting active (immunostimulatory) fractions, wherein said active fractions have the ability to stimulate interleukin-12 release from dendritic cells, said dendritic cells having been isolated from a mammal within 10 hours of assaying said ability (or as assayed by one or more assays described in Section 5.6 and Section 12, infra); (m) dialyzing the active fractions; (n) applying the dialyzed active fractions to a HPLC DEAE column and collecting one or more active (immunostimulatory) fractions, wherein said active fractions have the ability to stimulate interleukin-12 release from dendritic cells, said dendritic cells having been isolated from a mammal within 10 hours of assaying said ability (or as assayed by one or more assays described in Section 5.6 and Section 12, infra). In certain embodiments, the method of producing a polypeptide further comprising (O) applying the active fractions of step (n) to a reverse phase HPLC column; and (p) eluting bound protein from the reverse phase HPLC column, to produce eluted protein, wherein said protein has the ability (immunostimulatory ability) to stimulate interleukin-12 release from dendritic cells, said dendritic cells having been isolated from a mammal within 10 hours of assaying said ability (or as assayed by one or more assays described in Section 5.6 and Section 12, infra). The present invention also provides a purified polypeptide that is the product of this process. The present invention further provides a pharmaceutical composition comprising a therapeutically effective amount of the polypeptide and a pharmaceutically acceptable carrier.

The present invention further provides a method of isolating a polypeptide comprising the steps of: (1) producing a homogenate of a purified Apicomplexan organism or a cell infected with an Apicomplexan organism; (2) centrifuging the homogenate to obtain a pellet; (3) treating the pellet with a solution comprising a phospholipase; (4) centrifuging the solution to obtain a supernatant; (5) applying the supernatant to a reverse phase HPLC column; and (6) eluting bound protein from the reverse phase HPLC column, to produce eluted protein, wherein said protein has the ability (immunostimulatory ability) to stimulate interleukin-12 release from dendritic cells, said dendritic cells having been isolated from a mammal within 10 hours of assaying said ability (or as assayed by one or more assays described in Section 5.6 and Section 12, infra). The present invention also provides a purified polypeptide that is the product of this process. The present invention further provides a pharmaceutical composition comprising a therapeutically effective amount of the polypeptide and a pharmaceutically acceptable carrier.

The present invention provides an antibody which binds a first protein, the amino acid sequence of which first protein consists SEQ ID NO:26, which antibody does not bind to a second protein, the amino acid sequence of which second protein consists of SEQ ID NO:1 or SEQ ID NO:2. In a specific embodiment, the antibody is a monoclonal antibody. In another specific embodiment, the present invention provides a molecule comprising a fragment of said antibody, which fragment is capable of binding said first protein.

The present invention provides an isolated nucleic acid selected from the group consisting of: (a) an isolated nucleic acid comprising a nucleotide sequence, which nucleotide sequence encodes a polypeptide comprising SEQ ID NO: 3, 4, 6 or 7; (b) an isolated nucleic acid comprising a nucleotide sequence, which nucleotide sequence encodes a polypeptide comprising SEQ ID NOs: 3, 4, 5, 6 and 7; and (c) an isolated nucleic acid molecule comprising a nucleotide sequence, which nucleotide sequence encodes a polypeptide comprising an amino acid sequence which has at least 90%, at least 91%, at least 92%, at least 93%, at least 94%, or at least 95% identity to SEQ ID NO:29 as determined by a BLAST 2.0 algorithm set to default parameters. In one embodiment, the nucleic acid is purified. In another embodiment, the nucleic acid is a vector. In yet another embodiment, the vector further comprises a promoter operably linked to said nucleic acid sequence encoding said polypeptide.

The present invention also provides a host cell comprising an expression vector, wherein said expression vector comprises a promoter operably linked to a nucleotide sequence, wherein said promoter is non-native with respect to said nucleotide sequence, and wherein said nucleotide sequence encodes (a) a polypeptide comprising SEQ ID NO: 3, 4, 6 or 7; (b) a polypeptide comprising SEQ ID NOs: 3, 4, 5, 6 and 7; or (c) a polypeptide comprising an amino acid sequence which has at least 90%, at least 91%, at least 92%, at least 93%, at least 94%, or at least 95% identity to SEQ ID NO:29 as determined by a BLAST 2.0 algorithm set to default parameters.

In one embodiment, the host cell is a mammalian host cell. In another embodiment, the host cell is a yeast cell. In another embodiment, the host cell is an insect cell. In yet another embodiment, the host cell is a bacterial cell. In a specific embodiment, the bacterial cell is an *E. coli*. The present invention further provides a method of producing a polypeptide comprising growing said cell, such that the encoded polypeptide is expressed by the cell, and recovering the expressed polypeptide. In a specific embodiment, the expressed polypeptide is recovered by a method comprising the steps of: (1) producing an extract of said cell; (2) centrifuging the cell extract to produce a supernatant; (3) fractionating the supernatant by ammonium sulfate to precipitate proteins; (4) centrifuging the precipitate to obtain a pellet; (5) resuspending the pellet into a solution; (6) applying the solution to a low pressure column; (7) collecting active (immunostimulatory) fractions eluted from the low pressure column, wherein said active fractions have the ability to stimulate interleukin-12 release from dendritic cells, said dendritic cells having been isolated from a mammal within 10 hours of assaying said ability (or as assayed by one or more assays described in Section 5.6 and Section 12, infra); (8) dialyzing the active fractions; (9) applying the dialyzed active fractions to a HPLC DEAE column; (10) collecting one or more active (immunostimulatory) fractions eluted from the HPLC DEAE column, wherein said active fractions have the ability to stimulate interleukin-12 release from dendritic cells, said dendritic cells having been isolated from a mammal within 10 hours of assaying said ability (or as assayed by one or more assays described in Section 5.6 and Section 12, infra); (11) applying the active fraction to a size exclusion column; and (12) eluting the active (immunostimulatory) fractions from the size exclusion column, wherein said active fractions have the ability to stimulate interleukin-12 release from dendritic cells, said dendritic cells having been isolated from a mammal within 10 hours of assaying said ability (or as assayed by one or more assays described in Section 5.6 and Section 12, infra).

| Conventions and Abbreviations | |
|---|---|
| ARP | Apicomplexa-related protein (the active molecule of the invention) |
| SIE | Small intestine extract |
| BEX | Bovine small intestine extract |
| GM-CSF | Granulocyte macrophage-colony stimulating factor |
| IL2 | Interleukin 2 |
| IL12 | Interleukin 12 |
| IFN.gamma. | Interferon-gamma |
| DC | Dendritic cell |
| LGL | Large granular lymphocytes |

-continued

Conventions and Abbreviations

| | |
|---|---|
| NK or NK cells | Natural killer cells |
| n_NK | NK to target cell ratio, where n represents seeding ratio |
| CMC | Cell-mediated cytotoxicity |
| spp. | Various species of a given genus |
| cDNA | Complementary DNA |

BRIEF DESCRIPTION OF THE FIGURES

FIG. 4. Comparison of protein sequences from three *Eimeria* species. The sequences of *E. tenella* (EtU3) and *E. acervulina* (3-1E: Accession # AF1 13613) were obtained from cDNA translation. The cDNA for EtU3 was obtained from *E. tenella* mRNA as described in section 10. The segments from a presumed bovine *Eimeria* of unknown species was obtained by Edman and MS/MS amino acid sequencing of tryptic peptides.

FIG. 9. Anti-tumor activity of *E. tenella* extracts and recombinant *E. tenella* ARP in the murine tumor model. Three or five dosing groups for each treatment are shown. The dosing protocol consisted of the indicated dose in ng/mouse/day given daily for 5 consecutive days beginning one day after tumor injection. The amount of ARP in the extract was determined by C8 HPLC chromatography. The control group received a sham injection of buffer. A) recombinant *E. tenella* ARP from the EtU3 clone, B) recombinant *E. tenella* ARP from the E1 clone, C) *E. tenella* ARP extract from sporulated oocysts.

FIG. 17. DC activity and murine tumor index data of an *Eimeria* tenella crude membrane preparation. Dendritic cell IL12 production is shown for various dilutions of the *E. tenella* crude membrane fragment suspension, where 1.0 indicates no dilution of the suspension and is the concentration administered to mice in the in vivo anti-tumor assay. Tumor index for the ongoing test of membrane suspension activity is also shown. The lower value for the test treatment indicates positive anti-tumor activity.

FIG. 19. Alignment of various Apicomplexa expressed sequence tag (EST) translations. Alignments were performed by visual observation. A threshold for "similarity" at a position was that no more than two amino acids that would be considered non-conservative changes relative to the other amino acids that were present at that position. If this condition is satisfied, the recorded amino acid is the one occurring most commonly in the column. Average length from start Methionine is 191. Among the ESTs compared, 41 positions (41/191=21%) have 100% identity, and 106 positions (106/191=55%) have at least 80% similarity by amino acid property.

FIG. 20. Alignment of DNA sequences of *E. tenella* ARP E1 clone and the EtU3 (also referred as U3 in the figure) clone.

DETAILED DESCRIPTION OF THE INVENTION

Figure 1:
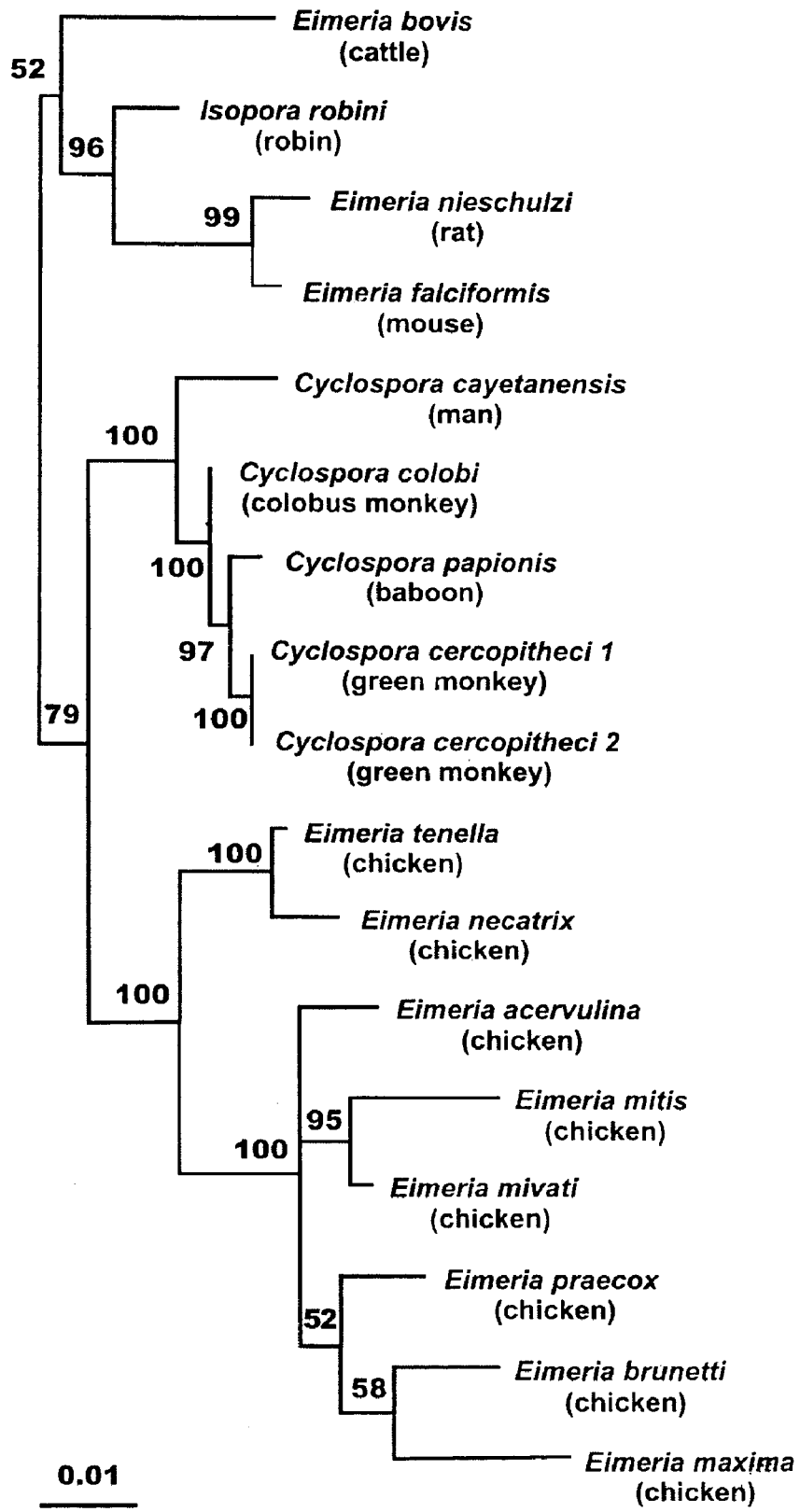
FIG. 1. Phylogenetic tree for small subunit ribosomal RNA sequences of Cyclospora and *Eimeria* species. Quartet puzzling maximum likelihood results are shown, with *Toxoplasma gondii* as the outgroup. After analysis, the outgroup branch was removed for clarity. Numbers to the left of the nodes indicate the quartet puzzling support for each internal branch. The scale bar indicates an evolutionary distance of 0.01 nucleotides per position in the sequence. Vertical distances are for clarity only. (This figure is taken from Eberhard et al., 1999, Emerging Infectious Diseases, 5(5): 651-658.)

The present invention provides compositions and methods for the prevention and treatment of primary and metastatic neoplastic diseases and infectious diseases, for stimulating an immune response in a subject, and for use as an alternative to interleukin-12 (IL-12) treatment. In particular, the present invention provides Apicomlexa-related proteins (ARPs) that have immune stimulatory activity and thus have uses in the treatment and prevention of cancer and infectious diseases, and in immune modulation. Compositions comprising ARPs are provided. Methods of use of ARPs for the prevention and/or treatment of cancer and infectious diseases, for use as an alternative to interleukin-12 (IL-12) treatment, and for eliciting an immune response in a subject, are also provided. While not bound by any theory, the invention is based, in part, on the Applicants' discovery that a molecule purified from *Eimeria* infected bovine small intestine extracts, which is highly homologous to a surface antigen (3-1E, Lellehoj et al., 2000, Avian Diseases 44: 379-389) of Apicomplexan protozoan *Eimeria acervulina*, is a robust activator of dendritic cells at pico- and femtomolar levels and has cross species immune stimulatory effects both in vitro and in vivo.

For clarity of disclosure, and not by way of limitation, the detailed description of the invention is divided into the following subsections:
(i) ARPs
(ii) ARPs of Purified Apicomplexa
(iii) Derivatives and Analogs of ARPs
(iv) Antibodies to ARPs, Derivatives and Analogs
(v) Structure Prediction and Functional Analysis of ARPs
(vi) Characterization and Demonstration of ARP activities
(vii) Uses of the Compositions of the Invention
(viii) Other Anti-cancer Therapies
(iv) Other Anti-infection Agents
(x) Dosage Regimens
(xi) Administrations, Formulations and Kits
(xii) Article of Manufacture
(xiii) Monitoring of Effects During Treatment ARPs In some embodiments, an ARP of the invention is a protein of an Apicomplexan organism that has immune stimulatory activity, as well as a fragment, a derivative, a variant, a homolog or an analog thereof. An Apicomplexan organism is one of those of the phylum Apicomplexa. Non-limiting examples of Apicomplexan organisms include but not limited to, those that are listed in Table 1, infra. In specific embodiments, an ARP of the invention include, but are not limited to, SEQ ID NO:1 (ARP of *E. tenella*), SEQ ID NO:2 (ARP of *E. acervulina*), and a protein that comprises SEQ ID NOs: 3-7 (partial amino acid sequence of bovine *Eimeria* spp. ARP. SEQ ID NOs: 3-7 are not necessarily contiguous, there may be intervening or adjacent sequences to each fragment. Preferably, a protein comprises SEQ ID NOs: 3, 4, 5, 6 and 7 in an order of SEQ ID NO:3 to SEQ ID NO:7 from the N terminus to the C terminus).

In a specific embodiment, an ARP of the invention is an Apicomplexan protein (encoded by genome of an Apicomplexan organism) that has at least 25%, at least 30%, at least 35%, at least 40%, at least 45%, at least 50%, at least 55%, at least 60%, at least 65%, at least 70%, at least 75%, at least 80%, at least 85% identity to the sequence of SEQ ID NO:1 or SEQ ID NO:2 as measured by a BLAST algorithm with default parameters using the BLAST 2.0 suite of programs (Altschul et al., Nucleic Acids Res, 2: 3389-3402, 1997), wherein the Apicomplexan protein has immune stimulatory and/or anti-cancer activity. Such activity (immunostimulatory) can be measured by, e.g., assays described in Section 5.6 and Section 12.3, infra. In a specific embodiment, an ARP of the invention is a naturally occurring Apicomplexan protein. In some embodiments, the ARPs of the invention exist in a soluble form. In some embodiments, the ARPs of the invention exist in a membrane-linked form. The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, Current Protocols in Molecular Biology, Chapter 19, Ausubel, et al., Eds., Greene Publishing and Wiley-Interscience, New York, 1995. New versions of the above programs or new programs altogether will undoubtedly become available in the future, and can be used with the present invention. It is to be understood that default settings of the parameters can be readily changed as needed in the future.

In a specific embodiment, an ARP of the invention is a protein that contains a conserved PROF (profilin) domain, wherein the protein has immune stimulatory and/or anti-cancer activity. Such activity can be measured by, e.g. assays described in Section 5.6 and Section 12.3, infra. Conserved domains are defined based on recurring sequence patterns or motifs. In one embodiment, the conserved PROF (profilin) is determined by using Conserved Domain Database (CDD v. 1.60) and an RPS-BLAST (Reverse Position-Specific BLAST) algorithm set to default parameters. Current CDD database contains domains derived from two popular collections, Smart and Pfam, plus contributions from NCBI. In Conserved Domain Database, the PROF (profilin) domain is also identified as smart 00392 or cd 00148 domain, or pfam 00235 domain (PSSM Id's 14983, 14824 and 801 correspondingly). To identify conserved domains in a protein sequence, the RPS-BLAST algorithm can be used. The query sequence is compared to a position-specific score matrix prepared from the underlying conserved domain alignment. Hits may be displayed as a pairwise alignment of the query sequence with a representative domain sequence, or as a multiple alignment. See, Marchler-Bauer et al., (2003) Nucleic Acids Research 31:383-387 (2003); Marchler-Bauer et al., (2002) Nucleic Acids Research 30:281-283, all of which are incorporated by reference in their entirety. The "PROF" domain is represented by profilin, which is ubiquitous in nature, occurring in organisms from amoeba to mammals. Profilin is involved in the regulation of actin polymerization and may link the cytoskeleton with major signaling pathways by interacting with components of the phosphatidylinositol and Ras pathway. See e.g. Korenbaum et al., Biochemistry (1998) 37(26):9274-83; Schluter et al., Biochim Biophys Acta. (1997) 1359(2):97-109, all of which are incorporated by reference in their entireties. In a specific embodiment, an ARP of the invention is a plant profilin e.g. SEQ ID NO: 11, 12, 13, or 14.

In a specific embodiment, an ARP of the invention is an Apicomplexan protein whose encoding nucleic acid (Apicomplexan cDNA or genomic nucleic acid) hybridizes under stringent conditions (high, moderate or low stringent condition) to an ARP nucleic acid (e.g., having a sequence as set forth in SEQ ID NO:16, SEQ ID NO:17, SEQ ID NO:18, SEQ ID NO:19, or SEQ ID NO:20, or to its reverse complement, or to a nucleic acid encoding an ARP derivative, or to its reverse complement), wherein the Apicomplexan protein has immune stimulatory and/or anti-cancer activity. Such activity can be measured by, e.g., assays described in Section 5.6 and Section 12.3, infra. Stringent conditions are sequence-dependent and circumstance-dependent, for example, longer sequences hybridize specifically at higher temperatures. An extensive guide to the hybridization of nucleic acids is found in Tijssen, Techniques in Biochemistry and Molecular Biology-Hybridization with Nucleic Probes, "Overview of principles of hybridization and the strategy of nucleic acid assays" (1993). See also Martin et al (EMBO J. 4: 1625-1630 (1985)) and Davies et al (Methods in Molecular Biology Vol 28: Protocols for nucleic acid analysis by non-radioactive probes, Isaac, P. G. (ed) pp 9-15, Humana Press Inc., Totowa N.J., USA). All of which are incorporated herein by reference in their entireties.

In a specific embodiment, a nucleic acid which is hybridizable to an ARP nucleic acid or its reverse complement under conditions of low stringency is provided. By way of example but not limitation, procedures using such conditions of low stringency are as follows (see also Shilo and Weinberg, 1981, Proc. Natl. Acad. Sci. U.S.A. 78, 6789-6792): filters containing DNA are pretreated for 6 hours at 40° C. in a solution containing 35% formamide, 5×SSC, 50 mM Tris-HCl (pH7.5), 5 mM EDTA, 0.1% PVP, 0.1% Ficoll, 1% BSA, and 500 μg/ml denatured salmon sperm DNA; hybridizations are carried out in the same solution with the following modifications: 0.02% PVP, 0.02% Ficoll, 0.2% BSA, 100 μg/ml salmon sperm DNA, 10% (wt/vol) dextran sulfate, and 5-20× $10^6$ cpm 32P-labeled probe is used; filters are incubated in hybridization mixture for 18-20 hours at 40° C., and then washed for 1.5 hours at 55° C. in a solution containing 2×SSC, 25 mM Tris-HCl (pH7.4), 5 mM EDTA, and 0.1% SDS; the wash solution is replaced with fresh solution and incubated an additional 1.5 hours at 60° C.; filters are blotted dry and exposed for autoradiography. If necessary, filters are washed for a third time at 65-68° C. and re-exposed to film. In another example, low stringency hybridization is carried out at 62° C. without formamide. Other conditions of low stringency which may be used are well known in the art (e.g., as employed for cross-species hybridizations).

In another specific embodiment, a nucleic acid which is hybridizable to an ARP nucleic acid, or its reverse complement, under conditions of high stringency is provided. By way of example but not limitation, procedures using such conditions of high stringency are as follows: prehybridization of filters containing DNA is carried out for 8 hours to overnight at 65° C. in buffer composed of 6×SSC, 50 mM Tris-HCl (pH7.5), 1 mM EDTA, 0.02% PVP, 0.02% Ficoll, 0.02% BSA, and 500 μg/ml denatured salmon sperm DNA; filters are hybridized for 48 h at 65° C. in prehybridization mixture containing 100 μg/ml denatured salmon sperm DNA and 5-20×$10^6$ cpm of $^{32}$P-labeled probe; washing of filters is done at 37° C. for 1 hour in a solution containing 2×SSC, 0.01% PVP, 0.01% Ficoll, and 0.01% BSA; this is followed by a wash in 0.1×SSC at 50° C. for 45 min before autoradiography. In another example, high stringency hybridization is carried out at 62° C. with 50% formamide. Other conditions of high stringency which may be used are well known in the art.

In another specific embodiment, a nucleic acid which is hybridizable to an ARP nucleic acid, or its reverse complement, under conditions of moderate stringency is provided. Selection of appropriate conditions for such stringencies is well known in the art (see e.g., Sambrook et al., 1989, Molecular Cloning, A Laboratory Manual, 2d Ed., Cold Spring Harbor Laboratory Press, Cold Spring Harbor, N.Y.; see also, Ausubel et al., eds., in the Current Protocols in Molecular Biology series of laboratory technique manuals, ©1987-1997, Current Protocols, ©1994-1997 John Wiley and Sons, Inc.). In one non-limiting example, moderate stringency hybridization can be carried out at 62° C. with 20% formamide.

In an embodiment where a bovine ARP (which comprises SEQ ID NOs: 3-7) or its derivatives are used therapeutically or prophylactically, the ARP comprises a disulfide bond. In one embodiment, a bovine ARP has not been subjected to reducing conditions that would disrupt a disulfide bond. ARP protein that has been reduced has activity that is 2-5 times greater than the oxidized form.

In some embodiments, an ARP of the invention is post-translationally modified. In some embodiments, an ARP of the invention is not post-translationally modified. In specific embodiments, an ARP of the invention is glycosylated. In specific embodiments, an ARP of the invention is unglycosylated.

In some embodiments, an ARP of the invention is membrane-linked. In some embodiments, an ARP of the invention is not membrane-linked. In specific embodiments, an ARP of the invention is glysosylphosphatidylinos-itol (GPI)-linked. In specific embodiments, an ARP of the invention is not GPI-linked. In one embodiment, an ARP of the invention is a lipoprotein. In another embodiment, an ARP of the invention is not a lipoprotein.

In a specific embodiment, an ARP of the invention is a native protein. In a specific embodiment, an ARP of the invention is a recombinantly produced protein. In specific embodiments, an ARP of the invention has a molecular weight in the range of 18 kD to 25 kD, and an isoelectric point (pI) between 4.0 and 4.7.

Therapeutic ARPs of the invention can be tested in vitro for the desired activity by any one or more assays known in the art or assays as described in Section 5.6.

An ARP of the invention typically has potent immune stimulatory activity, even at very low concentration (e.g., pico- or femtomolar levels). In specific embodiments, a therapeutic or prophylactic composition of the invention for eliciting an immune response and for the prevention and treatment of cancer and infectious diseases comprises an enriched ARP. As used herein, the term "enriched" in reference to a protein (e.g., a peptide, polypeptide or fusion protein) means that the protein constitutes a higher fraction of the total amount of protein present in the composition of interest, relative to the natural or original state from which the protein is derived. The enrichment can be achieved by preferential reduction in the amount of other protein present, or by a preferential increase in the amount of the specific protein of interest, or by a combination of the two. It should be noted that "enriched" does not imply that there are no other proteins present. The term also does not imply that there are no proteins present from other sources. The other source proteins may, for example, comprise protein(s) encoded by a genome of another species, or of a cloning vector. The term is meant to cover only those situations in which man has intervened to elevate the proportion of the desired protein. In specific embodiments, an ARP is greater than 0.001%, greater than 0.003%, greater than 0.01%, greater than 0.05%, greater than 0.1%, greater than 0.5%, greater than 1%, greater than 10%, greater than 20%, greater than 30% of total protein by weight.

The term "enriched" in reference to nucleic acid means that the nucleic acid constitutes a higher fraction of the total amount of nucleic acids present in the composition of interest, relative to the natural or original state from which the nucleic acid is derived. The enrichment can be achieved by preferential reduction in the amount of other nucleic acid present, or by a preferential increase in the amount of the specific nucleic acid of interest, or by a combination of the two. It should be noted that "enriched" does not imply that there are no other nucleic acids present. The term also does not imply that there are no nucleic acids present from other sources. The other source nucleic acids may, for example, comprise nucleic acid(s) encoded by a genome of another species, or of a cloning vector. The term is meant to cover only those situations in which man has intervened to elevate the proportion of the desired nucleic acid.

In a preferred embodiment, an ARP of the invention is purified. The term "purified" in reference to a protein or a nucleic acid means at least one order of magnitude of purification is achieved, preferably two or three orders of magnitude, most preferably four or five orders of magnitude of purification of the starting material or of the natural material. Thus, the term "purified" as used herein does not mean that the material is 100% purified and thus does not mean that a purified protein or a nucleic acid excludes any other material. In specific embodiments, a purified ARP is at least 60%, at least 80%, or at least 90% of total protein or nucleic acid, as the case may be, by weight. In a specific embodiment, a purified ARP is purified to homogeneity as assayed by, e.g., sodium dodecyl sulfate polyacrylamide gel electrophoresis, or agarose gel electrophoresis.

In a specific embodiment, an ARP of the invention is present in the form of purified viable or inactivated Apicomplexan organisms at any developmental stage or a protein fraction thereof (e.g., a protein-containing membrane preparation thereof, or a storage granule preparation thereof). In a specific embodiment, an Apicomplexan organism is an *Eimeria*, which is species-specific and usually cannot cause symptomatic infection in a host of a different species from its native host. In another specific embodiment, an inactivated Apicomplexan organism is a life cycle defective Apicomplexan organism.

Preparation and Purification of ARP

In some embodiments, the compositions of the invention that are used in prevention or treatment of cancer and/or infectious diseases comprise an enriched, an isolated, or a purified ARP. In accordance with the methods described herein, an ARP employed in a composition of the invention can be in the range of 0.001 to 100 percent of the total mg protein, or at least 0.001%, at least 0.003%, at least 0.01%, at least 0.1%, at least 1%, at least 10%, at least 30%, at least 60%, or at least 90% of the total mg protein. In one embodiment, an ARP employed in a composition of the invention is at least 4% of the total protein. In another embodiment, an ARP is purified to apparent homogeneity, as assayed, e.g., by sodium dodecyl sulfate polyacrylamide gel electrophoresis. The ARPs of the invention can be purified, e.g., from the homogenates of infected tissue or a purified Apicomplexan organism with the use of either soluble fractions (supernatants) or insolubles (pellets), or from intact cells (e.g., mammalian cells expressing a recombinant protein or Apicomplexa cells) with the use of enzymes acting on cell surface. Any techniques known in the art can be used in purifying an ARP, including but are not limited to, separation by precipitation, separation by adsorption (e.g., column chromatography, membrane adsorbents, radial flow columns, batch adsorption, high-performance liquid chromatography, ion exchange chromatography, inorganic adsorbents, hydrophobic adsorbents, immobilized metal affinity chromatography, affinity chromatography), or separation in solution (e.g., gel filtration, electrophoresis, liquid phase partitioning, detergent partitioning, organic solvent extraction, and ultrafiltration). See Scopes, PROTEIN PURIFICATION, PRINCIPLES AND PRACTICE, $3^{rd}$ ed., Springer (1994), the entire text is incorporated herein by reference. During the purification, the immune-stimulatory activity and/or the anti-tumor activity of the ARP should be monitored by one or more in vitro or in vivo assays as described in Section 5.6 and Section 12. The present invention also encompasses any modification to the methods of isolation of ARP that affects ARP activity and/or aggregation state through regulation of binding of divalent cations. The purity of ARP can be assayed by any methods known in the art, such as but not limited to, gel electrophoresis. See Scopes, supra.

Purification of Soluble ARPs from Tissue and Cell Extracts

In one embodiment, an ARP is purified from Apicomplexa infected tissue of a vertebrate animal (the animal may have symptomatic infection or non-symptomatic infection), including but not limited to, a cow, a sheep, a pig, a goat, a horse, a dog, a cat, a rodent, an avian, a primate (e.g., monkey), a mammal, and a human. In another embodiment, an ARP is purified from a cell culture infected with an Apicomplexan organism. In yet anther embodiment, an ARP is purified from a preparation of an Apicomplexan organism. A procedure that can be used to purify ARPs from infected tissues, a cell culture, or a preparation of Apicomplexan organism, is presented by way of example but not limitation in Section 6, infra.

Briefly, by way of example but not limitation, a preparation of infected tissue or cells (e.g., a homogenized small intestine tissue or a preparation of the cells of intestinal mucosa) is centrifuged. The resulting liquid supernatants are brought to 45% saturation with solid ammonium sulfate, centrifuged and the pellet is discarded. The supernatants are brought to 80% saturation using solid ammonium sulfate, centrifuged again, and the supernatant is discarded. The pellets are dissolved in 1.5 M Ammonium Sulfate/50 mM Sodium Phosphate (pH 6.8) after resuspending completely within the bottles or tubes. Non-dissolved material is removed by centrifugation.

In a preferred embodiment, to reduce the macromolecular load prior to size-exclusion chromatography, two bulk processing steps are used. The first step uses a hydrophobic interaction column (hereinafter "HIC" column. See Section 6.2.2., infra). A large amount of inactive material, particularly polynucleic acid, is removed in the flow-through and wash. The active (immunostimulatory) material (wherein said active fractions have the ability to stimulate interleukin-12 release from dendritic cells, said dendritic cells having been isolated from a mammal within 10 hours of assaying said ability (or as assayed by one or more assays described in Section 5.6 and Section 12, infra)) is eluted after a change to a buffer free of ammonium sulfate. The eluted material is prepared for DEAE chromatography by dialysis against 4 L of 0.2M NaCl/10 mM Sodium Phosphate (pH7.4) at 4° C. with buffer exchanges. The elution is processed in a similar fashion on DEAE ion exchange chromatography (see Section 6.2.2., infra) where the flow-through and wash are discarded. The elution at higher NaCl concentration is retained, concentrated on a membrane pressure cell, and added to a size exclusion column (e.g., a Superdex™ column). Specific activity (with respect to protein content, as assayed by one or more assays described in Section 5.6 and Section 12) is determined on the retained fractions from each step in the purification. Approximately 7000-fold purification is reached at the end of the size exclusion chromatography step. In specific embodiments (e.g., when small intestine extracts are used, bacterial endotoxin is always a contaminant), the endotoxin levels are monitored with the LAL assay (see Section 5.3., infra) at each step in the purification. Endotoxin levels are reduced approximately 1000-fold resulting in final levels that are well below those that can interfere with the DC assay (threshold of 1000 U/mL for minimal DC activity. See Section 5.6 and Section 12 for detailed description of the DC assay).

In some embodiments, to obtain enough material for final purification, pools are created that contained the extracts from multiple samples (e.g., animal intestines). Preferably, these are pre-selected for high activity in the crude supernatants (for an example of such pretesting of the activity, see Section 6.2.1). Several batches of intestinal or cell preparations are combined, concentrated, cleared of calcium binding proteins (by an HIC column, see Section 6.2.2., infra) and designated as a pool.

To obtain a purified product, a pool is initially separated on a high performance liquid chromatography (hereinafter "HPLC") HIC column. The active fractions (wherein said active fractions have the ability to stimulate interleukin-12 release from dendritic cells, said dendritic cells having been isolated from a mammal within 10 hours of assaying said ability (or as assayed by one or more assays described in Section 5.6 and Section 12, infra)) are dialyzed to remove ammonium sulfate and are applied to an HPLC DEAE column in 0.15M NaCl (see Section 6.2.2., infra). A NaCl gradient is applied and the activity (immunostimulatory activity, as assayed by one or more assays described in Section 5.6 and Section 12, infra) eluted with a major peak near 0.3M ionic strength. Preferably, DEAE runs are used to process the active material from the HIC. In specific embodiments, the pooled active region is applied to a reverse phase HPLC column (e.g., C8 reverse phase HPLC column, see Section 6.2.2., infra) and eluted with an aqueous-acetonitile gradient. The activity (immunostimulatory activity, as assayed by one or more assays described in Section 5.6 and Section 12) eluted near 40% acetonitrile on a slow, shallow gradient elution protocol. The question of purity of these active fractions is addressed by plotting activity versus absorbance along a finely-sampled separation. A reasonably robust linear regression line and the intersection near zero indicate the lack of contaminating molecules.

The reverse phase HPLC column purification step denatures most of the protein. In a preferred embodiment, the eluted protein from a reverse phase HPLC column is renatured by a method known in the art, preferably by the method described in Section 13. In another embodiment, reverse phase HPLC column is not used to purify an ARP of the invention.

In some embodiments, a soluble ARP can be isolated by a process comprising the steps of: (1) producing a solution with enriched ARP, e.g., an extract of cells expressing a recombinant ARP protein; (2) centrifuging the solution to obtain a supernatant; (3) fractionating the supernatant by ammonium sulfate to precipitate proteins, centrifuging the precipitate to obtain a pellet, and resuspending the pellet into a solution; (4) applying the solution to a low pressure HIC column and collecting active (immunostimulatory) fractions (wherein said active fractions have the ability to stimulate interleukin-12 release from dendritic cells, said dendritic cells having been isolated from a mammal within 10 hours of assaying said ability (or as assayed by one or more assays described in Section 5.6 and Section 12, infra)); (5) dialyzing the active fractions; (6) applying the dialyzed active fractions to HPLC DEAE column and collecting one or more active (immunostimulatory) fractions (wherein said active fractions have the ability to stimulate interleukin-12 release from dendritic cells, said dendritic cells having been isolated from a mammal within 10 hours of assaying said ability (or as assayed by one or more assays described in Section 5.6 and Section 12, infra)); and (7) applying the active fractions to a size exclusion column and collect eluted active (immunostimulatory) fractions (wherein said active fractions have the ability to stimulate interleukin-12 release from dendritic cells, said dendritic cells having been isolated from a mammal within 10 hours of assaying said ability (or as assayed by one or more assays described in Section 5.6 and Section 12, infra)) (see Section 10.2, infra).

In a specific embodiment, a soluble ARP is isolated by a process comprising the steps of: (1) producing mineral media spent by bacteria expressing a recombinant ARP; (2) applying the media to a DEAE column; (3) eluting material bound to the DEAE column with buffer to produce an eluted fraction; (4) applying the eluted fraction to a size exclusion column; and (5) collecting the fractions eluted from the size exclusion column.

In another embodiment, an ARP is purified from an Apicomplexan protozoan, 4 including but is not limited to, those that are listed in Table 1. FIG. 1 also provides phylogenetic information on some of the Apicomplexan protozoa. A non-limiting example of the purification process is given in Section 8.

TABLE 1

Apicomplexa

Coccidia
  Eimeriida
    Cryptosporidiidae
      *Cryptosporidium andersoni*
      *Cryptosporidium baileyi*
      *Cryptosporidium canis*
      *Cryptosporidium felis*
      *Cryptosporidium galli*
      *Cryptosporidium meleagridis*
      *Cryptosporidium muris*
      *Cryptosporidium parvum*
      *Cryptosporidium saurophilum*
      *Cryptosporidium serpentis*
      *Cryptosporidium wrairi*
      *Cryptosporidium* sp.
      unclassified *Cryptosporidium*
    Eimeriidae
      *Caryospora*
        *Caryospora bigenetica*
        *Caryospora* sp.
      *Choleoeimeria*
        *Choleoeimeria* sp.
      *Cyclospora*
        *Cyclospora cayetanensis*
        *Cyclospora cercopitheci*
        *Cyclospora colobi*
        *Cyclospora papionis*
        *Cyclospora* sp.
        *Cyclospora* sp. strain Gombe 22
        *Cyclospora* sp. strain Gombe 34
        *Cyclospora* sp. strain Gombe 40
      *Eimeria*
        *Eimeria acervulina*
        *Eimeria adeneodei*
        *Eimeria ahsata*
        *Eimeria alabamensis*
        *Eimeria albigulae*
        *Eimeria antrozoi*
        *Eimeria arizonensis*
        *Eimeria aubernensis*
        *Eimeria bovis*
        *Eimeria brunetti*

TABLE 1-continued

Apicomplexa

*Eimeria catronensis*
        *Eimeria chaetodipi*
        *Eimeria chobotari*
        *Eimeria crandallis*
        *Eimeria dipodomysis*
        *Eimeria falciformis*
        *Eimeria faurei*
        *Eimeria langebarteli*
        *Eimeria leucopi*
        *Eimeria maxima*
        *Eimeria meleagrimitis*
        *Eimeria mitis*
        *Eimeria mivati*
        *Eimeria necatrix*
        *Eimeria nieschulzi*
        *Eimeria onychomysis*
        *Eimeria ovinoidalis*
        *Eimeria papillata*
        *Eimeria peromysci*
        *Eimeria pilarensis*
        *Eimeria polita*
        *Eimeria porci*
        *Eimeria praecox*
        *Eimeria reedi*
        *Eimeria rioarribaensis*
        *Eimeria scabra*
        *Eimeria scholtysecki*
        *Eimeria separata*
        *Eimeria sevilletensis*
        *Eimeria stiedae*
        *Eimeria telekii*
        *Eimeria tenella*
        *Eimeria tropidura*
        *Eimeria weybridgensis*
      *Goussia*
        *Goussia janae*
      *Isospora*
        *Isospora belli*
        *Isospora felis*
        *Isospora gryphoni*
        *Isospora insularius*
        *Isospora ohioensis*
        *Isospora peromysis*
        *Isospora robini*
        *Isospora suis*
    Sarcocystidae
      *Toxoplasma*
  Eucoccidiorida
    Adeleorina
    Lankesterellidae
      *Lankesterella*
Colpodellidae
  *Colpodella*
    *Colpodella pontica*
    *Colpodella* sp. ATCC50594
Gregarinia
  Eugregarinida
    Gregarinidae
    Lecudinidae
    Leidyanidae
    Monocystidae
    Ophryocystidae
  *Pseudomonocystis*
    *Pseudomonocystis lepidiota*
Haemosporida (haemosporidians)
  *Haemoproteus*
    *Haemoproteus chelodinae*
    *Haemoproteus columbae*
    *Haemoproteus kopki*
    *Haemoproteus majoris*
    *Haemoproteus ptyodactylii*
    *Haemoproteus sylvae*
    *Haemoproteus* sp.
    unclassified *Haemoproteus*
  *Hepatocystis*
    *Hepatocystis* sp.
  *Leucocytozoon*

TABLE 1-continued

Apicomplexa

Leucocytozoon dubreuli
Leucocytozoon simondi
Plasmodium
    Plasmodium agamae
    Plasmodium atheruri
    Plasmodium azurophilum
    Plasmodium berghei
    Plasmodium brasilianum
    Plasmodium chabaudi
    Plasmodium chiricahuae
    Plasmodium cuculus
    Plasmodium cynomolgi
    Plasmodium elongatum
    Plasmodium fairchildi
    Plasmodium falciparum (malaria parasite P. falciparum)
    Plasmodium fieldi
    Plasmodium floridense
    Plasmodium fragile
    Plasmodium gallinaceum
    Plasmodium giganteum
    Plasmodium gonderi
    Plasmodium guanggong
    Plasmodium heteronucleare
    Plasmodium hylobati
    Plasmodium inui
    Plasmodium juxtanucleare
    Plasmodium knowlesi
    Plasmodium lophurae
    Plasmodium malariae
    Plasmodium cf. malariae
    Plasmodium mexicanum
    Plasmodium nucleophilum
    Plasmodium ovale (malaria parasite P. ovale)
    Plasmodium reichenowi
    Plasmodium relictum
    Plasmodium rouxi
    Plasmodium simiovale
    Plasmodium simium
    Plasmodium vinckei
    Plasmodium vivax (malaria parasite P. vivax)
    Plasmodium yoelii
    Plasmodium sp.
    unclassified Plasmodium
  unidentified Haemosporida
Piroplasmida (Piroplasmids)
  Babesiidae
    Babesia
  Theileriidae
    Cytauxzoon
    Theileria
    Theileria-related sp.
  unclassified Piroplasmida
    Piroplasmida gen. sp. BH1
    Piroplasmida gen. sp. BH3
    Piroplasmida gen. sp. CA1
    Piroplasmida gen. sp. CA3
    Piroplasmida gen. sp. CA4
    Piroplasmida gen. sp. FD1
    Piroplasmida gen. sp. MD1
    Piroplasmida gen. sp. WA1
    Piroplasmida gen. sp. WA2
unclassified Apicomplexa
  Tridacna hemolymph apicomplexan
  Apicomplexa sp. 72141
  unidentified symbiont Type N For more information, see e.g., the website at ncbi.nlm.nih.gov/Taxonomy/taxonomyhome.html/index.cgi, Plasmodium falciparum, Apicomplexa; the website at plasmodb.org; or the website at biology.unm.edu/biology/coccidia.

A purified Apicomplexan organism can be obtained by any method known in the art. See e.g., Tomley, Methods: A Companion to Methods in Enzymology 13: 171-176 (1997); Ryley et al., Parasitology, 73: 311-362 (1976); U.S. Pat. Nos. 6,001,363, 6,100,241, 5,792,644, 6,451,984 and 6,008,342. For a detailed example, also see Section 8.

In one embodiment, ARP is purified from the class coccidian. In another embodiment, ARP is purified from the family Eimeriidae. In yet another embodiment, ARP is purified from the genus Eimeria.

Briefly, by way of example but not limitation, ARP can be purified from E. tenella (see Section 8) as follows: sporulated oocysts are suspended in PBS and centrifuged. The supernatant is removed and retained. The pellet is suspended in 30 mM Hepes and homogenized on ice. This processing will result in most oocysts to be broken, releasing sporocysts that remain largely intact. The homogenate is transferred to a microcentrifuge tube and centrifuged.

In a second preparation, the homogenate is sonicated with care taken to keep the homogenate cooled during the sonication. Approximately 80% of the released sporocysts are disrupted. The suspensions are pooled and microcentrifuged. The pellet is retained and stored at 4° C. for future processing.

The starting material for the 3rd extract of sporulated oocysts is the residual pellet of the 2nd extract preparation. The pellet material is suspended in Hepes and transferred to a beadbeater tube containing glass beads. The tube is then completely filled with Hepes and processed in a Mini-Beadbeater with care taken to prevent excessive heating. The suspension is microcentrifuged briefly and the supernatant is separated from the glass beads. This supernatant is microcentrifuged and is filter-sterilized and used for purification of ARP by a reverse phase HPLC chromatography (e.g., C8 reverse phase HPLC chromatography). The pellet can be used for purification of the membrane-linked form of ARP.

Purification of Membrane-Linked ARPs

In a specific embodiment, the therapeutic or prophylactic compositions of the invention comprise a protein-containing membrane preparation of Apicomplexan protozoa (see section 9). While not bound by any theory, the ARP is believed to exist in two forms: a soluble form and a membrane-linked form. In a specific embodiment, an ARP of the invention is linked to a cell membrane through a glycosylphosphatidylinositol (GPI) anchor (for description of protozoan-derived GPI and its receptor (Toll-like receptor 2) see, e.g., Almeida et al., J. of Leukocyte Biology, 2001, 70: 467477; Campos et al., the J. of Immunology, 2001, 167: 416423; Ropert et al., Current Opinion in Microbiology, 2000, 3: 395-403). When an Apicomplexa organism infects a host, such as a cow, soluble ARP may also originate from the membranes of the Apicomplexa organism due to cleavage by endogenous phospholipase C or D present in the host's blood. An ARP can be extracted from a membrane by a non-enzymatic or a enzymatic method. In a specific embodiment, an ARP is extracted from a membrane by a detergent. In another specific embodiment, an ARP is released from a membrane by an enzymatic method, e.g., using internal or external phospholipase or a protease. Co-sedimenting large ARP aggregates (if any) are dissolved simultaneously if the incubation buffer is free of divalent cations.

In certain embodiments, a membrane-bound ARP is isolated by a process comprising the steps of: (1) producing a homogenate of a purified Apicomplexan organism, cells infected with an Apicomplexan organism, or cells expressing a recombinant ARP; (2) centrifuging the homogenate to obtain a pellet; (3) suspending the pellet in a solution and treating the solution to release the ARP by an enzymatic method (e.g., using a phospholipase); (4) centrifuging the solution to obtain a supernatant highly enriched in ARP; (5) applying the supernatant to a reverse phase HPLC column; and (6) eluting bound protein from the reverse phase HPLC column. In specific embodiments, the eluted bound protein of step (6) is renatured by any technique known in the art. The immunostimulatory activity of an ARP is monitored by one or more assays described in Section 5.6 and Section 12 during the isolation process. In a specific embodiment, a membrane-bound ARP is prepared by the following method:

Briefly, by way of example but not limitation, crude membrane preparation from the sporozoites of *E. tenella* can be prepared as follows: a suspension of oocysts in homogenization buffer (hereinafter "HB") (50 mM Tris pH 7.4, 1 mM PMSF, 50 µl/ml of protease inhibitors cocktail) is sonicated on ice followed by freeze-thaw cycles (liquid nitrogen/room temperature). This procedure results in almost complete breakage of oocysts, sporocysts and sporozoites. 10 mM $ZnCl_2$ can be added to inhibit the release of an ARP from membranes by internal phospholipase and/or facilitate ARP aggregation to increase the yield.

The cell homogenate is then centrifuged to pellet membranes. This centrifugation regime also pellets nuclei, other organelles, pelletable ARP aggregates and storage granules, if any. Organelles can be disrupted in further purification cycles in HB without $ZnCl_2$.

Pellet is suspended in 1 ml of HB and centrifuged again. Centrifugation/resuspension is repeated once more with and 2-3 times more without $ZnCl_2$ in the suspension buffer. Supernatants from centrifugation cycles done without $ZnCl_2$ contain significant amounts of ARP.

The final pellet is suspended in 100 µl of HB with or without protease inhibitors and incubated at 37° C. 1-4 hrs to release additional quantities of ARP. Phospholipase C at 16 U/ml facilitates the ARP release. The ARP released into solution can be separated from the insoluble material by centrifugation, followed by two washing cycles. All three supernatants are combined. They contain ARP with small amount of contaminants which can be removed by a single separation by reverse phase chromatography (e.g., C8 reverse phase chromatography).

Antibody-Affinity Purification of ARP

In another embodiment, antibody is used to purify an ARP or a fragment thereof. Any ARP preparations, e.g., an Apicomplexa infected tissue extract, cell culture, or a protein containing membrane preparation, can be used in antibody affinity purification of ARP. Antibodies can also be used in purifying a recombinant ARP product or a synthesized ARP. Antibodies can be monoclonal or polyclonal, and antibodies can be raised against the ARP or against a fragment of ARP (e.g., comprising a hydrophilic portion). In a specific embodiment, an antibody that binds to SEQ ID NO:26 (bovine ARP fragment 1 (SEQ ID NO:3) fused to bovine ARP fragment 2 (SEQ ID NO:4) fused to bovine ARP fragment 3 (SEQ ID NO:5) fused to bovine ARP fragment 4 (SEQ ID NO:6) and fused to bovine ARP fragment 5 (SEQ ID NO:7)) is used to purify an ARP or a fragment thereof. When ARP is engineered to express as a fusion protein, antibodies raised against a portion of the fused protein that is not ARP can be used to purify the ARP. Antibodies can be produced by any method known in the art or as described in Section 5.4., infra.

Methods of using antibodies to purify a protein are standard and well known in the art, and are not described in detail here. See, e.g., Scopes, PROTEIN PURIFICATION, PRINCIPLES AND PRACTICE, 3$^{rd}$ ed., Springer (1994), at pp 187-236, the entire text is incorporated herein by reference.

Recombinant Expression of ARP

Methods known in the art can be utilized to recombinantly produce ARP. A nucleic acid sequence encoding ARP can be inserted into an expression vector for propagation and expression in host cells.

An expression construct, as used herein, refers to a nucleotide sequence encoding ARP or a fragment thereof operably associated with one or more regulatory regions which enable expression of ARP in an appropriate host cell. "Operably-associated" refers to an association in which the regulatory regions and the ARP sequence to be expressed are joined and positioned in such a way as to permit transcription, and ultimately, translation.

The regulatory regions necessary for transcription of the ARP can be provided by the expression vector. A translation initiation codon (ATG) may also be provided if the ARP gene sequence lacking its cognate initiation codon is to be expressed. In a compatible host-construct system, cellular transcriptional factors, such as RNA polymerase, will bind to the regulatory regions on the expression construct to effect transcription of the modified ARP sequence in the host organism. The precise nature of the regulatory regions needed for gene expression may vary from host cell to host cell. Generally, a promoter is required which is capable of binding RNA polymerase and promoting the transcription of an operably-associated nucleic acid sequence. Such regulatory regions may include those 5' non-coding sequences involved with initiation of transcription and translation, such as the TATA box, capping sequence, CAAT sequence, and the like. The non-coding region 3' to the coding sequence may contain transcriptional termination regulatory sequences, such as terminators and polyadenylation sites.

In order to attach DNA sequences with regulatory functions, such as promoters, to the ARP gene sequence or to insert the ARP gene sequence into the cloning site of a vector, linkers or adapters providing the appropriate compatible restriction sites may be ligated to the ends of the cDNAs by techniques well known in the art (Wu et al., 1987, Methods in Enzymol, 152: 343-349). Cleavage with a restriction enzyme can be followed by modification to create blunt ends by digesting back or filling in single-stranded DNA termini before ligation. Alternatively, a desired restriction enzyme site can be introduced into a fragment of DNA by amplification of the DNA by use of PCR with primers containing the desired restriction enzyme site.

An expression construct comprising an ARP sequence operably associated with regulatory regions can be directly introduced into appropriate host cells for expression and production of ARP without further cloning. See, e.g., U.S. Pat. No. 5,580,859. The expression constructs can also contain DNA sequences that facilitate integration of the ARP sequence into the genome of the host cell, e.g., via homologous recombination. In this instance, it is not necessary to employ an expression vector comprising a replication origin suitable for appropriate host cells in order to propagate and express ARP in the host cells.

A variety of expression vectors may be used including, but not limited to, plasmids, cosmids, phage, phagemids or modified viruses. Such host-expression systems represent vehicles by which the coding sequences of interest may be produced and subsequently purified, but also represent cells which may, when transformed or transfected with the appropriate nucleotide coding sequences, express ARP in situ. These include, but are not limited to, microorganisms such as bacteria (e.g., *E. coli* and *B. subtilis*) transformed with recombinant bacteriophage DNA, plasmid DNA or cosmid DNA expression vectors containing ARP coding sequences; yeast (e.g., *Saccharomyces, Pichia*) transformed with recombinant yeast expression vectors containing ARP coding sequences; insect cell systems infected with recombinant virus expression vectors (e.g., baculovirus) containing ARP coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing ARP coding sequences; or mammalian cell systems (e.g., COS, CHO, BHK, 293, NS0, and 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli* and eukaryotic cells, especially for the expression of whole recombinant ARP molecule, are used for the expression of a recombinant ARP molecule. For example, mammalian cells such as Chinese hamster ovary cells (CHO) can be used with a vector bearing promoter element from major intermediate early gene of cytomegalocirus for effective expression of ARPs (Foecking et al., 1986, Gene 45: 101; and Cockett et al., 1990, Bio/Technology 8: 2).

In bacterial systems, a number of expression vectors may be advantageously selected depending upon the use intended for the ARP molecule being expressed. For example, when a large quantity of such an ARP is to be produced, for the generation of pharmaceutical compositions of an ARP molecule, vectors which direct the expression of high levels of fusion protein products that are readily purified may be desirable. Such vectors include, but are not limited to, the *E. coli* expression vector pCR2.1 TOPO (Invitrogen), in which the ARP coding sequence may be directly ligated from PCR reaction and may be placed in frame to the lac Z coding region so that a fusion protein is produced; pIN vectors (Inouye & Inouye, 1985, Nucleic Acids Res. 13: 3101-3109; Van Heeke & Schuster, 1989, J. Biol. Chem. 24: 5503-5509) and the like. Series of vectors like pFLAG (Sigma), pMAL (NEB), and pET (Novagen) may also be used to express the foreign polypeptides as fusion proteins with FLAG peptide, malE-, or CBD-protein. These recombinant proteins may be directed into periplasmic space for correct folding and maturation. The fused part can be used for affinity purification of the expressed protein. Presence of cleavage sites for specific protease like enterokinase allows to cleave off the APR. The pGEX vectors may also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system, many vectors to express foreign genes can be used, e.g., *Autographa californica* nuclear polyhedrosis virus (AcNPV) can be used as a vector to express foreign genes. The virus grows in cells like *Spodoptera frugiperda* cells. The ARP coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the ARP coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing ARP in infected hosts (see, e.g., Logan & Shenk, 1984, Proc. Natl. Acad. Sci. USA 81: 355-359). Specific initiation signals may also be required for efficient translation of inserted ARP coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see, e.g., Bittner et al., 1987, Methods in Enzymol. 153: 51-544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript and post-translational modification of the gene product, e.g., glycosylation and phosphorylation of the gene product, may be used. Such mammalian host cells include, but are not limited to, PC12, CHO, VERY, BHK, Hela, COS, MDCK, 293, 3T3, WI 38, BT483, Hs578T, HTB2, BT20 and T47D, NS0 (a murine myeloma cell line that does not endogenously produce any immunoglobulin chains), CRL7030 and HsS78Bst cells. Expression in a bacterial or yeast system can be used if post-translational modifications turn to be non-essential for the activity of ARP.

For long term, high yield production of properly processed ARP, stable expression in cells is preferred. Cell lines that stably express ARP may be engineered by using a vector that contains a selectable marker. By way of example but not limitation, following the introduction of the expression constructs, engineered cells may be allowed to grow for 1-2 days in an enriched media, and then are switched to a selective media. The selectable marker in the expression construct confers resistance to the selection and optimally allows cells to stably integrate the expression construct into their chromosomes and to grow in culture and to be expanded into cell lines. Such cells can be cultured for a long period of time while ARP is expressed continuously.

A number of selection systems may be used, including but not limited to, antibiotic resistance (markers like Neo, which confers resistance to geneticine, or G-418 (Wu and Wu, 1991, Biotherapy 3: 87-95; Tolstoshev, 1993, Ann. Rev. Pharmacol. Toxicol. 32: 573-596; Mulligan, 1993, Science 260: 926-932; and Morgan and Anderson, 1993, Ann. Rev. Biochem. 62: 191-217; May, 1993, TIB TECH 11 (5): 155-2 15); Zeo, for resistance to Zeocin; Bsd, for resistance to blasticidin, etc.); antimetabolite resistance (markers like Dhfr, which confers resistance to methotrexate, Wigler et al., 1980, Natl. Acad. Sci. USA 77: 357; O'Hare et al., 1981, Proc. Natl. Acad. Sci. USA 78: 1527); gpt, which confers resistance to mycophenolic acid (Mulligan & Berg, 1981, Proc. Natl. Acad. Sci. USA 78: 2072); and hygro, which confers resistance to hygromycin (Santerre et al., 1984, Gene 30: 147). In addition, mutant cell lines including, but not limited to, tk-, hgprt- or aprt-cells, can be used in combination with vectors bearing the corresponding genes for thymidine kinase, hypoxanthine, guanine- or adenine phosphoribosyltransferase. Methods commonly known in the art of recombinant DNA technology may be routinely applied to select the desired recombinant clone, and such methods are described, for example, in Ausubel et al. (eds.), Current Protocols in Molecular Biology, John Wiley & Sons, NY (1993); Kriegler, Gene Transfer and Expression, A Laboratory Manual, Stockton Press, NY (1990); and in Chapters 12 and 13, Dracopoli et al. (eds), Current Protocols in Human Genetics, John Wiley & Sons, NY (1994); Colberre-Garapin et al., 1981, J. Mol. Biol. 150:1.

The recombinant cells may be cultured under standard conditions of temperature, incubation time, optical density and media composition. However, conditions for growth of recombinant cells may be different from those for expression of ARP. Modified culture conditions and media may also be used to enhance production of ARP. Any techniques known in the art may be applied to establish the optimal conditions for producing ARP.

Isolation of ARP Gene

The gene encoding an ARP can be isolated by any technique known in the art. Specific embodiments for the isolation of an ARP gene follow. For example, a protozoa of genus Apicomplexa can be used to isolate its total RNA. Once the total RNA of an Apicomplexa protozoan is available, the ARP gene can be isolated by methods known in the art, including but are not limited to, screening of a cDNA library, affinity purification of ARP mRNA, and polymerase chain reaction (PCR).

In specific embodiments, an isolated ARP gene comprises a nucleic acid molecule encoding SEQ ID NO:1 (ARP of *E. tenella*), SEQ ID NO:2 (ARP of *E. acervulina*), or SEQ ID NOs: 3-7 (partial sequences of bovine *Eimeria* spp. ARP. SEQ ID NOs:3-7 are not necessarily contiguous, there may be intervening or adjacent sequences to each fragment. Preferably, the nucleic acid molecule encodes a protein comprising SEQ ID NOs:3, 4, 5, 6 and 7 in an order of SEQ ID NO:3 to SEQ ID NO:7 from the N-terminus to the C-terminus). In specific embodiments, an isolated ARP gene consists a nucleic acid molecule encoding SEQ ID NO:1, SEQ ID NO:2, or SEQ ID NO:26 (SEQ ID NO:3 fused to SEQ ID NO:4 fused to SEQ ID NO:5 fused to SEQ ID NO:6 and fused to SEQ ID NO:7).

In one embodiment, cDNA library is generated by using any method known in the art (e.g., OrientExpress cDNA Library Construction System (Novagen)). Total mRNA are used to synthesize the first strand, second strand, and ligated into lambda (λ) bacteriophage arms. The constructed phage DNA can be packaged into bacteriophage by, e.g., Phage-Maker Kit (Novagen). The bacteriophages containing different DNA inserts are used to infect the bacterial host to generate the lambda bacteriophage cDNA library. Normally, the library will contain $10^5$ to $10^6$ primary clones. The phage library are amplified and plated out to e.g., about $10^4$ clones per plate. The library can then be screened by membrane lifting technique, using an ARP gene probe (e.g., an *E. tenella* ARP). Alternatively, the cDNA library can be screened by induction of protein expression by isopropyl-1-thio-β-D-galactoside (IPTG). The membranes lifted from the plates contained the expressed proteins are screened by using antibody generated against an ARP (e.g., SEQ ID NO:1 or 2). The identified clones are analyzed by DNA sequencing. The correct DNA insert are subcloned into protein expression vector for protein expression. The recombinant protein can be tested for DC activating property.

In another embodiment, an ARP gene (e.g., SEQ ID NO:15, 16, 17, 18, 19, 20 or 27) is cloned into a vector (e.g., pET-Blue2 vector (Novagen)) in the inverse orientation. This plasmid is transformed into a bacterial host. The bacterial strain harboring the pET-Blue2 plasmid has the ability to generate single strand (ss) phage DNA after infection with the helper phage R408. The positive strand of the insert will be made during the phage formation. The positive strand with the inverse orientation would correspond to the negative strand of the original ARP gene cloned into the vector. This ssDNA will be complimentary to a targeted ARP mRNA. The ssDNA can be biotinylated and added to the total Apicomplexan protozoan mRNA preparation to allow hybridization of the two complimentary strands. The complex can be isolated by binding to streptavidin magnetic beads. After washing of the unbound mRNA, the bound targeted Apicomplexan ARP mRNA will be eluted under low salt condition, while the biotinylated ssDNA will remain bound to the magnetic bead through strong biotin-streptavidin binding. The resulting mRNA, which is specific for targeted Apicomplexan ARP gene, will be used for synthesizing first strand DNA, second strand DNA, and cloned into protein expression vector for DNA sequencing and protein expression. DNA sequence is confirmed by homology to an ARP gene. The recombinant protein is expressed to test DC activation function. In a specific embodiment, antitumor activity is confirmed by mouse test.

In another embodiment, using the total mRNA isolated from an Apicomplexa protozoan, the first strand can be synthesized by MMLV reverse transcriptase using oligo dT as primer. The resulting sample will be used to perform polymerase chain reaction (PCR) by using Taq polymerase and specific primers determined by an ARP gene sequence (e.g., SEQ ID NOs: 15, 16, 17, 18, 19, 20 or 27) or consensus of ESTs from GenBank. PCR products can be analyzed by DNA agarose gel to determine the molecular weight as compared to molecular weight standard and the expected value from an ARP gene. PCR products can be introduced into cloning vector (e.g., pCR 2.1 TOPO from Invitrogen) and the plasmids with the correct insert can be selected on a basis of analysis of their size, and PCR amplification pattern with primers specific to the ARP gene. Finally the gene can be re-cloned into an expression vector. The cloned gene can be subjected to DNA sequence analysis for final confirmation of ARP sequence and precise determination of the ARP gene.

In another embodiment, polymerase chain reaction (PCR) is used to amplify the desired sequence in a genomic or cDNA library, prior to selection. Oligonucleotide primers representing an ARP sequences can be used as primers in PCR. In a preferred aspect, the oligonucleotide primers represent at least part of conserved segments of strong homology between ARP genes of different species. The synthetic oligonucleotides may be utilized as primers to amplify sequences from a source (RNA or DNA), preferably a cDNA library, of potential interest. PCR can be carried out, e.g., by use of a Perkin-Elmer Cetus thermal cycler and Taq polymerase (e.g., Gene Amp™). The nucleic acid being amplified can include mRNA or cDNA or genomic DNA from any species. One may synthesize degenerate primers for amplifying homologs from other species in the PCR reactions.

It is also possible to vary the stringency of hybridization conditions used in priming the PCR reactions, to allow for greater or lesser degrees of nucleotide sequence similarity between the ARP nucleotide sequences and a nucleic acid homolog being isolated. For cross species hybridization, low stringency conditions are preferred. For same species hybridization, moderately stringent conditions are preferred. After successful amplification of a segment of an ARP homolog, that segment may be cloned and sequenced by standard techniques, and utilized as a probe to isolate a complete cDNA or genomic clone. This, in turn, permits the determination of the gene's complete nucleotide sequence, the analysis of its expression, and the production of its protein product for functional analysis, as described below. In this fashion, additional genes encoding ARPs and ARP analogs may be identified.

Peptide Synthesis

An alternative to producing ARP or a fragment thereof by recombinant techniques is peptide synthesis. For example, an entire ARP, or a peptide corresponding to a portion of ARP can be synthesized by use of a peptide synthesizer. Conventional peptide synthesis or other synthetic protocols well known in the art may be used.

Peptides having the amino acid sequence of ARP or a portion thereof may be synthesized by solid-phase peptide synthesis using procedures similar to those described by Merrifield, 1963, J. Am. Chem. Soc., 85: 2149. During synthesis, N-α-protected amino acids having protected side chains are added stepwise to a growing polypeptide chain linked by its C-terminal and to an insoluble polymeric support, i.e., polystyrene beads. The peptides are synthesized by linking an amino group of an N-α-deprotected amino acid to an α-carboxyl group of an N-α-protected amino acid that has been activated by reacting it with a reagent such as dicyclohexylcarbodiimide. The attachment of a free amino group to the activated carboxyl leads to peptide bond formation. The most commonly used N-α-protecting groups include Boc which is acid labile and Fmoc which is base labile. Details of appropriate chemistries, resins, protecting groups, protected amino acids and reagents are well known in the art and so are not discussed in detail herein (See, Atherton et al., 1989, Solid Phase Peptide Synthesis: A Practical Approach, IRL Press, and Bodanszky, 1993, Peptide Chemistry, A Practical Textbook, 2nd Ed., Springer-Verlag).

Purification of the resulting ARP or a fragment thereof is accomplished using conventional procedures, such as preparative HPLC using gel permeation, partition and/or ion exchange chromatography. The choice of appropriate matrices and buffers are well known in the art and so are not described in detail herein.

ARPs of Purified Apicomplexa

In specific embodiments, the present invention provides a purified Apicomplexan organism that containing an ARP for the treatment of cancer and infectious diseases, and for eliciting an immune response. In a preferred embodiment, the purified Apicomplexan organism is also an inactivated Apicomplexan organism or an Apicomplexan organism that can not cause the disease in an intended host. A purified or an inactivated Apicomplexan organism containing ARP can be directly administered, preferably orally, to a subject for treatment or prevention of cancer.

Some genus of Apicomplexa, such as *Eimeria*, is highly species-specific. For example, an *Eimeria* that infect avian species usually does not cause symptomatic infections in non-avian species. In one embodiment of the invention, an Apicomplexan organism containing ARP is administered to a subject that is not a natural host of the organism for the treatment and prevention of cancer.

In a preferred embodiment, *Eimeria* sporulated oocysts containing ARPs are administered to a subject that is not a natural host of the organism for the treatment or prevention of cancer.

In another embodiment of the invention, an Apicomplexan organism containing ARP is engineered to have a defective life cycle so that it cannot cause a symptomatic infection in a host, and the engineered Apicomplexan organism is administered to a subject for treatment or prevention of cancer. Any technique known in the art that is able to cause an Apicomplexan organism to have a defective life cycle can be used. Such techniques include but not limited to, genetic engineering, use of chemical toxins, or radiation. Whether an Apicomplexan organism is having a defective life cycle can be tested in animals by infection followed by biopsy to verify that the organism has entered cells. An appropriate waiting period would indicate if the organism is unable to complete its life cycle and create oocysts in the feces.

Apicomplexa have complex life cycles, and there is much variation among different apicomplexa groups. Both asexual and sexual reproduction are involved, although some apicomplexa skip one or the other stage. The basic life cycle may be said to start when an infective stage, or sporozoite, enters a host cell, and then divides repeatedly to form numerous merozoites. Some of the merozoites transform into sexually reproductive cells, or gamonts. Gamonts join together in pairs and form a gamontocyst. Within the gamontocyst, the gamonts divide to form numerous gametes. Pairs of gametes then fuse to form zygotes, which give rise by meiosis to new sporozoites, and the cycle begins again. Apicomplexans are transmitted to new hosts in various ways; some, like the malaria parasite, are transmitted by infected mosquitoes, while others may be transmitted in the feces of an infected host, or when a predator eats infected prey.

The class Coccidia tend to infect vertebrates through mucosal surfaces, such as the gut. The family Eimeriidae, within the order Eimeriida, within the Coccidia, is characterized by a life cycle that requires only one host and a brief passage through the environment in the oocyst stage. The genus *Eimeria* is characterized by sporozoite invasion, merogony, gamogony and oocyst formation confined to a region of the intestine that is specific to each *Eimeria* species. The oocysts sporulate in the environment, are ingested, and the oocyst walls are broken by bile salts and trypsin in the duodenum. The sporozoites penetrate the epithelial cell walls where they protect themselves with a specialized membrane. Within this safe haven, they produce as many as 120,000 merozoites as a schizont. Upon maturation, these burst out and invade other cells. This process is repeated two or three times and is followed by a gamont stage in which sexual reproduction occurs and oocysts are formed. These are excreted with the feces to complete the cycle.

In accordance with the present invention, an Apicomplexan organism at any developmental stage, e.g., a merozoite, a gamont, a gamontocyst, a gamete, a sporozoite, or an oocyst, can be used to treat or prevent cancer or an infectious disease, or to eliciting an immune response. In a preferred embodiment, a sporozoite, a merozoite or an oocyst of an Apicomplexan organism is used to treat or prevent cancer or an infectious disease, or to elicit an immune response. More preferably, a sporozoite, a merozoite or an oocyst of an *Eimeria* species is used to treat or prevent cancer or an infectious disease, or to eliciting an immune response.

In another embodiment of the invention, a dead Apicomplexan organism containing ARP is administered to a subject for treatment or prevention of cancer. An Apicomplexan organism can be killed by any method known in the art, including but not limited to, chemical toxins and radiations.

In yet another embodiment, a protein fraction, preferably, a membrane preparation or a storage granule preparation of an Apicomplexan organism containing ARP is administered to a subject for treatment or prevention of cancer.

Derivatives and Analogs of ARP

The invention further provides derivatives (including but not limited to fragments), and analogs of ARPs. The production and use of derivatives and analogs related to ARP are within the scope of the present invention.

In a specific embodiment, the derivative or analog is functionally active, i.e., capable of exhibiting one or more functional activities associated with a full-length, wild-type ARP. Preferably, the derivative or analog is an activator of dendritic cells as assayed by the DC assay (see section 5.6 and section 12.3). Derivatives or analogs of ARP can be tested for the desired activity by procedures known in the art, including but not limited to the assays described in Section 5.5 and Section 12, infra.

In particular, ARP derivatives can be made by altering ARP sequences by substitutions, insertions or deletions that provide for functionally equivalent molecules. Preferably, such alteration of an ARP sequence is done in a variable region (i.e., that is not highly conserved among different ARP molecules, for example, see FIG. 19), e.g. an alteration is done within the first fifteen amino acids of an ARP. Due to the degeneracy of nucleotide coding sequences, other DNA sequences which encode substantially the same amino acid sequence as an ARP gene may be used in the practice of the present invention. These include, but are not limited to, nucleotide sequences comprising all or portions of ARP genes which are altered by the substitution of different codons that encode a functionally equivalent amino acid residue within the sequence, thus producing a silent change. Likewise, the ARP derivatives of the invention include, but are not limited to, those containing, as a primary amino acid sequence, all or part of the amino acid sequence of an ARP including altered sequences in which functionally equivalent amino acid residues are substituted for residues within the sequence resulting in a silent change (i.e., conservative substitutions). For example, one or more amino acid residues within the sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. ARP derivatives of the invention also include, but are not limited to, those containing, as a primary amino acid sequence, all or part of the amino acid sequence of an ARP including altered sequences in which amino acid residues are substituted for residues with similar chemical properties (i.e., conservative substitutions). In specific embodiments, 1, 2, 3, 4, or 5 amino acids are substituted. In a specific embodiment, SEQ ID NO:1 amino acid residue 165 His can be changed to Tyr, and the new protein still has the same activity as SEQ ID NO: 1. In a specific embodiment, SEQ ID NO:1 amino acid residue 167 Ser can be changed to Ala, and the new protein still has the same activity as SEQ ID NO: 1. In anther specific embodiment, SEQ ID NO: 1 amino acid residue 165 His can be changed to Tyr, and amino acid residue 167 Ser can be changed to Ala, the new protein still has the same activity as SEQ ID NO:1.

Derivatives or analogs of ARP include, but are not limited to, those peptides which are substantially homologous to ARP or fragments thereof, or whose encoding nucleic acid is capable of hybridizing to an ARP nucleic acid sequence.

The ARP derivatives and analogs of the invention can be produced by various methods known in the art. The manipulations which result in their production can occur at the gene or protein level. For example, the cloned ARP gene sequence can be modified by any of numerous strategies known in the art (Maniatis, T., 1989, Molecular Cloning, A Laboratory Manual, 2d ed., Cold Spring Harbor Laboratory, Cold Spring Harbor, N.Y.). The sequence can be cleaved at appropriate sites with restriction endonuclease(s), followed by further enzymatic modification if desired, isolated, and ligated in vitro. In the production of the gene encoding a derivative or analog of ARP, care should be taken to ensure that the modified gene remains within the same translational reading frame as ARP, uninterrupted by translational stop signals, in the gene region where the desired ARP activity is encoded.

Additionally, the ARP-encoding nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Any technique for mutagenesis known in the art can be used, including but not limited to, in vitro site-directed mutagenesis (Hutchinson, C. et al., 1978, J. Biol. Chem. 253: 6551), use of TAB™ linkers (Pharmacia), etc.

Manipulations of the ARP sequence may also be made at the protein level. Included within the scope of the invention are ARP fragments or other derivatives or analogs which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited to, reagents useful for protection or modification of free NH2-groups, free COOH-groups, OH-groups, side groups of Trp-, Tyr-, Phe-, His-, Arg-, or Lys-; specific chemical cleavage by cyanogen bromide, hydroxylamine, BNPS-Skatole, acid, or alkali hydrolysis; enzymatic cleavage by trypsin, chymotrypsin, papain, V8 protease, $NaBH_4$; acetylation, formylation, oxidation, reduction; metabolic synthesis in the presence of tunicamycin; etc.

In addition, analogs and derivatives of ARP can be chemically synthesized. For example, a peptide corresponding to a portion of an ARP which comprises the desired domain, or which mediates the desired aggregation activity in vitro, or binding to a receptor, can be synthesized by use of a peptide synthesizer. Furthermore, if desired, nonclassical amino acids or chemical amino acid analogs can be introduced as a substitution or addition into the ARP sequence. Non-classical amino acids include, but are not limited to, the D-isomers of the common amino acids, α-amino isobutyric acid, 4-aminobutyric acid, hydroxyproline, sarcosine, citrulline, cysteic acid, t-butylglycine, t-butylalanine, phenylglycine, cyclohexylalanine, β-alanine, designer amino acids such as β-methyl amino acids, Cα-methyl amino acids, and Nα-methyl amino acids.

In a specific embodiment, the ARP derivative is a chimeric, or fusion, protein comprising an ARP or fragment thereof fused via a peptide bond at its amino- and/or carboxy-terminus to a non-ARP amino acid sequence. In a preferred embodiment, the non-ARP amino acid sequence is fused at the amino-terminus of an ARP or a fragment thereof. In another preferred embodiment, the non-ARP amino acid sequence is fused at a variable region of an ARP or a fragment thereof, e.g., the first 15 amino acids of an ARP gene. In one embodiment, such a chimeric protein is produced by recombinant expression of a nucleic acid encoding the protein (comprising an ARP-coding sequence joined in-frame to a non-ARP coding sequence). Such a chimeric product can be custom made by a variety of companies (e.g., Retrogen, Operon, etc.) or made by ligating the appropriate nucleic acid sequences encoding the desired amino acid sequences to each other by methods known in the art, in the proper coding frame, and expressing the chimeric product by methods commonly known in the art. Alternatively, such a chimeric product may be made by protein synthetic techniques, e.g., by use of a peptide synthesizer. In a specific embodiment, a chimeric nucleic acid encoding a mature ARP with a heterologous signal sequence is expressed such that the chimeric protein is expressed and processed by the cell to the mature ARP protein. The primary sequence of ARP and non-ARP gene may also be used to predict tertiary structure of the molecules using computer simulation (Hopp and Woods, 1981, Proc. Natl. Acad. Sci. U.S.A. 78: 3824-3828); the chimeric recombinant genes could be designed in light of correlations between tertiary structure and biological function. Likewise, chimeric genes comprising an essential portion of ARP molecule fused to a heterologous (non-ARP) protein-encoding sequence may be constructed. In a specific embodiment, such chimeric construction can be used to enhance one or more desired properties of an ARP, including but not limited to, ARP stability, solubility, or resistance to proteases. In another embodiment, chimeric construction can be used to target ARP to a specific site, e.g., a chimeric construction comprising an ARP fused to an antibody to a specific type of cancer allows ARP to be delivered to the cancer site. In yet another embodiment, chimeric construction can be used to identify or purify an ARP of the invention, such as a His-tag, a FLAG tag, a green fluorescence protein (GFP), β-galactosidase, a maltose binding protein (MalE), a cellulose binding protein (CenA) or a mannose protein, etc.

In another specific embodiment, the ARP derivative is a fragment of ARP of one specie of Apicomplexa comprising a region of homology with an ARP of another specie of Apicomplexa. As used herein, a region of a first protein shall be considered "homologous" to a second protein when the amino acid sequence of the region is at least 25%, at least 30%, at least 45%, at least 55%, at least 65%, at least 75% either identical or involving conservative changes, when compared to any sequence in the second protein of an equal number of amino acids as the number contained in the region.

In a specific embodiment, the invention provides ARP derivatives and analogs, in particular ARP fragments and derivatives of such fragments that comprise one or more domains of the ARP.

In a specific embodiment, relating to an ARP of a species other than *Eimeria*, preferably other species in the Apicomplexa phylum, the fragments comprising specific portions of ARP are those comprising portions in the respective ARP most homologous to specific fragments of an *Eimeria* ARP.

Antibodies to ARPs, Derivatives and Analogs

In various embodiments, monoclonal or polyclonal antibodies specific to ARP, or a domain of ARP, can be used in immunoassays to measure the amount of ARP or used in immunoaffinity purification of an ARP. A Hopp & Woods hydrophilic analysis (see Hopp & Woods, Proc. Natl. Acad. Sci. U.S.A. 78: 3824-3828 (1981) can be used to identify hydrophilic regions of a protein, and to identify potential epitopes of an ARP. In a specific embodiment, an antibody that binds to SEQ ID NO:26 (bovine ARP fragment 1 (SEQ ID NO:3) fused to fragment 2 (SEQ ID NO:4) fused to fragment 3 (SEQ ID NO:5) fused to fragment 4 (SEQ ID NO:6) and fused to fragment 5 (SEQ ID NO:7)) is used in immunoassays to measure the amount of an ARP or in immunoaffinity purification of an ARP.

The antibodies that immunospecifically bind to an ARP or an antigenic fragment thereof can be produced by any method known in the art for the synthesis of antibodies, in particular, by chemical synthesis or preferably, by recombinant expression techniques.

Polyclonal antibodies immunospecific for ARP or an antigenic fragment thereof can be produced by various procedures well-known in the art. For example, an ARP can be administered to various host animals including, but not limited to, rabbits, mice, and rats, to induce the production of sera containing polyclonal antibodies specific for the ARP. Various adjuvants may be used to increase the immunological response, depending on the host species, including but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling et al., in: Monoclonal Antibodies and T Cell Hybridomas 563 681 (Elsevier, N.Y., 1981). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art. Briefly, mice can be immunized with a non-murine antigen and once an immune response is detected, e.g., antibodies specific for the antigen are detected in the mouse serum, the mouse spleen is harvested and splenocytes isolated. The splenocytes are then fused by well known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

The present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with a non-murine antigen with myeloma cells and then screening the hybridomas resulting from the fusion for hybridoma clones that secrete an antibody able to bind to the antigen.

Antibody fragments which recognize specific particular epitopes may be generated by any technique known to those of skill in the art. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain. Further, the antibodies of the present invention can also be generated using various phage display methods known in the art.

In phage display methods, functional antibody domains are displayed on the surface of phage particles which carry the polynucleotide sequences encoding them. In particular, DNA sequences encoding $V_H$ and $V_L$ domains are amplified from animal cDNA libraries (e.g., human or murine cDNA libraries of affected tissues). The DNA encoding the $V_H$ and $V_L$ domains are recombined together with an scFv linker by PCR and cloned into a phagemid vector. The vector is electroporated in E. coli and the E. coli is infected with helper phage. Phage used in these methods are typically filamentous phage including fd and M13 and the $V_H$ and $V_L$ domains are usually recombinantly fused to either the phage gene III or gene VIII. Phage expressing an antigen binding domain that binds to a particular antigen can be selected or identified with antigen, e.g., using labeled antigen or antigen bound or captured to a solid surface or bead. Examples of phage display methods that can be used to make the antibodies of the present invention include those disclosed in Brinkman et al., 1995, J. Immunol. Methods 182: 41-50; Ames et al., 1995, J. Immunol. Methods 184: 177-186; Kettleborough et al., 1994, Eur. J. Immunol. 24: 952-958; Persic et al., 1997, Gene 187: 9-18; Burton et al., 1994, Advances in Immunology 57: 191-280; International application No. PCT/GB91/O1 134; International publication Nos. WO 90/02809, WO 91/10737, WO 92/01047, WO 92/18619, WO 93/11236, WO 95/15982, WO 95/20401, and WO97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743 and 5,969,108.

As described in the above references, after phage selection, the antibody coding regions from the phage can be isolated and used to generate whole antibodies or any other desired antigen binding fragment, and expressed in any desired host, including mammalian cells, insect cells, plant cells, yeast, and bacteria, e.g., as described below. Techniques to recombinantly produce Fab, Fab' and F(ab')2 fragments can also be employed using methods known in the art such as those disclosed in PCT publication No. WO 92/22324; Mullinax et al., 1992, BioTechniques 12(6): 864-869; Sawai et al., 1995, AJRI 34: 26-34; and Better et al., 1988, Science 240: 1041-1043.

To generate whole antibodies, PCR primers including $V_H$ or $V_L$ nucleotide sequences, a restriction site, and a flanking sequence to protect the restriction site can be used to amplify the $V_H$ or $V_L$ sequences in scFv clones. Utilizing cloning techniques known to those of skill in the art, the PCR amplified $V_H$ domains can be cloned into vectors expressing a $V_H$ constant region, e.g., the human gamma 4 constant region, and the PCR amplified $V_L$ domains can be cloned into vectors expressing a $V_L$ constant region, e.g., human kappa or lamba constant regions. Preferably, the vectors for expressing the $V_H$ or $V_L$ domains comprise an EF-1α promoter, a secretion signal, a cloning site for the variable domain, constant domains, and a selection marker such as neomycin. The $V_H$ and $V_L$ domains may also cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

For some uses, including in vivo use of antibodies in humans and in vitro detection assays, it may be preferable to use humanized antibodies or chimeric antibodies. Human antibodies can be made by a variety of methods known in the art including phage display methods described above using antibody libraries derived from human immunoglobulin sequences. See also U.S. Pat. Nos. 4,444,887 and 4,716,111; and International publication Nos. WO 98/46645, WO 98/50433, WO 98/24893, WO98/16654, WO 96/34096, WO 96/33735, and WO 91/10741.

A chimeric antibody is a molecule in which different portions of the antibody are derived from different immunoglobulin molecules. Methods for producing chimeric antibodies are known in the art. See e.g., Morrison, 1985, Science 229: 1202; Oi et al., 1986, BioTechniques 4: 214; Gillies et al., 1989, J. Immunol. Methods 125: 191-202; and U.S. Pat. Nos. 5,807,715, 4,816,567, 4,816,397, and 6,311,415.

A humanized antibody is an antibody or its variant or fragment thereof which is capable of binding to a predetermined antigen and which comprises a framework region having substantially the amino acid sequence of a human immunoglobulin and a CDR having substantially the amino acid sequence of a non-human immuoglobulin. A humanized antibody comprises substantially all of at least one, and typically two, variable domains (Fab, Fab', $F(ab')_2$, Fabc, Fv) in which all or substantially all of the CDR regions correspond to those of a non-human immunoglobulin (i.e., donor antibody) and all or substantially all of the framework regions are those of a human immunoglobulin consensus sequence. Preferably, a humanized antibody also comprises at least a portion of an immunoglobulin constant region (Fc), typically that of a human immunoglobulin. Ordinarily, the antibody will contain both the light chain as well as at least the variable domain of a heavy chain. The antibody also may include the CH1, hinge, CH2, CH3, and CH4 regions of the heavy chain. The humanized antibody can be selected from any class of immunoglobulins, including IgM, IgG, IgD, IgA and IgE, and any isotype, including IgG1, IgG2, IgG3 and IgG4. Usually the constant domain is a complement fixing constant domain where it is desired that the humanized antibody exhibit cytotoxic activity, and the class is typically $IgG_1$. Where such cytotoxic activity is not desirable, the constant domain may be of the $IgG_2$ class. The humanized antibody may comprise sequences from more than one class or isotype, and selecting particular constant domains to optimize desired effector functions is within the ordinary skill in the art. The framework and CDR regions of a humanized antibody need not correspond precisely to the parental sequences, e.g., the donor CDR or the consensus framework may be mutagenized by substitution, insertion or deletion of at least one residue so that the CDR or framework residue at that site does not correspond to either the consensus or the import antibody. Such mutations, however, will not be extensive. Usually, at least 75% of the humanized antibody residues will correspond to those of the parental framework region (FR) and CDR sequences, more often 90%, and most preferably greater than 95%. Humanized antibody can be produced using variety of techniques known in the art, including but not limited to, CDR-grafting (European Patent No. EP 239,400; International Publication No. WO 91/09967; and U.S. Pat. Nos. 5,225,539, 5,530,101, and 5,585,089), veneering or resurfacing (European Patent Nos. EP 592,106 and EP 519,596; Padlan, 1991, Molecular Immunology 28(4/5): 489-498; Studnicka et al., 1994, Protein Engineering 7(6): 805-814; and Roguska et al., 1994, PNAS 91: 969-973), chain shuffling (U.S. Pat. No. 5,565, 332), and techniques disclosed in, e.g., U.S. Pat. No. 6,407, 213, U.S. Pat. No. 5,766,886, WO 9317105, Tan et al., J. Immunol. 169: 1119-25 (2002), Caldas et al., Protein Eng. 13(5): 353-60 (2000), Morea et al., Methods 20(3): 267-79 (2000), Baca et al., J. Biol. Chem. 272(16): 10678-84 (1997), Roguska et al, Protein Eng. 9(10): 895-904 (1996), Couto et al., Cancer Res. 55 (23 Supp): 5973s-5977s (1995), Couto et al., Cancer Res. 55(8): 1717-22 (1995), Sandhu J S, Gene 150(2): 409-10 (1994), and Pedersen et al., J. Mol. Biol. 235(3): 959-73 (1994). Often, framework residues in the framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; and Riechmann et al., 1988, Nature 332: 323.)

Further, the antibodies that immunospecifically bind to ARP or an antigenic fragment thereof can, in turn, be utilized to generate anti-idiotype antibodies that "mimic" ARP or an antigenic peptide thereof using techniques well-known to those skilled in the art. (See, e.g., Greenspan & Bona, 1989, FASEB J. 7(5): 437-444; and Nissinoff, 1991, J. immunol. 147(8): 2429-2438).

Polynucleotide Sequences Encoding an Antibody

The invention provides polynucleotides comprising a nucleotide sequence encoding an antibody or fragment thereof that immunospecifically binds to ARP or an antigenic fragment thereof. The invention also encompasses polynucleotides that hybridize under high stringency, intermediate, or lower stringency hybridization conditions to polynucleotides that encode an antibody of the invention.

The polynucleotides may be obtained, and the nucleotide sequence of the polynucleotides determined, by any method known in the art. The nucleotide sequence of antibodies immunospecific for a desired antigen can be obtained, e.g., from the literature or a database such as GenBank. Once the amino acid sequences of an ARP or an antigenic fragment thereof is known, nucleotide sequences encoding this antibody or a fragment thereof (e.g., a CDR) can be determined using methods well known in the art, i.e., nucleotide codons known to encode particular amino acids are assembled in such a way to generate a nucleic acid that encodes the antibody. Such a polynucleotide encoding the antibody may be assembled from chemically synthesized oligonucleotides (e.g., as described in Kutmeier et al., 1994, BioTechniques 17: 242), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably poly A+ RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties), to generate antibodies having a different amino acid sequence, for example to create amino acid substitutions, deletions, and/or insertions.

In a specific embodiment, one or more of the CDRs is inserted within framework regions using routine recombinant DNA techniques. The framework regions may be naturally occurring or consensus framework regions, and preferably human framework regions (see, e.g., Chothia et al., 1998, J. Mol. Biol. 278: 457-479 for a listing of human framework regions). Preferably, the polynucleotide generated by the combination of the framework regions and CDRs encodes an antibody that specifically binds to a particular antigen. Preferably, as discussed supra, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

Recombinant Expression of an Antibody

Recombinant expression of an antibody of the invention, derivative, analog or fragment thereof, (e.g., a heavy or light chain of an antibody of the invention or a portion thereof or a single chain antibody of the invention), requires construction of an expression vector containing a polynucleotide that encodes the antibody. Once a polynucleotide encoding an antibody molecule or a heavy or light chain of an antibody, or portion thereof (preferably, but not necessarily, containing the heavy or light chain variable domain), of the invention has been obtained, the vector for the production of the antibody molecule may be produced by recombinant DNA technology using techniques well-known in the art. See, e.g., U.S. Pat. No. 6,331,415. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, a heavy or light chain of an antibody, a heavy or light chain variable domain of an antibody or a portion thereof, or a heavy or light chain CDR, operably linked to a promoter. Such vectors may include the nucleotide sequence encoding the constant region of the antibody molecule (see, e.g., International Publication No. WO 86/05807 and WO 89/01036; and U.S. Pat. No. 5,122,464) and the variable domain of the antibody may be cloned into such a vector for expression of the entire heavy, the entire light chain, or both the entire heavy and light chains.

The expression vector is transferred to a host cell by conventional techniques and the transfected cells are then cultured by conventional techniques to produce an antibody of the invention. Thus, the invention includes host cells containing a polynucleotide encoding an antibody of the invention or fragments thereof, or a heavy or light chain thereof, or portion thereof, or a single chain antibody of the invention, operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibody molecules of the invention (see, e.g., U.S. Pat. No. 5,807,715, and those described in Section 5.1.2, supra). The expression levels of an antibody molecule can be increased by vector amplification (for a review, see Bebbington and Hentschel, The use of vectors based on gene amplification for the expression of cloned genes in mammalian cells in DNA cloning, Vol. 3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., 1983, Mol. Cell. Biol. 3: 257).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, 1986, Nature 322: 52; and Kohler, 1980, Proc. Natl. Acad. Sci. USA 77: 2 197). The coding sequences for the heavy and light chains may comprise cDNA or genomic DNA.

Once an antibody molecule of the invention has been produced by recombinant expression, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies of the present invention or fragments thereof may be fused to heterologous polypeptide sequences described herein or otherwise known in the art to facilitate purification.

Structure Prediction and Functional Analysis of ARPs

The invention provides ARPs which can be from various species of Apicomplexa. Thus, it would be valuable if the structure of an ARP or a fragment thereof may be predicted based on the amino acid sequence. Structure prediction, analysis of crystallographic data, sequence alignment, as well as homology modeling, can be accomplished using computer software programs available in the art, such as BLAST, CHARMm release 21.2 for the Convex, and QUANTA v. 3.3, (Molecular Simulations, Inc., York, United Kingdom). For example, some ARPs comprise a conserved PROF (smart 00392 or cd 00148) domain in Conserved Domain Database (CDD v. 1.60) as determined by a RPS-BLAST (Reverse Position-Specific BLAST) algorithm set to default parameters.

Once an ARP is identified, it may be isolated and purified by standard methods including chromatography (e.g., ion exchange, affinity, and sizing column chromatography), centrifugation, differential solubility, or by any other standard technique for the purification of proteins. The in vitro activities and in vivo biological functions of the foregoing may be evaluated using any suitable assay (including immunoassays as described infra).

Alternatively, once an ARP produced by a recombinant host cell is identified, the amino acid sequence of the ARP(s) can be determined by standard techniques for protein sequencing, e.g., with an automated amino acid sequencer.

The ARP sequence can be characterized by a hydrophilicity analysis (Hopp, T. and Woods, K., 1981, Proc. Natl. Acad. Sci. U.S.A. 78: 3824). A hydrophilicity profile can be used to identify the hydrophobic and hydrophilic regions of the ARP and the corresponding regions of the gene sequence which encode such regions.

Secondary structural analysis (Chou, P. and Fasman, G., 1974, Biochemistry 13: 222) can also be done, to identify regions of the ARP that assume specific secondary structures.

Other methods of structural analysis can also be employed. These include, but are not limited to, X-ray crystallography (Engstom, A., 1974, Biochem. Exp. Biol. 11: 7-13) and computer modeling (Fletterick, R. and Zoller, M. (eds.), 1986, Computer Graphics and Molecular Modeling, in Current Communications in Molecular Biology, Cold Spring Harbor Laboratory, Cold Spring Harbor, N.Y.).

The functional activity of an ARP or a fragment thereof can be assayed by various methods known in the art.

For example, where one is assaying for the ability of an ARP from one genus to bind or compete with an ARP from another genus for binding to an antibody, various immunoassays known in the art can be used, including but not limited to, competitive and non-competitive assay systems using techniques such as radioimmunoassays, ELISA (enzyme linked immunosorbent assay), "sandwich" immunoassays, immunoradiometric assays, gel diffusion precipiting reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. Antibody binding can be detected by detecting a label on the primary antibody. Alternatively, the primary antibody is detected by detecting binding of a secondary antibody or reagent to the primary antibody, particularly where the secondary antibody is labeled. Many means are known in the art for detecting binding in an immunoassay and are within the scope of the present invention.

The half life of a protein is a measurement of protein stability and indicates the time necessary for a one half reduction in activity of the protein. The half-life of an ARP can be determined by any method measuring activity of ARP in samples from a subject over a period of time, such as but not limited to, DC assay and NK assay (see Section 5.6 and Section 12). The normalization to concentration of ARP in the sample can be done by immunoassays using anti-ARP antibodies (or antibody to a fused part of a gene wherein an ARP is fused to another moiety) to measure the levels of the ARP molecules in samples taken over a period of time after administration of the ARP, or detection of radiolabelled ARP molecules in samples taken from a subject after administration of the radiolabeled ARP molecules. In specific embodiments, techniques known in the art can be used to prolong the half life of an ARP in vivo. For example, albumin or inert polymer molecules such as high molecular weight polyethyleneglycol (PEG) can be used. See, e.g., International Publication Nos. WO 93/15199, WO 93/15200, and WO 01/77137; and U.S. Pat. No. 6,528,485.

Other methods will be known to the skilled artisan and are within the scope of the invention.

Characterization and Demonstration of ARP Activity

The immunostimulatory activity and/or anti-cancer activity of the ARPs used in accordance with the present invention can be determined by any method known in the art. In one embodiment, the immunostimulating activity and/or anti-cancer activity of an ARP is determined by using various experimental animal models, including but not limited to, cancer animal models such as scid mouse model or nude mice with human tumor grafts known in the art and described in Yamanaka, 2001, Microbiol Immunol 2001; 45(7): 507-14, which is incorporated herein by reference.

Various in vitro and in vivo assays that test the immunostimulatory activities and/or anti-cancer activities of an ARP are used in purification processes of an ARP. The protocols and compositions of the invention are also preferably tested in vitro, and then in vivo, for the desired therapeutic or prophylactic activity, prior to use in humans.

In one embodiment, a NK cell assay is used to assess ARP-induced cytotoxic activity of NK-like cells (see section 12.2). Briefly, by way of example but not limitation, a NK cell assay can be carried out as follows: large granular lymphocytes (LGLs) are co-cultured with tumor cells at various ratios (effector to target ratio) for four days at 37° C., 5% $CO_2$. The culture medium also contains a low concentration of IL2 plus an ARP to be tested. The culture is terminated at the end of day 4 and vitally stained using a MTT cell viability quantification assay (see Mossman, T. J. Immunol. Methods 65: 55 (1983); and Sigma Chemical MTT (M5655) product application note). Culture media is aspirated and the remaining cells are washed and replaced with DMEM/F12 plus FCS, containing MTT. The cells are further incubated for 4-5 hours at 37° C. Absorbance is measured with the aid of a plate reader. Decreased absorbance indicated a decrease in the number of viable cells per well (i.e., cytotoxicity). Absorbance is measured again after the MTT is solubilized by replacement of the medium with 2-propanol containing HCl, which gives a uniform color throughout the well. NK-inducing activity is calculated relative to negative (PBS/BSA) and positive (internal standard) controls.

In another embodiment, the ARP activity is measured by IFNγ assay (see section 12.4). By way of example but not limitation, the production and release of IFNγ by LGLs into the culture media is determined as follows: LGLs, enriched with NK cells, are isolated and seeded into 96 well plates at densities of 2.5 or $5.0 \times 10^5$ cells/well, in 200 uL of DMEM/F12 supplemented with 10% fetal calf serium, gentamycin (50 ug/mL), and IL2 (125 U/mL). The ARP to be tested is added and the cells are cultured overnight, following which the condition media (CM) is removed and then centrifuged to remove any aspirated cells. Aliquots of the CM are then measured for IFNγ using an commercially available ELISA kit.

In a preferred embodiment, dendritic cell (DC) assay is used to follow interleukin-12 (IL-12) release from freshly isolated dendritic cells as an index of DC activation (see section 12.3). This activity is highly correlated with both NK-CMC in vitro and anti-tumor activity in vivo of an ARP.

Briefly, by way of example but not limitation, a DC assay can be carried out as follows: freshly isolated dendritic cells ($CD11c^+$ splenocytes, e.g., isolated from the spleens of BALB/c mice within ten hours of assaying the activity) are suspended at a density of $0.5 \times 10^6$ cells per mL in cytokine supplemented culture media (GM-CSF, 1.0 ng/ml; IL-4, 1.0 ng/ml; IFNg, 3.0 ng/ml; anti mouse CD40, 0.5 mg/ml). The dendritic cells are then added (100 µL/well) to 96-well tissue culture plates containing ARP diluted in 100 µL media per well and cultured overnight at 37° C. in 5% $CO_2$, 95% air. Mouse IL-12 release from the dendritic cells ($CD11c^+$ splenocytes) is then measured using ELISA.

Compounds for use in therapy can be tested in suitable animal model systems prior to testing in humans, including but not limited to in rats, mice, chicken, cows, monkeys, rabbits, etc. The principle animal models for cancer known in the art and widely used include, but not limited to, mice, as described in Hann et al., 2001, Curr Opin Cell Biol 2001 December; 13(6): 778-84.

In a preferred embodiment, The S-180 cell line (ATCC CCL 8, batch F4805) is chosen as the tumor model because the same line is capable of growing both in animals and in culture (in both serum-containing and serum-free conditions). Tumors are established in mice (BALB/c) by injection of cell suspensions obtained from tissue culture. Approximately $1 \times 10^6$ to $3 \times 10^6$ cells are injected intra-peritoneally per mouse. The tumor developed as multiple solid nodules at multiple sites within the peritoneal cavity and cause death in most of the animals within 10 to 15 days. In addition to monitoring animal survival, their condition is qualitatively assessed as tumor growth progressed and used to generate a tumor index as described in the following paragraph.

To establish an estimate of drug activity in tumor model experiments, an index can be developed that combines observational examination of the animals as well as their survival status. For example, mice are palpated once or twice weekly for the presence, establishment and terminal progression of the intraperitoneal S180 tumor. Tumor development and progression is assessed in these mice according to the following scale: "0"—no tumor palpated; "1"—initial tumor appears to be present; small in size (~1 mm); no distended abdomen; "2"—tumor appears to be established; some distension of the abdomen; no apparent cachexia; "3"—tumor is well established, marked abdominal distension, animal exhibits cachexia; and, "4"—animal is dead. The index value for a treatment group is the average of the individual mouse indices in the group.

Further, any assays known to those skilled in the art can be used to evaluate the prophylactic and/or therapeutic utility of the combinatorial therapies disclosed herein for treatment or prevention of cancer and/or infectious diseases.

Uses of the Compositions of the Invention

The compositions of the invention may be administered to a subject in need thereof to stimulate an immune response, to prevent or treat a cancer or an infectious disease (including one or more symptoms thereof), or to use as an alternative to interleukin 12 (IL-12) treatment. The compositions of the invention may be administered alone or in combination with one or more other therapies useful for immune stimulation to a subject in need thereof to elicit an immune response. The compositions of the invention may administered alone or in combination with one or more other therapies to a subject in need thereof to elevate systemic levels of IL-12 in the subject. The compositions of the invention may also be administered alone or in combination with one or more other therapies useful for the prevention or treatment of cancer (including, but not limited to, the prophylactic or therapeutic agents listed in Section 5.8 hereinbelow) or infectious diseases (including, but not limited to, the prophylactic or therapeutic agents listed in Section 5.9 hereinbelow) to a subject in need thereof to prevent or treat a cancer or infectious diseases.

In one embodiment, the present invention provides a method of treating or preventing cancer or an infectious disease (including one or more symptoms thereof), wherein said infectious disease is not caused by infection with a human immunodeficiency virus (HIV), comprising administering to a subject in whom such treatment or prevention is desired a therapeutically or prophylactically effective amount of an ARP. In another embodiment, the present invention provides a method of treating or preventing cancer or an infectious disease (including one or more symptoms thereof), wherein said infectious disease is not caused by infection with a human immunodeficiency virus (HIV), comprising administering to a subject in whom such treatment or prevention is desired a therapeutically or prophylactically effective amount of a nucleic acid comprising a nucleotide sequence encoding one or more ARPs. In another embodiment, the present invention provides a method of treating or preventing cancer or an infectious disease (including one or more symptoms thereof), wherein said infectious disease is not caused by infection with a human immunodeficiency virus (HIV), comprising administering to a subject in whom such treatment or prevention is desired a therapeutically or prophylactically effective amount of a cell transformed with a nucleic acid comprising a nucleotide sequence encoding an ARP, wherein said nucleotide sequence is operably linked to a promoter. In yet another embodiment, the present invention provides a method of treating or preventing cancer or an infectious disease (including one or more symptoms thereof), wherein said infectious disease is not caused by infection with a human immunodeficiency virus (HIV), comprising administering to a subject in whom such treatment or prevention is desired a therapeutically or prophylactically effective amount of an ARP and a therapeutically or prophylactically effective amount of one or more agents other than ARP. In a specific embodiment, the cancer to be treated is an ovarian cancer. In specific embodiments, the infectious disease is caused by infection with an Apicomplexan organism. In other specific embodiments, the infectious disease is not caused by infection with an Apicomplexan organism.

In another embodiment, the present invention provides a method of stimulating an immune response comprising administering to a subject, with the proviso that said subject is not infected with a human immunodeficiency virus (HIV), an effective amount of an ARP. In another embodiment, the present invention provides a method of stimulating an immune response comprising administering to a subject, with the proviso that said subject is not infected with a human immunodeficiency virus (HIV), an effective amount of a nucleic acid comprising a nucleotide sequence encoding one or more ARPs. In another embodiment, the present invention provides a method of stimulating an immune response comprising administering to a subject, with the proviso that said subject is not infected with a human immunodeficiency virus (HIV), an effective amount of a cell transformed with a nucleic acid comprising a nucleotide sequence encoding an ARP, wherein said nucleotide sequence is operably linked to a promoter. In yet another embodiment, the present invention provides a method of stimulating an immune response comprising administering to a subject, with the proviso that said subject is not infected with a human immunodeficiency virus (HIV), an effective amount of an ARP and an effective amount of one or more immune stimulatory agents other than ARP. In specific embodiments, the subject is an avian species. In other specific embodiments, the subject is not an avian species.

In yet another embodiment, the present invention provides a method of elevating systemic level of interleukin-12 (IL-12) in a subject, wherein said subject is not infected with a human immunodeficiency virus (HIV), comprising administering to the subject in whom such elevation of interleukin-12 level is desired an effective amount of an ARP. In another embodiment, the present invention provides a method of elevating systemic level of interleukin-12 (IL-12) in a subject, wherein said subject is not infected with a human immunodeficiency virus (HIV), comprising administering to the subject in whom such elevation of interleukin-12 level is desired an effective amount of a nucleic acid comprising a nucleotide sequence encoding one or more ARPs. In another embodiment, the present invention provides a method of elevating systemic level of interleukin-12 (IL-12) in a subject, wherein said subject is not infected with a human immunodeficiency virus (HIV), comprising administering to the subject in whom such elevation of interleukin-12 level is desired an effective amount of a cell transformed with a nucleic acid comprising a nucleotide sequence encoding an ARP, wherein said nucleotide sequence is operably linked to a promoter. In yet another embodiment, the present invention provides a method of elevating systemic level of interleukin-12 (IL-12) in a subject, wherein said subject is not infected with a human immunodeficiency virus (HIV), comprising administering to the subject in whom such elevation of interleukin-12 level is desired an effective amount of an ARP and an effective amount of one or more immune stimulatory agents other than ARP.

Several adjuvants are used experimentally to enhance the immune response to administered antigens. Only aluminum hydroxide (alum), however, is approved by the FDA as an adjuvant for human use. This inert inorganic molecule has been shown to be safe, but is only a moderately good adjuvant. Other adjuvants (e.g. Bacille Calmette-Guerin (BCG), Freund's adjuvants, keyhole limpet hemocyanin (KLH), dinitrophenol, QS-21, CAP have been used in animal studies or are currently under investigation for humans. Unfortunately, they are either non-specific (CAP, QS-21, dinitrophenol) or toxic (BCG, KLH, Freund's adjuvant).

In a further embodiment of the invention, the very potent dendritic cell activation properties of ARP make it an ideal candidate to provide a superior adjuvant for vaccine production. Inorganic adjuvants are considered non-specific activators of the immune system. In contrast, ARP appears to be a specific activator of innate immunity. Thus, it activates a cascade of genetically preprogrammed events that upregulate the antigen presenting activity of dendritic cells while simultaneously generating the release of the cytokines associated with the activation of immediate cellular responses (e.g. NK cells) and, more importantly, the activation of adaptive immunity (both cellular and humoral). This latter function would facilitate the generation of memory T-cells (cellular response) and circulating antibodies (humoral response).

The subject as used herein refers to an animal, preferably a mammal. In some embodiments, the subject is a domestic animal, including but not limited to, chicken, pig, cow, horse and goat. In some embodiments, the subject is a pet, including but not limited to, cat, dog, and bird. In a preferred embodiment, the subject is a human.

Target Infectious Diseases

Infectious diseases that can be treated or prevented by the methods of the present invention are caused by infectious agents including, but not limited to, viruses, bacteria, fungi, protozoa and parasites.

Viral diseases that can be treated or prevented by the methods of the present invention include, but are not limited to, those caused by hepatitis type A, hepatitis type B, hepatitis type C, influenza, varicella, adenovirus, herpes simplex type I (HSV-I), herpes simplex type II (HSV-II), rinderpest, rhinovirus, echovirus, rotavirus, respiratory syncytial virus, papilloma virus, papova virus, cytomegalovirus, echinovirus, arbovirus, huntavirus, coxsackie virus, mumps virus, measles virus, rubella virus, and polio virus. In accordance with the present invention, the disease that is treated or prevented by the methods of the present invention is not caused by a human immunodeficiency virus (human immunodeficiency virus type I (HIV-I), or human immunodeficiency virus type II (HIV-II); e.g., the disease is not AIDS).

Bacterial diseases that can be treated or prevented by the methods of the present invention are caused by bacteria including, but not limited to, mycobacteria, *rickettsia*, mycoplasma, *neisseria* and *legionella*.

Fungal diseases that can be treated or prevented by the methods of the present invention include, but not limited to, aspergilliosis, crytococcosis, sporotrichosis, coccidioidomycosis, paracoccidioidomycosis, histoplasmosis, blastomycosis, zygomycosis, and candidiasis.

Protozoal diseases that can be treated or prevented by the methods of the present invention are caused by protozoa including, but not limited to, *leishmania* kokzidioa, and *trypanosoma*. In specific embodiments, protozoal diseases that can be treated or prevented by the methods of the present invention are not caused by Apicomplexa protozoa.

Parasitic diseases that can be treated or prevented by the methods of the present invention are caused by parasites including, but not limited to, chlamydia and amebiasis.

Target Cancer

Therapeutic Uses

In some embodiments, the present invention provides a method of treating a cancer (including ameliorating a symptom thereof) comprising administering to a subject in whom such treatment is desired a therapeutically effective amount of a composition comprising an ARP. A composition of the invention may, for example, be used as a first, second, third or fourth line cancer treatment. In some embodiments, the invention provides methods for treating a cancer (including ameliorating a symptom thereof) in a subject refractory to one or more conventional therapies for such a cancer, said methods comprising administering to said subject a therapeutically effective amount of a composition comprising an ARP. A cancer may be determined to be refractory to a therapy when at least some significant portion of the cancer cells are not killed or their cell division are not arrested in response to the therapy. Such a determination can be made either in vivo or in vitro by any method known in the art for assaying the effectiveness of treatment on cancer cells, using the art-accepted meanings of "refractory" in such a context. In a specific embodiment, a cancer is refractory where the number of cancer cells has not been significantly reduced, or has increased.

The invention provides methods for treating a cancer (including ameliorating one or more symptoms thereof) in a subject refractory to existing single agent therapies for such a cancer, said methods comprising administering to said subject a therapeutically effective amount of a composition comprising an ARP and a therapeutically effective amount of one or more therapeutic agents other than ARP. The invention also provides methods for treating cancer by administering a composition comprising an ARP in combination with any other anti-cancer treatment (e.g., radiation therapy, chemotherapy or surgery) to a patient who has proven refractory to other treatments. The invention also provides methods for the treatment of a patient having cancer and immunosuppressed by reason of having previously undergone one or more other cancer therapies. The invention also provides alternative methods for the treatment of cancer where chemotherapy, radiation therapy, hormonal therapy, and/or biological therapy/immunotherapy has proven or may prove too toxic, i.e., results in unacceptable or unbearable side effects, for the subject being treated.

In specific embodiments, a composition comprising an ARP of the invention is administered to a subject for the treatment of cancer, wherein the subject does not have an infection with an Apicomplexan organism.

Cancers that can be treated by the methods encompassed by the invention include, but are not limited to, neoplasms, malignant tumors, metastases, or any disease or disorder characterized by uncontrolled cell growth such that it would be considered cancerous. The cancer may be a primary or metastatic cancer. Specific cancers that can be treated according to the present invention include, but are not limited to, those listed in Table 2 (for a review of such disorders, see Fishman et al., 1985, Medicine, 2d Ed., J.B. Lippincott Co., Philadelphia):

TABLE 2

MALIGNANCIES AND RELATED DISORDERS

Leukemia
  acute leukemia
  acute lymphocytic leukemia
  acute myelocytic leukemia
    myeloblastic
    promyelocytic
    myelomonocytic
    monocytic
    erythroleukemia
  chronic leukemia
  chronic myelocytic (granulocytic) leukemia
  chronic lymphocytic leukemia
Polycythemia vera
Lymphoma
  Hodgkin's disease
  non-Hodgkin's disease
Multiple myeloma
Waldenstrom's macroglobulinemia
Heavy chain disease
Solid tumors
  sarcomas and carcinomas
    fibrosarcoma
    myxosarcoma
    liposarcoma
    chondrosarcoma
    osteogenic sarcoma
    chordoma
    angiosarcoma
    endotheliosarcoma
    lymphangiosarcoma
    lymphangioendotheliosarcoma
    synovioma
    mesothelioma
    Ewing's tumor
    leiomyosarcoma
    rhabdomyosarcoma
    colon carcinoma
      rectal cancer

TABLE 2-continued

MALIGNANCIES AND RELATED DISORDERS pancreatic cancer
breast cancer
ovarian cancer
prostate cancer
squamous cell carcinoma
basal cell carcinoma
adenocarcinoma
sweat gland carcinoma
sebaceous gland carcinoma
papillary carcinoma
papillary adenocarcinomas
cystadenocarcinoma
medullary carcinoma
bronchogenic carcinoma
renal cell carcinoma
hepatoma
bile duct carcinoma
choriocarcinoma
seminoma
embryonal carcinoma
Wilms' tumor
curvical cancer
testicular tumor
lung carcinoma
small cell lung carcinoma
bladder carcinoma
epithelial carcinoma
glioma
astrocytoma
medulloblastoma
craniopharyngioma
ependymoma
pinealoma
hemangioblastoma
acoustic neuroma
oligodendroglioma
menangioma
melanoma
neuroblastoma
retinoblastoma Prophylactic Uses The compositions of the invention can be administered to prevent progression to a neoplastic or malignant state, including but not limited to those disorders listed in Table 2. Such prophylactic use is indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, 1976, Basic Pathology, 2d Ed., W.B. Saunders Co., Philadelphia, pp. 68-79.). Hyperplasia is a form of controlled cell proliferation involving an increase in cell number in a tissue or organ, without significant alteration in structure or function. As but one example, endometrial hyperplasia often precedes endometrial cancer. Metaplasia is a form of controlled cell growth in which one type of adult or fully differentiated cell substitutes for another type of adult cell. Metaplasia can occur in epithelial or connective tissue cells. A typical metaplasia involves a somewhat disorderly metaplastic epithelium. Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation, and is often found in the cervix, respiratory passages, oral cavity, and gall bladder.

Alternatively or in addition to the presence of abnormal cell growth characterized as hyperplasia, metaplasia, or dysplasia, the presence of one or more characteristics of a transformed phenotype, or of a malignant phenotype, displayed in vivo or displayed in vitro by a cell sample from a patient, can indicate the desirability of prophylactic/therapeutic administration of the composition of the invention. Such characteristics of a transformed phenotype include morphology changes, looser substratum attachment, loss of contact inhibition, loss of anchorage dependence, protease release, increased sugar transport, decreased serum requirement, expression of fetal antigens, disappearance of the 250,000 dalton cell surface protein, etc. (see also id., at pp. 84-90 for characteristics associated with a transformed or malignant phenotype).

In a specific embodiment, leukoplakia, a benign-appearing hyperplastic or dysplastic lesion of the epithelium, or Bowen's disease, a carcinoma in situ, are pre-neoplastic lesions indicative of the desirability of prophylactic intervention.

In another embodiment, fibrocystic disease (cystic hyperplasia, mammary dysplasia, particularly adenosis (benign epithelial hyperplasia)) is indicative of the desirability of prophylactic intervention.

The prophylactic use of the compositions of the invention is also indicated in some viral infections that may lead to cancer. For example, human papilloma virus can lead to cervical cancer (see, e.g., Hernandez-Avila et al., Archives of Medical Research (1997) 28: 265-271), Epstein-Barr virus (EBV) can lead to lymphoma (see, e.g., Herrmann et al., J Pathol (2003) 199(2): 140-5), hepatitis B or C virus can lead to liver carcinoma (see, e.g., El-Serag, J Clin Gastroenterol (2002) 35(5 Suppl 2): S72-8), human T cell leukemia virus (HTLV)-I can lead to T-cell leukemia (see e.g., Mortreux et al., Leukemia (2003) 17(1): 26-38), and human herpesvirus-8 infection can lead to Kaposi's sarcoma (see, e.g., Kadow et al., Curr Opin Investig Drugs (2002) 3(11): 1574-9).

In other embodiments, a patient which exhibits one or more of the following predisposing factors for malignancy is treated by administration of an effective amount of a composition of the invention: a chromosomal translocation associated with a malignancy (e.g., the Philadelphia chromosome for chronic myelogenous leukemia, t (14; 18) for follicular lymphoma, etc.), familial polyposis or Gardner's syndrome (possible forerunners of colon cancer), benign monoclonal gammopathy (a possible forerunner of multiple myeloma), a first degree kinship with persons having a cancer or precancerous disease showing a Mendelian (genetic) inheritance pattern (e.g., familial polyposis of the colon, Gardner's syndrome, hereditary exostosis, polyendocrine adenomatosis, medullary thyroid carcinoma with amyloid production and pheochromocytoma, Peutz-Jeghers syndrome, neurofibromatosis of Von Recklinghausen, retinoblastoma, carotid body tumor, cutaneous melanocarcinoma, intraocular melanocarcinoma, xeroderma pigmentosum, ataxia telangiectasia, Chediak-Higashi syndrome, albinism, Fanconi's aplastic anemia, and Bloom's syndrome; see Robbins and Angell, 1976, Basic Pathology, 2d Ed., W.B. Saunders Co., Philadelphia, pp. 112-113) etc.), and exposure to carcinogens (e.g., smoking, and inhalation of or contacting with certain chemicals).

In another specific embodiment, a composition of the invention is administered to a human patient to prevent progression to breast, colon, ovarian, or cervical cancer.

Gene Therapy

In one embodiment, one or more nucleic acid molecules comprising sequences encoding one or more ARPs are administered to a subject to stimulate an immune response and/or to prevent or treat cancer or infectious diseases by way of gene therapy. Gene therapy refers to therapy performed by the administration to a subject of an expressed or expressible nucleic acid.

Any of the methods for gene therapy available in the art can be used according to the present invention. Exemplary methods are described below.

For general reviews of the methods of gene therapy, see Goldspiel et al., 1993, Clinical Pharmacy 12: 488-505; Wu and Wu, 1991, Biotherapy 3: 87-95; Tolstoshev, 1993, Ann. Rev. Pharmacol. Toxicol. 32: 573-596; Mulligan, 1993, Science 260: 926-932; and Morgan and Anderson, 1993, Ann. Rev. Biochem. 62: 191-217; May, 1993, TIBTECH 11(5): 155-215). Methods commonly known in the art of recombinant DNA technology which can be used are described in Ausubel et al. (eds.), 1993, Current Protocols in Molecular Biology, John Wiley & Sons, NY; and Kriegler, 1990, Gene Transfer and Expression, A Laboratory Manual, Stockton Press, NY.

In a preferred embodiment, a composition of the invention comprises nucleotide sequences encoding one or more ARPs, said nucleic acid sequences being part of expression vectors that express ARPs in a suitable host. In particular, such nucleic acids have promoters, preferably heterologous (non-native) promoters, operably linked to the ARP coding region, said promoter being inducible or constitutive, and, optionally, tissue-specific. In another particular embodiment, nucleic acid molecules are used in which the ARP coding sequences and any other desired sequences are flanked by regions that promote homologous recombination at a desired site in the genome, thus providing for intrachromosomal expression of the ARP nucleic acids (Koller and Smithies, 1989, Proc. Natl. Acad. Sci. USA 86: 8932-8935; Zijlstra et al., 1989, Nature 342: 435-438).

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, 1987, J. Biol. Chem. 262: 4429-4432) (which can be used to target cell, types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g, PCT Publications WO 92/06180 dated Apr. 16, 1992 (Wu et al.); WO 92/22635 dated Dec. 23, 1992 (Wilson et al.); WO92/20316 dated Nov. 26, 1992 (Findeis et al.); WO93/14188 dated Jul. 22, 1993 (Clarke et al.), WO 93/20221 dated Oct. 14, 1993 (Young)). Alternatively, the nucleic acid can be introduced intracellularly and incorporated within host cell DNA for expression, by homologous recombination (Koller and Smithies, 1989, Proc. Natl. Acad. Sci. USA 86: 8932-8935; Zijlstra et al., 1989, Nature 342: 435-438).

In one embodiment, viral vectors that contain nucleic acids encoding one or more ARPs are used in accordance with the invention (see Miller et al., 1993, Meth. Enzymol. 217: 581-599). A retroviral vector, for example, can be used in gene therapy to deliver an ARP to a subject. These retroviral vectors have been modified to delete retroviral sequences that are not necessary for packaging of the viral genome and integration into host cell DNA. More detail about retroviral vectors can be found in Boesen et al., 1994, Biotherapy 6: 291-302; Clowes et al., 1994, J. Clin. Invest. 93: 644-651; Kiem et al., 1994, Blood 83: 1467-1473; Salmons and Gunzberg, 1993, Human Gene Therapy 4: 129-141; and Grossman and Wilson, 1993, Curr. Opin. in Genetics and Devel. 3: 110-114.

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson (1993, Current Opinion in Genetics and Development 3: 499-503) present a review of adenovirus-based gene therapy. Bout et al. (1994, Human Gene Therapy 5: 3-10) demonstrated the use of adenovirus vectors to transfer genes to the respiratory epithelia of rhesus monkeys. Other instances of the use of adenoviruses in gene therapy can be found in Rosenfeld et al., 1991, Science 252: 431-434; Rosenfeld et al., 1992, Cell 68: 143-155; Mastrangeli et al., 1993, J. Clin. Invest. 91: 225-234; PCT Publication WO94/12649; and Wang et al., 1995, Gene Therapy 2: 775-783. In a preferred embodiment, adenovirus vectors are used in gene therapy to deliver ARPs to a subject to prevent or treat cancer.

Adeno-associated virus (AAV) has also been proposed for use in gene therapy (Walsh et al., 1993, Proc. Soc. Exp. Biol. Med. 204: 289-300; U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, 1993, Meth. Enzymol. 217: 599-618; Cohen et al., 1993, Meth. Enzymol. 217: 618-644; Cline, 1985, Pharmac. Ther. 29: 69-92) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include, but are not limited to, epithelial cells, endothelial cells, keratinocytes, fibroblasts, muscle cells, hepatocytes; blood cells such as T lymphocytes, B lymphocytes, NK cells, dendritic cells, monocytes, macrophages, neutrophils, eosinophils, megakaryocytes, granulocytes, autologous cancer cells; various stem or progenitor cells, in particular hematopoietic stem or progenitor cells, e.g. as obtained from bone marrow, umbilical cord blood, peripheral blood, fetal liver, etc.

In a preferred embodiment, the cell used for gene therapy is autologous to the patient.

In one embodiment in which recombinant cells are used in gene therapy, one or more nucleotide sequences encoding one or more ARPs are introduced into the cells such that the nucleotide sequences are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see e.g. PCT Publication WO 94/08598, dated Apr. 28, 1994; Stemple and Anderson, 1992, Cell 71: 973-985; Rheinwald, 1980, Meth. Cell Bio. 21A: 229; and Pittelkow and Scott, 1986, Mayo Clinic Proc. 61: 771). In another specific embodiment, cancer cells are used.

In a specific embodiment, the nucleic acid to be introduced for purposes of gene therapy comprises a constitutive, tissue-specific, or inducible promoter operably linked to the coding region. In a preferred embodiment, the nucleic acid to be introduced for purposes of gene therapy comprises an inducible promoter operably linked to the coding region, such that expression of the nucleic acid is controllable by controlling the presence or absence of the appropriate inducer of transcription.

Other Anti-Cancer Therapies

The present invention provides methods of preventing or treating cancer comprising administering to a subject in need thereof a composition comprising ARP alone or in combination with one or more prophylactic or therapeutic agents other than ARP. Other therapeutic or prophylactic agents include, but are not limited to, peptides, polypeptides, proteins, fusion proteins, nucleic acid molecules, small molecules, mimetic agents, synthetic drugs, inorganic molecules, and organic molecules. Any agent or therapy (e.g., chemotherapies, radiation therapies, surgery, hormonal therapies, and/or biological therapies/immunotherapies) which is known to be useful, or which has been used or is currently being used for the prevention or treatment of cancer can be used in combination with a composition of the invention in accordance with the invention described herein.

Examples of such agents (i.e., anti-cancer agents) include, but are not limited to, DNA-interactive agents including, but not limited to, the alkylating agents (e.g., nitrogen mustards, e.g. Chlorambucil, Cyclophosphamide, Isofamide, Mechlorethamine, Melphalan, Uracil mustard; Aziridine such as Thiotepa; methanesulphonate esters such as Busulfan; nitroso ureas, such as Carmustine, Lomustine, Streptozocin; platinum complexes, such as Cisplatin, Carboplatin; bioreductive alkylator, such as Mitomycin, and Procarbazine, Dacarbazine and Altretamine); the DNA strand-breakage agents, e.g., Bleomycin; the intercalating topoisomerase II inhibitors, e.g., Intercalators, such as Amsacrine, Dactinomycin, Daunorubicin, Doxorubicin, Idarubicin, Mitoxantrone, and nonintercalators, such as Etoposide and Teniposide; the non-intercalating topoisomerase II inhibitors, e.g., Etoposide and Teniposde; and the DNA minor groove binder, e.g., Plicamydin; the antimetabolites including, but not limited to, folate antagonists such as Methotrexate and trimetrexate; pyrimidine antagonists, such as Fluorouracil, Fluorodeoxyuridine, CB3717, Azacitidine and Floxuridine; purine antagonists such as Mercaptopurine, 6-Thioguanine, Pentostatin; sugar modified analogs such as Cytarabine and Fludarabine; and ribonucleotide reductase inhibitors such as hydroxyurea; tubulin Interactive agents including, but not limited to, colcbicine, Vincristine and Vinblastine, both alkaloids and Paclitaxel and cytoxan; hormonal agents including, but note limited to, estrogens, conjugated estrogens and Ethinyl Estradiol and Diethylstilbesterol, Chlortrianisen and Idenestrol; progestins such as Hydroxyprogesterone caproate, Medroxyprogesterone, and Megestrol; and androgens such as testosterone, testosterone propionate; fluoxymesterone, methyltestosterone; adrenal corticosteroid, e.g., Prednisone, Dexamethasone, Methylprednisolone, and Prednisolone; leutinizing hormone releasing hormone agents or gonadotropin-releasing hormone antagonists, e.g., leuprolide acetate and goserelin acetate; antihormonal antigens including, but not limited to, antiestrogenic agents such as Tamoxifen, anti-androgen agents such as Flutamide; and antiadrenal agents such as Mitotane and Aminoglutethimide; cytokines including, but not limited to, IL-1.alpha., IL-1β, IL-2, IL-3, IL-4, IL-5, IL-6, IL-7, IL-8, IL-9, IL-10, IL-11, IL-12, IL-13, IL-18, TGF-β, GM-CSF, M-CSF, G-CSF, TNF-α, TNF-β, LAF, TCGF, BCGF, TRF, BAF, BDG, MP, LIF, OSM, TMF, PDGF, IFN-α, IFN-β IFN-γ, and Uteroglobins (U.S. Pat. No. 5,696,092); anti-angiogenics including, but not limited to, agents that inhibit VEGF (e.g., other neutralizing antibodies (Kim et al., 1992; Presta et al., 1997; Sioussat et al., 1993; Kondo et al., 1993; Asano et al., 1995, U.S. Pat. No. 5,520,914), soluble receptor constructs (Kendall and Thomas, 1993; Aiello et al., 1995; Lin et al., 1998; Millauer et al., 1996), tyrosine kinase inhibitors (Siemeister et al., 1998, U.S. Pat. Nos. 5,639,757, and 5,792,771), antisense strategies, RNA aptamers and ribozymes against VEGF or VEGF receptors (Saleh et al., 1996; Cheng et al., 1996; Ke et al., 1998; Parry et al., 1999); variants of VEGF with antagonistic properties as described in WO 98/16551; compounds of other chemical classes, e.g., steroids such as the angiostatic 4,9(11)-steroids and C21-oxygenated steroids, as described in U.S. Pat. No. 5,972,922; thalidomide and related compounds, precursors, analogs, metabolites and hydrolysis products, as described in U.S. Pat. Nos. 5,712,291 and 5,593,990; Thrombospondin (TSP-1) and platelet factor 4 (PF4); interferons and metalloproteinase inhibitors; tissue inhibitors of metalloproteinases (TIMPs); anti-Invasive Factor, retinoic acids and paclitaxel (U.S. Pat. No. 5,716,981); AGM-1470 (Ingber et al., 1990); shark cartilage extract (U.S. Pat. No. 5,618,925); anionic polyamide or polyurea oligomers (U.S. Pat. No. 5,593,664); oxindole derivatives (U.S. Pat. No. 5,576,330); estradiol derivatives (U.S. Pat. No. 5,504,074); thiazolopyrimidine derivatives (U.S. Pat. No. 5,599,813); and LM609 (U.S. Pat. No. 5,753,230); apoptosis-inducing agents including, but not limited to, bcr-abl, bcl-2 (distinct from bcl-1, cyclin D1; GenBank accession numbers M14745, X06487; U.S. Pat.

Nos. 5,650,491; and 5,539,094) and family members including Bcl-x1, Mcl-1, Bak, A1, A20, and antisense nucleotide sequences (U.S. Pat. Nos. 5,650,491; 5,539,094; and 5,583,034); Immunotoxins and coaguligands, tumor vaccines, and antibodies.

Specific examples of anti-cancer agents which can be used in accordance with the methods of the invention include, but not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; interleukin II (including recombinant interieukin II, or rIL2), interferon alpha-2a; interferon alpha-2b; interferon alpha-n1; interferon alpha-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride. Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesinei; pentosan polysulfate sodium; pentostatin; pentrozole; perflubron; perfosfamide; perillyl alcohol; phenazinomycinii; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B 1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; 5-fluorouracil; leucovorin; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; thalidomide; velaresol; veramine; verdins; verteporfin; vinorelbine; vinxaltine; vitaxin; vorozole; zanoterone; zeniplatin; zilascorb; and zinostatin stimalamer.

The invention also encompasses administration of a composition comprising ARP in combination with radiation therapy comprising the use of x-rays, gamma rays and other sources of radiation to destroy the cancer cells. In preferred embodiments, the radiation treatment is administered as external beam radiation or teletherapy wherein the radiation is directed from a remote source. In other preferred embodiments, the radiation treatment is administered as internal therapy or brachytherapy wherein a radiaoactive source is placed inside the body close to cancer cells or a tumor mass.

In a preferred embodiment, a composition of the invention is used in combination with an interleukin-18 (IL-18), a CD40 ligand, an interferon-γ (INFγ), an interleukin-4 (IL-4), a granulocyte macrophage-colony stimulating factor (GM-CSF), other cytokines, an anti-CD40 antibody and a co-stimulatory agonist in stimulating an immune reponse and/or in prevention or treatment of cancer. In a specific embodiment, an ARP of the invention may exhibit synergistic immune-stimulatory effects with these agents.

In specific embodiments, a patient with ovarian cancer is administered a prophylactically or therapeutically effective amount of a composition comprising ARP in combination with a prophylactically or therapeutically effective amount of one or more other agents useful for ovarian cancer therapy, including but not limited to, intraperitoneal radiation therapy, such as $P^{32}$ therapy, total abdominal and pelvic radiation therapy, cisplatin, the combination of paclitaxel (Taxol) or docetaxel (Taxotere) and cisplatin or carboplatin, the combination of cyclophosphamide and cisplatin, the combination of cyclophosphamide and carboplatin, the combination of 5-FU and leucovorin, etoposide, liposomal doxorubicin, gemcitabine or topotecan. In a particular embodiment, a prophylactically or therapeutically effective amount of a composition of the invention is administered in combination with the administration of Taxol for patients with platinum-refractory disease. A further embodiment is the treatment of patients with refractory ovarian cancer including administration of: ifosfamide in patients with disease that is platinum-refractory, hexamethylmelamine (HMM) as salvage chemotherapy after failure of cisplatin-based combination regimens, and tamoxifen in patients with detectable levels of cytoplasmic estrogen receptor on their tumors.

Cancer therapies and their dosages, routes of administration and recommended usage are known in the art and have been described in such literature as the *Physician's Desk Reference* ($56^{th}$ ed., 2002).

Other Anti-Infection Agents

The present invention provides methods of preventing or treating an infectious disease, said methods comprising administering to a subject in need thereof a composition comprising ARP alone or in combination with one or more prophylactic or therapeutic agents other than ARP. Any agent or therapy which is known to be useful, or which has been used or is currently being used for the prevention or treatment of infectious disease can be used in combination with the composition of the invention in accordance with the invention described herein.

Examples of such agents to treat bacteria infections include, but are not limited to, folate antagonists (e.g., mafenide, silver sulfadiazine, succinylsulfathiazole, sulfacetamide, sulfadiazine, sulfamethoxazole, sulfasalazine, sulfisoxazole, pyrimethoamine, trimethoprim, co-trimoxazole), inhibitors of cell wall synthesis (e.g., penicillins, cephalosporins, carbapenems, monobactams, vacomycin, bacitracin, clavulanic acid, sulbactam, tazobactam), protein synthesis inhibitors (e.g., tetracyclines, aminoglycosides, macrolides, chloramphenicol, clindamycin), fluoroquinolones (e.g., ciproloxacin, enoxacin, lomefloxacin, norfloxacin, ofloxacin), nalidixic acid, methenamine, nitrofurantoin, aminosalicylic acid, cycloserine, ethambutol, ethionamide, isoniazid, pyrazinamide, rifampin, clofazimine, and dapsone.

Examples of agent that can be used in combination with ARP to treat fungal infections include, but not limited to, amphotericin B, fluconazole, flucytosine, itraconazole, ketoconazole, clotrimazole, econazole, griseofulvin, miconazole, and nystatin.

Examples of agent that can be used in combination with ARP to treat protozoal infections include, but not limited to, chloroquine, dehydroemetine, diloxanide furoate, emetine, metronidazole, paramomycin, chloroquine, mefloquine, primaquine, pyrimethamine, quinine, quinidine, melarsoprol, nifurtimox, pentamidine, suramin, sodium stibogluconate, pyrimethamine, and quinacrine.

Examples of antihelmintic agents that can be used in combination with ARP to treat helminth (worm) infections include, but not limited to, ivermectin, mebendazole, pyrantel pamoate, thiabendazole, praziquantel, and niclosamide.

Examples of antiviral agents that can be used in combination with ARP to treat viral infections include, but not limited to, amantadine, ribavirin, rimantadine, acyclovir, famciclovir, foscamet, ganciclovir, trifluridine, vidarabine, didanosine (ddI), stavudine (d4T), zalcitabine (ddC), zidovudine (AZT), lamivudine, abacavir, delavirdine, nevirapine, efavirenz, saquinavir, ritonavir, indinavir, nelfinavir, amprenavir, lopinavir and interferon.

Dosage Regimens

Toxicity and efficacy of the prophylactic and/or therapeutic protocols of the present invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Prophylactic and/or therapeutic agents that exhibit large therapeutic indices are preferred. While prophylactic and/or therapeutic agents that exhibit toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage of the prophylactic and/or therapeutic agents for use in humans. The dosage of such agents lies preferably within a range of circulating concentrations that include the $ED_{50}$ with little or no toxicity. The dosage may vary within this range depending upon the dosage form employed and the route of administration utilized. For any agent used in the method of the invention, the therapeutically effective dose can be estimated initially from cell culture assays (see Section 5.6 and Section 12). A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

The amount of the composition of the invention which will be effective in the treatment of a particular disorder or condition will depend on the nature of the disorder or condition, and can be determined by standard clinical techniques. The precise dose to be employed in the formulation will also depend on the route of administration, and the seriousness of the disease or disorder, and should be decided according to the judgment of the practitioner and each patient's circumstances.

The dosage of ARP for intravenous administration in a human patient provided by the present invention is preferably less than 100 µg/kg body weight, less than 50 µg/kg body weight, less than 10 µg/kg body weight, less than 5 µg/kg body weight, less than 1 µg/kg body weight, less than 0.5 µg/kg body weight, less than 0.1 µg/kg body weight, less than 0.05 µg/kg body weight, less than 0.01 µg/kg body weight, or less than 0.001 µg/kg body weight. In a preferred embodiment, ARP is given at a dosage of 0.1 µg per person per day (or about 0.14 ng per kg body weight).

In the case of treating for an infection with influenza virus the dosage for treating a human can be derived from a suitable dose in the mouse which has been found to be about 10,000 ng per mouse. Given the difference in body weight, a comparable dose in a human would be 28 mg. For treatment of influenza virus infection in a human patient using the present invention, the dose is preferably from about 2.8 mg to about 280 mg, more preferably from about 5 mg to about 100 mg and most preferably from about 10 mg to about 50 mg.

Prior to administering the first full dose, each patient preferably receives a subcutaneous injection of a small amount (e.g., {fraction (1/100)} to {fraction (1/10)} of the prescribed dose) of a composition of the invention to detect any acute intolerance. The injection site is examined one and two hours after the test. If no reaction is detected, then the full dose is administered.

The compositions of the invention can also be administered orally. In one embodiment, intact sporulated oocysts of an Apicomplexan genus (e.g., *Eimeria* tenella) are given orally with drinking water. The dosage can be, by way of example, 100 to 10,000 oocysts in a single administration depending on the cross-species infectivity of the protozoan.

The compositions of the invention can be administered in various forms. In one embodiment, a composition of the invention comprises an ARP in a membrane-linked form. In another embodiment, a composition of the invention comprises live or dead bacteria with recombinant ARP expressed. In another embodiment, a composition of the invention comprises live bacteria, which are specific to a particular organ, expressing recombinant ARP (e.g., *Lactobacillus* would live in intestinal tissue, while some air-born non-pathogenic bacteria may be specific to lungs, or the nasal cavity, etc).

Administrations, Formulations and Kits

The invention provides methods of treatment and/or prophylaxis by administration to a subject of an effective amount of a composition comprising ARP. In a preferred aspect, the ARP is purified. The subject is preferably an animal, including but not limited to animals such as cows, pigs, chickens, etc., and is preferably a mammal. In a preferred embodiment, the subject is a domestic animal, including but not limited to chickens, pigs, cows, goats and horse. In another preferred embodiment, the subject is a pet, including but not limited to, cats, dogs, and birds. In another preferred embodiment, the subject is a human.

Various delivery systems are known and can be used to administer a composition of the invention, e.g., encapsulation in liposomes, microparticles, microcapsules, expression by recombinant cells, receptor-mediated endocytosis (see, e.g., Wu and Wu, 1987, J. Biol. Chem. 262: 4429-4432), construction of an ARP nucleic acid as part of a retroviral or other vector, etc. Methods of introduction include, but are not limited to, intradermal, intramuscular, intraperitoneal, intravenous, subcutaneous, intranasal, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

In a specific embodiment, it may be desirable to administer the pharmaceutical compositions of the invention locally to the area in need of treatment; this may be achieved by, for example, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of a malignant tumor or neoplastic or pre-neoplastic tissue.

In another embodiment, a chimeric construction of an ARP is used to target a specific area, i.e., even systemic administration of the composition would direct the composition to the organ of choice (e.g., an antibody to a specific type of cancer fused to an ARP would let the chimeric construct to be delivered to the surface of the tumor).

In a specific embodiment, the ARP nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., 1991, Proc. Natl. Acad. Sci. USA 88: 1864-1868), etc. Alternatively, an ARP nucleic acid can be introduced intracellularly and incorporated within host cell DNA for expression, by homologous recombination.

The present invention also provides pharmaceutical compositions. Such compositions comprise a therapeutically effective amount of a composition of the invention, and a pharmaceutically acceptable carrier or excipient. Such a carrier includes but is not limited to saline, buffered saline, dextrose, water, glycerol, ethanol, and combinations thereof. The carrier and composition can be sterile. The formulation should suit the mode of administration.

The composition, if desired, can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

In one embodiment, purified Apicomplexan organisms are given orally. In a specific embodiment, intact sporulated oocysts of an Apicomplexa genus (e.g., *Eimeria* species, such as *E. tenella*) are given orally with drinking water.

In addition to the formulations described previously, the compositions may also be formulated as a depot preparation. Such long acting formulations may be administered by implantation (for example, subcutaneously or intramuscularly) or by intramuscular injection. Thus, for example, the compositions may be formulated with suitable polymeric or hydrophobic materials (for example, as an emulsion in an acceptable oil) or ion exchange resins, or as sparingly soluble derivatives, for example, as a sparingly soluble salt. Liposomes and emulsions are well known examples of delivery vehicles or carriers for hydrophilic drugs.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

The invention also provides kits for carrying out the therapeutic regimens of the invention. Such kits comprise in one or more containers therapeutically or prophylactically effective amounts of the composition of the invention in pharmaceutically acceptable form. The composition in a vial of a kit of the invention may be in the form of a pharmaceutically acceptable solution, e.g., in combination with sterile saline, dextrose solution, or buffered solution, or other pharmaceutically acceptable sterile fluid. Alternatively, the composition may be lyophilized or desiccated; in this instance, the kit optionally further comprises in a container a pharmaceutically acceptable solution (e.g., saline, dextrose solution, etc.), preferably sterile, to reconstitute the composition to form a solution for injection purposes.

In another embodiment, a kit of the invention further comprises a needle or syringe, preferably packaged in sterile form, for injecting the formulation, and/or a packaged alcohol pad. Instructions are optionally included for administration of the formulations of the invention by a clinician or by the patient.

In some embodiments, the present invention provides kits comprising a plurality of containers each comprising a pharmaceutical formulation or composition comprising a dose of the composition of the invention sufficient for a single administration.

In a specific embodiment, a kit comprises a first container containing a composition comprising ARP; and a second container containing a different treatment modality in an amount that, when administered before, concurrently with, or after the administration of the ARP in the first container, is effective to improve overall treatment effectiveness over the effectiveness of the administration of each component alone, or is effective to decrease side effects of the treatment when each component is used alone. In a preferred specific embodiment, the invention provides a kit comprising in a first container, a composition of the invention; and in a second container, a composition comprising a purified cytokine.

The appropriate and recommended dosages, formulation and routes of administration for treatment modalities such as chemotherapeutic agents, radiation therapy and biological/immunotherapeutic agents such as cytokines are known in the art and described in such literature as the Physician's Desk Reference (56th ed., 2002).

Article of Manufacture

The present invention also encompasses a finished packaged and labeled pharmaceutical product. This article of manufacture includes the appropriate unit dosage form in an appropriate vessel or container such as a glass vial or other container that is hermetically sealed. In the case of dosage forms suitable for parenteral administration the active ingredient is sterile and suitable for administration as a particulate free solution. In other words, the invention encompasses both parenteral solutions and lyophilized powders, each being sterile, and the latter being suitable for reconstitution prior to injection. Alternatively, the unit dosage form may be a solid suitable for oral, transdermal, topical or mucosal delivery.

In a preferred embodiment, the unit dosage form is suitable for intravenous, intramuscular or subcutaneous delivery. Thus, the invention encompasses solutions, preferably sterile, suitable for each delivery route.

In another preferred embodiment, compositions of the invention are stored in containers with biocompatible detergents, including but not limited to, lecithin, taurocholic acid, and cholesterol; or with other proteins, including but not limited to, gamma globulins and serum albumins. More preferably, compositions of the invention are stored with human serum albumins for human uses, and stored with bovine serum albumins for veterinary uses. While not bound by any theory, a low concentration of ARP tends to be denaturing on the surface of plastic or glass containers. The handling and storage as described herein would minimize the loss of ARP on surfaces of containers and keep an ARP in its active form. Other methods known in the art can also be used. See Wang, International J. of Pharmaceutics, 185: 129-188 (1999).

As with any pharmaceutical product, the packaging material and container are designed to protect the stability of the product during storage and shipment. Further, the products of the invention include instructions for use or other informational material that advise the physician, technician or patient on how to appropriately prevent or treat the disease or disorder in question. In other words, the article of manufacture includes instruction means indicating or suggesting a dosing regimen including, but not limited to, actual doses, monitoring procedures (such as methods for monitoring mean absolute lymphocyte counts, tumor cell counts, and tumor size) and other monitoring information.

More specifically, the invention provides an article of manufacture comprising packaging material, such as a box, bottle, tube, vial, container, sprayer, insufflator, intravenous (i.v.) bag, envelope and the like; and at least one unit dosage form of a pharmaceutical agent contained within said packaging material. The invention also provides an article of manufacture comprising packaging material, such as a box, bottle, tube, vial, container, sprayer, insufflator, intravenous (i.v.) bag, envelope and the like; and at least one unit dosage form of each pharmaceutical agent contained within said packaging material. The invention further provides an article of manufacture comprising packaging material, such as a box, bottle, tube, vial, container, sprayer, insufflator, intravenous (i.v.) bag, envelope and the like; and at least one unit dosage form of each pharmaceutical agent contained within said packaging material. The invention further provides an article of manufacture comprising a needle or syringe, preferably packaged in sterile form, for injection of the formulation, and/or a packaged alcohol pad.

In a specific embodiment, an article of manufacture comprises packaging material and a pharmaceutical agent and instructions contained within said packaging material, wherein said pharmaceutical agent is an ARP or a derivative, fragment, homolog, analog thereof and a pharmaceutically acceptable carrier, and said instructions indicate a dosing regimen for preventing, treating or managing a subject with cancer. In another embodiment, an article of manufacture comprises packaging material and a pharmaceutical agent and instructions contained within said packaging material, wherein said pharmaceutical agent is an ARP or a derivative, fragment, homolog, analog thereof, a prophylactic or therapeutic agent other than an ARP or a derivative, fragment, homolog, analog thereof, and a pharmaceutically acceptable carrier, and said instructions indicate a dosing regimen for preventing, treating or managing a subject with a cancer. In another embodiment, an article of manufacture comprises packaging material and two pharmaceutical agents and instructions contained within said packaging material, wherein said first pharmaceutical agent is an ARP or a derivative, fragment, homolog, analog thereof and a pharmaceutically acceptable carrier, and said second pharmaceutical agent is a prophylactic or therapeutic agent other than an ARP or a derivative, fragment, homolog, analog thereof, and said instructions indicate a dosing regimen for preventing, treating or managing a subject with a cancer.

Monitoring of Effects During Treatment

The effect of immunotherapy with an ARP compositions of the invention on development and progression of neoplastic diseases can be monitored by any methods known to one skilled in the art, including but not limited to measuring: a) delayed hypersensitivity as an assessment of cellular immunity; b) activity of cytolytic T-lymphocytes in vitro; c) levels of tumor specific antigens, e.g., carcinoembryonic (CEA) antigens; d) changes in the morphology of tumors using techniques such as a computed tomographic (CT) scan; e) changes in levels of putative biomarkers of risk for a particular cancer in subjects at high risk, and f) changes in the morphology of tumors using a sonogram.

Delayed Hypersensitivity Skin Test

Delayed hypersensitivity skin tests are of great value in the overall immunocompetence and cellular immunity to an antigen. Inability to react to a battery of common skin antigens is termed anergy (Sato, T., et al, 1995, Clin. Immunol. Pathol., 74: 35-43).

Proper technique of skin testing requires that the antigens be stored sterile at 4 C, protected from light and reconstituted shorted before use. A 25- or 27-gauge needle ensures intradermal, rather than subcutaneous, administration of antigen. Twenty-four and 48 hours after intradermal administration of the antigen, the largest dimensions of both erythema and induration are measured with a ruler. Hypoactivity to any given antigen or group of antigens is confirmed by testing with higher concentrations of antigen or, in ambiguous circumstances, by a repeat test with an intermediate test.

In Vitro Activation of Cytotoxic T Cells $8 \times 10^6$ peripheral blood derived T lymphocytes isolated by the Ficoll-Hypaque centrifugation gradient technique, are restimulated with $4 \times 10^6$ mitomycin C treated tumor cells in 3 ml RPMI medium containing 10% fetal calf serum. In some experiments, 33% secondary mixed lymphocyte culture supernatant or IL-2, is included in the culture medium as a source of T cell growth factors.

In order to measure the primary response of cytolytic T-lymphocytes after immunization, T cells are cultured without the stimulator tumor cells. In other experiments, T cells are restimulated with antigenically distinct cells. After six days, the cultures are tested for cytotoxicity in a 4 hour 51 Cr-release assay. The spontaneous 51 Cr-release of the targets should reach a level less than 20%. For the anti-MHC class I blocking activity, a tenfold concentrated supernatant of W6/32 hybridoma is added to the test at a final concentration of 12.5% (Heike M., et al., *J. Immunotherapy*, 15: 165-174).

Levels of Tumor Specific Antigens

Although it may not be possible to detect unique tumor antigens on all tumors, many tumors display antigens that distinguish them from normal cells. The monoclonal antibody reagents have permitted the isolation and biochemical characterization of the antigens and have been invaluable diagnostically for distinction of transformed from nontransformed cells and for definition of the cell lineage of transformed cells. The best-characterized human tumor-associated antigens are the oncofetal antigens. These antigens are expressed during embryogenesis, but are absent or very difficult to detect in normal adult tissue. The prototype antigen is carcinoembryonic antigen (CEA), a glycoprotein found on fetal gut and human colon cancer cells, but not on normal adult colon cells. Since CEA is shed from colon carcinoma cells and found in the serum, it was originally thought that the presence of this antigen in the serum could be used to screen patients for colon cancer. However, patients with other tumors, such as pancreatic and breast cancer, also have elevated serum levels of CEA. Therefore, monitoring the fall and rise of CEA levels in cancer patients undergoing therapy has proven useful for predicting tumor progression and responses to treatment.

Several other oncofetal antigens have been useful for diagnosing and monitoring human tumors, e.g., alpha-fetoprotein, an alpha-globulin normally secreted by fetal liver and yolk sac cells, is found in the serum of patients with liver and germinal cell tumors and can be used as a marker of disease status.

Computed Tomographic (CT) Scan

CT remains the choice of techniques for the accurate staging of cancers. CT has proved more sensitive and specific than any other imaging techniques for the detection of metastases.

Measurement of Putative Biomarkers

The levels of a putative biomarker for risk of a specific cancer are measured to monitor the effect of the molecular complex of the invention. For example, in subjects at enhanced risk for prostate cancer, serum prostate-specific antigen (PSA) is measured by the procedure described by Brawer, M. K., et. al., 1992, *J. Urol.*, 147: 841-845, and Catalona, W. J., et al., 1993, *JAMA*, 270: 948-958; or in subjects at risk for colorectal cancer, CEA is measured as described above in Section 5.10.3; and in subjects at enhanced risk for breast cancer, 16-hydroxylation of estradiol is measured by the procedure described by Schneider, J. et al., 1982, *Proc. Natl. Acad. Sci.* USA, 79: 3047-3051.

Sonogram

A sonogram remains an alternative choice of technique for the accurate staging of cancers.

Monitoring Adverse Effects During Treatment

Any adverse effects during the use of an ARP alone or in combination with another therapy (including another therapeutic or prophylactic agent) are preferably also monitored. Examples of adverse effects of chemotherapy during a cancer treatment or treatment of an infectious disease include, but are not limited to, gastrointestinal toxicity such as, but not limited to, early and late-forming diarrhea and flatulence; nausea; vomiting; anorexia; leukopenia; anemia; neutropenia; asthenia; abdominal cramping; fever; pain; loss of body weight; dehydration; alopecia; dyspnea; insomnia; dizziness, mucositis, xerostomia, and kidney failure, as well as constipation, nerve and muscle effects, temporary or permanent damage to kidneys and bladder, flu-like symptoms, fluid retention, and temporary or permanent infertility. Adverse effects from radiation therapy include, but are not limited to, fatigue, dry mouth, and loss of appetite. Other adverse effects include gastrointestinal toxicity such as, but not limited to, early and late-forming diarrhea and flatulence; nausea; vomiting; anorexia; leukopenia; anemia; neutropenia; asthenia; abdominal cramping; fever; pain; loss of body weight; dehydration; alopecia; dyspnea; insomnia; dizziness, mucositis, xerostomia, and kidney failure. Adverse effects from biological therapies/immunotherapies include, but are not limited to, rashes or swellings at the site of administration, flu-like symptoms such as fever, chills and fatigue, digestive tract problems and allergic reactions. Adverse effects from hormonal therapies include but are not limited to nausea, fertility problems, depression, loss of appetite, eye problems, headache, and weight fluctuation. Additional undesired effects typically experienced by patients are numerous and known in the art. Many are described in the *Physicians' Desk Reference* ($56^{th}$ ed., 2002).

EXAMPLE 1 PURIFICATION OF ARP FROM BOVINE SMALL INTESTINE EXTRACTS

Material

Source of intestines used in the examples: large animal intestines were obtained from freshly slaughtered cows. These were routinely obtained from Bellingar Packing, Ashley, Mich. Rat and mouse intestines were obtained from Sprague Dawley rats or BALB-c mice, purchased from Harlan Industries, Indianapolis, Ind. Pig intestines were obtained from Bellingar Packing. Some pig and cow intestines were also obtained from Bain's Packing & Refrigeration, Howell, Mich.

Methods

Enriched or Isolated ARP

Extraction and Centrifugation

Bovine small intestine ileal sections (25 feet or 40 feet) proximal to the cecum were excised from animals immediately after slaughter. Each section was slit down its length and the contents flushed free. Washing was initiated at the slaughterhouse in phosphate buffered saline (PBS) plus ciprofloxacin (10 mg/L) and was completed in the laboratory. The tissue was transported on ice to the laboratory where it was cut into 1 foot long strips and the external fatty deposits removed. Each section was washed in a solution of PBS containing ciprofloxacin. This was followed by serial washes through 6 beakers (on ice) containing PBS without ciprofloxicin. Each section was blotted free to remove excess fluid and then the soft tissue was scraped from the serosal casing and the serosa was discarded. The soft tissue was minced in a kitchen-variety motorized mini food processor in 50 mL aliquots using 10 start and stop cycles of the processor. An equal volume of cold 30 mM Hepes was added and the mixture was homogenized in a 55 mL glass homogenizer tube with a Teflon pestle. After five down-up cycles in the homogenizer, the material was centrifuged at 18,000 rpm (25,000 G) in a refrigerated SS-34 Sorvol rotor. The resulting liquid supernatants were prefiltered through a double layer of Millipore pre filters (#API507500) housed in a sterilizing stainless 90 mm filter holder to remove fatty particulates in suspension. The filtrate was flash frozen in liquid nitrogen and stored frozen at −80° C.

Pretesting of Prefiltered BEX
Preparation:
(a) Prepare 2.0 L of 1×PBS buffer from 10×PBS and acclimate to 4° C.
(b) Soak an appropriate number (one greater than the number of intestines to be pre-tested) of 100 mm long, 10 mm wide regenerated cellulose dialysis membranes, MWCO 6-8000, in r.o.deionized water until pliable.
(c) Defrost the 1.2 ml/intestine aliquots of prefiltered BBX and the intestinal mix.
Test for Activity:
(a) Dialyze 1.0 ml of the individual intestinal extracts and intestinal mix against 1 L of PBS for 3 hours at 4° C.
(b) Change buffer and dialyze overnight.
(c) Transfer dialysates to sterile 1.2 ml cryotubes.
(d) Prepare individual samples for the dendritic cell activity test by diluting the dialyzed stock BBX 1:10 (1 part BBX plus 9 parts sterile 0.1% BSA in PBS). From each stock serially dilute 1:2 (501 μl stock plus 50 μl 0.1% BSA/PBS) 4×.
(e) Graphically compare pre-test samples with an appropriate pre-test control with predetermined activity.
(f) Flash freeze and store pre-test leftovers in the −80° C. freezer.
Process Control:
Discard extracts from intestines generating dendritic cell activity less than 20% of the pre-test control.

Procipitate™ and Cleanascite™
The initial reductions of non-active macromolecules were facilitated with two commercial bulk-processing products from Ligochem, Inc. (Cleanascite™ and Procipitate™). Three parts extract was treated with one part Cleanascite™, which is a non-ionic adsorbent which selectively removes lipids, floating cells, cell debris and mucinous impurities. After centrifugation, the resulting supernatant was treated with the synthetic, water insoluble, anionic polyelectrolyte Procipitate™ at a ratio of four parts supernatant to one part Procipitate™ to remove selective proteins. This was spun at low speeds according the manufacturers recommendation and the supernatant retained for further purification.

Ultra-Filtration
A small sample of each week's batch was purified for testing using an Amicon stirred cell (series 800) initially fitted with a 300 kD disc membrane to remove impurities greater than 300 kD in size followed by a 10 kD disc membrane to remove impurities less than 10 kD as well as to concentrate the sample. During this procedure phosphate buffered saline was used to wash the >300 kD retentate. The resulting 10 to 300 kD sample was tested on the NK assay and/or in mice.

If the sample was active, the whole batch was processed in a large-scale procedure. The solution was filtered through 300 kD filter plates in a Millipore Pelicon™ ultrafiltration system and the <300 kD flow-through material together with its 30 mM HEPES wash(es) were concentrated in Amicon™ stirred cells on 10 kD disc membranes. The resulting material, denoted Stage 1 BEX (Bovine Extract), was sterile-filtered with Serum Acrodisc™ 0.22 μm (Gelman Cat# 4525) filters, flash frozen, and stored at −80° C. awaiting Stage 2 BEX purification.

Superdex™ Size Exclusion
Gel filtration chromatography was used to further purify Stage 1 into Stage 2. A 1200 ml column (Amicon Cat# 9644100) was packed with Superdex-75 prep grade (Pharmacia Cat# 17-1044-01) and equilibrated in 15 mM Sodium Phosphate, 120 mM Sodium Chloride pH 7.0 (PBS). PBS buffer was used for isocratic elution of fractions. Prior to loading, Stage 1 BEX was concentrated in CentriPrep-10™ (Amicon Cat# 4304) to 35-40 mg/ml, filtered using Serum Acrodisc™ 0.22 μm (Gelman Cat# 4525). Glycerol was added to a final concentration of 5%, and the sample was loaded onto the column at 0.1-1% of column volume (1.2-12 ml). Chromatographic parameters used: 280 nm, 1.0 Absorbance full scale, 4.0 ml/min (18-26 psi) flow rate, 5 cm/hr chart speed and 2.0 minutes/8.0 mL fractions size.

Active fractions were pooled and concentrated to ~40 mg/ml using Amicon Stir Cell™ Model #8200 (Amicon Cat# 5123) with a YM10™ disc membrane (Amicon Cat# 13632). Stage 2 was sterile filtered and stored at −80° C. for the next purification step.

DEAE
A DEAE-Sepharose column (1.5×6 cm, DEAE-Sepharose Fast Flow, Pharmacia Biotech Inc. Piscataway, N.J.) was equilibrated with 30 mM Hepes and 0.1 M NaCl, pH 7.4. The sample obtained from Superdex 75™ (Stage 2) in PBS was applied to the column. The column was then washed with 100 ml of 0.1 M NaCl in 30 mM Hepes and then 200 ml of 0.2 M NaCl in the same buffer. The column was eluted isocratically with approximately 120 ml of 0.3 M NaCl in Hepes buffer. Fractions were collected every 4 min at 2.5 ml/fraction. The column was further eluted with 0.5 M NaCl in 30 mM Hepes. Fractions were analyzed by the NK-mediated cytotoxicity assay and SDS-polyacrylamide gel electrophoresis.

Purification of ARP: Modified Method

Extraction and Centrifugation
See the same step in section 6.2.1.

Pretesting of Prefiltered BEX
See the same step in Section 6.2.1.

Ammonium Sulfate Fractionating
The extract supernatant was brought to 45% ammonium sulfate at 4° C. using solid chemical and stirred for 1 hour. This was centrifuged in 250 mL centrifuge bottles at 13,000 RPM (17,300 G) for 30 minutes and in 40 mL centrifuge tubes at 15,000 RPM (17,500 G) for 20 min. The supernatant was decanted into a 4 L glass beaker and the pellets were discarded. The supernatants were brought to 80% saturation using solid ammonium sulfate, centrifuged as above, and the supernatant discarded. The pellets were dissolved in 1.5M Ammonium Sulfate/50 mM Na Phosphate (pH 6.8) after resuspending completely within the bottles or tubes. Non-dissolved material was removed by centrifugation in 250 mL centrifuge bottles at 10,000 RPM (10,200 G) for 30 minutes. The supernatants were pre-filtered through a double layer of Millipore pre-filters (AP1507500) housed in a sterilizing stainless 90 mm filter holder. Samples were taken after each step for quality control monitoring.

Hydrophobic Interaction Column (Hereinafter "HIC") Step-Elution Chromatography

A 5 cm×20 cm chromatography column, packed with 300 mL phenyl sepharose 6 fast flow (high substitution)—Amersham Pharmacia Biotech 17-0973-05, was equilibrated with 1.5M ammonium sulfate/50 mM Sodium Phosphate buffer at pH 6.8. At room temperature the pre-filtered ammonium sulfate treated BBX was pumped onto the column at a rate of ~18 mL/min. Flow was collected from the column until no longer cloudy (~1200 mL). The column was washed with 900 mL of 1.5M Ammonium Sulfate/50 mM Sodium Phosphate. The active material was eluted with 700 ml of 0.5 M Sodium Phosphate buffer.

The eluted material was prepared for DEAE chromatography by dialysis against 4 L of 0.2M NaCl/10 mM Na Phosphate (pH7.4) at 4° C. with buffer changes after 3 and 6 hours followed by a final dialysis overnight.

DEAE Step-Elution Chromatography

After the sample was dialyzed against 0.2 M NaCl, 10 mM sodium phosphate, pH 7.4, the sample was filtered through a 0.45 µm membrane to remove particulates, and then applied to the DEAE-Sepharose column (0.5×8 cm). The column was washed with about 800 mL of the same buffer (0.2 M NaCl, 10 mM Na Phosphate, pH 7.4). When the absorbance at 280 nm was down to baseline, the bound material was eluted with about 400 mL of the eluted buffer (0.5 M NaCl, 10 mM Na Phosphate, pH 7.4). The eluted fraction was concentrated to about 20 mL by Amicon stir cell with YM 10 membrane. The sample was divided into two halves and flash frozen in liquid nitrogen and then stored at −80° C.

Superdex™ Size Exclusion

Gel filtration chromatography was used to further purify the material from the DEAE step-elution. A 1200 mL column (Amicon Cat# 9644100) was packed with Superdex-75 prep grade (Pharmacia Cat# 17-1044-01) and equilibrated in 15 mM Sodium Phosphate, 120 mM Sodium Chloride pH 7.0 (PBS). PBS buffer was used for isocratic elution of fractions. Prior to loading, the samples was filtered using Serum Acrodisc™ 0.22 µm (Gelman Cat# 4525) and loaded onto the column at 0.1-1% of column volume (1.2-12 ml). Chromatographic parameters used: 280 nm, 1.0 Absorbance full scale, 4.0 ml/min (18-26 psi) flow rate, 5 cm/hr chart speed and 2.0 minutes/8.0 ml fractions size. The sample was flash frozen in liquid nitrogen and stored at −80° C.

Concentration of Superdex™ Samples and Calmodulin Removal

The active regions from 7 batches were thawed and pooled, which typically generated approximately 1,200 mL. The sample was centrifuged at 10,000 rpm (10,200 G) for 30 min with GSA rotor to remove any precipitate. The sample was then filtered with 0.45 µm syringe filter and applied to the DEAE-Sepharose column (0.3×5.5 cm). The column was washed with 0.2 M NaCl, 10 mM Na Phosphate, pH 7.4 (about 200 mL). The bound material was eluted with 1 M NaCl, 0.1 mM $CaCl_2$, 10 mM Tris, pH 7.0. The protein peak was collected in approximately 50-60 mL and was dialyzed overnight against 1 liter of 1 M NaCl, 0.1 mM $CaCl_2$, 10 mM Tris, pH 7.0.

To remove calmodulin and other calcium-binding proteins, an HIC column (1.5×6 cm) was equilibrated with 1 M NaCl, 0.1 mM $CaCl_2$, 10 mM Tris, pH 7.0 before the sample was loaded onto the column. After applying the sample, the column was washed with the same buffer. The flow through fraction was collected and constituted about 75 to 80 ml. The column was washed with the same buffer (about 100 mL) then the bound material was eluted with 1 mM EGTA (ethylene glycol-bis(β-aminoethyl ether)-N,N,N',N'-tetraacetic acid), in 10 mM Tris, pH 7.0. The flow through fraction, which contained all DC activity, was used for the next step.

HIC Gradient Chromatography

All high performance liquid chromatography (hereinafter "HPLC") was performed with a Waters Associates (Milford, Mass.) 626 LC system and a Linear Instruments (Reno, Nev.) 200 Uvis absorbance detector at either 280 nm (HIC) or 215 nm (DEAE and C-8 separations). All chemicals are Ultrapure Bioreagent grade from J. T. Baker (Phillipsburg, N.J.) unless otherwise noted.

Sample volume was measured and mixed with an equal volume of 3.0 M ammonium sulfate (ACS grade, Mallinckrodt, Paris Ky.) solution in 50 mM phosphate buffer, pH 7.2. The sample was loaded via the solvent inlet manifold on the HPLC. Solvents are: Buffer A, 1.5 M ammonium sulfate in 50 mM phosphate buffer, pH 7.2 and Buffer B, 50 mM phosphate buffer, pH 7.2. Samples were applied to 21.5×150 mm Phenyl-5PW column, (TosoHaas, Montgomeryville, Pa.) with 13 µm particle size, equilibrated in Buffer A at a flow rate of 4 mL/min at room temperature. At this time a linear gradient was performed from 0-100% Buffer B over 90 minutes at 4 mL/min. Fractions were collected at 2.5 minutes using a fraction collector (LKB-Frac-100, Pharmacia, Piscataway N.J.). Fractions were diluted with phosphate buffered saline (PBS) and assayed on the DC assay. Active fractions were pooled and dialyzed in Spectra/Por 1 Membrane dialysis tubing, 6-8000 MWCO (Fisher, Pittsburgh Pa.) against two changes of PBS.

DEAE Gradient Chromatography

Samples were loaded via the solvent inlet manifold on the HPLC. Solvents are: Buffer C, PBS, pH 7.2 and Buffer D, 0.5 M NaCl in 15 mM phosphate buffer, pH 7.2. Samples were applied to DEAE-5PW column, 10 µm bead, 8×75 mm (TosoHaas) equilibrated in Buffer C at 1 mL/min at room temperature. The column was flushed with Buffer C until a stable baseline was established. At this time a linear gradient was performed from 0-100% Buffer D over 90 minutes at 1 mL/min. Fractions were collected by hand to capture either individual peaks or at five-minute intervals using the fraction collector. Fractions were diluted with PBS and assayed on the DC assay.

C8 Reverse-Phase Chromatography

Samples were loaded either via the solvent inlet manifold for large volumes (>5 mL) or via the injector loop for smaller samples. Solvents are: Buffer E, 5% Acetonitrile (HPLC grade, Burdick and Jackson, Muskegon Mich.)/95% water (HPLC grade, Burdick and Jackson)/0.1% Trifluoroacetic acid (TFA); and Buffer F, 90% HPLC Acetonitrile/10% HPLC water/0.08% TFA. Samples were applied to C8, 5 µm bead, 300 Å, 4.6×150 mm column (Vydac 208TP5415, The Separations Group, Hesperia Calif.) equilibrated with Buffer E at 1 mL/min at 55° C. The column was flushed with Buffer E until a stable baseline was established. At this time, a linear gradient was performed from 30%-55% Buffer F in 150 minutes at 1 mL/min and 55° C. Fractions were collected either at five-minute intervals or for individual peaks. Fractions were diluted with PBS and assayed for activity on the DC assay. The bulk of the fractions were flash frozen in liquid nitrogen and stored at −80° C.

Results

Enriched or Isolated ARP:

Small intestine tissues were obtained approximately once per week, typically from six freshly slaughtered cattle. The extraction & centrifugation, Procipitate™ & Cleanascite™, and ultra-filtration steps produced a soluble mixture of macromolecules with the approximate size range of 10-300 kD. This material was non-toxic, could cure S-180 tumors in mice, induce NK cytotoxicity in vitro, induce IFNγ in NK cells in vitro, and induce IL-12 release from dendritic cells in vitro. The solution was sampled for mycoplasma and bacterial testing (MSU Animal Health Diagnostic Laboratory) and measured for LAL reactivity. It was prepared for size exclusion (Stage 2) purification by concentration on ultrafiltration membranes. Separation on the Superdex™ molecular sieving column yielded activity confined to a single region, which is centered around 20-30 kD.

To enhance purity of Stage 2 (size exclusion purification) material and reduce any endotoxin burden, the concentrated active fractions of the 1st Superdex™ separation were applied to the column again. The central portion of the peak in the re-run was retained and denoted BBX-01 and used in the 1st leg of the phase 1 clinical trial approved by the FDA. This material was sterile filtered and concentrated on ultrafiltration membranes prior to sterile filling in dosage forms at the GMP formulating facility at the University of Iowa.

DEAE ion exchange chromatography was used to purify Stage 2 material into Stage 3 material. The active portions of the re-run material from the Superdex™ separations were applied to a freshly cleaned DEAE Sepharose™ column. Due to the high ionic strength (0.15M) of the Stage 2 material, the majority of the protein passed through the column unbound. This is denoted Fraction A. The bound material was eluted in two steps of increasing ionic strength (0.2M and 0.5M). The first elution is denoted Fraction B and the second, Fraction C. Two types of activity have been detected in Fractions A and C, respectively, but Fraction B has routinely exhibited weak activity. The activity of Fraction A is associated with induction of high levels of IFNγ, which was proved to be IL18. Fraction C contains the majority of the NK-inducing activity and antitumor activity and is the only fraction that activates dendritic cells. The C fraction contains only 5% of the protein and is denoted BBX-01c. This material was used for the 2nd leg of the human phase 1 clinical trial.

Purification of ARP: Modified Method

The modified purification procedures were developed to enhance recovery and specific activity. The modified procedure increased the yield of ARP at the final step possibly by as much as $10^2$-$10^3$ fold. The first part of the procedure used an implementation of a long-standing method to process crude material utilizing ammonium sulfate fractionation. It was done in two steps. The first step removed approximately 50% of protein contaminants together with some other material, and inhibited proteolysis of ARP by internal proteases, while the second step precipitated ARP allowing to reduce the volume and speed up further purification steps, also minimizing proteolysis. Prevention of proteolysis was most probably responsible for the yield increase and for the increase in the average length of sequenced ARP peptides, which allowed identification of the *Eimeria* surface antigen by database searches. Experiments to find the best conditions yielded 45% saturation ammonium sulfate for the first precipitation, followed by 80% saturation for the second precipitation. The activity was recoverable in the final precipitation pellet, which was resuspended for further purification.

Figure 2A:
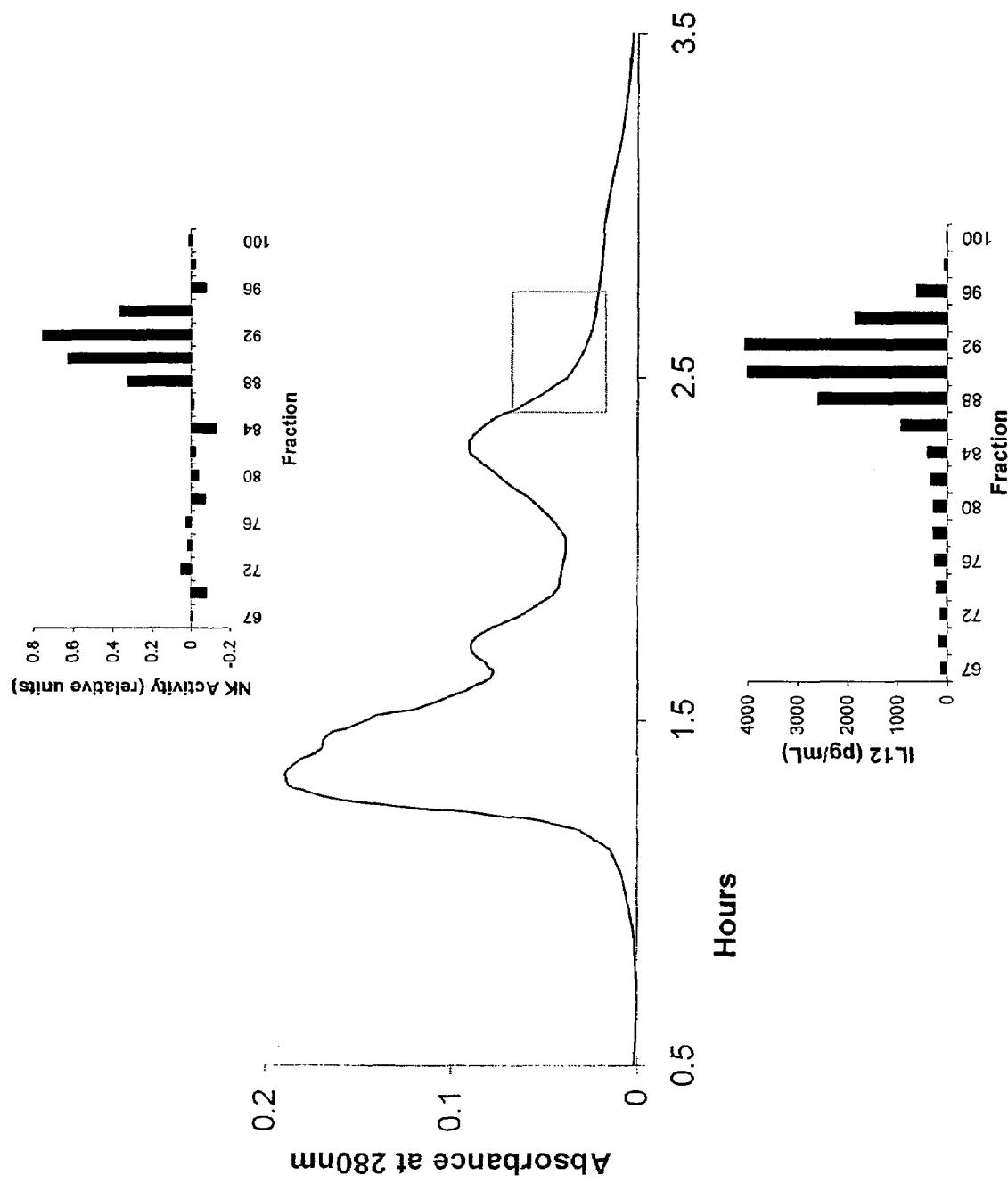
FIG. 2. (A) Example of a molecular sieving chromatography step using Superdex™ 75 and the activity on the NK and DC assays. (B) Typical total recovery from the purification scheme outlined in section 6, at the end of the Superdex™ size exclusion step. The activity within the crude material (corrected for total volume) is shown on the far left. The total recovered after Superdex™ chromatography is shown at the far right.
Figure 2B:
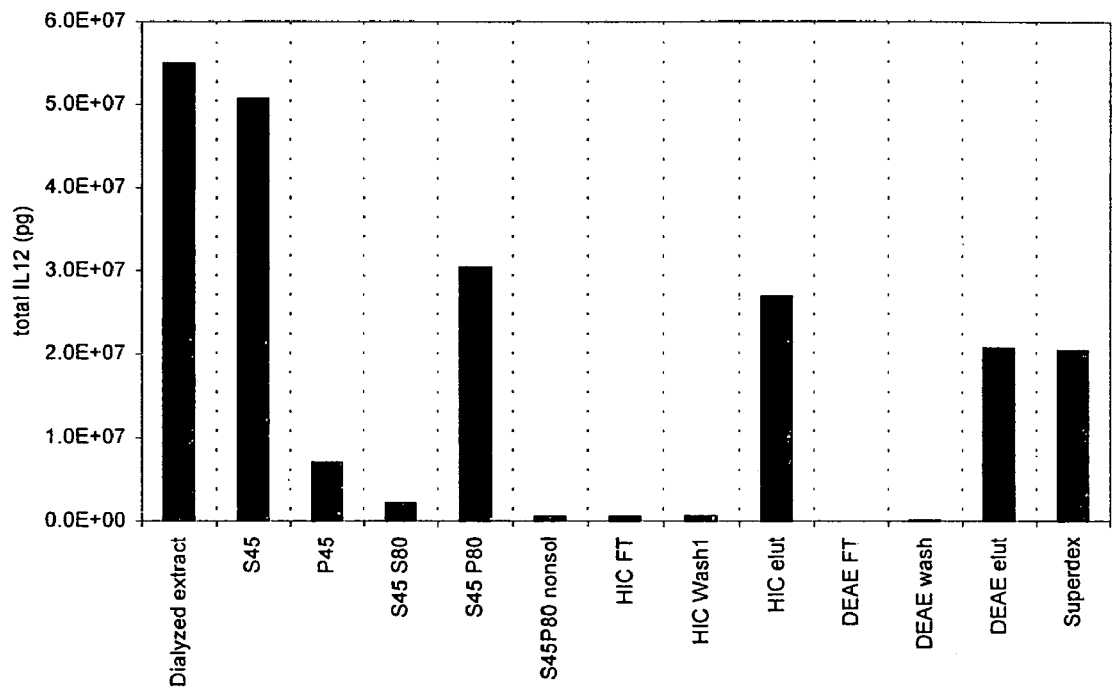

To reduce the macromolecular load prior to Superdex™ size-exclusion chromatography, two bulk processing steps were incorporated. The first step used an HIC column, which is compatible with the re-dissolved pellet of the ammonium sulfate fractionating process. A large amount of inactive material, particularly nucleic acid, was removed in the flow-through and wash. The active material was eluted after a change to a buffer free of ammonium sulfate. The elution was processed in a similar fashion on DEAE ion exchange chromatography where the flow-through and wash were discarded. The elution at higher NaCl concentration was retained, concentrated on a membrane pressure cell, and added to the Superdex™ column and the activity was eluted in a region of low absorbance (FIG. 2(A)). The total recovery of activity, for a typical batch (I week) is shown in FIG. 2(B). Specific activity (with respect to protein content) was determined on the retained fractions from each step in the purification (Table 3). Approximately 7000-fold purification was reached at the end of the Superdex step.

TABLE 3

Purification steps that were performed on each batch

| Purification Step | Activity Location | Activity Recovery | Total Protein | Sepcific Activity |
|---|---|---|---|---|
| Extract | Supernatant | 100 | 25504 | 1.0 |
| 45% Ammonium Sulfate cut | Supernatant | 102 | 11684 | 2.2 |
| 80% Ammonium Sulfate cut | Pellet | 80 | 11035 | 1.8 |
| Hydrophobic Interaction Step Elution | PBS Elution | 59 | 6683 | 2.2 |
| DEAE Step Elution | Salt Elution | 65 | 460 | 36.2 |
| Size Exclusion (Superdex ™) Chromatography | Selected Fraction | 62 | 2.3 | 6820.0 |

Since bacterial endotoxin was always a contaminant from small intestine extracts, the endotoxin levels were monitored with the LAL assay (see section 13) at each step in the purification. This is shown in FIG. 2(B) for the steps shown in FIG. 2(A). Endotoxin levels are reduced approximately 1000-fold resulting in final levels that are well below those that can interfere with the DC assay (see section 12.3, threshold of 1000 U/mL for minimal DC activity).

To obtain enough material for final purification, pools were created that contained the extracts from 21 cattle intestines. These were pre-selected for high activity in the crude homogenate supernatants and processed three-at-a-time. Seven batches of 3 intestinal preparations were combined, concentrated, cleared of calcium binding proteins and designated as a pool. Four such pools were created. The first pool was used for method development and the second pool was used to obtain the first sequenceable product.

Figure 3A:
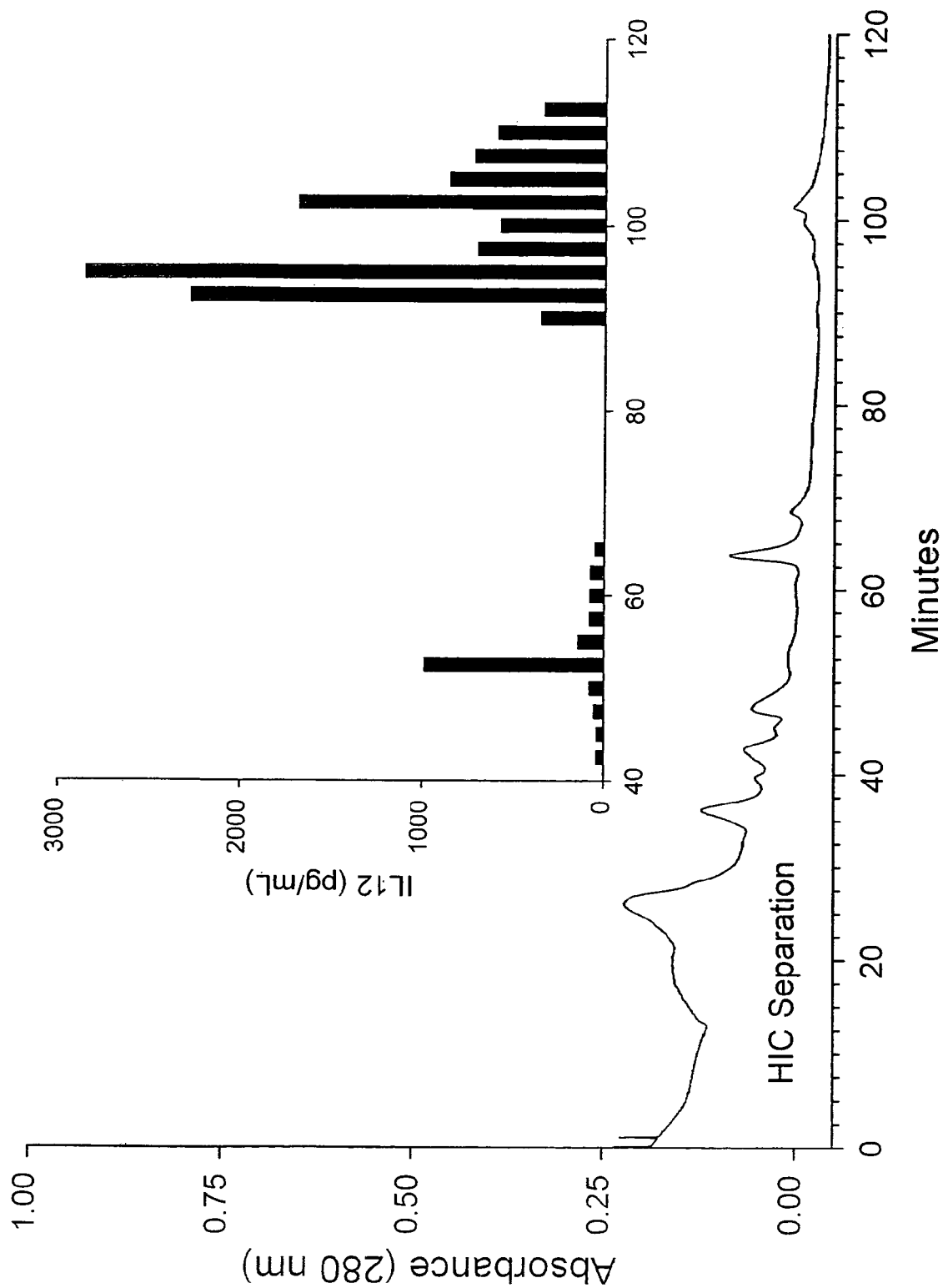
FIG. 3. (A) HIC gradient chromatography of BBX after Calcium-binding protein removal step. (B) DEAE gradient chromatography of the active fractions from the HIC gradient. (C) C8 reverse phase gradient of the active fractions from the DEAE gradient. (D) Correlation of absorbance and activity in C8 active fractions.
Figure 3B:
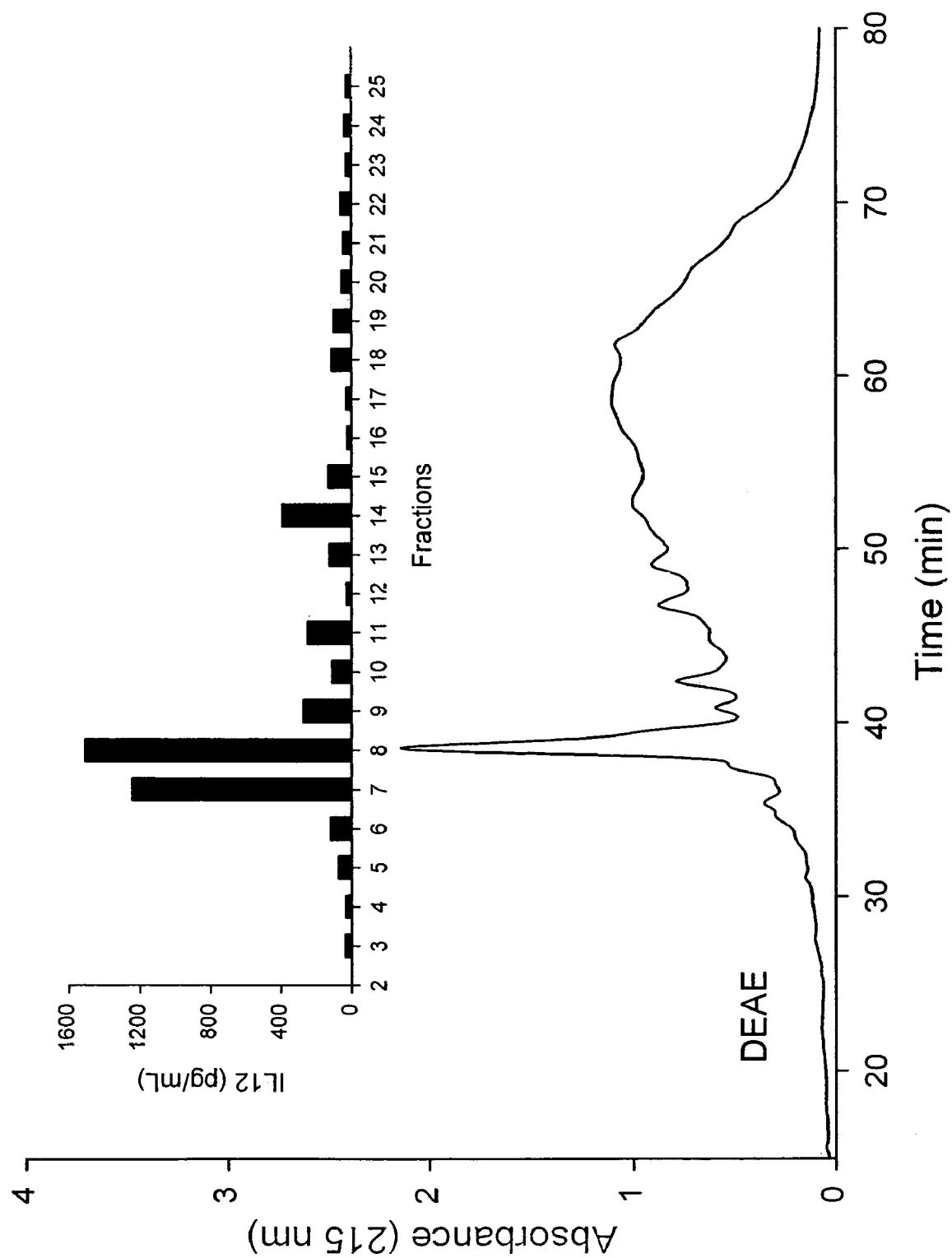
Figure 3C:
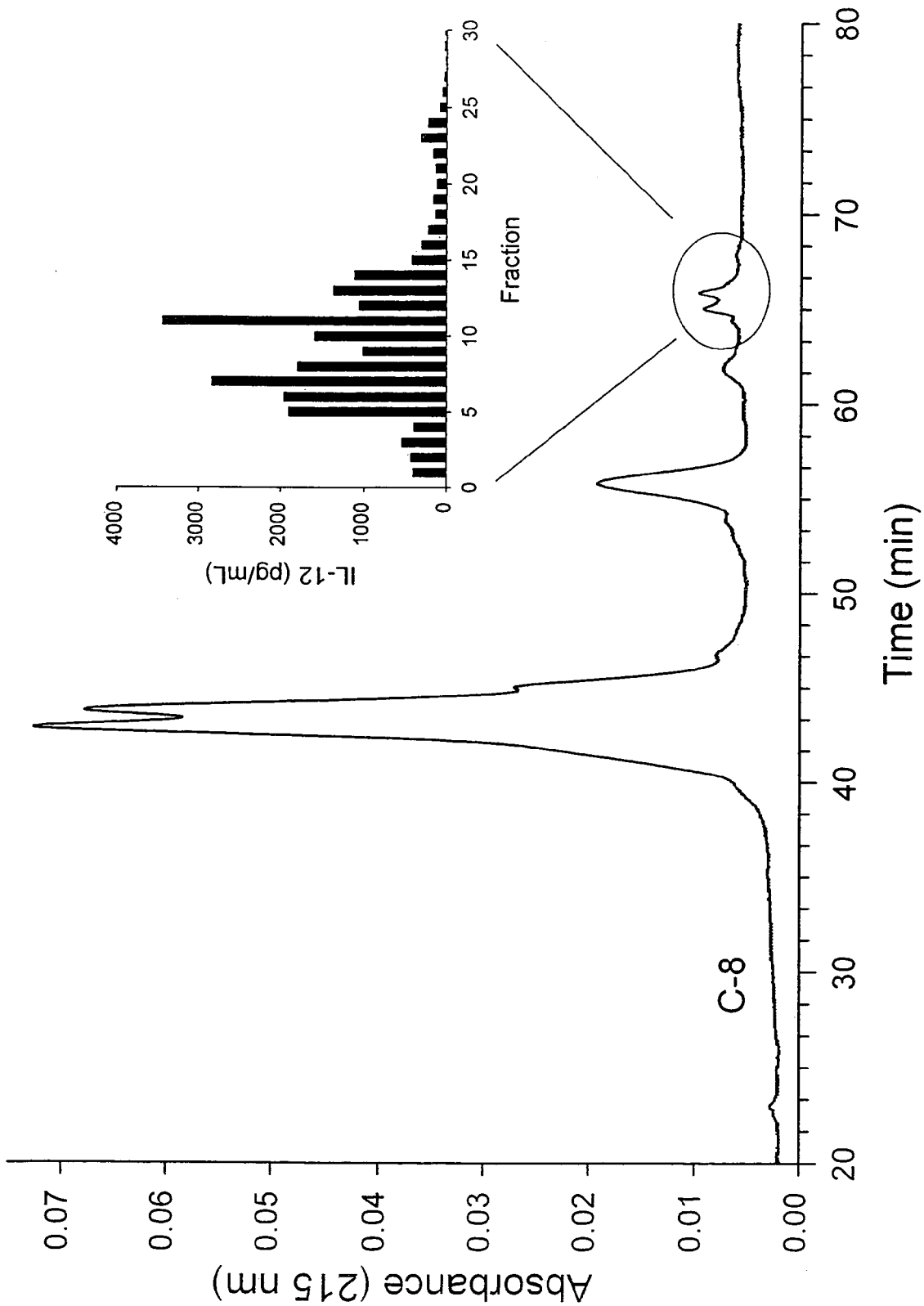
Figure 3D:
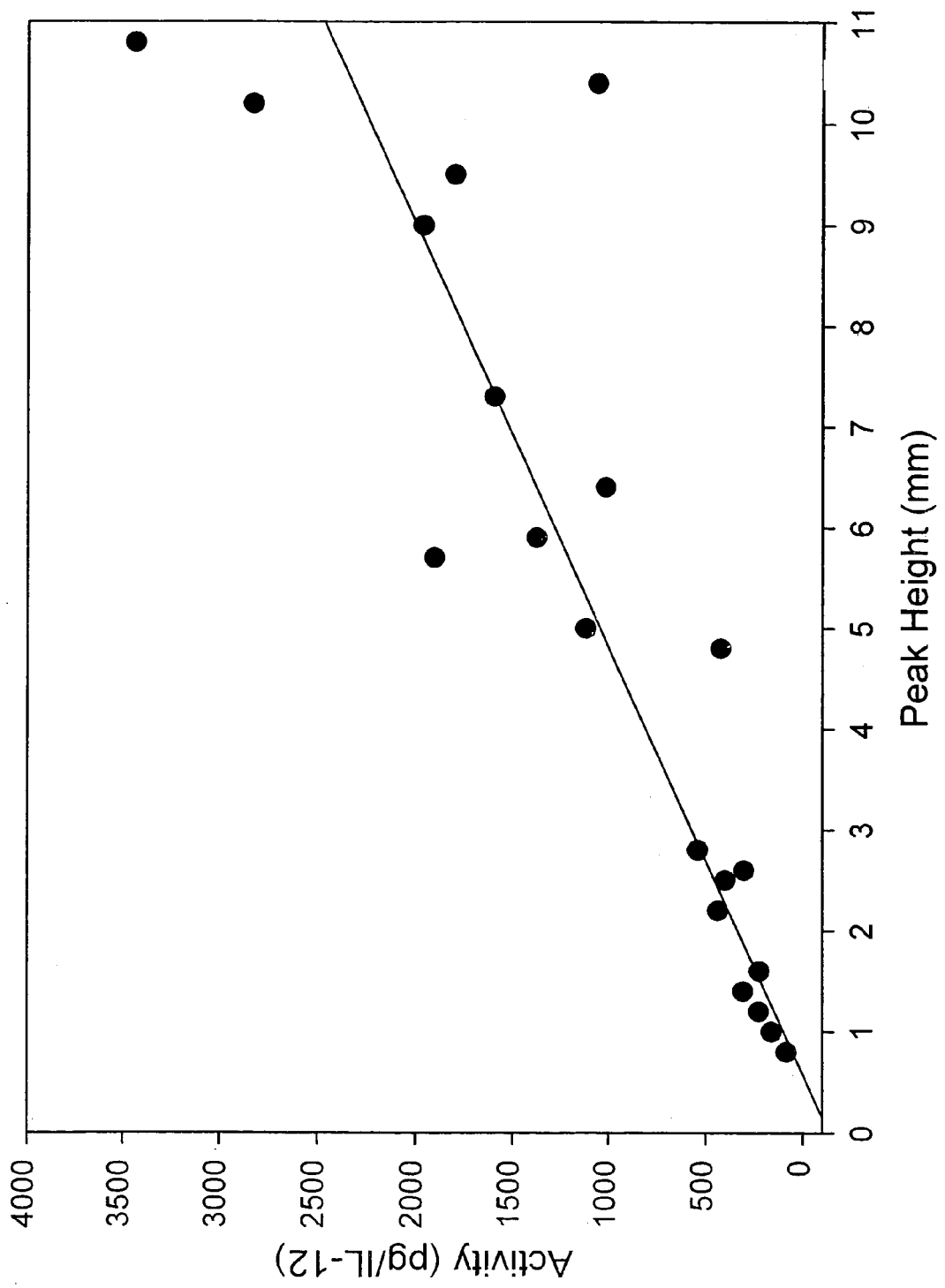

To obtain a purified product, a pool was initially separated on an HPLC HIC column, one-half of the pool at a time. The activity was located near the end of the chromatogram (see FIG. 3(A)), which is indicative of a moderately hydrophobic molecule. Some earlier activity was occasionally detected, but was weak and sporadic. The active fractions were dialyzed to remove ammonium sulfate and were applied to an HPLC DEAE column in 0.15M NaCl. A NaCl gradient was applied and the activity eluted with a major peak near 0.3M ionic strength. The chromatogram and activity are shown in FIG. 3(B). Three DEAE runs were required to process the active material from the HIC. The pooled active region was applied to the C8 reverse phase HPLC column and eluted with an aqueous-acetonitile gradient (FIG. 3(C)). The activity eluted near 40% acetonitrile on a slow, shallow gradient elution protocol. Fourteen separations were performed to process the material from the DEAE separation. The activity was associated with two major neighboring peaks and two or three minor peaks or shoulders. This appeared to represent minor variations in the molecule, but these differences have not been quantified. The question of purity of these active fractions was addressed by plotting activity versus absorbance along a finely-sampled separation. This is shown in FIG. 3(D). The linear regression line is reasonably robust and the intersection near zero indicates the lack of contaminating molecules.

The first major peak, denoted alpha, was obtained from approximately one-half of the C8 separations and was concentrated by roto-evaporation, digested with trypsin, and submitted for peptide separation and Edman sequencing at the MSU Macromolecular Structure Facility. Considerable amount of the protein was apparently lost during the concentrating step. Four peaks generated sequence information, one of them containing two sequences from different regions of the bovine ARP. The information was still sufficient to begin searching database by using PattinProt program (PattinProt searching can be done, e.g., at the website phil.ibcp.fr (select NPS@, and then PattinProt)) and led to identification of ARP as one of the proteins in the mixture. Since the concentrating step involved the multiple transfer of collected fractions into a single tube, we considered that the loss of material must have resulted from protein sticking to the plastic conical tubes. Experiments demonstrated that to move the molecule between tubes required the addition of acetonitrile. Incorporating that methodology change separately on the $2^{nd}$ half of the alpha peak and the $1^{st}$ half of the second major peak (beta), generated much higher tryptic peptide quantities. These peptides provided sufficient sequences to extend searching the available public databases (e.g., BLAST, PattinProt) for sequence matches.

EXAMPLE 2

Identification of Sporozoite Antigen Protein

Protein sequencing services were provided by the Macromolecular Structure Facility at MSU (Edman procedure) and M-Scan Inc., West Chester, Pa. (MS-MS procedure).

Tryptic peptides for Edman sequencing were prepared using the following procedure. Active fractions, typically 1 mL, from several C8 separations were placed in microcentrifuge tubes and evaporated to near dryness under vacuum (Centrivap Concentrator, Labconco, Kansas City Mo.) at 35° C. All sample tubes were washed three times with 200 μL of 60% HPLC acetonitrile/40% HPLC water/0.1% TFA, each time reducing the volume to near dryness. After the third wash, all fractions were combined into a single microcentrifuge tube and were washed twice with 500 μL of HPLC water again reducing to near dryness after each wash. The combined sample, reduced to approximately 15 μL, was diluted to 125 μL in the digestion buffer (100 mM Tris (reagent grade, Sigma-Aldrich, St. Louis Mo.) pH 8.4, 2 mM $CaCl_2$). Trypsin (sequence grade, Sigma-Aldrich) was added to 2% (w/w) and the sample incubated at 37° C. for four hours. The pH of the sample was checked and an additional 50 μL of digestion buffer was added. Digestion was halted by flash freezing the sample in liquid nitrogen after 18-20 hours of digestion.

Purification of tryptic peptides was performed at the MSU Macromolecular Structure Facility on a microbore reversed phase HPLC using a Vydac C18 column, 5 μm, 300 Å, ID 800 μm, using a linear gradient from 5% H to 70% H in 160 minutes. G buffer consists of 0.1% TFA in water. H buffer consists of 90% HPLC grade Acetonitrile, 10% HPLC Grade water, and 0.985% TFA. Absorbance was monitored by a Kratos Analytical Spectroflow 783 detector at 214 μm. N-terminal sequencing of selected peptide fragments was performed on a Perkin Elmer/Applied Biosystems 494 cLC Procise Protein Sequencer which utilizes Edman Degradation chemistry.

Samples for MS-MS analysis were isolated and digested as described above. Two samples were sent to M-Scan Inc. (West Chester, Pa.); a Trypsin autodigest and digested sample. Each sample was applied to a C18 ZipTip and desalted by washing with 0.1% aqueous formic acid. Peptides were eluted using a solution of 60% acetonitrile, 40% water containing 0.1% formic acid. The peptide mixture obtained from each sample was analyzed initially by positive ion ESI-MS using a Sciex Q-Star/Pulsar mass spectrometer. The sample was introduced using a nanospray needle and data was collected in the MCA mode. The same instrument and sample introduction method were used for the MS/MS sequencing.

The amino acid sequences from the tryptic peptides, generated by the Edman and MS/MS procedures, are shown in Table 4. Several robust reads were obtained from various peaks using the Edman procedure, although some reads were the convolution of two or more separate sequences and most were contaminated, resulting in multiple reads in almost every position of every peptide. Most commonly used programs, like BLAST, could not perform a search with such complicated data. Therefore, the sequences were assigned by usage of PATTINPROT program (Network Protein Sequence Analysis (NPS@); TIBS 2000, 25: 147-150). Multiple amino acid reads at each position were searched by the program at the desired level of similarity (usually higher than 70%), and a list of proteins matching those parameters was generated. Since the list normally contained several dozen of different entries, it was searched again with sequence of a second peptide. This procedure usually produced a list containing only the entries related to sporozoite antigen. In case any identifiable contaminants were on the first list (trypsin, keratin, albumin), their sequences were subtracted from the amino acid reads and the search repeated with the remainder reads. Once the *Eimeria* sporozoite antigen was considered as a likely candidate, some of the multiple reads were deconvoluted by finding a match for one possible sequence and then determined if the remaining sequence also matched a different part of the protein. The strategy was successful in multiple cases, and resulted in generating several most probably peptide sequences for bovine ARP.

TABLE 4

Probable sequences generated from Edman tryptic peptides or MS/MS analysis

| Fragment source | Generated sequence |
|---|---|
| $\alpha_1 18, \alpha_2 18/\beta_1 18^1$ SEQ ID NO:31 | EWLVDTGKVF |
| MS/MS SEQ ID NO:32 | LVDTGK |
| $\alpha_2 25$ SEQ ID NO:33 | VFAGGVASIADG |
| $\alpha_2 25$ SEQ ID NO:34 | AGYQIESVQEDNGTVQ |
| $\alpha_2 35, \alpha_2 32/\beta_1 30, \alpha_1 28, \beta_1 32$ SEQ ID NO:35 | [3]MFGASTDSGGDPNAELVQYN |
| MS/MS[2] SEQ ID NO:36 | [3]MFGASTDS |
| $\alpha_2 13/\beta_1 14$, MS/MS SEQ ID NO:37 | APDGVYIGGVK |

TABLE 4-continued

Probable sequences generated from Edman tryptic peptides or MS/MS analysis

| Fragment source | Generated sequence |
|---|---|
| $\alpha_1 18, \alpha_2 18/\beta_1 18$ SEQ ID NO:38 | GGGFLIK |
| $\alpha_2 50/\beta_1 46, \alpha_2 49/\beta_1 45$ SEQ ID NO:39 | TPNENIAIALYDEEKEQNKA |
| MS/MS SEQ ID NO:40 | TPNXXXXIALYDEEKEQNK |
| $\alpha_2 53/\beta_1 49, \alpha_1 40, \alpha_1 37$ SEQ ID NO:41 | ADALTTALNFADFLYQ |

[1]Reads of combined peptides are marked with "/", e.g., $\alpha_2 18/\beta_1 18$.
[2]MS/MS method cannot distinguish between I and L, and often between Q and K, so all the positions with one of those amino acids are not certain from MS/MS reads.
[3]Since tryptic peptides were used, the position preceding the first readable amino acid is either R, or K, but it cannot be conclusively determined which one of these two is the correct amino acid.

Possible errors in amino acid assignments cannot be eliminated, however, due to the quality of some of the data. Table 5 lists possible errors (where plain text represents highly confident data, i.e., multiple read and multiple samples; underlined text represents lower confidence; and bold text represents lowest confidence):

TABLE 5

Possible errors in SEQ ID NO: 3, 4, 5, 6 and 7

| SEQ ID NO:3 | Glu Trp Leu Val Asp Thr Gly Lys Val Phe Ala Gly Gly Val Ala Ser Ile Ala Asp Gly[1] |
| SEQ ID NO:4 | Arg Met Phe Gly Ala Ser Thr Asp Ser Gly Gly/Asn Asp Pro Asn Ala Glu Leu Val Lys Ala/Val Gly/Phe Tyr/Ala Gln/Gly Ile/Gly Glu/Val Ser/Ala Val/Ser Gln/Ile Glu/Ala Asp Asn/Gly[2] |
| SEQ ID NO:5 | Gln Ala Ile Val[3] |
| SEQ ID NO 6 | Ala Pro Asp Gly Val Tyr Ile Gly Gly Val Lys[4] |
| SEQ ID NO.7 | Gly/Glu Gly/Trp Gly/Leu Phe/Val Leu/Asp Ile/Thr Lys/Gly Thr Pro Asn Glu Asn Ile Ala Ile Ala Leu Tyr Asp Glu Glu Lys Glu Gln Asn Lys Ala Asp Ala Leu Thr Thr Ala Leu Asn Phe Ala Asp Phe Leu Tyr Gln[5] |

[1]Lower confidence: two reads convoluted in a single sample. The read with identity to an Eimeria acervulina conserved region is assigned here (see SEQ ID NO:4 for other read).
[2]Lowest confidence: two reads in one sample. The second choice in each case was assigned to SEQ ID NO:3, due to match in Eimeria. The first choice is assigned here, due to partial match to Eimeria.
[3]Lowest confidence: Low S/N (signal to noise ratio) and derived from only one sample.
[4]Lower confidence: slightly lower S/N, but no other amino acid reads present for these positions.
[5]Lower confidence: obtained from only one sample, but S/N is good. Lowest confidence: deconvoluted data from two samples containing two sequences. The second choice in each case was assigned to fragment 1, due to match with Eimeria. The corresponding region in fragment 1 was also corroborated by MS/MS data making it high confidence. The first choice from each double read is assigned here, due to match to Eimeria. This makes the sequence fairly reliable, but the three Gly have a low S/N.

The second half of the beta peak was sent to M-Scan Inc. for MS/MS sequence analysis. Several peptides were identified, and the match to the *Eimeria* antigen was verified. A rather long variable region was also detected, which still matched the known ARP sequences with low similarity and was therefore assigned to a portion of molecule.

When all peptide sequences were evaluated, evidence for a homologue to the sporozoite antigen was overwhelming. The alignment to the *Eimeria* 19 kD antigen 3-1E is shown in FIG. 4. Most of other sequences could be assigned to the understandable contaminants, keratin, trypsin, and bovine albumin, though a small number of the generated sequences remained non-assigned.

EXAMPLE 3

Extraction of Activity from *e. tenella* Oocysts

Oocysts can be obtained from intentionally infected animals, from barnyard soils, or from feces of infected animal. Methods of isolating oocysts are known in the art. See, e.g., Tomley, Methods: A companion to Methods in Enzymology 13: 171-176 (1997), which is incorporated herein in its entirety by reference. For example, one protocol that can be used to obtain sporulated oocysts is as follows: infect 6- to 8-week old Light Sussex chickens by oral dosing with between $10^3$ and $6 \times 10^3$ sporulated oocysts and recover oocysts from the ceca 7 days later using either enzymatic or chemical treatment (e.g., remove and cut ceca, add phosphate-buffered distilled water, pH 8.0, and homogenize to a fine pulp with a commercial blender; add trypsin (Difcon 1:250 powder) to a final concentration of 1.5% w/v; incubate at 41° C. for 30 min, strain through two thicknesses of muslin, and centrifuge at 1000 g for 10 min; discard the supernatant, replace with a similar volume of saturated sodium chloride solution, mix well, and centrifuge again; collect the oocysts from the top of the salt using a syringe fitted with a cannula or a long needle; and wash them repeatedly by centrifugation and resuspension in buffered water) and then sporulate the oocysts (e.g., suspend oocysts in 2% (w/v) potassium dichromate and incubate at 28-30° C. for 48 hours with forced aeration; remove the potassium dichromate by repeated centrifugation and dilution in water; add sodium hypochlorite to a final concentration of 10% (v/v) and incubate on an ice bath for 5-10 min; centrifuge and mix the pellet with saturated sodium chloride solution; overlay the tube contents with distilled water and centrifuge for 5 min; collect clean, bacteria-free oocysts from the interface of the salt and water into sterile distilled water and wash repeatedly by centrifugation into water).

Approximately $3 \times 10^8$ sporulated oocysts (a gift of Dr. Ray Fetterer, USDA) was suspended in 9.0 mL of PBS and centrifuged for 10 minutes at 200×G. The supernatant ("wash") was removed and retained. The pellet (~0.5 mL packed volume) was suspended in 0.5 mL 30 mM Hepes and homogenized on ice with a glass homogenizer for a total of approximately 15 min (prep 1). Most of the oocysts were broken, releasing sporocysts that remained largely intact. A few less rigid, smaller structures (perhaps sporozoites) were observable. Continued homogenization did not appear to appreciably increase the number of these structures. The homogenate was transferred to a microcentrifuge tube and centrifuged for 20 minutes at 6000×G. The supernatant (~200 μg/mL protein) was sterile filtered (0.22 μm) and designated the soluble protein extract of *E. tenella* sporulated oocysts (EtH-1).

In a second preparation, the homogenate was divided into 3 microcentrifuge tubes each with a total volume of approximately 500 μL. Each suspension was sonicated with 30 1-second bursts using a Fisher Scientific Ultrasonic Dismembrator™ (Model 100), with care taken to keep the homogenate cooled during the sonication. Approximately 80% of the released sporocysts were disrupted into non-light refractory "disrupted" sporozoites. The suspensions were pooled and microcentrifuged for 20 minutes at 6000×G. The resulting supernatant was retained, sterile filtered, and designated EtH-2. The pellet was retained and stored at 4° C. for future processing (see $3^{rd}$ extract).

The starting material for the 3rd extract of *Eimeria* tenella sporulated oocysts was the residual pellet of the 2nd extract preparation. This pellet was stored at +4° C. for 18 days. The pellet material was suspended in 500 μL 30 mM Hepes and transferred to a 2 mL beadbeater tube containing approximately 1.3 mL of 0.5 mm glass beads (BioSpec Products #11079105). The tube was then completely filled with 30 mM Hepes and processed in a Mini-Beadbeater (BioSpec Products Model #3110BX) for 2 cycles of 3 minutes each at 4800 cpm. The tube was placed on ice for 15 minutes in between the 3 minute cycles to prevent excessive heating. The suspension was microcentrifuged briefly and the supernatant was separated from the glass beads. This supernatant was microcentrifuged for 20 minutes at 8000×G and was filter-sterilized and tested in the DC/mLl2 release assay for activity.

Figure 5A:
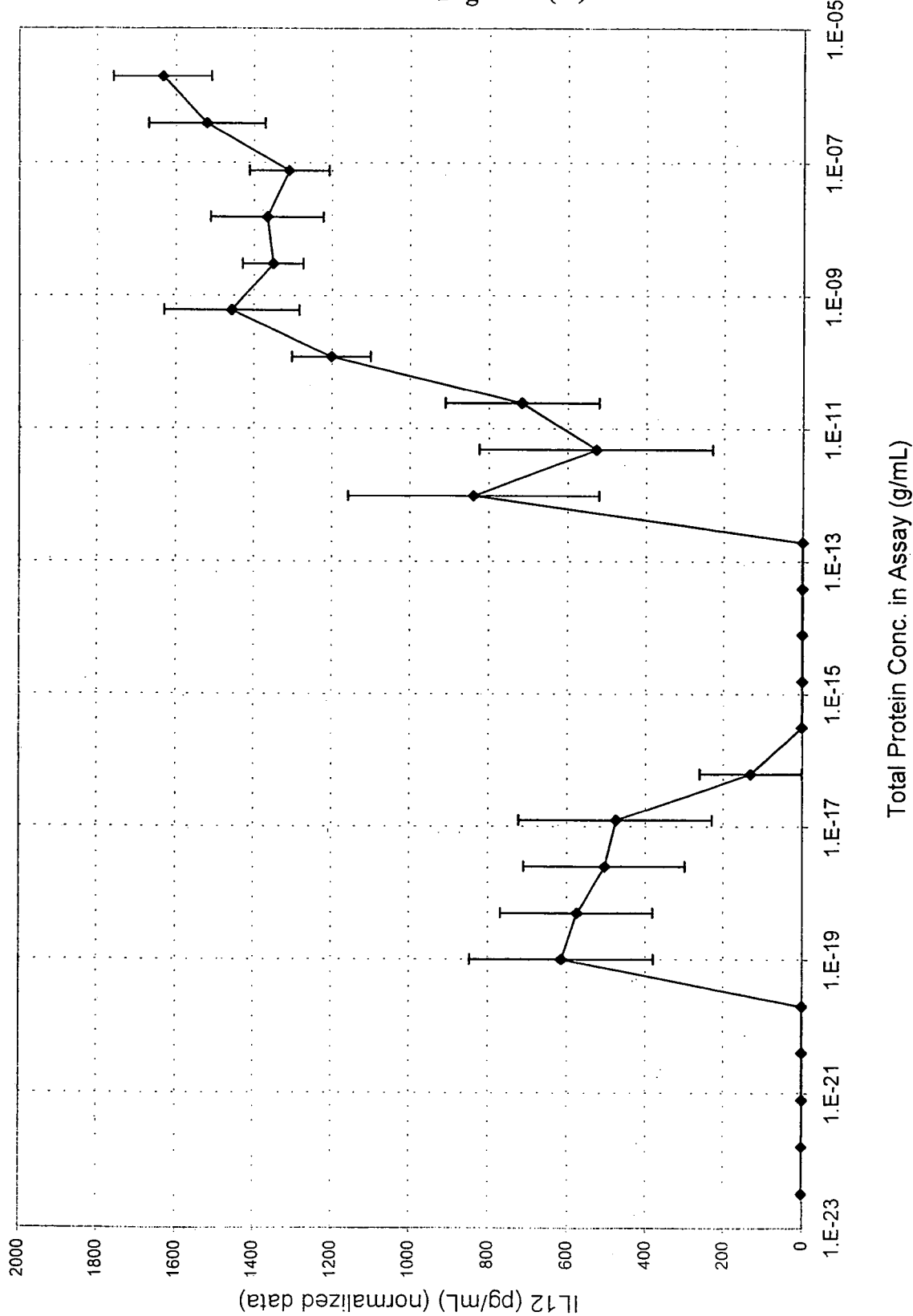
FIG. 5. (A) Dilution profile of unpurified *E. tenella* extracts on the DC assay. Samples were prepared according to first extraction of section 8. Five replicate dilution curves, spanning two separate DC assays, were averaged. The error bars indicate the standard deviation of the 5 replicates. (B) C8 HPLC separation of the second *E. tenella* extract and the corresponding DC assay activity of the fractions.

The supernatants from the partially homogenized and washed mixture of broken oocysts, sporocysts, broken sporocysts, and sporozoites contained a large amount of DC activity in a small amount of protein. As shown FIG. 5(A), the first extract supernatant yielded dilution curves that were active to low picogram levels of total protein. For a 20 kD protein, this is approximately 50 fM. This assumes that all the protein in the extract is active, which is unrealistic. Therefore, the active molecule is probably active below this level. An unusual second region of activity appeared in all five replicates on two different assay days, which may due to possibility that the active molecule forms inactive complexes (dimer, trimer, multimer) with itself or another molecule, such that its active site is sequestered. Upon sufficient dilution, this complex dissociates and activity reappears.

Figure 6:
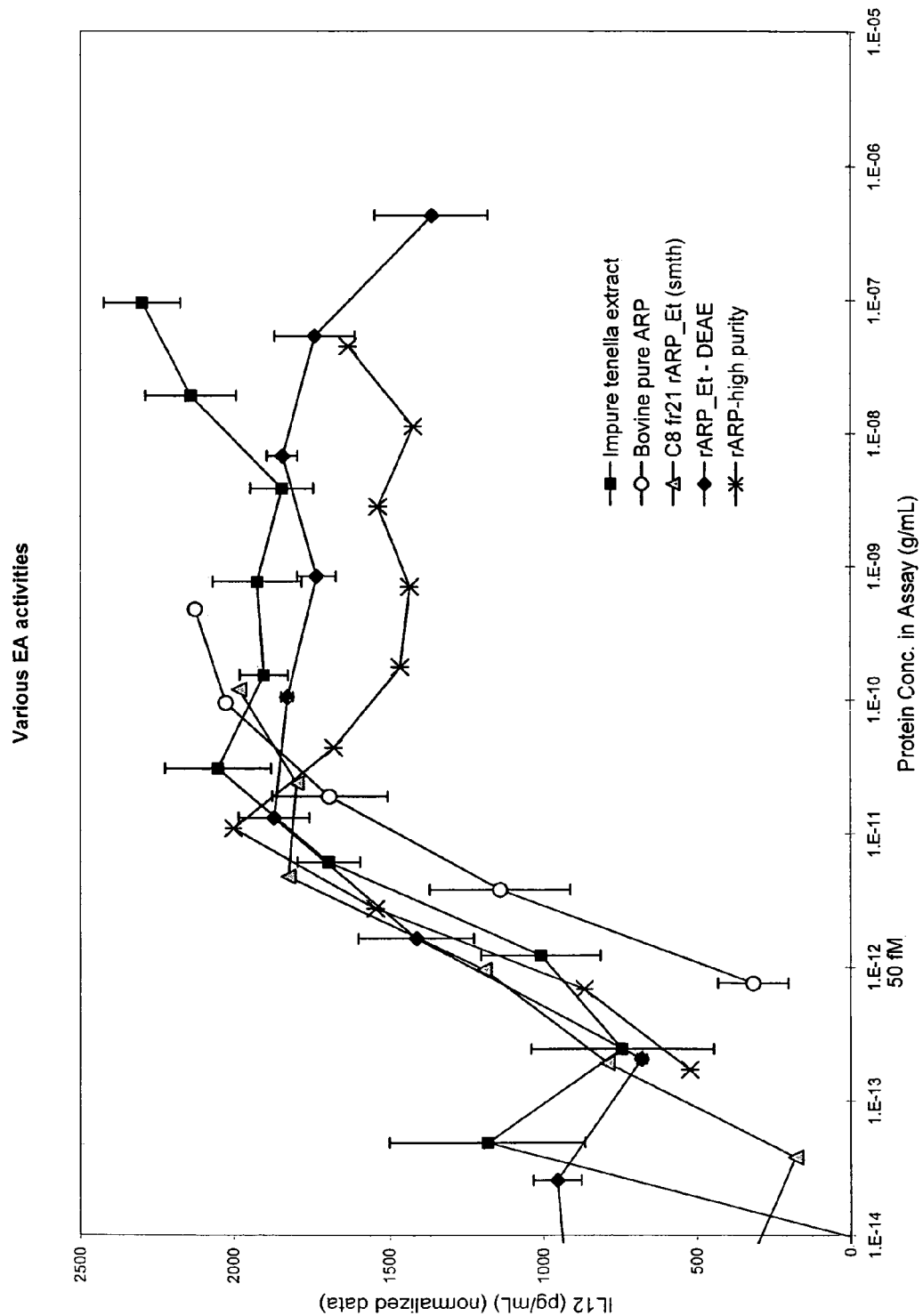
FIG. 6: Dose/response curves for various sources of ARP. The impure *E. tenella* extract and the DEAE-purified recombinant sample contain ARP that is about 4% of total protein weight. The pure bovine extract and the recombinant *E. tenella* protein are pure but approximately 95% denatured from the reverse-phase chromatographic conditions. These estimates were used to calculate protein concentration in assays. The highly pure rARP sample was obtained from size-exclusion chromatography from the DEAF active fraction. Its purity and protein content were evaluated on a small sample by C8 reverse-phase chromatography and its activity was plotted without corrections for concentration. Response curves were normalized to similar maximal levels.

A second extract utilized sonication to facilitate the breakage of oocysts and sporocysts. This did substantially change the yield of active material and there was a repeat of the reappearance of activity at high dilution. A third extract, utilizing the Bead Beater™ to break the cysts with micro beads, generated an anomalously high level of activity in the first DC assay, but subsequent assays were very similar to FIG. 6. The amount of dilution required to reach zero activity is truly remarkable. This extended dose/response may be related to the low dilution "hump" described above. If different size complexes, with different dissociation constants are releasing activity, then this long, flat response may result.

Figure 5B:
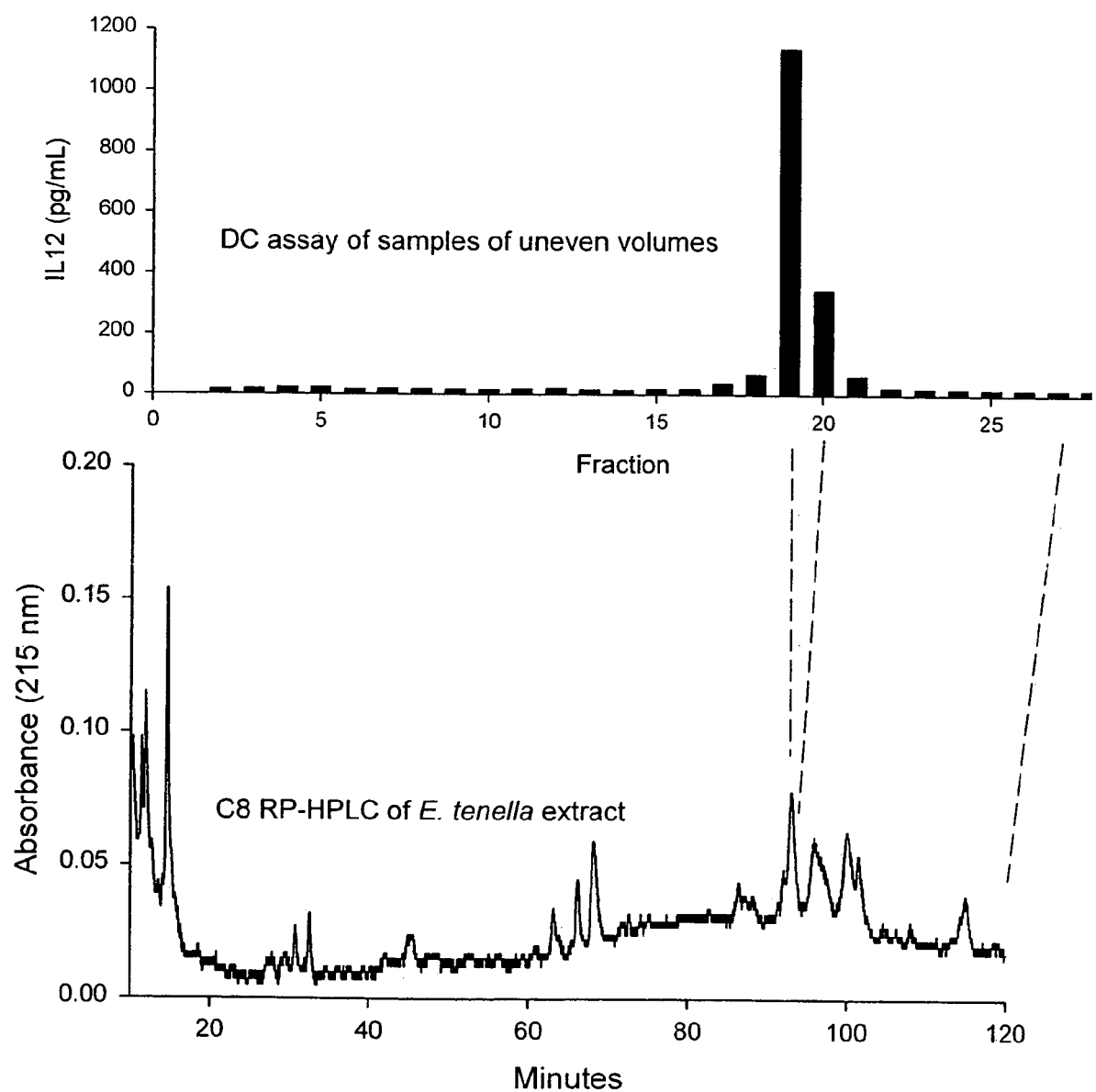

Samples of the extracts were separated on C8 HPLC using the same protocol as for the bovine extract. The chromatogram and activity are shown in FIG. 5(B). The position of the activity is shifted to higher retention time compared to the highly pure bovine molecule. This appears to indicate a higher hydrophobicity to the *Eimeria* molecule, when extracted directly from the protozoan.

EXAMPLE 4

Crude Membrane Preparation and Purification of the Membrane-Linked Form of ARP from the Sporozoites of *e. tenella*

Protocols (1) Disruption of Oocysts.

1 ml of suspension of oocysts at $3\times10^7$/ml in homogenization buffer (HB): 50 mM Tris pH 7.4, 1 mM PMSF, 50 μl/ml protease inhibitors cocktail and 10 mM $ZnCl_2$ (in some experiments) was homogenized for 20 minutes in glass homogenizer, followed by 15 freeze-thaw cycles (liquid nitrogen/37° C.) or by sonication (Fisher Scientific Ultrasonic Dismembrator, model 100) 10 seconds×36-45 bursts on ice with three freeze-thaw cycles. The homogenization resulted in almost complete oocyst breakage into sporocysts. Sonication resulted in almost complete breakage of all structures present except sporocyst walls.

(2) Membrane Sedimentation and Washing.

The cell homogenate was spun at 15000 g 15 min, 4° C. to pellet membranes. This centrifugation regime is sufficient to pellet also nuclei, other organelles, pelletable ARP aggregates and storage granules, if any. Organelles should be disrupted in further purification cycles in HB without $ZnCl_2$ Pellet was suspended in 1 ml of HB and centrifuged again. Centrifugation/resuspension was repeated once more with and 2-3 times more without 10 mM $ZnCl_2$ in the suspension buffer. The pellet obtained by this procedure with two washing cycles in the presence of 10 mM $ZnCl_2$ was used as a crude membrane preparation in immune-stimulatory activity test, described in Section 12.5.1.

(3) Release of ARP from the Membranes.

For purification of the membrane-linked ARP, the final pellet was suspended in 100 μl of HB without $ZnCl_2$ and incubated at 37° C. 1-4 hours with or without protease inhibitors and phospholipase C from *Bacillus cereus*, 16 U/ml.

(4) Membrane Sedimentation and Washing.

ARP released into solution was separated from the insoluble material by centrifugation as described in step 2, followed by two washing cycles. All three supernatants were combined.

(5) C8 Reverse Phase Chromatography.

Figure 18:
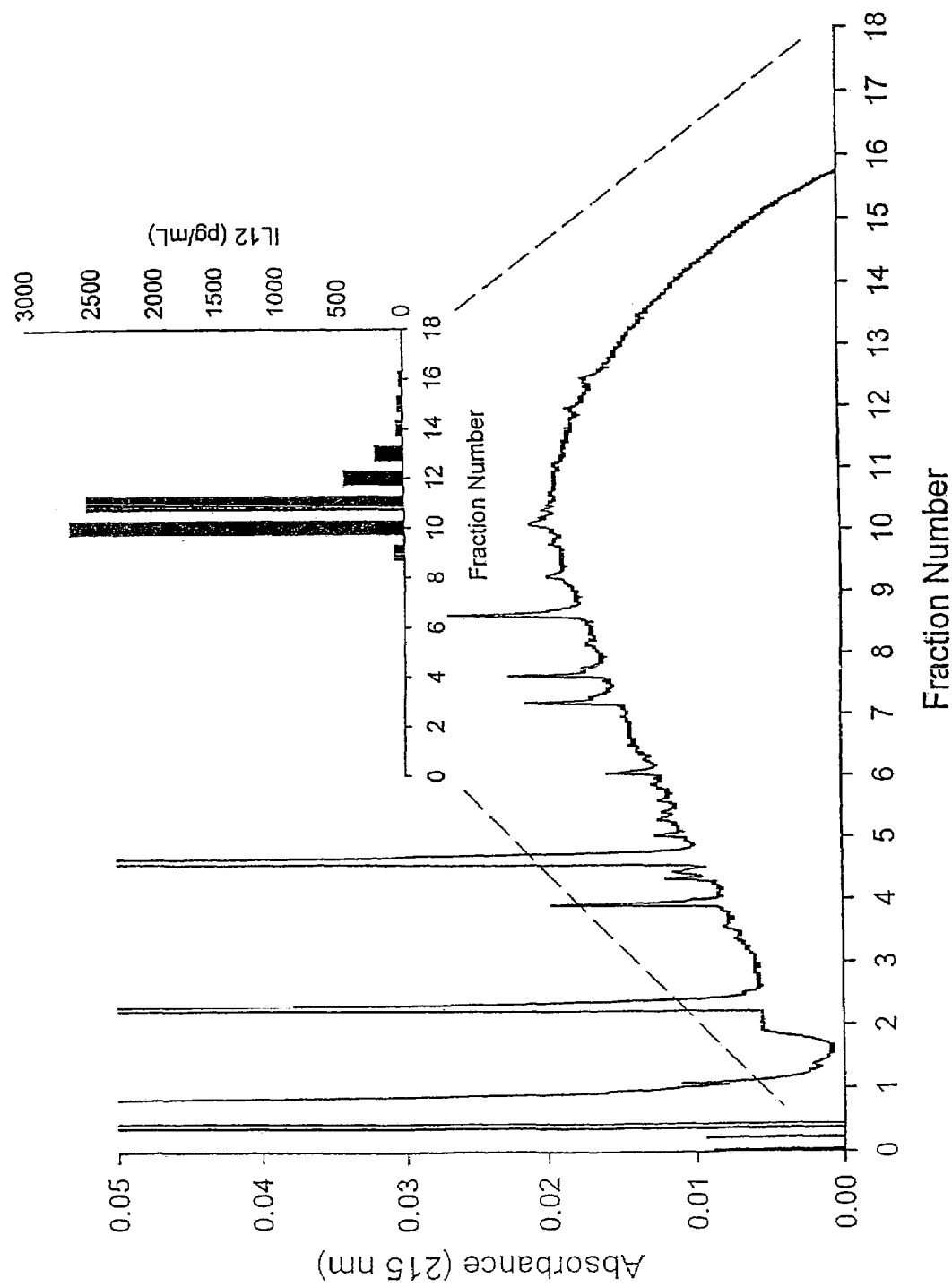
FIG. 18. C8 reverse phase chromatography of ARP released from the crude membrane preparation from *E. tenella* oocysts after incubation in 50 mM tris-HCl pH 7.4, 1 mM PMSF at 37° C. 4 hours (section 9).
Figure 21:
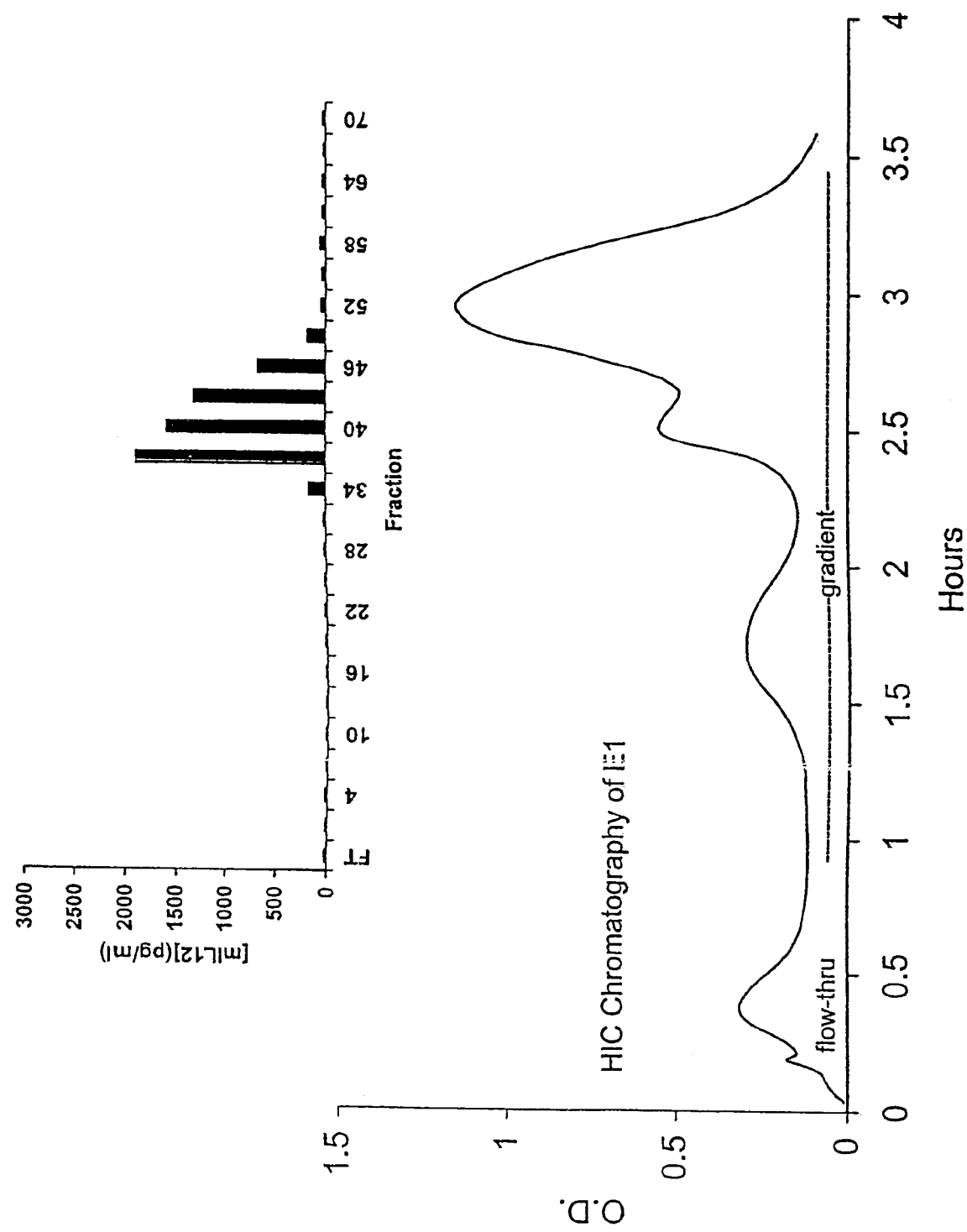
FIG. 21. Chromatogram of the HIC gradient chromatography separation of the 80% ammonium sulfate fraction obtained from the E1 clone extract and the corresponding DC assay activity profile.
Figure 22:
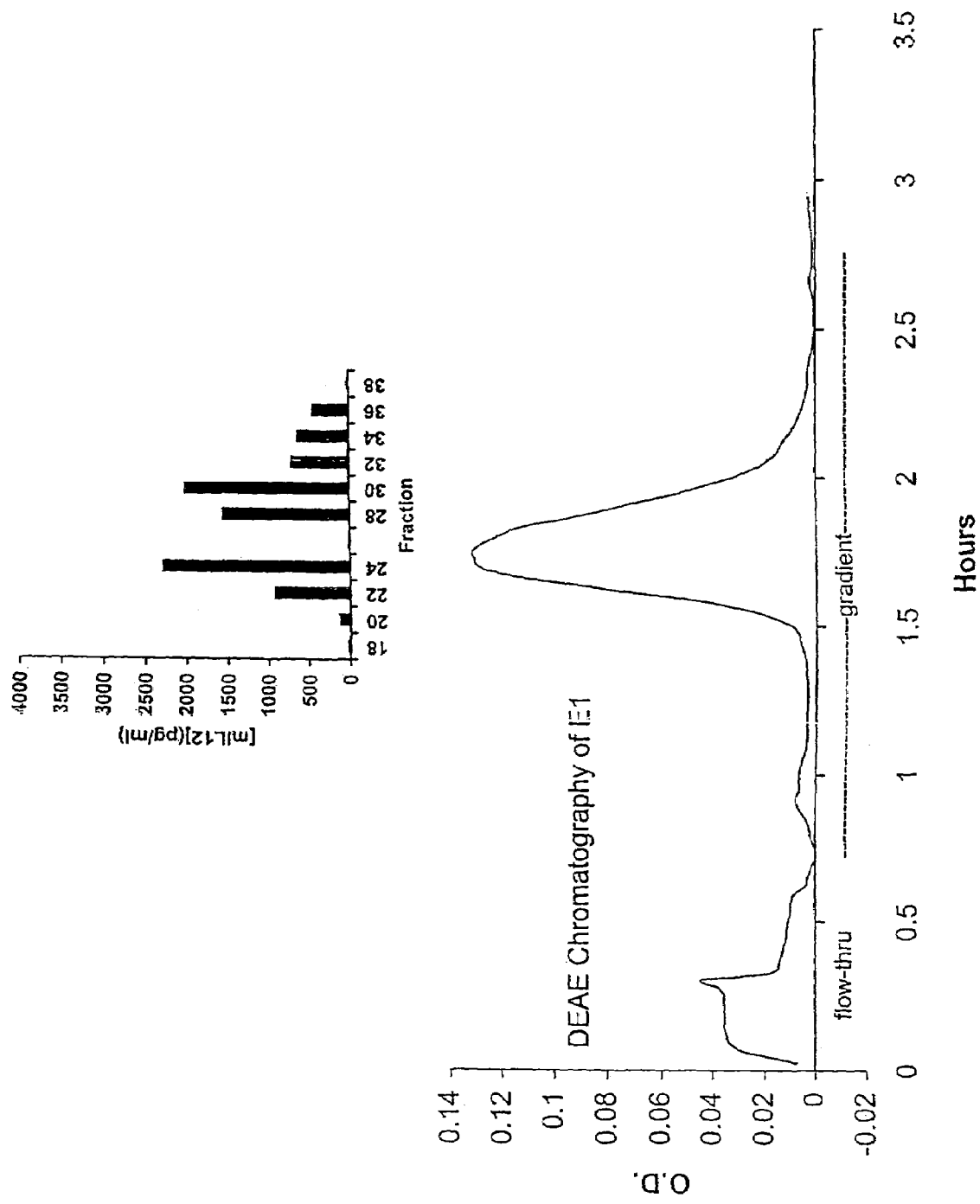
FIG. 22. Chromatogram of the DEAE gradient chromatography separation of the active fractions from the HIC chromatography of the E1 clone extract and the corresponding DC assay activity profile FIG. 23. Chromatogram of the Superdex isocratic chromatography separation of the active fractions from the DEAE chromatography of the E1 clone extract and the corresponding DC assay activity profile FIG. 24. Chromatogram of the C8 HPLC separation of a small portion of the pooled active fractions from the Superdex chromatography of the E1 clone extract. This indicates that the Superdex product is highly pure.
Figure 23:
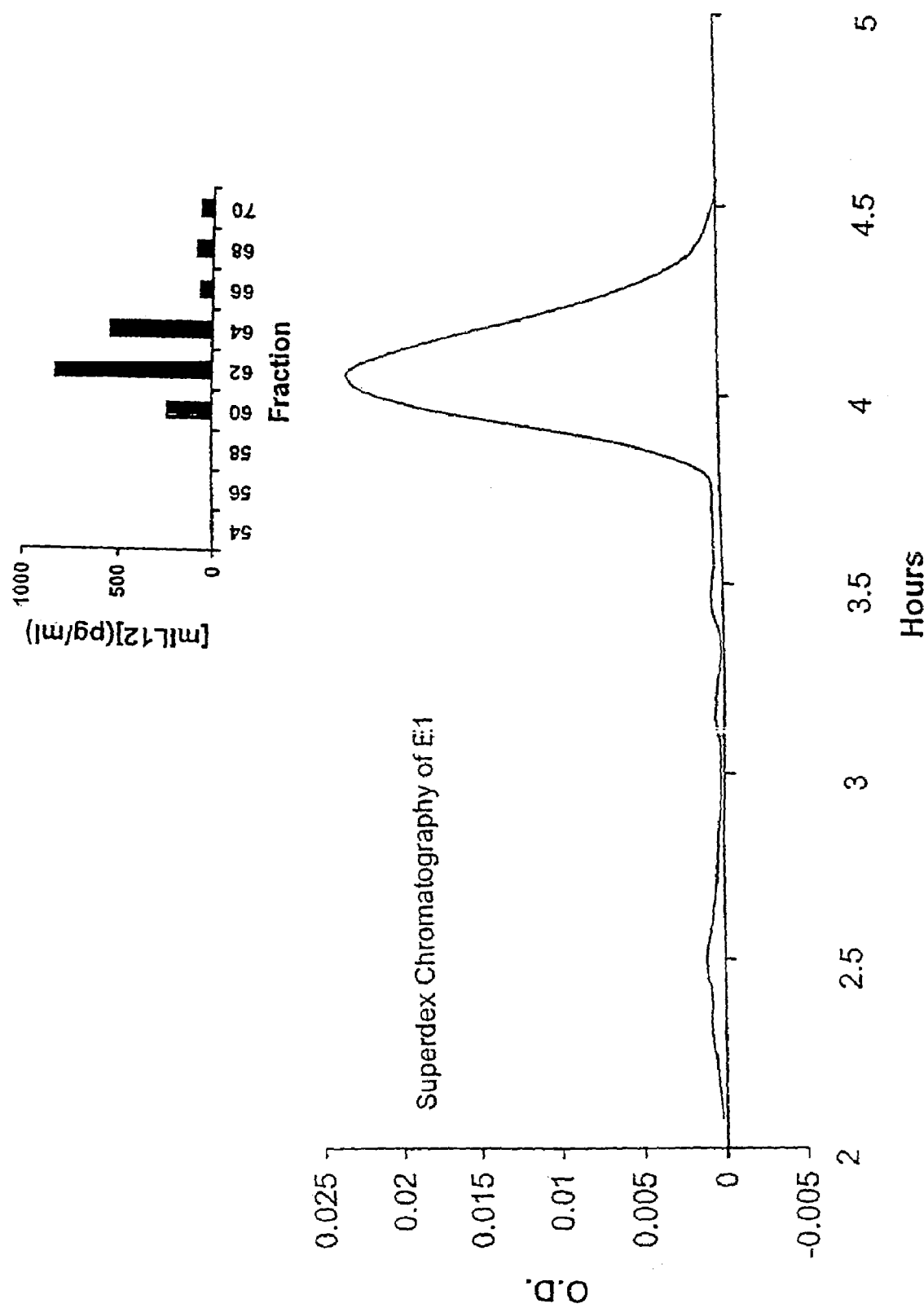
Figure 24:
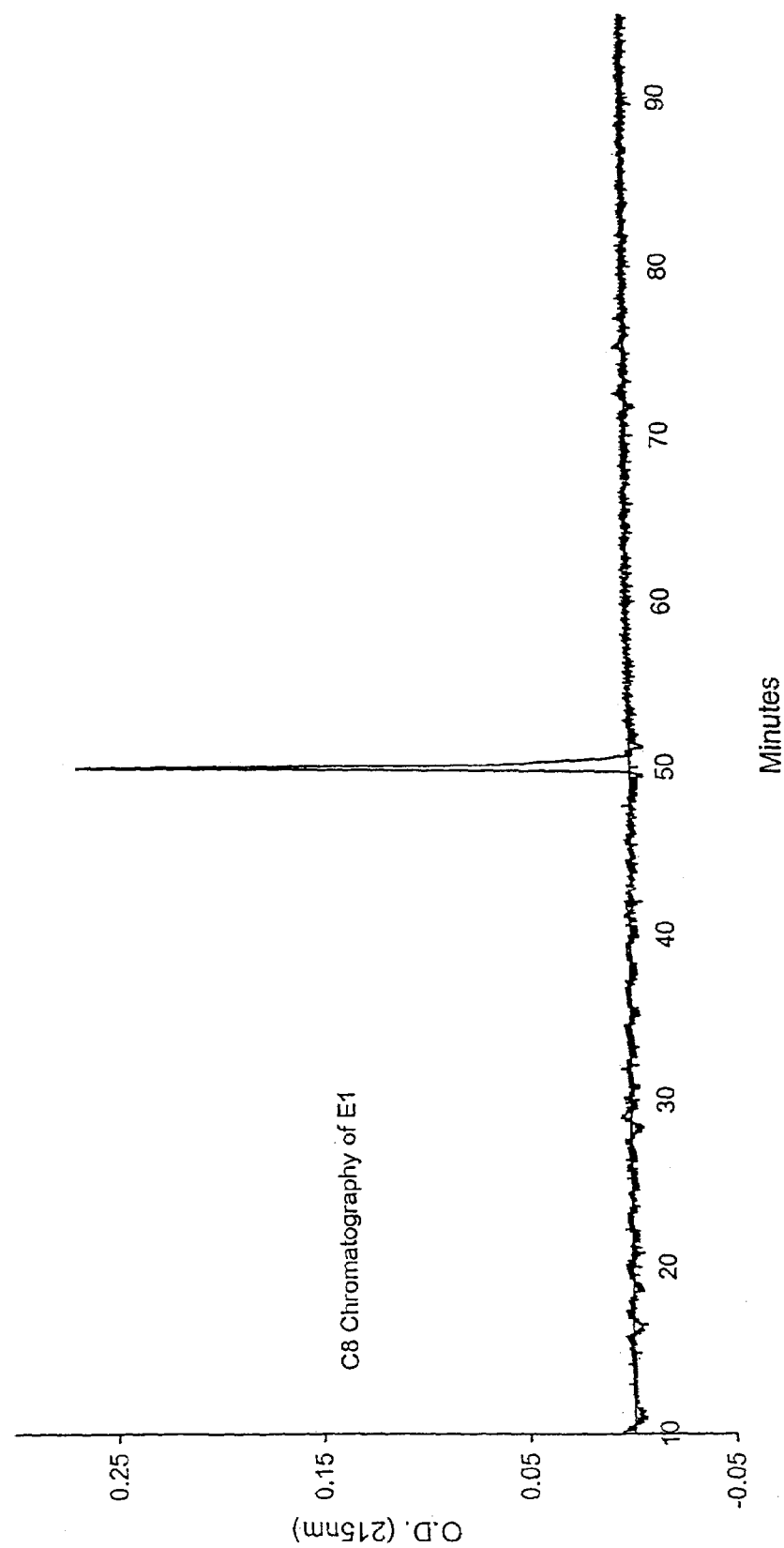

C8 chromatography was performed as described in Section 6 with linear gradient from 100% buffer E to 100% buffer F in 90 minutes. An aliquot from each fraction was assayed for DC activity after renaturing (FIG. 18).

CONCLUSIONS

It was determined that in control samples (without PLC) significant amount of DC-factor is released into solution spontaneously. Upon addition of external PLC the amount of released activity increased in all four experiments, the increase ranging from 10-fold to 25%, the data suggesting that the DC-factor is indeed GPI linked to the outer cell membrane.

Material released into solution spontaneously as well as after PLC digestion was pure enough to be analyzed by reverse phase HPLC chromatography. The region where the DC-activity eluted (41-55% buffer F) was quite clean, containing 2-3 peaks with UV absorbance at 215 nm below 0.01. The position of DC-activity on the gradient was the same for all samples analyzed: supernatants generated by membrane washing in step 2 and supernatants generated by membrane washing in step 4 after incubation at 37° C. for 4 hrs with or without PLC.

The presence of 10 mM $ZnCl_2$ in the oocyst suspension during sonication and membrane washing in step 2 was shown to significantly inhibit the ARP loss in the first two washing steps, the effect, probably, being due to inhibition of the internal phospholipase and to a smaller extent—to aggregation of ARP. Less than 1% ARP loss was obtained in the presence of $ZnCl_2$ as opposed to ca. 50% loss in the absence of $ZnCl_2$. This allows to wash away the intracellular material generated by cell breakage thus obtaining a clean membrane preparation without any loss of DC-factor (ARP) (presence of ARP aggregates in this preparation is possible). Removal of $ZnCl_2$ by resuspending the membrane pellet in $ZnCl_2$-free buffer restores the spontaneous activity release. By washing the pellet in $ZnCl_2$-free buffer combined with incubation at 37° C. for 1 hr about 35-50% of DC-activity of the pellet can be removed into solution, thus producing a clean preparation of DC-factor (ARP). The whole procedure takes one day.

EXAMPLE 5

Gene Cloning and Expression of *emeria tenella* cDNA

Cloning and Expression of *E. Tenella* ARP

Total RNA was obtained from *E. tenella* by treating ~$10^7$ oocysts to Proteinase K™ digestion (Sigma) at a final concentration of 1 mg/mL, in 200 µL of buffer containing 50 mM Tris-HCl pH 7.5, 10 mM EDTA, 1M guanidine thiocyanate (Sigma), and 0.5% of N-lauroylsarcosine (Sigma). The mix was shaken for 16 hr at 37° C. in a sealed Eppendorf™ tube followed by addition of 120 mg of guanidine thiocyanate, and 1 ml of TRI™ reagent (MRC, Inc.). Isolation of total RNA was performed according to the manufacturer recommendations based on Chomczynsky and Sachi (1987). The final pellet of total RNA was washed twice with 75% ethanol, air dried, and dissolved in 20 µL of sterile distilled, deionized water (DDW) pre-treated with 0.4% diethyl pyrocarbonate (DEP) to inhibit RNases.

The first strand cDNA was obtained with SuperScript RT™ (Life Technologies) in accordance with manufacturer recommendations. About 1 µg (6 µL) of total RNA, and 1 µg of oligo(dT$_{20}$) (Genemed) were mixed together in total volume 11 µL (adjusted with DEP-treated sterile DDW), heated at 90° C. for 2 min, and placed on ice. To the mixture, 4 µL of 5× first strand buffer, 2 µL of 0.1M DTT, 1 µL of a mixture of all four dNTP's (at 25 mM each, Life Technologies) and 30 U of anti RNase (Ambion) were added. This was incubated for 2 min at 37° C. followed by addition of 200 U of SuperScript RT™ and a brief low-speed centrifugation. The reaction proceeded for 100 min at 37° C. followed by 15 min at 70° C. to inactivate the enzyme. RNase H (4 U, Life Technologies) was added for 30 min at 37° C. to digest the RNA from the RNA:DNA duplex formed at the previous step.

Preparation of double-stranded cDNA was performed by using PCR with the first strand cDNA, obtained above, and the following primers (Retrogen Inc): forward primer, specific to the sequences of ARP gene derived from *E. tenella* ESTs, CCAGTTTTTGCTTTCTTTTCC (SEQ ID NO:42), and reverse primer, designed to be complementary to the gene from several genera related to *Eimeria*, TARAASCCRSM-CTGGTRMAGGTACTC (SEQ ID NO:43), where R=A or G; S=C or G; and M=A or C. A degenerated second primer was chosen because of the lack of sequence information for the C-terminal region of ARP from *E. tenella* at the time. Taq-polymerase™ (Life Technologies) was used with 2 mM of MgCl$_2$ and 0.2% BSA. The program performed in PCR Express™ (Hybaid) was the following: a) one cycle consisting of 2 min at 94° C., 45 sec at 50° C., 1 min at 72° C.; b) 20 cycles consisting of 30 sec at 92° C., 30 sec at 53° C. (with ramp 1° C./sec), 60 sec at 72° C. (with time increasing 5 sec/cycle); c) 15 cycles consisting of 30 sec at 92° C., 45 sec at 55° C., 100 sec at 72° C. (with time increase 5 sec/cycle); and, d) one cycle consisting of 10 min at 72° C. followed by hold step at 4° C. First strand cDNA (0.2 uL) in 19.8 µL of the polymerase mixture was reacted in 0.2 ml MµlTI Ultra™ tubes (Sorenson BioScience, Inc.). After the completion of the program, the whole volume was separated at 50 V in 0.8% agarose gel made on 0.5×TAE (Tris-acetate: Acetic Acid, pH 8.5) buffer using RunOne™ cell and power supply unit (EmbiTec). The gel was visualized by staining for 10 min in freshly prepared 0.05% ethidium bromide, briefly washed with distilled water, and viewed on Transilluminator Model M-20E (VWR). One major band was spotted, cut from the gel, and cleaned with Wizard PCR™ kit (Promega) using the manufacturer's procedure. The fragment was eluted from the resin into 50 µL of sterile DDW.

The cDNA was inserted in the pCR2.1 TOPO cloning vector (Invitrogen) in accordance with manufacturer's recommendations. The individual fragment (4 µL in water) was mixed with 1 µL of vector, incubated for 5 min at room temperature, and placed on ice. For transformation procedure, 40 µL of *E. coli* of either NovaBlue™ competent cells (Novagen), or TransforMax EC 100 Electrocompetent™ cells (Epicentre) were mixed with 1-2 µl of the above mixture, and either electroporated by 1500V, 5 msec in 0.1 cm cuvette (BTX) in Model ECM399 electroporator (BTX) (for EC 100 cells), or transformed by heat-shock procedure (30 sec, at 43° C., for NovaBlue cells). The transformed mixtures were diluted by 500 µL of SOC medium, and incubated for 1 hr at 37° C. The bacterial suspension was then plated at 100 µL/plate onto pre-heated (37° C.) plates with LB medium containing ampicillin (100 µg/mL). IPTG and X-gal were spread over the plate immediately before plating. White colonies (with an insert) were selected and re-plated onto LB plates with 40 ug/mL kanamycin to obtain single colonies. A single colony from each clone was used for analysis of the insert size by PCR, with primers (M13 forward (−40), and M13 reverse) specific for the vector. The conditions for the PCR were the same as described above, with the exceptions that magnesium concentration was 3 mM and final volume was 10 µL per tube. The fragments were visualized with ethidium bromide, as above. The clones with insert size 0.5-0.6 kB were analyzed by PCR with primers (synthesized by Retrogen Inc.) designed to be specific to the *E. tenella* ARP on the basis of comparative analysis of available ESTs: forward primer AAATGGGAGAAGCAGACACC (SEQ ID NO:44), and reverse primer TCCGCGAAGTTAAGAGCT-GTTG (SEQ ID NO:45). The PCR program was the same as above with the exception that the annealing temperature was 56° C. at the second stage, and 58° C. at the third stage. The clones that showed a single band in the agarose gel were chosen for further investigation.

Samples for DC/IL12 assay were prepared by growing selected clones aerobically (shaking for 20 hr at 37° C.) in 3 mL of liquid LB medium supplemented with 40 µg/mL of kanamycin within sterile 15-mL polypropylene centrifuge tubes (Fisher). The bacterial cells were collected into 1.7 mL SafeSeal MµlTI™ microcentrifuge tubes (Sorenson BioScience, Inc.) by centrifugation at 10,000×g for 5 min, +4° C., microcentrifuge HSC10K™ (Savant). The supernatant was removed and filter sterilized in Spin-X centrifuge tube with 0.22 µm cellulose acetate filter (Costar) (5 min at 3,000×g). The bacterial cells were washed with 0.5 mL of filter sterilized PBS, re-pelleted at the same conditions as above, and re-suspended in 0.2 mL of sterile PBS. Bacterial cells were disrupted by ultrasound in the Sonic Dismembrator Model 100 (Fisher), 3 pulses of 10 sec each at 30 sec intervals; with all procedures performed on ice. The samples were clarified by centrifugation (10,000×g, 10 min, +4° C.) in HSC10K, and the supernatants were filter sterilized in Spin-X tubes as above. For DC assay, 10 µL from each spent medium, and supernatants of disrupted bacteria, was used per each well of the assay.

The recombinant form of ARP, generated in *E. coli* from the *E. tenella* cDNA, have approximately the same specific activity as purified bovine molecule and ARP extracted from *E. tenella* oocyts. See FIG. 5. 50% activity occurs at approximately 50 femtomolar active protein concentration. The recombinant material was obtained from the cloning vector, pCR2.1 TOPO. The vector allows for expression from cDNA placed in frame to LacZ gene. The whole construction as ARP protein fused to β-galactosidase was obtained from the supernatant of a Liter of minimal growth media. The supernatant was purified using DEAE chromatography, with the method described in section 6, and was separated by C8 HPLC, using the method of section 6. One of two active peaks, containing approximately 200 ng of protein, was assayed on the DC assay to yield the response in FIG. 6.

Figure 7B:
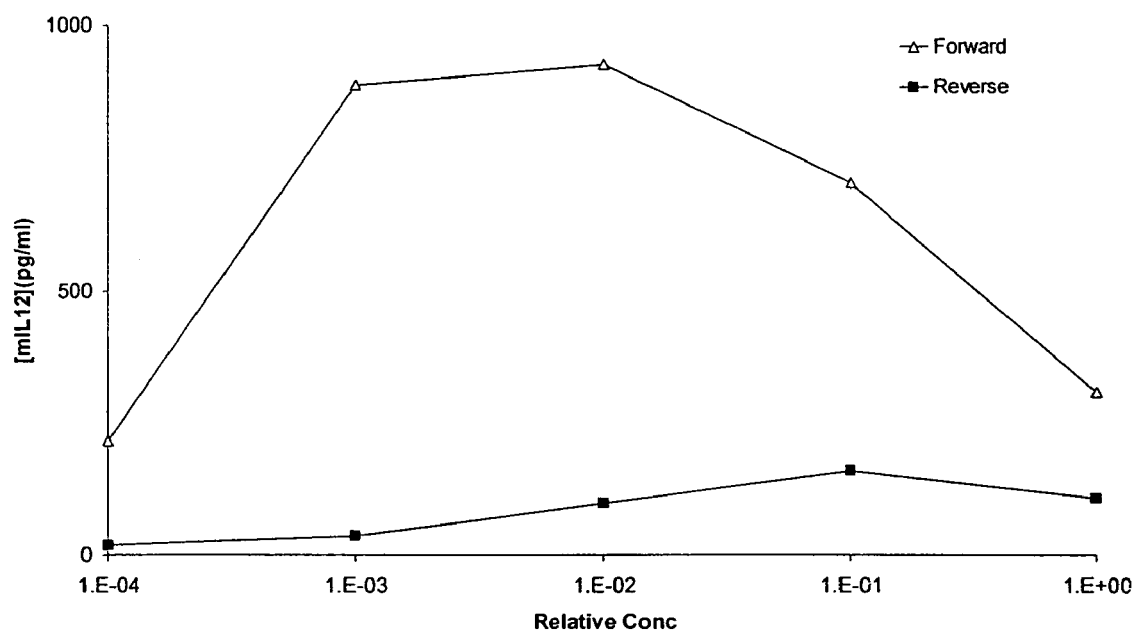
FIG. 7. (A) DNA sequence of the cDNA clone obtained from *E. tenella* mRNA using primers described in section 10. (B) Activity from two cultures of *E. coli* containing plasmids incorporating either forward or reverse orientations of the cDNA shown in (A). (C) C8 HPLC separation of the purified minimal media conditioned by *E. coli* containing the cloning plasmid with the cloned ARP for *E. tenella*, and the corresponding DC assay activity of the fractions.

The cDNA for *E. tenella* ARP was inserted in the pCR2.1 TOPO cloning vector (Invitrogen). Appropriate clones were selected by their insert size, sequence, and orientation. While not an optimized expression vector, some protein was produced from the insert in a form of fusion protein and exhibited DC activity. The DNA sequence of the insert, denoted EtU3, is given in FIG. 7(A). These inserts are being transferred to expression vectors for *E. coli* and eukaryotic cells. The expressed protein will contain a removable tag sequence to facilitate identification and purification. Activities of the products from two *E. coli* cultures containing the cloning vector, with the insert introduced in either direct or reverse orientation to LacZ promoter, are shown in FIG. 7(B). Only the correctly oriented ARP gene exhibited DC activity. This demonstrates proof that the activity is associated with this molecule because everything else between the two cultures is identical.

Figure 7C:
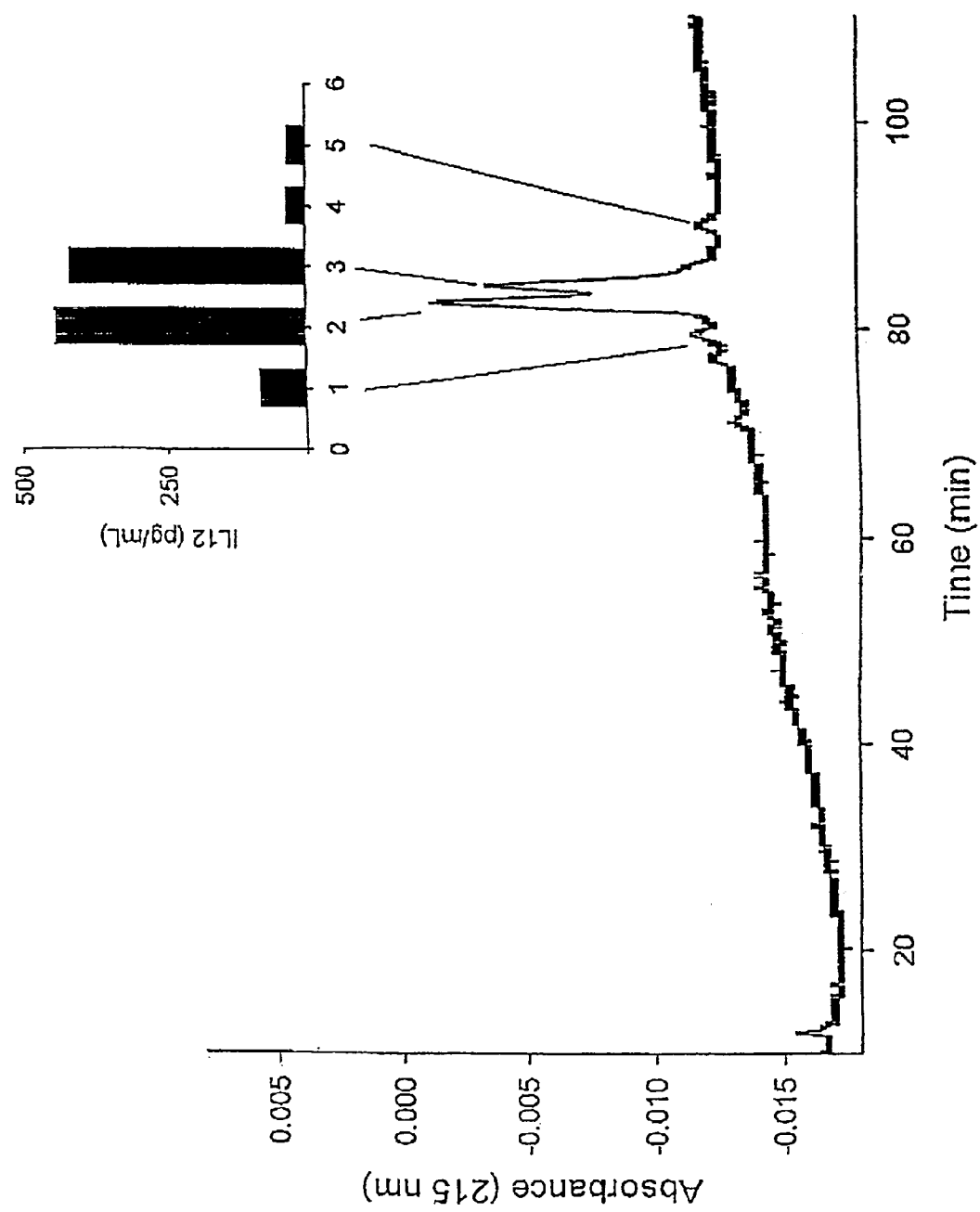

C8 chromatographic purification of the protein produced by the cloning vector in *E. coli*, growing in minimal mineral media, is shown in FIG. 7 (C), with DC activity included in the inserted graph. The activity is weak but is located at the similar retention time as the activity extracted from the sporozoites. The *E. coli* media was first purified by DEAE chromatography followed by Superdex™ chromatography (see Section 6 for detailed description of the procedures), yielding a highly pure product. The purity is shown as two active peaks on the analytical C8 chromatography column (FIG. 7 (C)). The data suggest that N-terminal region can be extended significantly without any loss in DC-activity. The ARP molecule, fused at the N-terminus, to either a portion of β-Galactosidase, maltose binding protein (MalE), FLAG peptide, or cellulose binding protein (CenA), retained significant activity. Point mutations at two positions nearby the C-terminal end (Y to H, and G to either A, or S) apparently did not change the DC-activity of the mutant as well. To reveal the importance of the C-terminus for activity of the ARP molecule, a truncated ARP molecule was created by introduction of a termination codon 14 amino acids prior to C-terminus by PCR (primer: CTATGTGAGAGCATCAGCTTTG, SEQ ID NO:46). It showed significantly (several orders of magnitude) lower DC-activity compared to full-length control. Both were expressed from T7 promoter with Shine-Dalgarno ribosomal binding site (RBS) introduced in front of the ATG start codon by PCR (primer: GAAGGAGTTTGCAAAATGGGAA, SEQ ID NO:47). Therefore, the missing sequence (TALN-FAEYLHQSGF, SEQ ID NO:48) is important for either structure or activity of ARP.

Transferring the cDNA to an expression vector (pMAL-pZE, New England Biolabs) have successfully generated clones with DC activity. This vector contains the malE gene (for fusion to maltose binding protein at N-terminus) adjacent to enterokinase cleavage site, which allows rapid separation and purification of the expressed protein. The fused ARP protein was expressed by IPTG induction, and appeared to be active as checked by DC assay. Release of the ARP protein from the fusion construction by cleavage with enterokinase did not result in enhancement in DC activity, arguing that the foreign part of the recombinant molecule may not impact the activity.

For stable expression of ARP in mammalian cells, the *E. tenella* ARP gene was re-cloned into two vectors: pTracer-CMV2 (Invitrogen) or p3xFLAG-CMV9 (Sigma). Uni-directional cloning into vector pTracer-CMV2 was performed into KpnI and XbaI sites. The fragment for cloning was created by PCR amplification of the gene with primers bearing newly created sites Kpn I (in front of start codon) and Xba I (after the stop codon). The ARP gene missing the start codon and cut out of the construction in pMal-p2e vector flanked by Hind III sites was used for cloning into a Hind III site of the vector p3xFLAG-CMV9. Orientation and in-frame position of the gene relative to secretion signal peptide as well as 3xFLAG peptide were confirmed by complete sequencing of the insert. Both plasmids were used to transform CHO-KI and S-180 cell lines with Lipofectamine 2000 (Invitrogen) according to manufacturer recommendations. Individual clones of transformed cells were obtained after selection in growth media containing antibiotic (Zeocine for pTracer-CMV2, and G-418 for p3xFLAG-CMV9), followed by re-seeding at low cell density into 96-well plate. In both cases the spent media showed high activity on DC-assay (up to 103 dilution) implying that ARP is secreted out of the cells. Analysis of the media by C8 RP-chromatography revealed the presence of a single peak of DC-activity eluting in the position close to that of bacterially expressed ARP. Preliminary calculations showed that specific activity of ARP expressed in mammalian cells is comparable to or higher than that of bacterially expressed protein.

The genes of numerous cytokines, chemokines and growth factors which influence the survival and growth of cancer have recently been incorporated into the gene therapy of cancer. In particular, the gene for interleukin 12 (IL12), has been introduced into various experimental cancer cells, resulting in a marked reduction in the tumorgenicity of the cells and/or the growth of the tumor. Presumably, the IL12 released by the cancer cells stimulates a local innate immune response which either retards the growth of the tumor or eliminates the tumor all together.

The successful isolation and expression of the ARP gene now makes it possible to propose a similar use in cancer immunotherapy. The use of the ARP gene would likely be more effective than the use of genes of specific factors (e.g. IL12), since ARP likely induced numerous pathways involved in DC maturation and activation in addition to IL12 release. Therefore, a more "complete" immune response is triggered.

An example of the use of the ARP gene in the immunotherapy of cancer is summarized as follows. The tumor is excised from the cancer patient and put into short term culture. The cultured cancer cells are transfected with the ARP gene in an exportable expression vector, other potentially useful genes such as cytokines and chemokines may be transfected as well. Lethally irradiated transfected cancer cells are re-introduced into the patient. The transfected cancer cells would release ARP locally in situ which would activate nearby DCs to release IL12 and possible other immune modulators. This response could stimulate local immune responses against the transfected cancer cells. Cancer cells are killed and release tumor associated antigens which are taken up, processed and presented by DCs, generating a specific adaptive (memory) immune response against other tumor cells existing in the body (primary tumor, metastases, recurrences). The patient now possesses a permanent immunity to the cancer.

Isolation of *E. Tenella* ARP from E1 Clone

The *E. tenella* gene coding for ARP was cloned by PCR using forward primer (ATGGGTGAAGAGGCTGATACT-CAGG, SEQ ID NO:49) and reverse primer (TTAGAAGC-CGCCCTGGTACAGGTACTCAGCGA, SEQ ID NO:50). The PCR fragment was ligated to the pET-Blue-1 acceptor vector (Novagen) with clonableRT (Novagen) overnight at 16° C. The resulting plasmid was transformed into *E. coli* host Nova Blue with carbenicillin/tetracycline and white/blue clone selection. Positive clones were identified by colony PCR using the same forward primer and pET Blue Down primer #70603-3 (Novagen) to assure DNA insert of correct orientation. The DNA sequence of the insert was confirmed by sequencing. The plasmid of the positive clone was isolated and transformed into host strain Turner™ (DE3) pLacI (Novagen) for protein expression. One stable clone was designated as E1. (See FIG. 20.) Clone E1 was deposited with the American Type Culture Collection on Jul. 15, 2004 and assigned patent deposit number PTA-6120.

Single clone of E1 from agar culture was inoculated in 10 ml LB medium supplemented with 1% glucose in the presence of 50 μg/ml carbenicillin and 34 μg/ml chloramphenicol. The culture was maintained overnight at 37° C. with shaking at 250 rpm. The culture was then added to 1 liter of the same medium and allowed to grow for 2.5 hours to absorbance of about 0.6-0.8 at 600 nm. Protein expression was induced by addition of isopropyl-1-thio-β-D-galactospyranoside (IPTG) to 0.5 mM final concentration. After 4 hours, the bacteria were harvested by centrifugation at 8,000 rpm (6,500×g), for 20 min. The supernatant was removed and saved and the pellet was frozen until used.

The bacterial pellet was resuspended in 30 ml PBS and passed through a French press three times at 1,600 psi to disrupt the cells. The press cell was rinsed with PBS to recover residual cell sample. The sample was centrifuged at 15,000 rpm (17,500×g) with SS34 rotor for 30 min to remove cell debris. The supernatant and the pellet were separately saved. Total volume of the supernatant totaled to about 38 ml. Ammonium sulfate was then added to the supernatant to 30% saturation. After 1 hour at 4° C. with stirring, the precipitate was removed by centrifugation. The ammonium sulfate was further added to 45% saturation. After 1 hour, the precipitate was removed. Ammonium sulfate was added to 80% saturation. The sample was stirred overnight at 4° C. The precipitate was recovered by centrifugation. The pellet was resuspended in 1.5 M ammonium sulfate, 50 mM sodium phosphate, pH 7.0. The sample was then centrifuged to remove undisolved material.

Hydrophobic Chromatography on Phenyl-Sepharose™ Column:

The soluble fraction was subjected to hydrophobic chromatography on a phenyl-Sepharose column (Fast Flow, (low sub), by Pharmacia 3×3.3 cm). After the sample was applied to the column, it was washed with the same buffer until the baseline was obtained. A reverse linear gradient of 1.5 M to 0 M ammonium sulfate, 50 mM Na phophate, pH 7.0 (200 ml for each buffer chamber) was applied at room temperature at a flow rate of 2 ml/min. 5 ml fractions were collected. Selected fractions were analyzed by DC assay and SDS-PAGE. The active fractions were pooled and dialyzed overnight at 4° C. against 0.2 M NaCl, 10 mM Na phosphate, pH7.0 to be ready for the DEAE-Sepharose™ chromatography.

DEAE-Sepharose Chromatography:

The DEAE-Sepharose™ column (Fast Flow, by Pharmacia; 1.5×5.5 cm) was equilibrated with the initial buffer (0.2 M NaCl, 10 mM Na phosphate, pH 7.0). After the sample was applied, the column was washed with the same buffer to remove unbound material as monitored by Abs280. When the absorbance came to the baseline, a linear gradient (0.2 M-0.6 M NaCl in 10 mM Na phosphate, pH 7.0, 200 ml for each buffer) was applied. Fractions of 5 ml were collected. The eluted fractions were analyzed by DC assay, and SDS-PAGE.

Superdex™ Size Exclusion Chromatography

Final purification and elimination of endotoxin was accomplished by Superdex™ 75 chromatography using the method described in Section 6. Active samples were stored at 4° C. instead of freezing.

C8 Chromatography for Quality Control

Reverse phase HPLC (as described in Section 9) was performed on a sample of the pooled active material from the Superdex chromatography.

EXAMPLE 6

Physical Properties of ARP

During the many years of dealing with an impure preparation of ARP, it was difficult to obtain information on the physical characteristics of the molecule. Initially, for example, it was not obvious if it was a protein or another type of macromolecule. In retrospect, it is clear that the extremely potent nature of the protein meant that it was always a very minor component in any partially pure preparation. Some findings related to the nature of ARP molecule are contained in the following subsections.

Molecular Weight

Several experiments have indicated that the molecular weight range of ARP is centered near 20 kD. A large amount of indirect evidence for this molecular weight has come from gel banding in SDS-PAGE for known active fractions. Similarly, activity has routinely eluted from sieving chromatography columns in this range. Direct evidence has been obtained from large SDS-PAGE slab gels. Active material has been applied to this system, with a slight modification in sample preparation to avoid boiling in SDS, and after electrophoresis, the gel was sliced and the proteins were eluted, renatured and tested. The only recoverable activity was located in the 20 kD (18.+−3 kD) range.

This has been validated with final purification and sequencing. The homologous protein from avian *Eimeria* is reported to have an 18.5 kD predicted mass and antibodies to a peptide segment react with a 20 kD band from *E. tenella* and *E. acervulina* (Lillihoj et al., 2000).

pI Determination

Several experiments on extracting and re-folding proteins from an acrylamide gel after isoelectric focusing revealed a pI being in range of 4.0-4.7 for protein active in NK assay, while the predicted pI for *E. acervulina*, and *E. tenella* ARP proteins is 4.3-4.5. These results are consistent with acidic protein containing a significant number of carboxyl groups.

Isoelectric focusing was performed with the use of a precast pH 3-7 IEF gel (Novex) according to company instructions. Broad pI calibration kit (Pharmacia) was used as a standard for pI calculation.

pH Dependence of ARP Activity

Several experiments revealed significant dependence of ARP activity on pH. In crude materials, NK activity was found to decline significantly at both high pH>0, and low pH<4. In some experiments, minimal activity was observed below pH4.0, while one experiment showed minimal activity in the range 3.4<pH<3.7. While the loss of activity at high pH can be at least partially reversed by re-naturation process, the impact of low pH in many cases (specially at pH<2.0) was irreversible.

Temperature Stability

The stability of drug product BBX-01 was evaluated at several temperatures to help determine shelf life and storage conditions. The results are shown in Table 6.

TABLE 6

Estimates of BBX-01 Thermo-stability

| Condition | Time to 50% loss (estimated from presumed exponential loss) | Comments (activity measured with NK Assay) |
|---|---|---|
| −80° C. | >>1 yr | No detectable loss in 24 months |
| 4° C. | >18 months | No detectable loss in 18 months |
| Ambient (~24° C.) | ~6 weeks | ~20% loss at two weeks |
| 37° C. | ~6 days | |
| 56° C. | ~11 min | |
| 16 Freeze-thaw cycles (liquid $N_2$ to ambient) | | No detectable loss of activity |

Activity was undiminished for extended periods in frozen and refrigerated conditions, while it decreased as the temperature increased. Even at 37° C., however, the half-life was nearly one week, suggesting that the usefulness as a drug would not be limited to auto-degradation at body temperature.

Stability of E1 in Human Serum Albumin

Preliminary studies on the stability of the recombinant ARP, E1 (1 μg/mL) in the presence of HSA (Human Serum Albumin) at 1, 5, or 10% w/v indicate no loss in activity at 4, 11, 25, 39 and 54 days when stored at 4° C. Higher temperature studies also indicate remarkable stability. No loss of activity was detected after 41 days at 37° C., 6 hours at either 55° C., or 2 hours 70° C. while in the presence of HSA. The increase in stability over BBX-01 is probably due to the higher purity of the E1 preparation, which avoids possible protease contaminants. For use in human clinical trials, ARP E1 has been formulated at 1 μg/ml with 3% HSA and stored at 4° C. for at least 55 weeks without loss of activity as measured by the DC assay.

Enzyme Sensitivities of ARP

There was compelling evidence that the partially purified material contained a protein and not a nucleic acid, glycolipid, lipopolysaccharide, or some complex of these with a peptide component. Treatment of the partially purified fraction with the proteases trypsin, chymotrypsin, V8, subtilisin, and papain were all successful in eliminating activity. Careful titration experiments indicated that, on average, a single cut from the protease subtilisin was sufficient to eliminate all activity, while chymotrypsin required three cuts to reduce activity 10-fold. These results gave strong evidence that a major component of the active molecule was protein. Additional catabolic enzymes were tested to test the possibility that a modified protein or complex was important to activity.

In several experiments with the nucleases, e.g., RNase A and DNase I, the activity of ARP was followed in the NK and IFNγ assays. For both enzymes, there was no loss of activity after 9 and 24 hours of incubation at 37° C. as compared to ARP incubated in the same conditions without the enzyme. In neither case, migration of the NK-active component in 4% agarose gel was affected by the treatment with the enzymes, while the visible nucleic acid bands disappeared. This indicated that no nucleo-protein complex was important to the activity.

Several experiments were also performed with deglycosylases on deglycosylation of crude bovine protein preparations with peptide-N-Glycosidase F from *Flavobacterium meningosepticum*, specific for N-linked carbohydrate moieties. These showed that the position of the active molecule did not move on polyacrylamide gels after digestion. Activity, however, was reduced by approximately 40% after incubation with the enzyme. This provides evidence for a short carbohydrate chain that may provide stability to the molecule or its removal reduces the activity due to introduction of an extra negative charge (Asn>Asp). Two potential N-glycosylation sites (Asn-Gly-Thr) are present in the bovine ARP sequence (see Table 4).

Effect of Divalent Cations on DC-Activity and Aggregation State of ARP

Salts of alkaline earth metals ($CaCl_2$, $MgCl_2$) and transitional metals ($ZnCl_2$ and $CuCl_2$) were tested for inhibition of DC-activity induced by semi-purified ARP preparations from bovine intestine and recombinant ARP. With crude ARP preparations, $ZnCl_2$ and $CuCl_2$ consistently showed inhibition of activity in mM-μM concentration range (which is in physiological range), while $CaCl_2$ and $MgCl_2$ did not. Some differences exist in the interaction of copper and zinc with ARP and must be explored further. Both transitional metals also inhibited the DC-activity of purified recombinant ARP. However, preliminary experiments involving pre-incubation with 10 mM salts of alkaline earth metals on recombinant ARP showed different effects in ARP preparations from bacteria grown on either mineral media (M9 with 2 mM $MgSO_4$, 0.1 mM $CaCl_2$, and no trace metals) or rich (LB) media. The former was inhibited by both—calcium and magnesium ions, while the latter—only by magnesium ions. The difference can be due to different local concentrations of divalent metals or other co-factors during synthesis and folding, producing different sets of conformational isomers of ARP.

Experiments on the mechanism of activity inhibition by $Zn^{2+}$ revealed that aggregation of ARP occurred in the presence of 10 mM $ZnCl_2$ yielding high molecular weight structures pelletable by centrifugation at 15000 g for 30 min. The data suggest that binding of divalent cations induces a change in the tertiary structure of ARP, exposing inner hydrophobic regions that result in aggregation and/or interaction with other proteins and this leads to a loss of activity.

Inhibition by representatives of both metal groups can have an impact on design of ARP treatment and purification protocols. The alkaline earth metals are abundant in all tissues and organs. The physiological concentration of $Zn^{2+}$ varies from 10 μM in serum to 3 mM in seminal fluid. Concentration of $Zn^{2+}$ and $Cu^{2+}$ was shown to change during some diseases including malignancies. In some tissues and/or pathological conditions the concentration of these metals may be high enough to interfere with anti-tumor activity of ARP. In these cases the local administration of metal-chelators might have to be included in ARP treatment protocols.

EXAMPLE 7

Measurement of ARP Activities

Tumor Protection Measurement Using Animal Tumor Models

BALB/c male mice were routinely used and were obtained from Harlan Industries at approximately 7 weeks of age. They were allowed to acclimate for 2 days before any treatments were given. Mice were housed 5 or less per cage in 16 cm×26 cm plastic cages with wire tops equipped with water bottles and food pellets (mouse chow). Animals were allowed ad libitum access to water and food. Litter was changed once per week; water and food was checked daily. Room lighting was on 24 hours per day.

The S-180 cell line (ATCC CCL 8, batch F4805) was chosen as the tumor model because the same line was capable of growing both in animals and in culture (in both serum-containing and serum-free conditions). Tumors were established in mice by injection of cell suspensions obtained from tissue culture. Approximately $1\times10^6$ to $3\times10^6$ cells were injected intra-peritoneally per mouse. The tumor developed as multiple solid nodules at multiple sites within the peritoneal cavity and caused death in most of the animals within 10 to 15 days. In addition to monitoring animal survival, their condition was qualitatively assessed as tumor growth progressed and used to generate a tumor index.

Treatment Protocol

Each experimental treatment group consisted of 5 animals, randomized from the total used in each experiment. Treatments consisted of 5 daily intra-peritoneal injections (near midday) beginning one day after injection of S-180 tumor cells. Injection volume was held constant at 0.5 ml for all treatment. Negative control groups received sham injections of only the buffer used for the treatment solutions. Animals were followed until death due to tumor growth or until day 100 if regression occurred. Some animals were allowed to live out their natural lifespan to monitor any delayed reaction to treatment.

Tumor Index

To establish an estimate of drug activity on incomplete tumor model experiments, an index was developed that combined observational examination of the animals as well as their survival status. Mice were palpated once or twice weekly for the presence, establishment and terminal progression of the intraperitoneal S180 tumor. Tumor development and progression was assessed in these mice according to the following scale: "0"—no tumor palpated; "1"—initial tumor appears to be present; small in size (~1 mm); no distended abdomen; "2"—tumor appears to be established; some distension of the abdomen; no apparent cachexia; "3"—tumor is well established, marked abdominal distension, animal exhibits cachexia; and, "4"—animal is dead. The index value for a treatment group was the average of the individual mouse indices in the group.

NK Assay

Materials

DMEM/F12 culture media, fetal calf serum (FCS), and human recombinant interleukin 2 (hr-IL2) (R & D Systems, Inc) were obtained from Gibco/BRL. Percoll™ (Pharmacia, Inc), gentamicin and MTT were obtained from Sigma Chemical Co. Mouse epidermal growth factor (EGF), bovine insulin and human transferrin were purchased from Collaborative Research Corp. Male Balb/C mice used in tumor studies, isolation of small intestinal extracts (MEX-SI) and isolation of spleen-derived NK cells were purchased from Harlan Bioproducts for Science (Indianapolis, Ind.).

NK (LGL) Cell Isolation

Spleens (10-15 per experiment) were aseptically removed from male Balb/C mice 6-10 weeks of age. Splenocytes were "squeezed" out of spleens using 2 sterile glass microscope slides. Cells were collected in approximately 10 ml of DMEM/F 12 containing 10% fetal calf serum (FCS) and gentamicin (50 µg/ml). Single cell suspensions were generated by passing collected cells through a 70 µm nylon mesh screen. After washing the cell pellet once with PBS (centrifuged at 675×g for 5 min), red blood cells were lysed by brief hypotonic shock (i.e. exposure to sterile distilled, deionized water, followed immediately with appropriate volumes of 10×PBS to return to isotonicity). Remaining cells were centrifuged and resuspended in DMEM/F12+10% FCS and transferred to 75 cm² flasks each containing 25 mls DMEM/F12+10% FCS (cells from 5 spleens per flask). The cells were incubated for 60 min. at 37° C. to selectively remove readily adherent cells (mainly fibroblasts and macrophages). After the incubation, the flasks were gently shaken and the non-adherent cells were removed, pelleted by centrifugation, and resuspended in DMEM/F12 (no supplements) (1.0 mL/10⁸ cells). A 1.0 mL volume of these cell suspensions were carefully layered onto a 70%/60%/40% (2 mL/4 mL/4 mL) Percoll™ gradients in 15 ml centrifuge tubes and centrifuged for 30 min at 675×G. The cells which sediment at the 40/60 interface represent primarily large granular lymphocytes (LGLs), enriched with NK cells. These cells were carefully removed with a pasteur pipet, centrifuged, washed once with PBS and resuspended in approximately 5 mL DMEM/F12 supplemented with gentamicin (50 µg/mL) and 10% fetal calf serum. Cell counts and appropriate dilutions of LGL cells were made with these cells, as described below. For convenience this LGL cell preparation is interchangeably referred to as NK cells.

NK Cell-Mediated Cytotoxicity (NK-CMC) Assay

Mouse sarcoma 180 cells were seeded into 96 well plates at a density of $5\times10^3$ cells per well in 100 µl DMEM/F12, supplemented with 10% FCS and gentamicin (50 µg/mL). After several hours to ensure proper attachment, test samples (e.g., samples containing an ARP protein, positive or negative controls) were added to each well in volumes of 10-25 µL. NK cells were added in 100 µL of supplemented DMEM/F12 at designated densities: 0 NK cells/well; $5\times10^4$ NK cells/well (1:10 target/effector ratio); $1.25\times10^5$ NK cells/well (1:25 target/effector ratio); $2.5\times10^5$ NK cells/well (1:50 target/effector ratio); and, $5\times10^5$ NK cells/well (1:100 target/effector ratio). (Note: routinely, only the 1:50 and 1:100 ratios were used for screening purposes. IL2 was added as a media supplement with final concentration of 125 U/mL.). Co-cultures were incubated for 4 days at 37° C., 5% $CO_2$, and terminated and vitally stained using a MTT cell viability quantification assay (see Mossman, T. J. Immunol. Methods 65:55 (1983); and Sigma Chemical MTT (M5655) product application note). Culture media was carefully aspirated from each well and the remaining cells were washed twice and replaced with 100 µL DMEM/F12+10% FCS, containing MTT (50 µg/mL). The plates were further incubated for 4-5 hours at 37° C. Absorbance was measured with the aid of a plate reader (600 nm filter). Decreased absorbance indicated a decrease in the number of viable cells per well (i.e. cytotoxicity). Absorbance was measured again after the MTT was solubilized by replacement of the medium with 200 µL of 2-propanol containing 0.04M HCl. This gave a uniform color throughout the well and minimized discrepancies in absorbance readings due to uneven cell distribution. NK-inducing activity was calculated relative to negative (PBS/BSA) and positive (internal standard) controls.

Dendritic Cell (DC) Assay

To follow the activity in semi-purified preparations of BEX, an assay which follows IL12 release from freshly isolated dendritic cells (DCs) as an index of DC activation was developed. This activity is highly correlated with both NK-CMC in vitro and anti-tumor activity in vivo.

Special Reagents

Mouse recombinant GM-CSF, IL4 and IFNγ and anti-mouse CD40 were obtained from R&D Systems (Minneapolis, Minn.). Collagenase D was obtained from Boehringer Mannheim (Indianapolis, Ind.). MiniMACS magnetic cell isolation system was obtained from Miltenyi Biotech (Auburn, Calif.).

Isolation and Culture of DCs

DCs were isolated from the spleens of male BALB/c mice 8-12 weeks of age (Harlan Bioproducts for Science, Indianapolis, Ind.), using the magnetic assisted cell separation (MACS) system purchased from Miltenyi Biotech. In summary: Spleens were aseptically removed from mice and placed into a petri dish containing 5 mL holding media (DMEM/F12 supplemented with 10% FCS and antibiotics). Each spleen was then injected with ~0.5 mls collagenase D solution (1 mg/mL in 10 mM Hepes-NaOH, pH 7.4, 150 mM NaCl, 5 mM $MgCl_2$, 1.8 mM $CaCl_2$), placed into 5-10 mL collagenase D, cut into 5-6 pieces and incubated at 37° C. for 45-60 min. Collagenase-digested spleens were then processed with glass slides and passed through a 70 μm nylon mesh cell strainer. After the strainer was flushed with 40 mL culture media, cells were centrifuged (8 min@200×G), suspended in 1 mL PBS and subjected to red blood cell lysis by incubating the cell suspension for 5 min at room temperature in 10 mL lysis buffer (155 mM $NH_4Cl$, 10 mM $KHCO_3$, 0.1 mM EDTA), followed by dilution in PBS to 50 mL and centrifugation (8 min@200×g). The splenocytes were then suspended in 10 mL MACS buffer (PBS pH 7.2, supplemented with 2 mM EDTA and 0.5% BSA), passed through a 40 μm nylon mesh cell strainer which was flushed with 40 mL MACS buffer. A preliminary cell count was taken at this time, prior to centrifugation (8 min@ 200×G). The splenocytes were suspended at a density of $10^8$ cells per 400 μL MACS buffer. Paramagnetic MicroBeads coated with anti-CD11c$^+$ antibody were mixed with the splenocyte suspension (100 μL per $10^8$ cells), incubated at +4° C. for 15 min, washed, suspended in 1.0 mL MACS buffer and passed through a MS+ separation column placed within a strong magnetic field. CD11c$^+$ cells were retained in the column whereas CD11c$^-$ cells were washed off the column as the flow-through cell fraction. CD11c$^+$ cells were then collected by removing the column out of the magnetic field and flushing the column twice with 1 mL of MACS buffer. CD11c$^+$ cells were washed once with culture media and suspended at a density of 0.5× $10^6$ cells per mL in cytokine supplemented culture media {DMEM/F12 supplemented with 10% FCS and gentamicin containing mouse GM-CSF (1 ng/1 mL), mouse IL-4 (1 ng/mL), mouse IFNγ (3 ng/mL) and anti mouse CD40 (0.5 mg/mL)}. CD11c$^+$ cells were then added (100 μL/well) to 96-well tissue culture plates containing test samples (e.g., samples containing an ARP protein, positive or negative controls) diluted in 100 μL media per well and cultured overnight at 37° C. in 5% $CO_2$, 95% air.

Determination of Mouse IL12 (p70) Release from DCs

Mouse IL12 release from CD11c$^+$ splenocytes was measured using ELISA. Briefly, CD11c+ cell culture supernatants were sampled following an overnight incubation (usually 15-18 hrs). Media samples (1100 μL) were added to ELISA plates coated with anti mouse IL12 (p70) capture antibody (R&D #MAB419; 250 ng in 100 μL per well) and incubated either at 37° C. or room temperature for 2 hrs. The ELISA plates were washed extensively with wash buffer after which 100 μL per well of detection antibody/detection reagent (biotinylated anti-mouse IL12; R&D #BAF419 at 50 ng/mL and streptavidin-HRP) was added. The ELISA plates were again incubated for 2 hours, washed and exposed to TMP substrate solution (Pierce #34021) for 20 min. The substrate reaction was stopped by adding 100 μL/well 2M $H_2SO_4$. ELISA plates were read at 450 nm (corrected at 540 nm) and mIL12(p70) levels were calculated using an intra-ELISA standard curve (range: 2000-31.25 pg/mL).

IFN-γ Assay

The production and release of IFNγ by LGLs into the culture media was assessed as follows: LGLs, enriched with NK cells, were isolated as described above in Section 12.2. and seeded into 96 well plates at densities of 2.5 or 5.0×$10^5$ cells/well, in 200 uL of DMEM/F12 supplemented with 10% fetal calf serum, gentamycin (50 ug/mL), and IL2 (125 U/mL). Test samples (e.g., samples containing an ARP protein, positive or negative controls) were added and the cells were cultured overnight, following which the condition media (CM) was removed and centrifuged to remove any aspirated cells. Aliquots of the CM were then measured for IFNγ using an ELISA kit purchased from various sources (BD PharMingen Inc., Genzyme Corp., and R&D Systems Inc.). Briefly, in the ELISA assay, CM or serum samples (and IFNγ standard) are incubated in ELISA plate wells, previously coated with a capture antibody (hamster monoclonal anti-mouse IFNγ), for 1 hr at 37° C. After extensive washing the wells are exposed to a biotinylated second antibody (polyclonal anti-mouse IFNγ) for 1 hr at 37° C. After washing, the wells are then exposed to a detection reagent (streptavidin conjugated with horseradish peroxidase) for 15-20 min. at 37° C. Once again, after extensive washing, 100 μL TMB substrate is added to the wells and incubated for 5-7 min. at room temperature. The reaction is stopped by adding 100 μL 2M $H_2SO_4$. Absorbance at 450 nm is read using a plate reader and IFNγ concentrations are calculated from the standard curve.

Anti-Tumor Activity of ARP

Activity in the Murine S-180 Model

Enriched or Isolated ARP

Figure 8:
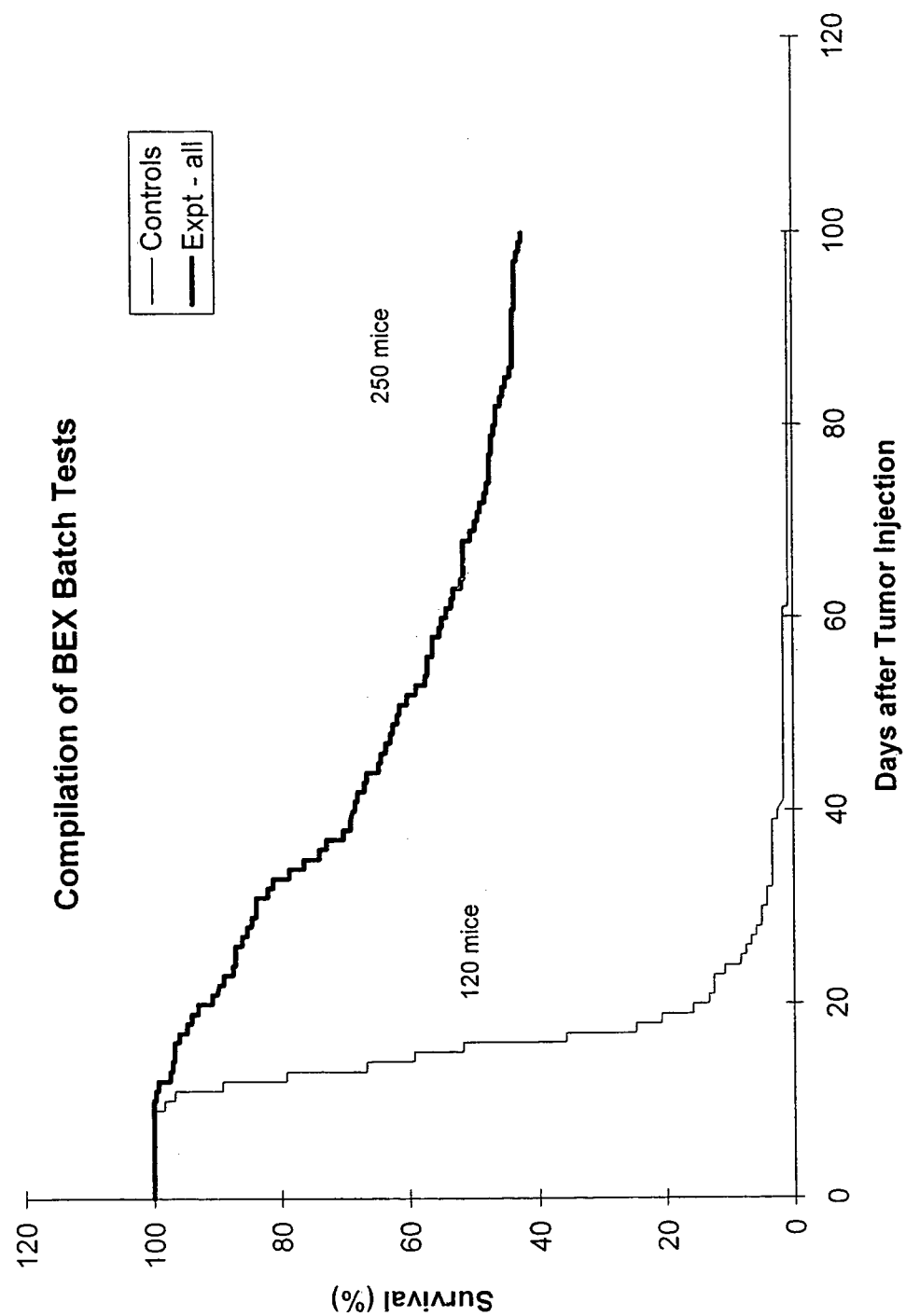
FIG. 8. Compilation of survival data of tumor-bearing Balb/c mice from control and partially purified ARP (stage 1 BEX) treated groups. These survival times were obtained from screening experiments designed to check the efficacy of the enriched ARP (stage 1 extraction) product. The number of control is not equal to the number in the treatment group because several batches were often screened simultaneously against the same control.

A series of routine screening experiments, which were used to determine the quality of BBX-01c, were compiled into a single survival plot. This is shown in FIG. 8. Approximately half of the animals in the treatment group were considered cured—survival greater than 100 days. Of those that died, the average increased lifespan over controls was approximately 2.5 fold.

In one experiment, the five day dose schedule was started at different times with respect to the injection of S180 tumor: days −5 to −1; days −2 to +2; days 1 to 5; and, days 4 to 8. Anti-tumor activity was optimal with injections begun 2 days before tumor injection (4 of 5 cures). Results were also very good for injections begun on day 1 (3 of 5 cures). When the injections were given from days −5 to −1 or days 4 to 8, the anti-tumor activity was poor. In these cases, increased life span was only ~150% with no cures.

Anti-Tumor Activity of Crude Membrane Preparation from *E. tenella*

The crude membrane preparation was generated as described in Section 9 from 50 μl of oocyst suspension. Preliminary results are shown in FIG. 17. The tumor index indicates that the preparation displays anti-tumor activity and can be used as well as purified soluble ARP.

Antitumor Activity as Purity Increased

Verification of the purification methodology always yielded a successful treatment of tumors in the mouse model. Samples from different purification steps were collected, verified active on the NK assay, then injected into tumor-bearing mice according to the standard 5-day protocol. High activity was observed at each step, including a C8 chromatography sample, from pool 1, which was above 50% pure.

Anti-Tumor Activity of E. tenella Extracts

An extract from E. tenella oocysts was generated using the second procedure described in section 8. Five groups of mice, bearing S-180 tumor, were injected for five days with different doses of ARP-containing extracts. These doses are shown in FIG. 9 (right side). Preliminary results, 40 days into the experiment, indicate that an optimal dosage may exist for this extract (0.36 ng/mouse/day). Good responses are observed spanning three orders of magnitude in dose, down to 0.048 ng/mouse/day.

Antitumor Activity of Recombinant E. tenella ARP, EtU3 and E1

The purified recombinant ARP molecule from the EtU3 or E1 clones (see FIG. 20) or from an extract of E. tenella sporulated oocysts was injected at three or five different doses into S-180 tumor-bearing mice. These doses are shown in FIG. 9 (right side). Mice were followed for 100 days at which point mice without observable tumor were considered "cured". Optimal therapeutic dose ranges for all versions of the ARP molecule were between 0.1 and 10 ng/mouse/day. Responders are mice that survived more than two standard deviations beyond the mean of the corresponding control group. An estimate of the effective dose for 50% response for the mouse antitumor model was obtained by fitting the Hill equation to the number of responders versus dose giving a value of 0.011 ng/mouse/day (regression coefficient=0.86, CV=7.5%).

Correlation of Anti-Tumor Activity to In Vitro Assays

Figure 10:
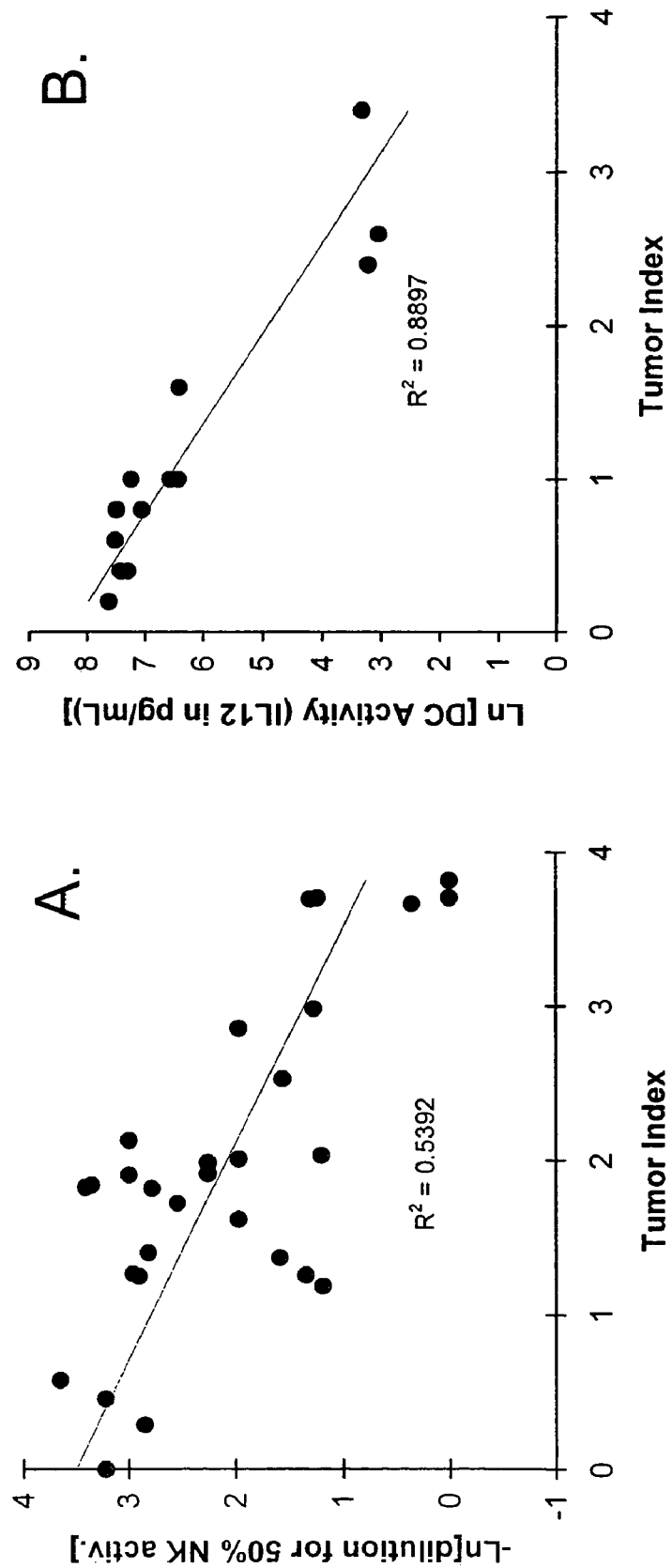
FIG. 10. Correlation of the in vitro NK and DC assays with anti-tumor response in mice. (A) Each batch of BEX was routinely tested in mice and in the NK assay. A series of batches, spanning approximately 1 year of extracts, were used in this figure. The in vivo anti-tumor activity was represented by a tumor index calculated from increased life span and survival, with 0 representing 100% cures and 4 representing no survival advantage over negative controls. The in vitro NK assay activity was represented by the logarithm of the dilution need to reach 50% cell kill. The solid line represents the best linear regression through the points. (B) Experimental dosages were pre-tested in the DC assay and the log of the activity observed for the dose was plotted against a tumor index based on degree of palpable tumors, presence of cachexia, and survival status. This index has the same endpoints as above. The regression fit parameters are displayed on each plot.

Early anti-tumor studies on partially purified ARP material was also tested simultaneously on the NK assay. The correlation between the two assays is shown in FIG. 10(A). Samples tested in the murine tumor model have also been tested in the NK and DC assays to help establish starting doses. The correlation of the DC assay to animal survival is shown in FIG. 10(B). This correlation has routinely allowed us to follow activity during purification without resorting to the use of animals for tumor studies and without the extended delay inherent in the anti-tumor experiments.

Responses in Human Patients

The anti-cancer activity of ARP was also tested in a phase 1 clinical trial. While the trial was designed to evaluate toxicity, attention was always paid to possible positive tumor status of the patients. In the $2^{nd}$ leg of the trial, using enriched ARP composition (BBX-01c), a single patient with a germ cell ovarian carcinoma demonstrated elevated serum IL-12 levels (FIG. 11), a dramatic reduction in an 8 cm pelvic tumor mass after a single 5-day course of partially purified ARP (BBX-01c) (Table 7) and complete elimination of the tumor and all peritoneal ascites after a second 5-day course. Other masses in her liver and spleen were refractory, but they remained static for nearly two years. She went from severe pain and bed-ridden to a pain-free status allowing her to return to work. Subsequent to the success in this patient, two other terminal ovarian epithelial carcinoma patients were recruited. The evaluation of the primary oncologist indicates that their disease has remained stable longer than anticipated.

TABLE 7

CT Scan Summaries for Patient #5-RW

| Date | Pelvic Mass | Liver & Spleen Masses | Ascites | Comments |
|---|---|---|---|---|
| Dec. 4, 2000 | 8 × 8 cm | 8 × 9 cm liver mass 6 × 6 cm spleen mass | yes | prior to BBX-01c therapy |
| Feb. 1, 2001 | 2 × 3 cm | unchanged | no | 2 wks after BBX-01c $1^{st}$ course |
| Mar. 6, 2001 | 2 × 3 cm | unchanged | yes | 7 wks after BBX-01c $1^{st}$ course |
| May 9, 2001 | not detectable | unchanged | no | 6 wks after BBX-01c $2^{nd}$ course |
| Nov. 9, 2001 | not detectable | unchanged | no | 32 wks after BBX-01c $2^{nd}$ course |
| Jun. 30, 2002 | not detectable | unchanged | no | 66 wks after BBX-01c $2^{nd}$ course |

Immuno-Stimulatory Activities of ARP

NK Activation

Early in this project it was discovered that cytotoxic lymphocytes isolated from mouse spleens were central mediators of the cytotoxic effects of mouse and bovine small intestinal extracts against S180 cells in vitro and also are most likely centrally involved in the anti-tumor effects of these extracts in vivo. Therefore, a novel in vitro assay to assess induced cytotoxic activity of NK-like cells was formulated and implemented using large granular lymphocytes (LGLs) isolated from mouse spleens using discontinuous Percoll™ gradients. The natural killer (NK) cells are routinely referred as the primarily mediators of the cytolytic effects of SIE in vitro and in vivo. It should be noted, however, that other lymphocytes contained in the LGLs population of spleenocyte may also be involved, such as lymphocyte activated killer cells (LAKs).

The LGLs were co-cultured with S180 tumor cells, at various effector to target (E:T) cell ratios, for 4 days. This protocol is not typically used in other reported experiments on NK activity. It is unique because tumor cells are dividing while the NK activation occurs. This creates a more complex environment that may mimic the in vivo conditions more closely. The culture medium contained a low concentration of IL2 (125 U/ml) plus any experimental (purification) preparation of intestinal extract to be tested. The "basal" activity induced by IL2 alone, at the highest NK:S180 ratio (100_NK), was normally low (10-15%), suggesting that S180 cells are relatively resistant to the cytolytic action of the LGLs cells induced by IL2. However, in the presence of partially purified bovine small intestinal extracts, the cytolytic activity of these LGLs was dramatically and synergistically increased, often resulting in nearly 100% cytotoxicity at effector: target ratios as low as 50:1. (It should be noted that the effector: target ratios are determined at the time of seeding the cells—Day 0, Since the S180 cells undergo 3-4 population doublings during the subsequent culture period and the LGLs do not proliferate under these conditions, the actual E:T ratios at the time of NK cell activation are probably much lower than stated here.)

The induced natural killer cell mediated cytotoxicity (NK-CMC) is not associated with any direct cytotoxic or growth inhibitory effects of the extracts on the S180 cells. The SIE-induced NK-CMC can be demonstrated over a tremendous dose range, with no observable effect on S180 cell growth or viability in the absence of NK cells (0_NK effects). Microscopic observations of NK/S180 co-cultures treated with SIE have described a clustering and clumping of NK cells in "activated" cultures. The clustering of NK cells appears to be especially focused around S180 cells. Time course experiments indicate that 2-3 days of exposure of NK cells to the SIEs are required for the cytolytic activity to be induced. The induction of SIE-induced NK-CMC is blocked by treatment of the LGLs/S180 co-cultures with anti-asialo-GM1 antibody, which specifically blocks NK cell cytolytic effects. These results indicate that NK cells are primarily involved in mediating the in vitro cytotoxic responses of SIEs against S180 tumor cells.

Figure 11:
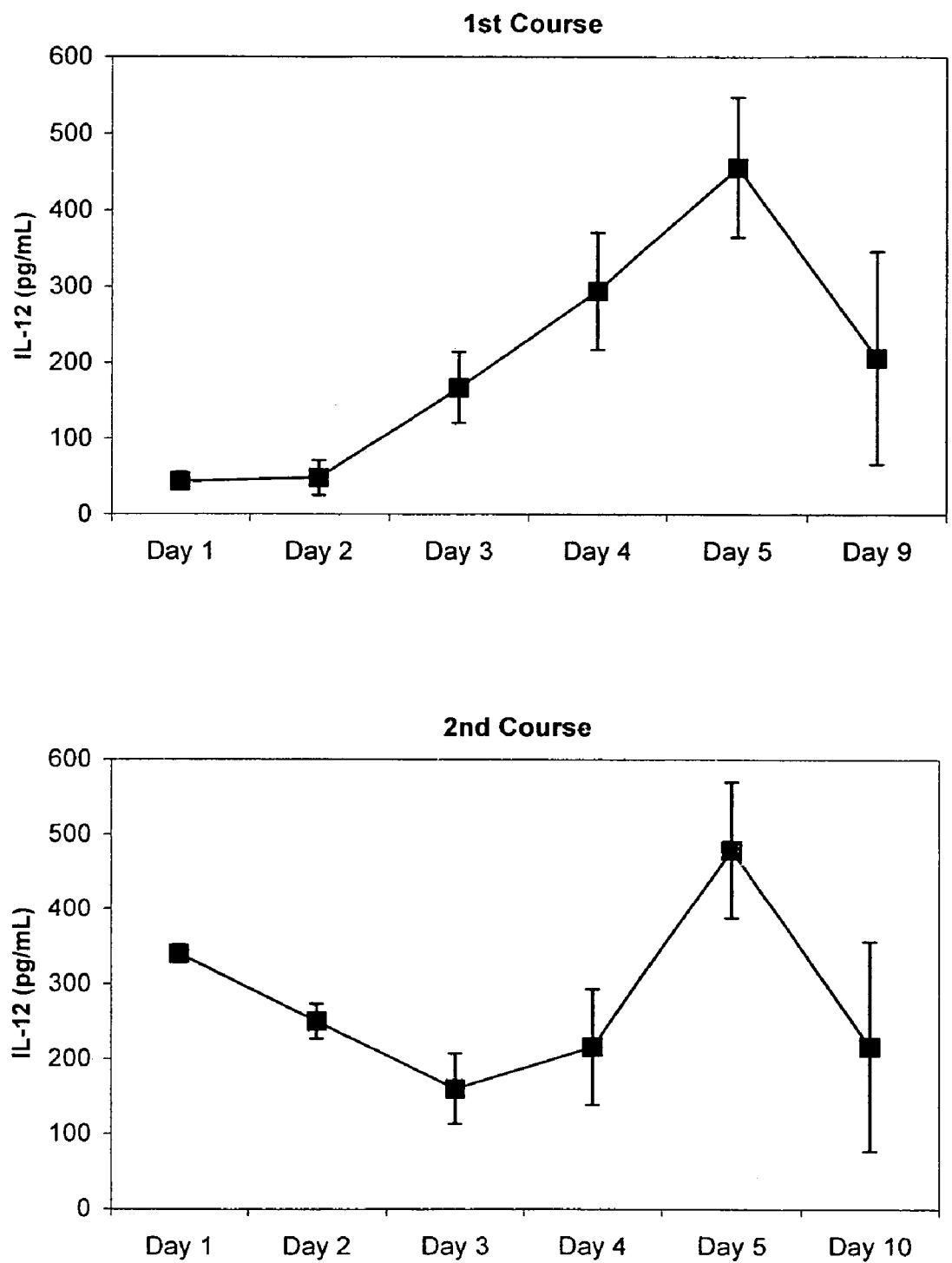
FIG. 11. Serum IL-12 levels in patient #5-RW, during two courses of the 5 day low-dose BBX-01c. Serum levels were measured prior to injections of BBX-01c on day 1 through day 5. A final sample was drawn either on day 9 or 10.
Figure 12:
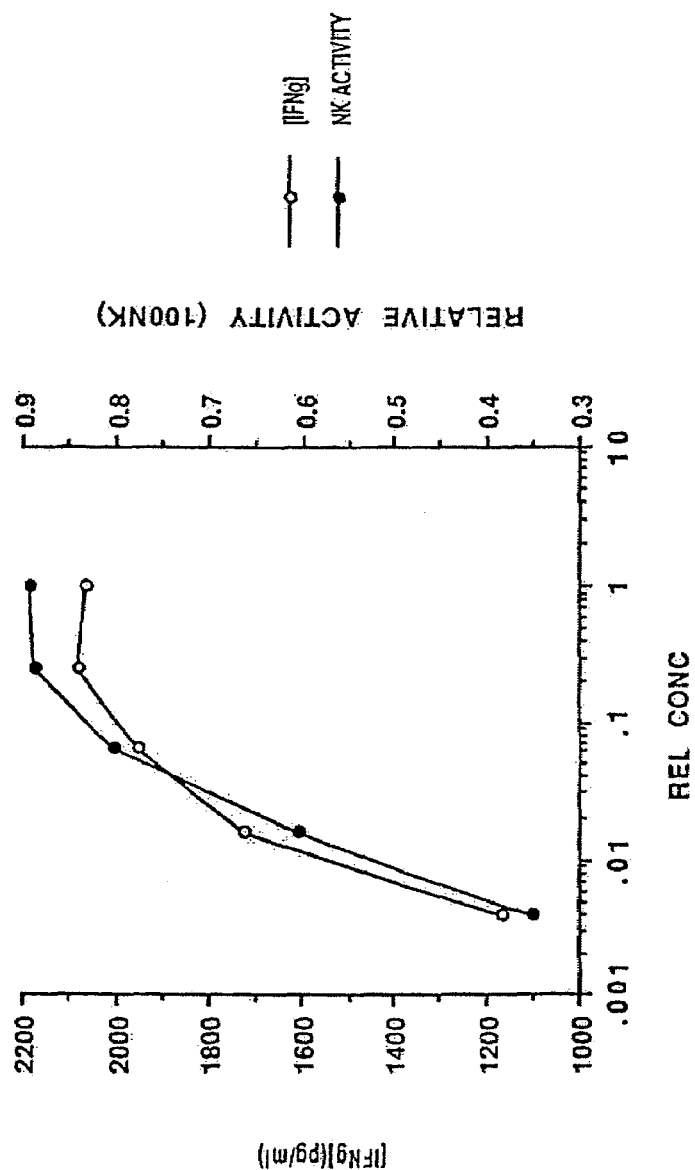
FIG. 12. Correlation of induced NK-CMC with elevated levels of IFNγ in the media of treated LGL cultures. LGL/S 180 co-cultures were treated with varying concentrations of BEX and analyzed for NK-CMC with the standard 4 day in vitro NK assay. LGL cultures were treated with the same concentrations of BEX and the conditioned media was analyzed for IFNγ concentration following an overnight culture.

The induction of NK-CMC by SIEs in vitro is closely associated with an increase in IFNγ levels in the media of these cultures. When the concentration of IFNγ ([IFNγ]) is measured in the conditioned media of LGL cultures exposed to SIEs, the [IFNγ] is dramatically increased within 18 hours of treatment. Dose response relationships show a closely linked association between increases in [IFNγ] and induced NK-CMC (FIG. 11). Treatment of NK/S180 cell co-cultures with a neutralizing antibody against mouse IFNγ (anti-mouse IFNγ antibody), markedly reduces and/or blocks NK-CMC induced by SIEs. However, adding mouse recombinant IFNγ directly to NK/S180 co-cultures only results in slight increase in NK-CMC, far below the maximal NK-CMC induced by SIEs. These results suggest that increased [IFNγ] induced by SIEs is an early and required event in mediating SIE-induced NK-CMC but is not by itself sufficient to induce NK-CMC.

The rapid induction of IFNγ in LGL cultures by SIEs provided a more rapid method to test for activity in various purification stages. An IFN assay was devised (see Section 12.4) and was used for several years to provide a one-day test of activity.

A large number of biological response modifiers have been reported to influence NK-CMC. We have screened a number of these factors in our NK-CMC assay in an attempt to duplicate SIE-induced activity in vitro. Table 8 lists the agents that have been tested.

TABLE 8

Summary of Effects of Various Cytokines[1] on NK-CMC and DC Assays.

| Cytokines | NK-CMC Activity | DC mIL12 Release[2] |
|---|---|---|
| Interleukins | | |
| IL-1β | −[3] | − |
| IL-2 | +[4] | − |
| IL-3 | − | − |
| IL-4 | − | + |
| IL-5 | − | − |
| IL-6 | − | − |
| IL-7 | − | nt |
| IL-10 | − | inhibitory |
| IL-11 | − | nt |
| IL-12 | ++[5] | na |
| IL-15 | − | nt |
| IL-18 | ++ | − |

TABLE 8-continued

Summary of Effects of Various Cytokines[1] on NK-CMC and DC Assays.

| Cytokines | NK-CMC Activity | DC mIL12 Release[2] |
|---|---|---|
| Interferons | | |
| IFNα | − | nt |
| IFNγ | +[6] | − |
| Defensins, Anti-microbial peptides | | |
| Corticostatin | − | nt |
| Magainin I | − | nt |
| Magainin II | − | nt |
| Cecropin A | − | nt |
| Cecropin B | − | nt |
| Cecropin P1 | − | nt |
| Defensin 1 | − | nt |
| Chemokines | | |
| MIP-1α | − | nt |
| JE/MCP-1 | − | nt |
| KC | − | nt |
| Misc. Cytokines, Growth Factors | | |
| TNFα | +[5] | − |
| TGFα | − | nt |
| TGFβ | − | − |
| FGFbasic | − | − |

[1]Each agent was tested in the in vitro NK assay (LGL assay) over a wide range of concentrations both in the presence and absence of IL-2 (125 U/ml).
[2]Agents were tested for synergism and inhibition.
[3]Indicates little or no additive or synergistic effect, nt = not tested, na = not applicable.
[4]IL-2 significantly increases NK-CMC only at high concentrations.
[5]IL-12 synergistically increases NK-CMC at low concentrations of IL-2. However, these effects, unlike MEX or BEX, are restricted by NK: S180 cell ratios (see text). Weakly activates NK cells in the presence of IL-2 (maximal response <50% cytotoxicity).
[6]Weakly activates NK cells in the presence of IL-2 (maximal response <50% cytotoxicity).

Only IL-12, IL-18, TNFα, and IFNγ have demonstrated any capability to increase NK-CMC when tested under the same conditions as BEX (enriched ARP). However, TNFα and IFNγ were relatively weak enhancers when compared to BEX. Furthermore, as described below, the capacity of IL-12 to increase NK-CMC is linked to its production by dendritic cells in the LGL mixture. Finally, IL18, while a major component of the A fraction (DEAE flow-through fraction), is not present in the C fraction (DEAE eluted fraction). Therefore, no known enhancer of NK-CMC tested under the in vitro conditions of our LGL/S180 assay system stimulates NK cell mediated cytotoxicity in a fashion similar to extracts from the small intestine.

Dendritic Cell Activation

We have recently established that dendritic cells (DCs) play a central role in activities induced by ARP in vitro. This has been based on the observations that removal of DCs from the standard NK assay eliminates overall NK-CMC activity. Furthermore, BBX-01c induces mIL-12 (murine IL-12) release from enriched DC suspensions obtained with magnetic assisted cell separation (MACS). Anti-mIL-12 (neutralizing antibody) also markedly reduces BBX-induced NK-cell-mediated-cytotoxicity (NK-CMC).

Figure 13A:
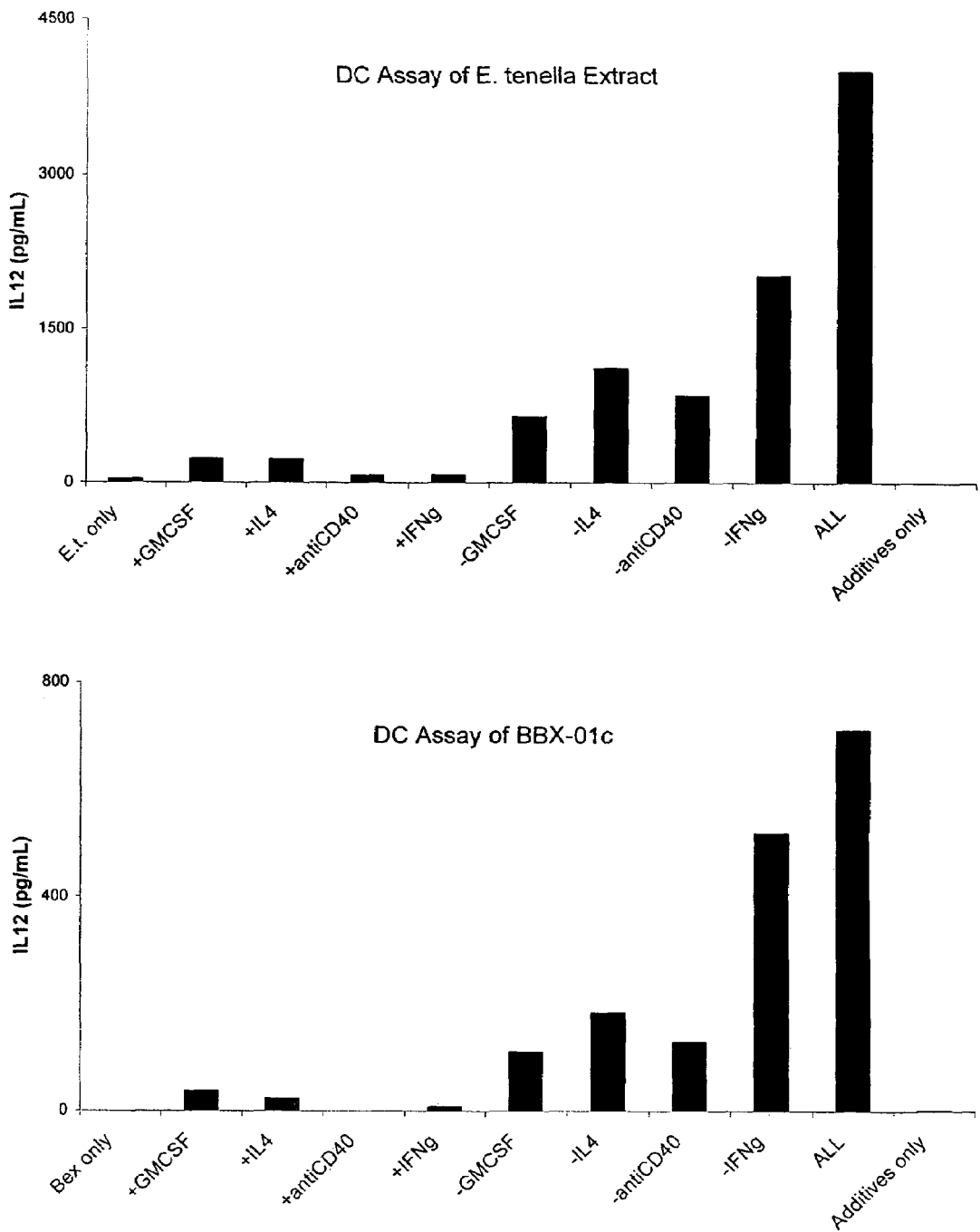
FIG. 13. (A) Response of the DC assay to *E. tenella* and Bovine BBX-01c as a function of synergistic additives. In each panel, activity is measured for the antigen alone, the additives alone, the antigen with all the additives (ALL), the antigen plus a single additive (denoted with +), and the antigen with only one additive missing (denoted with a −). The two panels represent two separate assays and absolute values between the two are not comparable. (B) Loss of sensitivity of freshly isolated CD11c$^+$ dendritic cells to BBX-01c as a function of time in tissue culture conditions.

Attempts to exploit these observations into a useful assay for BBX-01c material were largely limited because BBX-01c induced only a modest amount of mIL-12 from spleen DCs in the absence of other activating factors. Exploration of other dendritic cell agonists and co-stimulatory molecules revealed powerful synergisms with the C component of BBX (FIG. 13(A)—lower panel). The four additives give maximal response in the presence of BBX-01c, but have no activity in its absence. Removal of one of the four additives results in varying reductions in IL-12 release. The anti-CD40 antibody, which substitutes for CD40 ligand, is the most important synergistic agent, followed by GM-CSF and then IL-4. The latter two cytokines are known to lead to maturation of dendritic cells while CD40 ligand mimics the presence of CD4 T-cells and causes dendritic cells to release their activating cytokines. The E. tenella extract behaves in a virtually identical manner to the BBX sample (FIG. 13(A)—upper panel), which reinforces the similarity of the two active molecules, but more importantly, indicates that no other molecule of the small intestine tissue is part of the activity.

Optimization of the four additives has created a very robust assay for BBX-01c and *Eimeria* activity. The DC/mL-12 release activity correlates extremely well with NK-CMC activity in samples from Superdex, HIC, various HPLC chromatographic separations as well as other fractionations. Furthermore, dose/response relationships indicate that the DC/mL-12 release assay is significantly more sensitive than the NK-CMC assay in detecting low levels of the active C component in BBX-01c. It is completely insensitive to the A component, making it an ideal assay for following the component in BBX that is most highly correlated with anti-tumor activity. Other cytokines that were reported to be active in dendritic cells were also tested for synergism with C, these are reported in Table 8, supra.

Figure 13B:
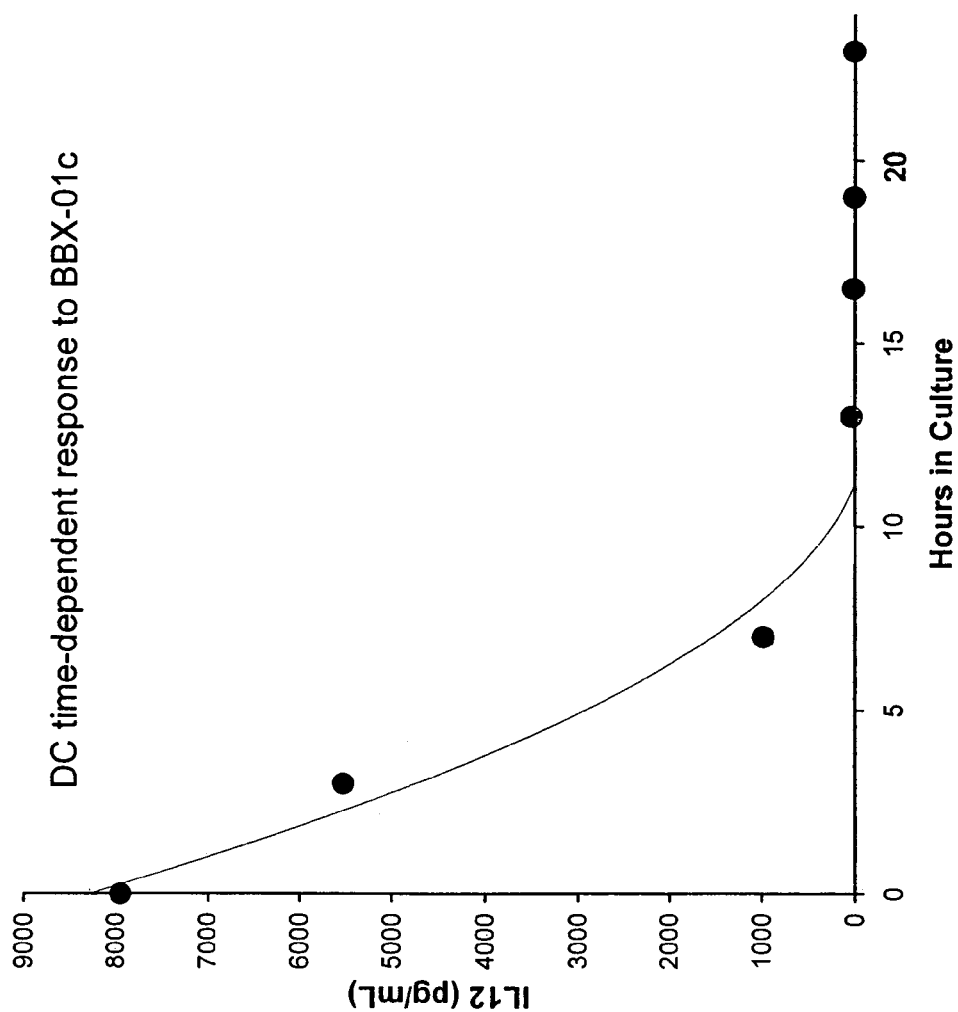

Another important observation regarding the activity of BBX is the need to use freshly isolated spleen cells from which to purify dendritic cells. If DC-like cells are created in culture from peripheral blood monocytes by incubation with IL4 and GM-CSF, they are not responsive to BBX. Furthermore, if freshly isolated spleen cells are allowed to acclimate to culture conditions, they loose their responsiveness. This is shown in FIG. 13 (B). It appears that a particular stage of dendritic cell maturation is required for activity. The current immunotherapy protocols that expose dendritic cells to tumor antigens in vitro may not benefit from *Eimeria* antigen stimulation. Whereas those protocols that operate in vivo may be greatly enhanced.

Synergism with GM-CSF in Murine Tumor Model

During the development of the IL-12 release assay from dendritic cells, several cytokines were shown to synergize with BBX-01c. The relevance of this to the clinical setting needs to be explored and may be important in future human trials. An in vivo examination of the synergism with GM-CSF (granulocyte macrophage—colony stimulating factor) was performed in two experiments in a mouse tumor model. GM-CSF was chosen because of its substantial history and relative safety in human therapy. Furthermore, its mode of action is primarily to expand cell population numbers, which may provide the most complementary function to BBX-01c.

Figure 14:
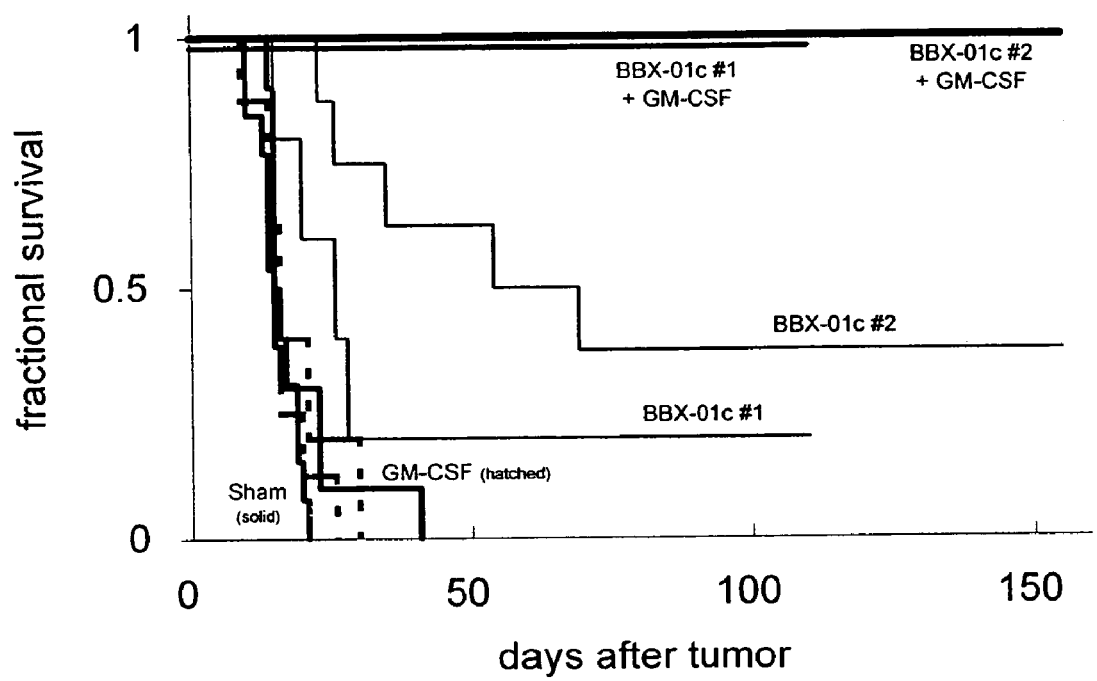
FIG. 14. Synergism of BBX-01c (enriched ARP) and GM-CSF in mouse tumor model. Two sub-therapeutic doses of BBX-01c, with and without GM-CSF, were injected one day after tumor. GM-CSF alone was not significantly different from sham injection with vehicle.

The results for two combinations of doses are shown in FIG. 14. Those animals receiving sham injections or GM-CSF alone followed similar survivorship curves. Those with the sub-optimal BBX-01c dosages exhibited some cures and extension of median survival in the remaining animals. The combined treatments were 100% curative with no evidence of tumor growth.

The dose of GM-CSF was 20 ng/mouse/day, which is approximately equivalent to a human dose of 0.1 µg/kg/day. Such a human dose is well below the 2-32 µg/kg/day dosage range for rhGM-CSF (recombinant human GM-CSF) used in cancer treatment to elevate white blood cell counts prior to or following chemotherapy. This dose suggests that human tolerance to GM-CSF will not be a problem in possible combinations with BBX-01c.

Induction of Interleukin-12

One of the major effects of an ARP both in vitro and in vivo is the induction of interleukin-12 (IL12) release from dendritic cells. IL12 has been proposed for a variety of uses, e.g., in immune regulation. However, such uses have been limited by severe toxicity associated with administration of IL12. An ARP of the invention provides an alternative to systemic IL 12 administration and provide the benefits of IL 12 administration without the associated toxicity.

The preliminary assessment of the pharmacodynamics of an ARP molecule in vivo was tested in mice utilizing the extremely high sensitivity of the DC/mL 12 bioassay to detect ARP at very low concentrations. Mice were injected either ip or sc with a single dose of ARP EtU3 (352.5 ng active protein) diluted in 0.5 ml 0.1% BSA in PBS or a single dose of *E. tenella* extract (containing 36 ng of active ARP). Mice were bled via orbital sinus puncture technique using light ether anesthesia at the following time intervals: 1 hr, 3.5 hrs, 7.5 hrs, 12 hrs, 24 hrs, and 42 hrs. Blood was collected into heparinized micro-hematocrit capillary tubes and centrifuged for 10 min at ~7000 rpm. Blood plasma was isolated and stored at +4° C. until the blood collection was completed.

Figure 25:
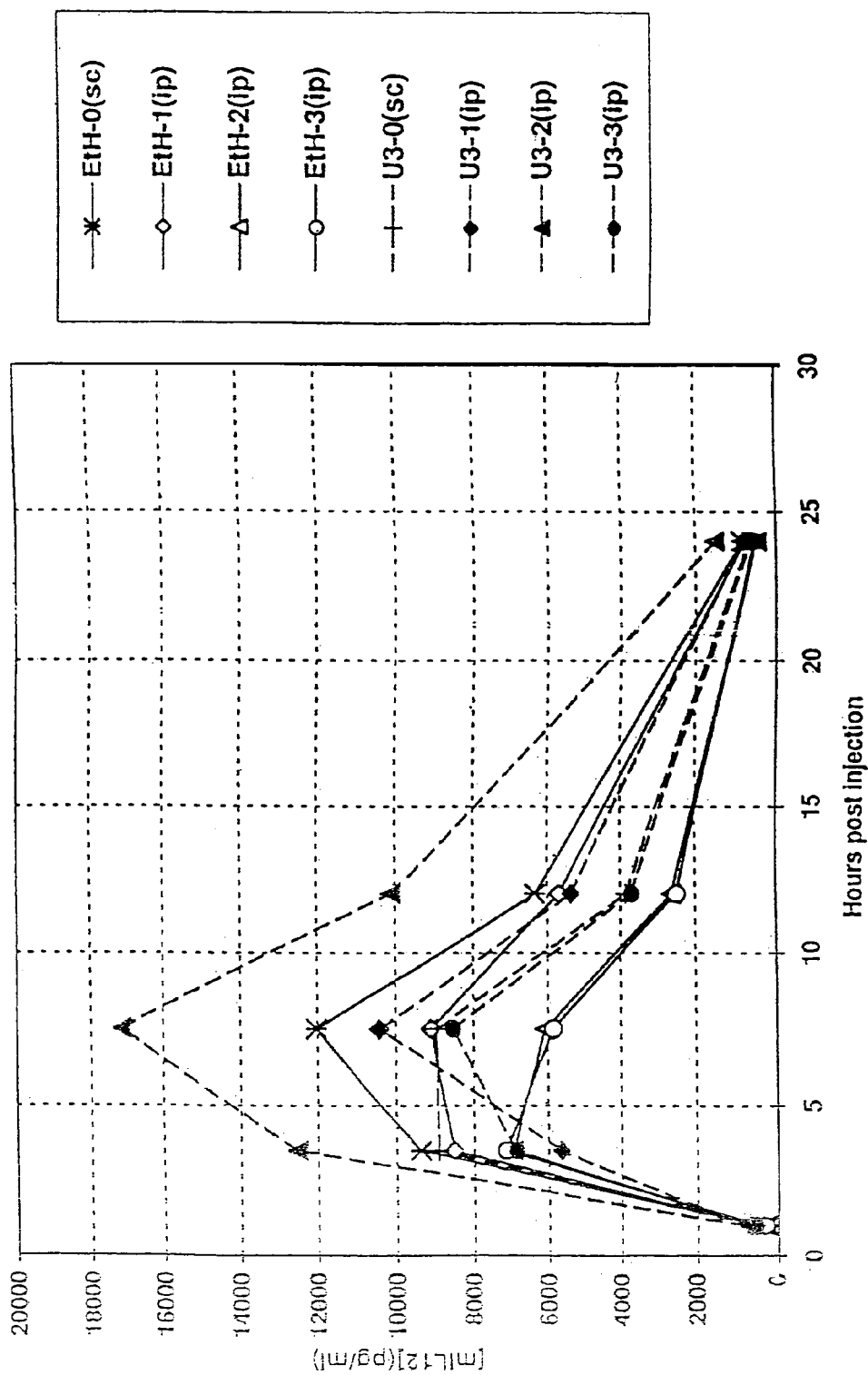
FIG. 25. ELISA assessment of IL-12 within the mice that were treated with an *E. tenella* ARP (EtU3).

To assess the degree to which ARP can induce IL12 within the animal, aliquots of the plasma samples were diluted into the culture media and directly applied to the IL12 ELISA. The results, from three mice injected ip and one mouse injected sc for each treatment, are shown in FIG. 25. Plasma IL12 reached a peak at approximately 5 hours post injection and exhibited an exponential rise in concentration, with a rate constant 0.92 hr-1, and an exponential decay in concentration, with a rate constant of −0.15 hr-1.

These experiments have demonstrated proof of principle for the induction of IL12 from *E. tenella*-derived ARP drug treatment. The level of ARP injected in this experiment is significantly above the effective dose range in mice (~0.05-5 ng/mouse/day), thus the rise and fall rates for induced in vivo IL12 must be considered tentative.

Moreover, BBX-01 induced serum IL12 concentrations in selective patients in the phase 1 clinical trial (see FIG. 11).

EXAMPLE 8

Other Assays Used in the Purification of ARP

LAL for Endotoxin

Endotoxin is routinely examined by the LAL gel clot assay (obtained from the Associates of Cape Cod Incorporated, 704 Main St., Falmouth Mass.). Samples were taken at various points during the purification process (Stage 1 and 2 processing) and were tested for endotoxin levels using the standard method described by the manufacturer. Early stages of intestine processing contained endotoxin above acceptable levels for human use, but these were reduced to safe levels by further purification. Processing on the Superdex™ 75 column provides a >10-fold reduction in endotoxin levels after each run. Therefore, re-processing the material through the column allowed reduction of endotoxin to any desired level, up to the native background levels in USP water. Target endotoxin levels have been set to yield material with a final concentration that meets the FDA guideline for parenteral drugs (<5 EU/kg). For the highest proposed dose of BBX-01 (100 mg/person), this yields a maximal target endotoxin level of approximately 70 kg/person×5 EU/kg÷100 mg/person, or 3.5

EU/mg for a 70 kg patient. Verification of the pyrogen safety of BBX-01 has been provided by independent testing at STS, Rush, N.Y. The rabbit pyrogen test on Superdex™ re-processed material, which had an endotoxin level of 0.4 (±0.2) EU/mg, yielded no pyretic effect.

Renaturation

Renaturation of collected fractions containing ARP, after reverse phase chromatography, SDS-gel electrophoresis (e.g., determining molecular weight), iso-electrofocusing (determining of pI), and some chemical modifications, used the method described for a different application (refolding of insoluble recombinant proteins) by Cabilly et al. Proc Natl Acad Sci USA. 81(11): 3273-7 (1984), with several modifications. The fractions, collected from C-4, C-8, or C 18 HPLC column chromatography, or extracted from slices of acrylamide gel, were put into a molecular porous dialysis tubing with MW cut-off of 6-8,000 kD (Spectra/Por, Houston, Tex.). BSA was added to each bag to a final concentration of 0.5 mg/mL. The bags were then dialyzed at 4° C. for 16 hr against 50 volumes of 8M urea/50 mM sodium glycinate, pH 10.8, 1 mM cysteine, and 0.1 mM cystine, this was followed by 24 hr dialysis against 100 vol of the same buffer containing 1 M urea, and finally, two-changes (8 hr, and 16 hr) against 100 vol of PBS with 2 mM EDTA, 1 mM cysteine, and 0.1 mM cystine. The fractions were filter sterilized by using Spin-X™ tube (Costar, Cambridge, Mass.) and diluted for in vitro assays.

SDS-PAGE Electrophoresis:

The Modular-Mini PROTEAN II™ Electrophoresis System (BioRad Cat# 165-2940) was used with 15% T, 0.8% C Tris/Glycine SDS Polyacrylamide gels. SDS-gel electrophoresis was performed according to Laemmli, U.K. (1970) Nature 227, 680-685. Gels were silver stained, photographed, and dried for storage (Gel Drying Kit from Promega, Fisher Cat# PR-V7120) or stored wet in sealed bags. For estimation of the molecular weight of ARP, gels were cut into slices, placed in a tube and extracted with buffer containing 0.1-0.5% SDS, followed by re-naturing. Extracts were tested for NK- and DC activity. SDS-PAGE standards (Bio-Rad) were used for calculation of molecular weight.

Chemical Modification Protocols

Chemical modifications of impure active bovine samples were used to determine the importance of various amino acids in an ARP. Reactions were performed according to "The Protein Protocols CD-ROM" (Walker, 1998, Protein Protocols on CD, Humana Press, Totowa, N.J.) designed for pure proteins. Modifications were added to allow the use of crude protein mixtures. For free COOH residue modification (in Asp, Glu, and C-terminus), the reagent EDC (1-ethyl-3-(3-dimethylaminopropyl)carbodiimi-de) was used. For His modification (ethoxyformylation), the reagent DEP (diethyl pyrocarbonate) was used. For Trp modification, Koshland's reagent (2-hydroxy-5-nitrobenzyl bromide) was used. For modification of guanidine groups (in Arg), the CHD (1,2-cyclohexanedione) reagent was used. For modification of free SH-groups (in Cys), two methods were utilized; a) Ellman's reagent, DTNB (5-5'-Dithiobis(2-nitrobenzoic acid)) and, b) NEM (N-ethylmaleimide). For modification of free $NH_2$ groups (amidination) (in Lys, and possible N-terminus), the amidination reagent MAH (methyl acetimidate hydrochloride) was used. For general oxidation/nitration reactions, TNM (tetranitromethane) was used. Treatment with, either $NaBH_4$, $Na_2S_2O_4$, or $Na_2SO_3$ was used for conducting reduction reactions (red-ox potentials for these reagents are 1.24, 2.96, and 0.92V). Hydroxylamine at basic pH was used for cleavage of the molecule at Asn-Gly site.

EXAMPLE 9

Toxicology in Animals and Humans

Early Toxicity Studies

No toxicity was observed during the standard (ip.) treatment with small intestine extract or any of its purified fractions. No overt changes were noticed in the health of the animals, in their activity levels, or growth weights.

Acute toxicity of porcine small intestine extract was tested in 3 mice which were given up to 1.0 ml in a single dose. To test for induction of hypersensitivity or anaphylaxis, repeat doses of 0.5 and 0.9 ml porcine extract were given 7 and 8 days later, respectively. These did not induce any observable changes.

In high subcutaneous doses of BBX-01c, a very mild phenotypic change was noticed in the mice, but only during the 5 days of injection. There was no pathological effects observed in tissue samples from various organs.

Treated animals routinely showed splenomegaly. This has been observed for other immune stimulators, such as IL-12. Since there were no pathological changes to the spleen, the enlargement is considered a beneficial and desirable outcome of treatment with the intestinal extract.

Safe Passage of BBX-01 in Dogs

Under the recommendation of the FDA, an initial safe passage study was performed on the original BBX-01 formulation on two male and two female beagles. This was contracted to MPI Research, Mattawan, Mich. The purpose of the study was to inject the animals with the initial dose that would be used in humans, without conversion to the lower body mass of the dog. This was considered by the FDA to provide some assurance that the first doses in humans could be administered safely and provide a base level from which dosage escalation could proceed. The summary of the report indicated that there was no adverse reaction to the drug.

Toxicity in Patients, BBX-01 ($1^{st}$ Leg of Study)

The only toxicity observed in this leg of the phase 1 clinical trial was a mild, reversible erythema at the site of injection. This was not raised and did not itch. It occurred to large or smaller degree in all patients, but was not considered dangerous. No other side effects were observed in blood chemistries, cell counts, or in careful physical exams.

Toxicity in Patient, BBX-01c (2nd Leg of Study)

The higher purity formulation, BBX-01c, did not exhibit the erythema of the previous formulation even with higher equivalent doses in half of the patients. Very high doses were not pursued, due to a lack of drug, but the one strong response in the germ cell ovarian cancer patient indicated that the therapeutic index for this material was likely to be high.

Preliminary Toxicity of E. tenella Extracts in Mice

A preparation from the oocysts of E. tenella, using the method described in Section 8, was injected at a single high dose into two mice. The dose was 40 times the highest dose given for the anti-tumor test described in Section 12.1. The mice tolerated the injection with no observable behavioral changes and no signs of any acute reactions have occurred.

Preliminary Toxicity of E. tenella Recombinant ARP, EtU3

Preliminary toxicity testing was conducted on a recombinant APR (EtU3). Three male BALB/c mice were each injected (ip) daily for 4 consecutive days with 4.3 μg of EtU3 in 1 ml buffer containing 0.1% BSA. A single non-injected mouse was retained as a control. Body weights were measured during and following the injections. Twenty-four days following the 4th injection the mice were given a 5th injection. Approximately 1 hour after the 5th injection, blood was sampled from each mouse for measurements of serum IL12 levels and for preliminary pharmacokinetic analysis. In addition, the following organs were removed and fixed in 10% buffered formalin for future histopathological analysis: spleen, liver, lung, kidney, adrenal, heart, and brain. No obvious indications of toxicity were observed during or following the treatment with EtU3. These include no significant changes in body weight, no "scruffiness", no lethargy and no diarrhea.

Toxicity of rBBX-01 in Mice

The acute toxicity of rBBX-01 (E1 formulated with 3% HSA) was evaluated in mice using an intraperitoneal (i.p.) route of administration. Three male mice were injected i.p. daily for 4 consecutive days with 4.27 µg/kg/day of rBBX-01. On day 27 each mouse received a 5$^{th}$ dose. One hour after the 5$^{th}$ dose, all animals were killed and necropsied. Selected organs and tissues were processed for histopathology.

There were no gross signs of toxicity in any of the treated mice. The body weights of the three treated mice showed an expected slight increase during the treatment period. Organs (liver, spleen, kidney, adrenal gland, heart, lungs and brain) were sampled, fixed and examined histopatholigically. No toxic effect was observed in any of the tissues sampled.

In a larger study, the acute and chronic toxicity of rBBX-01 was evaluated in mice under an intraperitoneal (i.p.) route of administration. Twenty-five male mice were injected i.p. with a single administration of rBBX-01 as follows: 5 mice were injected with vehicle control (3% HSA in PBS); 10 mice were injected with 400 ng ARP E; 5 mice were injected with 20 ng rBBX-01; 5 mice were injected with 1 mg rBBX-01. On day 4 post-injection 3 mice from the 400 ng treatment group were killed and necropsied. The remainder of the mice were necropsied on either day 17 or day 19. Selected organs and tissues were processed for histopathology. Body weights were recorded on days 4, 8, 10 and 13 of the study. Wet spleen weights were measured at necropsy on day 17 or 19.

There were no gross signs of toxicity in any of the treated mice. Body weights were not significantly different in any treatment group. There was a slight increase in wet spleen weight in mice treated with 400 ng rBBX-01 when compared with vehicle control treated animals. Organs and tissues were sampled, fixed and examined histopathologically. No significant toxic effect was observed in any of the tissues sampled.

Toxicity of rBBX-01 in Rats

A study was conducted to evaluate the potential toxicity of rBBX-01 following five days of once daily subcutaneous administration in rats. The study consisted of three groups of male and female CD®[Crl: CD® (SD)IGS BR] rats (10/sex/group). Two groups received the test article, rBBX-01, at dose levels of 7.5 and 300 ng/animal, and one group served as the control and received the vehicle, 3% human serum albumin (HSA) in phosphate buffered saline (PBS). The dose volume for all groups was 0.3 mL/animal. The first five animals/sex/group were necropsied on Day 6, while the last five animals/sex/group were necropsied on Day 15.

Observations for mortality and clinical signs, and body weight measurements were recorded throughout the study. Blood samples were collected on Days 2, 6, and 15 for the evaluation of clinical pathology parameters. At the respective interim and terminal necropsies (Days 6 and 15), complete necropsy examinations were performed, organ weights were measured, and selected tissues were collected, preserved for possible future processing and evaluation.

No treatment-related effects on survival, clinical signs, body weights, hematology/clinical chemistry evaluations, and macroscopic evaluations were noted during the study. No treatment-related organ weight changes occurred in either sex at the interim necropsy or in females at the terminal necropsy. However, terminal necropsy males exhibited a dose-related increase in prostate weights at 7.5 and 300 ng/animal (34% and 90% heavier than controls, respectively). In a subsequent study, rats receiving the same treatment showed a non-significant increase in prostate weight and microscopic evaluation of the prostate for all animals that were necropsied on Day 15 (Groups 1, 3, and 4; respective dose levels of 0, 7.5, and 300 ng/animal) determined that there were no treatment-related effects in this organ.

Based on the conditions and findings of this study, once daily-subcutaneous administration of rBBX-01 to rats for five consecutive days was well tolerated at dose levels up to 300 ng/animal.

EXAMPLE 10

Natural Abundance and Distribution of ARP

Animal Distribution

Various Species

During the course of many years, extracts were taken from mice, rats, pigs, and cattle. The activities from this early work are shown in Table 9. Different tissues were examined in these species but extracts from the small intestine were consistently active in the mouse anti-tumor model, indicating that the active factor is not strongly species specific. As we clarified the existence of A component (containing IL18) and C component (containing ARP), IL-18 in the A fraction was speculated to be a major contributor in these extracts, since it can cross species barriers to some extent. The DC assay demonstrated that laboratory mice and rats contained no ARP (C fraction) activity. A porcine sample from MSU was also devoid of activity, whereas a 10-yr old frozen sample from a slaughterhouse pig retained high activity. This suggested an agent with an environmental component was involved in ARP activity and that not all animals were exposed to the agent. We have trapped wild mice from the MSU cattle farms and a shrew from the BRI property, which allowed testing non-laboratory animals that might be analogous to farm-raised cattle. The shrew contained ARP activity, but several mice did not.

TABLE 9

Summary of early extracts from four species

| Treatment | ILS[1] | Cures[2] |
|---|---|---|
| Porcine Ileum Extract | | |
| of Jun. 4, 1991 | — | 6/6 |
| of Jun. 19, 1991 | 130% (4/6)[3] | 2/6 |
| of Aug. 7, 1991 | 150% (5/6) | 1/6 |
| of Aug. 7, 1991 | 162% (5/6) | 1/6 |
| of Aug. 7, 1991 | 145% (5/6) | 1/6 |
| Mucosa | 185% (5/6) | 1/6 |
| Sub-mucosa | 209% (2/6) | 4/6 |
| Smooth muscle | 133% (6/6) | — |
| Murine (Balb/c) | | |
| Brain | 115% (5/5) | — |
| Small Intestine[4] | 195% (2/24) | 22/24 |
| Large Intestine | 120% (6/6) | — |
| Large Intestine | 85% (5/5) | — |

TABLE 9-continued

Summary of early extracts from four species

| Treatment | ILS[1] | Cures[2] |
|---|---|---|
| Spleen (supernat.) | 78% (5/5) | — |
| Spleen (pellet) | 69% (4/5) | 1/6 |
| Rat (Sprague Dawley) | | |
| Brain | 98% | — |
| Small Intestine | 200% (5/6) | 1/6 |
| Small Intestine | — | 6/6 |
| Large Intestine | 166% (1/6) | 5/6 |
| Large Intestine | — | 6/6 |
| Bovine | | |
| Ileum mucosa | 254% (2/6) | 4/6 |
| Ileum sub-mucosa | — | 6/6 |
| Ileum smooth musc. | — | 6/6 |
| Distal ileum (all layers) | 200% (1/5) | 4/5 |
| Proximal ileum (all layers) | 214% (2/5) | 3/5 |
| Duodenum | 83% (5/5) | — |
| Jejunum | 74% (5/5) | — |

[1] ILS = 100% indicates survival identical to controls.
[2] Tumor-free survival beyond 50 days.
[3] Number of animals in this category, versus total in group.
[4] Representative sample of many experiments.

The identification of an *Eimeria* protein in cattle validated the notion that an environmental agent was critical to activity. The lack of activity in wild mice, however, suggested that *Eimeria* from mice may not work in our assay because the DC assay is based on murine splenic dendritic cells. It further suggests that only cross-species presentation of the *Eimeria* protein is effective when using the non-intestinal dendritic cells of the spleen. Further work to clarify this is being planned.

Cattle Breeds

Figure 15:
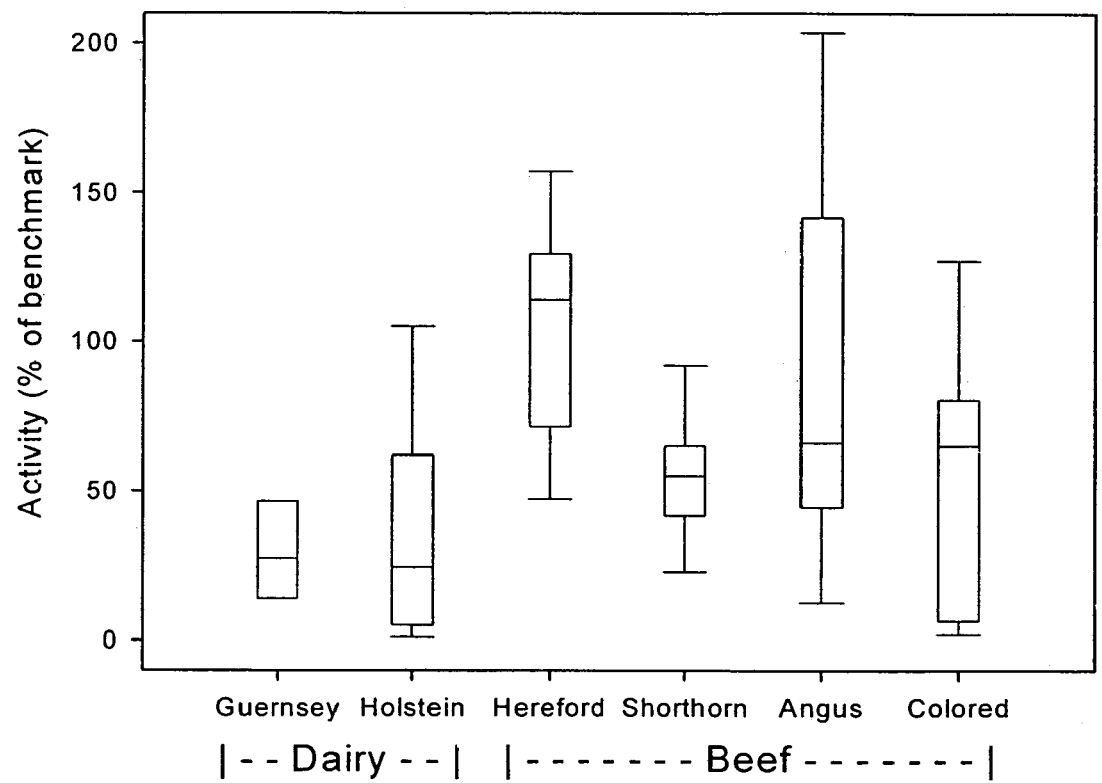
FIG. 15. DC assay activities of various bovine breeds compared to a benchmark pool. Boxes represent 25$^{th}$ percentile (bottom) to 75$^{th}$ percentile (top). Lines above and below boxes are the 95$^{th}$ and 5$^{th}$ percentile indicators, respectively. The median in denoted as a line inside the box.

We obtained hundreds of intestinal segments from cattle and routinely observed the wide variation in activity between animals and pools of animal extracts. Some of this variation was attributed to different breeds, as shown in FIG. 15, but the intra-breed variation was also very high. With beef cattle routinely containing higher levels of activity, these were selected more often from the slaughterhouse. The higher yields allowed for more quickly reaching quantities sufficient for purification to homogeneity (see Section 6).

Tissue Distribution

Various Organs

A limited set of organs and tissues have been examined over the years to test the hypothesis that the observed activity is confined to the intestinal tract. Brain and spleen from rodents examined showed no anti-tumor activity. Recent tissue samples from the spleen, liver, and lung of cattle have shown no activity in the DC and NK assays. However, due to the limited sample size and the sensitivity of the test, the absence of ARP in other organs is not conclusive.

Distribution of Activity Along the Intestine

Figure 16A:
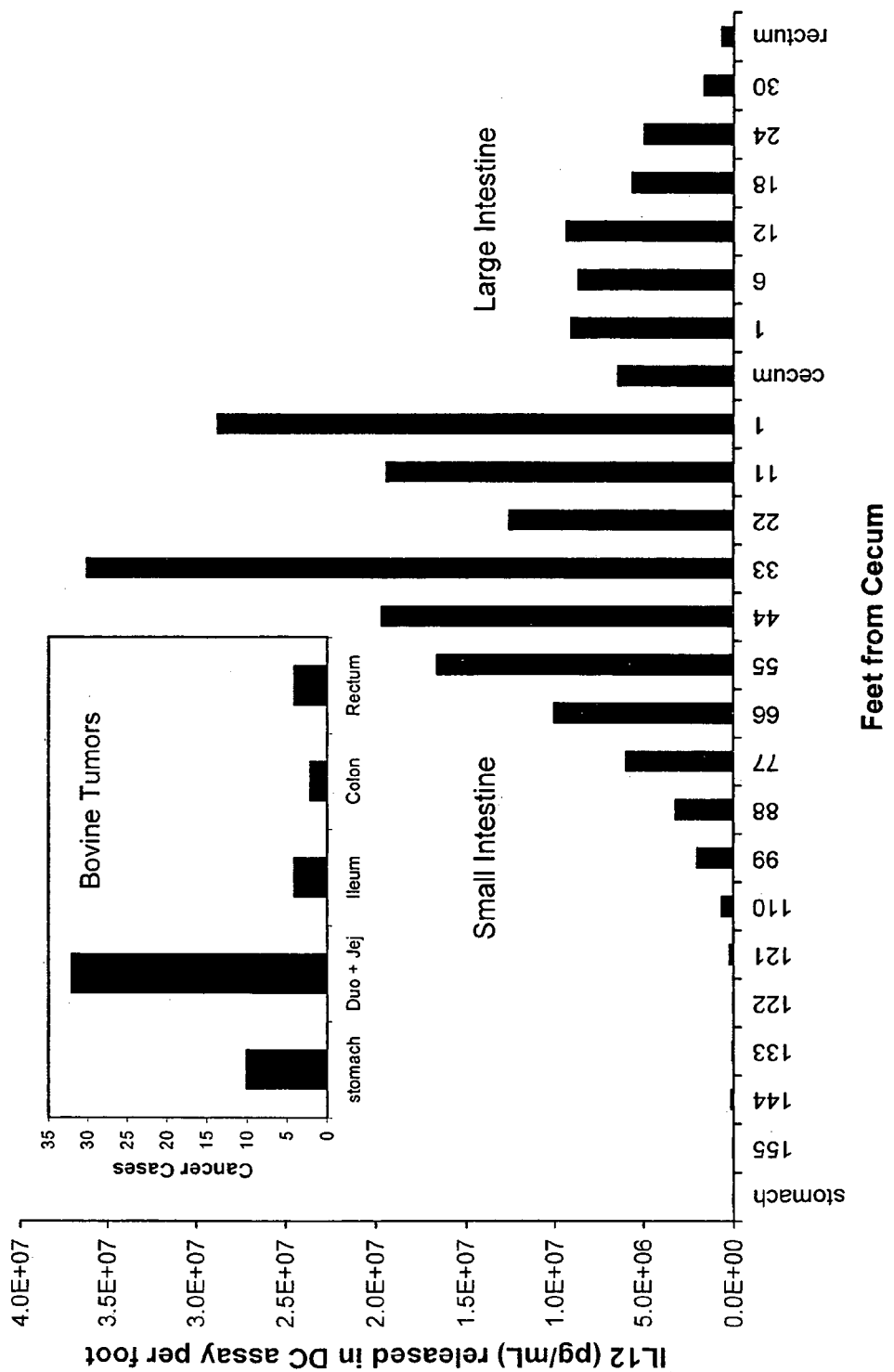
FIG. 16. (A) DC activity of extracts from sections of the bovine intestinal system with comparison to natural tumor incidence. (B) Antitumor activity of bovine intestinal extracts in the murine tumor model. The tumor index, as described in section 12.1.2, was used to evaluate an experiment in progress. Pools of three adjacent fractions along the small and large intestine were included with the cecum sample. Each group consisted of a group of 5 mice following the protocol of section 12.1.1.
Figure 16B:
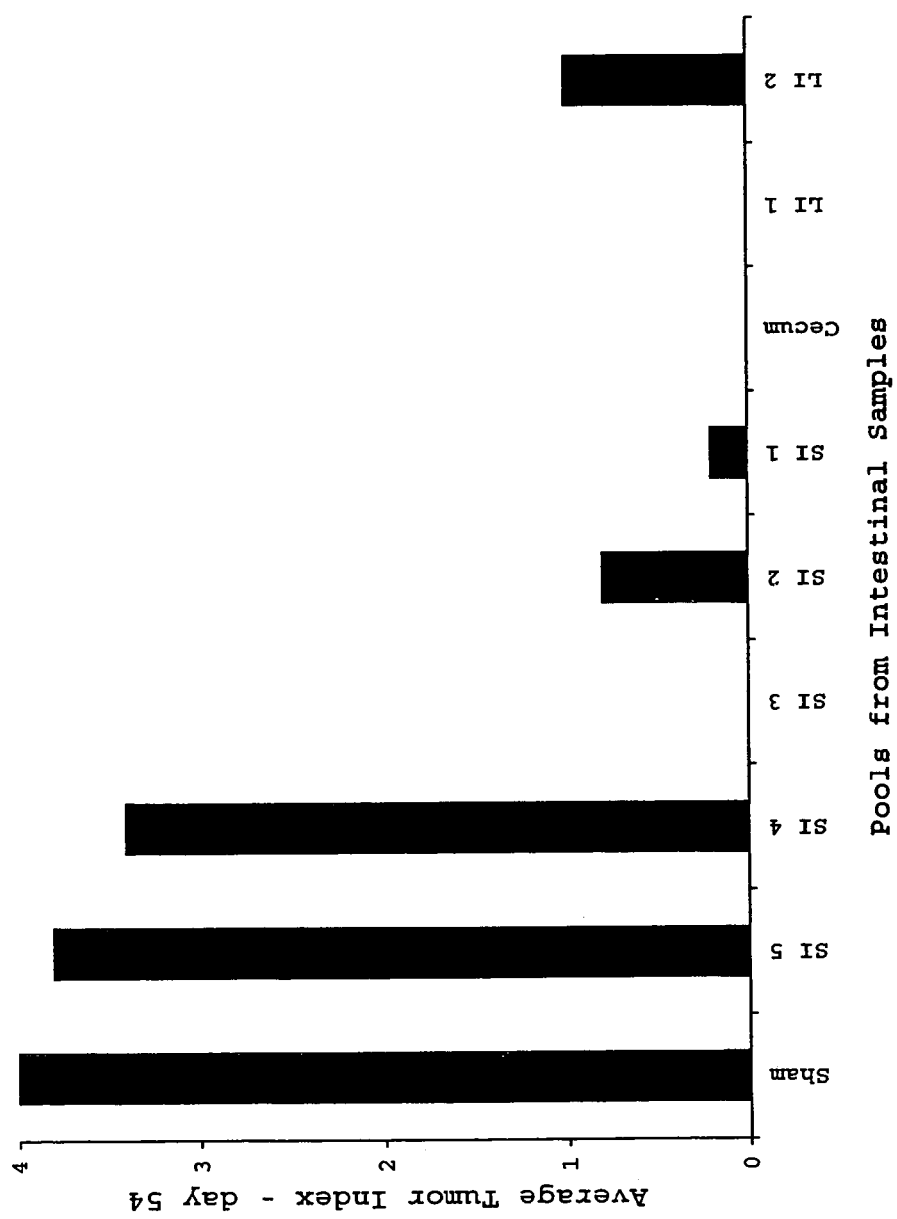

Initial studies in activity along the intestinal tract in cattle revealed that the ileum of small intestine contained the highest anti-tumor activity in mice (Table 9, supra). This was examined again when ARP-specific activity could be identified with the DC assay. The average of three experiments is shown in FIG. 16(A). Preliminary murine anti-tumor results for pooled samples along the intestinal tract is shown in FIG. 16(B). These results validate the previous findings and give a finer detail to the distribution of activity along the intestinal tract. This distribution is consistent with the locations of *Eimeria* life stages in cattle. More importantly, this distribution matches the prevalence of cancer in cattle (Lingeman and Garner, J. Natl. Cancer Inst. 48(2): 325-46 (1972)). Unlike humans, many animals have a low incidence of large intestine cancer along with the low incidence in the ileum. For cattle, the intestinal tract cancer is only observed in the jejunum and the rectum. This coincides very closely to the distribution of DC activating capacity shown in FIG. 16 (A).

Distribution of Activity Across the Intestinal Wall 70-90% of NK-activity, 80-100% of IFNγ-inducing activity and 80-100% of DC-activity could be extracted from the intestinal tissue with the use of 30 mM EDTA.

Small intestinal ileal sections were prepared and washed as described in Section 6. The washed pieces approximately 3 ft total length were cut into 2-3 cm pieces and incubated in PBS with 0.5-1 mM DTT 5-10 min to remove mucus. The solution was decanted and tissue pieces were stirred in 3-4×60 ml changes of PBS, 30 mM EDTA, 1 mM PMSF for 30-60 min at 40° C. The procedure removed cells from the mucosal layer containing most of the NK-, DC- and IFNγ-inducing activity as verified by analysis of the amount of activity in the residual tissue. Quantitative extraction of all activity types into the mucosal cell fraction is consistent with the known confinement of *Eimeria* infections to the intestinal mucosa.

EXAMPLE 11

Domain Studies

The importance of the disulfide bridge has been verified in semi-pure samples of both bovine and *E. tenella* ARPs. Cleavage of bovine ARP at Asn-Gly site drastically reduced both NK-, and DC-activities. Since the bovine ARP has at least one such site in the middle of the molecule (FIG. 4), it shows that the resulting fragments of the ARP molecule contain no domains responsible for either NK-, or DC-activity.

A synthetic peptide (50-mer) was constructed from a combination of the variable region of the bovine molecule and the flanking regions of the 3-1E protein (FIG. 4). This peptide was synthesized by Alpha Diagnostic International, Inc. and was received as a dry powder. It was tested in both the freshly reconstituted state and in a renatured form. Neither form exhibited any activity when tested over concentrations spanning 7 orders-of-magnitude starting at approximately 0.1 mg/mL. This synthetic peptide encompasses the domain between the disulfide bonds and its lack of activity indicates that either a different domain is important to dendritic cell binding or more of the molecule is needed for correct folding of this domain.

Experiments on recombinant ARP from *E. tenella* showed that the N-terminal end of the molecule can tolerate fusion of large non-related proteins and peptides without big changes in DC-activity (Section 10). The truncated molecule with an ATG start codon in 6th position (lacking GEADT, SEQ ID NO:51) was at least as active as the full protein, but activity was lost when the start codon was moved to the 21$^{th}$ position (forming a truncated molecule lacking GEADTQAWDTS-VREWLVDT, SEQ ID NO:52). This suggests that the distal part of N-terminus is probably not involved in formation of any domains important for manifestation of at least DC-activity. Two C-terminal mutants of the *E. tenella* ARP (one with double exchange Tyr to His and Gly to Ser, the other one with exchange Gly to Ala; Section 10) have been obtained and appeared to be equally active on DC-assay. Another mutant lacking three amino acids from C-terminus (SGF) retained significant activity while the mutants lacking 7, 10 or 14 amino acids from the C-terminus showed significantly lower (if any) DC-activity (Section 10), it suggests that the C-terminal part of the molecule is part of some domain determining DC-activity. This part of the molecule contains no regions highly conserved in the known Apicomplexan ARPs. A common motif in the region is: T/S-A/I-L-A/N-F-A-E-(Y)-L, which, as judged by comparison of ESTs, is conserved within *Eimeria, Neurospora*, and the most often found ARP sequences from *Toxoplasma*.

EXAMPLE 12

Antibodies to Variable and Constant Regions

Polyclonal antibodies to two 20-mer epitopes are being generated in rabbits by Alpha Diagnostics International, Inc. One epitope is from the non-conserved region of the bovine sequence and spans CRMFGASTDSGGDPYAELVQ (SEQ ID NO:53). The other is from the *E. acervulina* sequence and spans CALYDEEKEQNKADALTTAL (SEQ ID NO:54). In the first case, the cysteine is part of the molecule, while in the second case it was added at the beginning to allow conjugation to keyhole limpet haemocyanin, which is used to improve its antigenicity.

EXAMPLE 13

Evidence for Hydrophobic Membrane Anchors

In some embodiments, ARP is an outer surface antigen of *Eimeria* parasites. We investigated the mechanism of its linkage to the cell membranes (GPI-linkage vs. integral membrane protein) by studying the possibility of ARP release by phospholipase C (PLC), the enzyme specific for GPI-linked proteins. The results presented in Example 4 suggest that ARP is GPI-linked to the outer membrane of *E. tenella* sporozoites.

Spontaneous release of ARP from the membranes was observed in these experiments, which is described in literature for other parasites as "shedding" of surface proteins (Zambrano-Villa et al., Trends Parasitol. 18(6): 272-8 (2002)). The process was stimulated by elevated temperature, 10 mM EGTA, and was inhibited in the presence of 10 mM $ZnCl_2$, an inhibitor of endogenous protozoan PLC from *Trypanosoma*. These observations are consistent with the possibility of enzymatic nature of ARP release, probably due to endogenous PLC. However, non-enzymatic mechanisms are not excluded.

Many surface proteins of protozoa are anchored by GPI moieties (Ropert and Gazzinelli, Curr Opin Microbiol. 3(4): 395-403 (2000); Almeida and Gazzinelli, J Leukoc Biol. 70(4): 467-77 (2001)) and this moiety alone has previously demonstrated macrophage activation capacity (Magez et al., J. Immunol. 15; 160(4): 1949-56 (1998)) and is known to bind to the toll-like receptor-2 (Campos, 2001, J. of Immunology 167: 416-423), probably through its lipid moiety. Our experiments suggest that the release of ARP is regulated by protozoan metabolism through control of the GPI linkage and that the membrane linkage, disrupted by PLC is not required for activation of DC cells. Further evidence was generated by comparing the location of activity on C8 RP-HPLC separations of highly active *E. tenella* extracts with and without phospholipase treatments. In both cases, the activity remained unchanged and appeared in the same fractions. This distinguishes ARP from the DC activators that depend on lipid components, such as GPI itself, LPS, and bacterial lipoproteins (Brightbill et al., Science 285(5428): 732-6 (1999); Aliprantis et al., Science 285(5428): 736-9 (1999)). Preliminary data on testing the membrane preparation from sporozoites of *E. tenella* for anti-tumor activity in vivo imply, as one of the possible interpretations, that a membrane-linked form of ARP can be an effective therapeutic agent, giving it enhanced stability and/or slow-release characteristics.

EXAMPLE 14

Oral Administration of *E. tenella* Oocysts

Murine tumor model is used to determine if oral administration of a cross-species *Eimeria* can generate the anti-tumor response seen by administration of *E. tenella* extracts. Tumor-bearing mice, fed with oocysts, are examined for increased lifespan. Mice without tumor, receiving oocysts, are examined for DC activity in their spleens and small intestines approximately 2-3 weeks after oocysts ingestion. This will indicate whether ARP can be elevated in the SI tissue and whether this can extend to other tissues. Oocysts are delivered to mice in their drinking water after overnight water restriction. Each mouse drink approximately 0.5 mL, containing approximately 100,000 oocysts.

EXAMPLE 15

Evidence for Anti-Viral Activity of ARP in Humans

During the Phase I human trial of BBX-01, a terminal lung cancer patient reported the complete disappearance of long-term warts, likely to be of papillomavirus origin, from two body regions. The first along the left and central region of the back (along the line of the spine), and the second along the upper region of the left arm. The report stated that the warts suddenly dried up and disappeared. This occurred after the patient received three progressively larger single doses of BBX-01 spaced at approximately two-week intervals, but before receiving a multiple-dose course. The patient was under no other therapy during this period.

EXAMPLE 16

Identification of Proteins

Homologous to the *Eimeria* 19 kd Sporozoite Antizen

Sequence homology searches were performed, using the *E. acervulina* ARP (SEQ ID NO:2) and the variable region of the Bovine *Eimeria* protein sequence of the invention in order to identify other proteins with similar sequence and/or structure to that found for the isolated peptide of the invention. The Basic Local Alignment Research Tool (BLAST)®, available through the website managed by the National Library or Medicine (www.ncbi.nlm.nih.gov/BLAST), was used to identify homologues of the bovine *Eimeria* protein (Table 10). Alternatively, databases containing *Plasmodium falciparum* genome sequences were used for comparisons between the *Eimeria* 19 kD sporozoite antigen and sequences of the *Plasmodium falciparum* genome, using the BLAST algorithm available at the following website: plasmodb.org/plasmodb/serylet/sv?page=blast (Table 10).

In brief, the *Eimeria* 19 kD sporozoite antigen peptide sequence was used in a BLAST query of 1) the database of *Homo sapiens* protein sequences with a total of 39,196 sequences, 2) the database of GenBank+EMBL+DDBJ+PDB (but no EST, STS, GSS, or phase 0, 1 or 2 HTGS) sequences with a total of 1,687,930, and 3) the database of GenBank+EMBL+DDBJ sequences from EST divisions with a total of 15,724,693 sequences. All of these databases were available for public searching through the website of the National Center for Biotechnology Information (NCBI) at the National Library of Medicine (NLM) and could be found at the aforementioned website.

Pairwise BLAST comparisons, within the database of *Homo sapiens* protein sequences were made using the "blastp" program option, which is suitable for protein—protein comparisons. No significant homology between the *Eimeria* 19 kD sporozoite antigen and the sequences on deposit in the *Homo sapiens* protein database were found.

Pairwise BLAST comparisons within the database of GenBank+EMBL+DDBJ+PDB (but no EST, STS, GSS, or phase 0, 1 or 2 HTGS) sequences were made using the "tblastn" program option, which compares the protein "Sequence 1" against the nucleotide "Sequence 2" which has been translated in all six reading frames. Significant sequence and structural homology was found between the *Eimeria* 19 kD sporozoite antigen and the known protein sequences on deposit in this database.

Pairwise BLAST comparisons within the database of GenBank+EMBL+DDBJ sequences from EST divisions were made using the "tblastn" program option, which compares the protein "Sequence I" against the nucleotide "Sequence 2" which has been translated in all six reading frames. Significant homology was found between the *Eimeria* 19 kD sporozoite antigen and the known EST sequences on deposit in this database. Interestingly, only members of Apicomplexa resulted from this search.

The variable region sequence of the Bovine *Eimeria* protein of the invention was used in a BLAST query of the database of GenBank+EMBL+DDBJ+PDB (but no EST, STS, GSS, or phase 0, 1 or 2 HTGS sequences) sequences.

Pairwise BLAST comparisons within the database of GenBank+EMBL+DDBJ+PDB (but no EST, STS, GSS, or phase 0, 1 or 2 HTGS sequences) sequences were made using the "tblastn" program option, which compares the protein "Sequence 1" against the nucleotide "Sequence 2" which has been translated in all six reading frames. No reasonable homology was found between the variable region of the Bovine *Eimeria* protein of the invention and any known protein on deposit in the bovine database.

Identified ARPs have also been analyzed for conserved domains using Conserved Domain Database (CDD v. 1.60) and a Reverse Position-Specific BLAST® algorithm set to default parameters, which are available at the website ncbi.nlm.nih.gov/Structure/cdd/wrpsb.cgi. The analysis showed that the identified ARPs have a conserved PROF (profilin) domain, which is represented by profilin. Data showed that a preparation containing birch pollen (e.g., SEQ ID NO:13) was active in DC-assay. Based on the alignment on protein level, birch pollen profilin has 28% identity and 54% similarity to the *E. tenella* ARP; 31% identity and 57% similarity to the *E. acervulina* ARP.

TABLE 10

Representative BLAST ® Results

| Input Sequence | Accession # | SEQ ID NO. | Description | Bit Score | Percentage of Identity | Percentage of Positives[1] |
|---|---|---|---|---|---|---|
| EA 19 kD sporozoite antigen | 11561738 | 8 | Plasmodium (chr9.phat__327) | 116 | 39 | 56 |
| EA 19 kD sporozoite antigen | 11562004 | 9 | Plasmodium (chr9.gen__161) | 116 | 38 | 58 |
| EA 19 kD sporozoite antigen | 11562590 | 10 | Plasmodium (chr9.glm__372) | 100 | 40 | 58 |
| EA 19 kD sporozoite antigen | 11513601 | 11 | Latex profilin Hevb8 chain A from *Hevea Brasiliensis* | 35 | 26 | 42 |
| EA 19 kD sporozoite antigen | 2781152 | 12 | Profilin I from *Arabidopsis Thaliana* | 31 | | |
| EA 19 kD sporozoite antigen | 1942360 | 13 | Birch pollen profilin from *Betula Pendula* | 31 | 31 | 57 |
| EA 19 kD sporozoite antigen | 15224838 | 14 | Profilin I from *Arabidopsis Thaliana* | 31 | | |
| EA 19 kD sporozoite antigen | BG235691 | 21 | EtESTedl1f08.y1 *Eimeria tenella* S5-2 cDNA Neg Selected *Eimeria tenella* cDNA 5' similar to TR: Q24777 Q24777 19 KDA SPOROZOITE ANTIGEN. [2] TR: Q03777;, MRNA sequence | 285 | 83 | 91 |
| EA 19 kD sporozoite antigen | CB070888 | 22 | TgESTzye83c06.y1 TgME49 invivo Bradyzoite cDNA size selected *Toxoplasma gondii* cDNA clone TgESTzye83c06.y1 5' similar to TR: Q24777 Q24777 19 KDA SPOROZOITE ANTIGEN. [2] TR: Q03777;, MRNA sequence | 169 | 51 | 72 |

TABLE 10-continued

Representative BLAST ® Results

| Input Sequence | Accession # | SEQ ID NO. | Description | Bit Score | Percentage of Identity | Percentage of Positives[1] |
|---|---|---|---|---|---|---|
| EA 19 kD sporozoite antigen | BM189297 | 23 | TgESTzyb37c04.y1 TgRH Tachyzoite Subtracted cDNA Library *Toxoplasma gondii* cDNA clone TgESTzyb37c04.y1 5' similar to TR: Q24777 Q24777 19 KDA SPOROZOITE ANTIGEN. [2] TR: Q03777;, MRNA sequence | 169 | 51 | 72 |
| EA 19 kD sporozoite antigen | AA167907 | 24 | CpEST.071 uniZAPCpIOWAsporoLib1 *Cryptosporidium parvum* cDNA 5' similar to *Eimeria acervulina* 19 kDa sporozoite antigen, MRNA sequence | 129 | 46 | 64 |
| EA 19 kD sporozoite antigen | CA856473 | 25 | PfESToac08g05.y1 *Plasmodium falciparum* 3D7 gametocyte cDNA library *Plasmodium falciparum* 3D7 cDNA 5' similar to TR: Q24777 Q24777 19 KDA SPOROZOITE ANTIGEN. [2] TR: Q03777;, MRNA sequence | 122 | 38 | 57 |

[1] Percentage of positives: the extent of similarity between two sequences, which can be based on percent sequence identity and/or conservation.

EXAMPLE 17

Evidence for Anti-Viral Activity of ARP in Mice

Specific pathogen-free female BALB/c mice were infected intranasally with an LD90 dose of influenza virus A/NWS/33 (HINI). The mice were then treated with ARP E1 by one of two treatment protocols. In the first protocol mice received 100 ng of ARP E1 given intraperitoneally 48 hours before viral exposure, 4 hours after viral exposure (day 0) and on days 3 and 6 after viral exposure. In the second protocol mice received 100, 1,000, or 10,000, ng of ARP E1 intraperitoneally 4 hours after viral exposure (day 0) and on days 3 and 6 after viral exposure. Placebo treated mice received bovine serum albumin in phosphate-buffered saline. Mice were observed daily for death. The survival of the mice is shown in Table 11.

TABLE 11

Survival of Mice Exposed to Influenza

| Compound | Dose (ng/day) | Treatment Schedule | Survive/Total | Mean Day to Death[a] ± SD |
|---|---|---|---|---|
| ARP E1 | 100 | −2, 0, 3, 6 | 0/10 | 12.3 ± 1.2* |
| ARP E1 | 100 | 0, 3, 6 | 2/10 | 12.1 ± 1.6 |
| ARP E1 | 1,000 | 0, 3, 6 | 3/10 | 12.7 ± 2.7 |
| ARP E1 | 10,000 | 0, 3, 6 | 5/10* | 12.0 ± 1.4* |
| Placebo | | 0, 3, 6 | 2/20 | 11.3 ± 1.2 |

[a] Mean day to death of mice dying before day 21
*P < 0.05

There was a significant increase in the number of survivors and time to death in the mice treated with 10,000 ng of ARP E1. Arterial oxygen saturation was also measured in these mice on days 3-11. There was a statistically significant reduction of the decline in oxygen saturation in the mice treated with 1,000 ng and 10,000 ng of ARP E1.

EXAMPLE 18

Use of ARP as an Immunosuppressant by Initiation of Dendritic Cell Paralysis While the primary activity of ARP is to induce IL-12 production in dendritic cells it has been noted that at high doses (~1000 times stimulatory dose) ARP can suppress the production of IL-12. Based on this observation it may be possible to use ARP as an immunosuppressant in the treatment of diseases that are caused by an overactive or inappropriate immune response. This hypothesis was tested in the experimental autoimmune encephalomyelitis (EAE) model in SJL mice. EAE is induced in mice by immunization with spinal cord derived myelin basic protein which induces a disease in the mice which is very similar to multiple schlerosis (MS) in humans.

The SJL mice were immunized with the myelin basic protein on day 0 and on day 10 they received daily treatments of 0.1 μg, 1.0 μg or 10 μg ARP E1 given i.p. or with 5 mg Linomide given s.c. or with vehicle alone. Treatments were given daily for 5 days. Linomide is a drug that is known to inhibit EAE and is used as a positive control. EAE exhibits itself in mice as progressive paralysis beginning in the tail and progressing forward until death occurs. Severity of EAE is measured by means of the EAE score which starts at for normal and increases to a score of 5 when death occurs. For ethical reasons mice are sacrificed when a score of 4 is reached. The experiment was terminated on day 15 and the mean EAE scores are shown in Table 12.

TABLE 12

Effect of ARP on EAE in SJL Mice

| Treatment | Day 15 EAE Score ± SD |
|---|---|
| Vehicle | 1.8 ± 1.9 |
| Linomide | 0.6 ± 1.3 |

TABLE 12-continued

Effect of ARP on EAE in SJL Mice

| Treatment | Day 15 EAE Score ± SD |
|---|---|
| ARP E1 0.1 µg | 2.7 ± 1.3 |
| ARP E1 1.0 µg | 1.5 ± 1.6 |
| ARP E1 10.0 µg | 1.1 ± 1.5 |

Although the EAE scores in the ARP treated groups are not significantly different from the vehicle control, the trend in the scores is consistent with the proposed mechanism of action of ARP. At the lowest dose, where ARP is expected to act as an immunostimulant, it did appear to make the disease slightly worse. However, at the high dose where ARP's immunosupressant activity may expected the disease does appear to be suppressed giving a score intermediate between the vehicle treated control and the Linomide positive control.

EXAMPLE 19

Use of ARP to Treat *Candida albicans* Infection in Mice

The object of this study was to determine if administration of ARP following infectious challenge with *Candida albicans* increased the survival of mice. Groups of female CDI mice were inoculated intravenously (i.v.) on Day 0 with an infectious dose of *Candida albicans* calculated to provide 60-100% mortality in the control group. Groups of mice were administered, by i.p. injection, one of three concentrations of the test material (0.1, 1.0 or 10.0 ng/mouse/day) or vehicle on Day 0, approximately 1.5 hours following infectious challenge, and again on Days 1 through 4, for a total of five doses. An additional assay control group of mice was administered approximately 80 mg of fluconazole per kg of body weight by oral gavage approximately 1, 24, 48 and 72 hours following infectious challenge. The mice were observed for up to 14 days for mortality following infectious inoculation.

TABLE 13

Survival of *Candida albicans* challanged mice treated with ARP

| Treatment | Dose | Mean Time to Death[a] | Mean Survival Time[b] | Percent Mortality |
|---|---|---|---|---|
| Vehicle | — | 6.0 | 10.4 | 40 |
| ARP | 0.1 ng | 13.0 | 13.6 | 20 |
| ARP | 1.0 ng | 4.0 | 7.8 | 60 |
| ARP | 10.0 ng | 6.0 | 12.2 | 20 |
| Fluconazole | ~80 mg/kg | — | 14.0 | 0 |

[a]Time (days) relative to challenge, spontaneous deaths only
[b]Time (days) relative to challenge, all animals No statistically significant differences in percent mortality, mean survival time or mean time to death were observed between the test groups and the vehicle treated group. There may have been an effect at the 0.1 ng dose of ARP but it was not apparent at the higher doses.

EXAMPLE 20

Use of ARP to Treat Malaria in Mice

The object of this study was to determine if administration of ARP following infectious challenge with *Plasmodium yoelii* increased the survival of mice. Groups of male C57BL/6 mice were inoculated i.v. on Day 0 with an infectious dose of *Plasmodium yoelii*. Groups of mice were administered, by i.p. injection, one of three concentrations of the test material (0.1, 1.0 or 10.0 ng/mouse/day) or vehicle on Day 1 and again on Days 2 through 5, for a total of five doses. An additional assay control group of mice was administered approximately 40 mg of Chloroquine per kg of body weight by i.p. injection on Days 1 through 5 as well.

TABLE 14

Survival of *Plasmodium yoelii* challanged mice treated with ARP

| Treatment | Dose | Survival (Days) ± SD | Parasitized Erytthrocytes % |
|---|---|---|---|
| Vehicle | — | 24.0 ± 0.7 | 42 |
| ARP | 0.1 ng | 26.3 ± 1.2 | 34 |
| ARP | 1.0 ng | 25.9 ± 1.2 | 33 |
| ARP | 10.0 ng | 26.4 ± 1.1 | 36 |
| Chloroquine | 40 mg/kg | 37.0 ± 0.7 | 12 |

As an additional marker of activity the body temperature and heart rate of the mice was also monitored. All three doses of ARP delayed and reduced the rise in body temperature and heart rate typically seen in mice infected with malaria. There was further indication of activity of ARP in this model, as evidenced by the small increase in survival and reduction in level of parasitized erythrocytes, these differences were not statistically significant.

EXAMPLE 21

Use of ARP to Treat Chronic Hepatitis in Woodchucks

Woodchucks which are chronically infected with hepatitis were monitored both for levels of hepatitis DNA and anti-hepatitis antibody titer. Three woodchucks were treated daily for two weeks with 25 ng/kg of ARP and three additional woodchucks served as untreated controls. Blood samples were collected on days 3, 7, 15, 21, 28 and 42 after start of treatment for analysis of hepatitis DNA levels and antibody titers. There was no effect of ARP treatment seen on either hepatitis DNA level or anti-hepatitis antibody titer at the dose of ARP used.

EXAMPLE 22

Use of ARP to Treat Tuberculosis in Mice

Groups of mice were exposed to *Mycobacterium tuberculosis* Erdman strain (M.tb) by inhalation on day 0. On days 1, 2, 3, 4 and 5 the mice received 0.1 ng, 1.0 ng or 10.0 ng of ARP E1 in 3% BSA and phosphate buffered saline given by intraperitoneal injection. A control group of mice received vehicle only. On day 0, 21 and 42 the colony forming units (cfu) of M.tb in the lung were determined. There was no statistically significant difference in cfu between the control group and any of the treatment groups. While this particular treatment regimen did not have a significant effect on M.tb infection, the use of different doses, routes of administration or time of treatment may provide a beneficial effect.

EXAMPLE 23

Determination of the Number of Cys Residues in E1

The amino acid sequence of E1 (ARP E1) as predicted by the nucleic acid sequence inserted into the production plasmid should contain two cysteines. Because of sulfur reactivity and the potential role of disulfide bond formation in protein stability, it is necessary to evaluate the sulfhydryl content of the recombinant protein as well as its redox state. The mass spectrometry data obtained on each batch yielded a consistent mass of 18,414 Da. This is the exact mass predicted for the amino acid sequence given for sequence E1 (FIG. 20) provided both sulfhydryls are reduced. A mass of 18,412 Da would be expected 1 a disulfide bond were present. While mass spectrometry is highly accurate, concluding that a mass of 18,414 Da is indicative of a reduced form is difficult in the absence of corroborating data. To obtain such data, the sulfhydryls of the protein were modified by Ellman's reagent and the mass re-determined.

Ellman's reagent is a dimer of two thio-nitro-benzoic acid residues linked through a disulfide bridge. This will react with the cysteine thiols in proteins to form mixed disulfides, yielding adducts of well defined mass. Depending on the local redox environment of the protein and the proximity of the thiols, these mixed disulfides can exchange, yielding a disulfide on the protein and the re-generation of Ellman's reagent. This reaction also yields a reduced Ellman monomer for each protein cysteine oxidized.

If the E1 protein contains two sulfhydryls, the first of two products from the Ellman's reaction should be the double adduct, with mass:

18,414.24+396.3(Ellman)−2(hydrogen lost)=18,808.54 Da. The second product should be the disulfide form of the protein with mass 18,412.24 Da.

The protocol for this reaction is given below, followed by the mass spectrometry data for the E1 drug substance. The only major components detected by mass spectrometry are the two expected products.

Results

Figure 26:
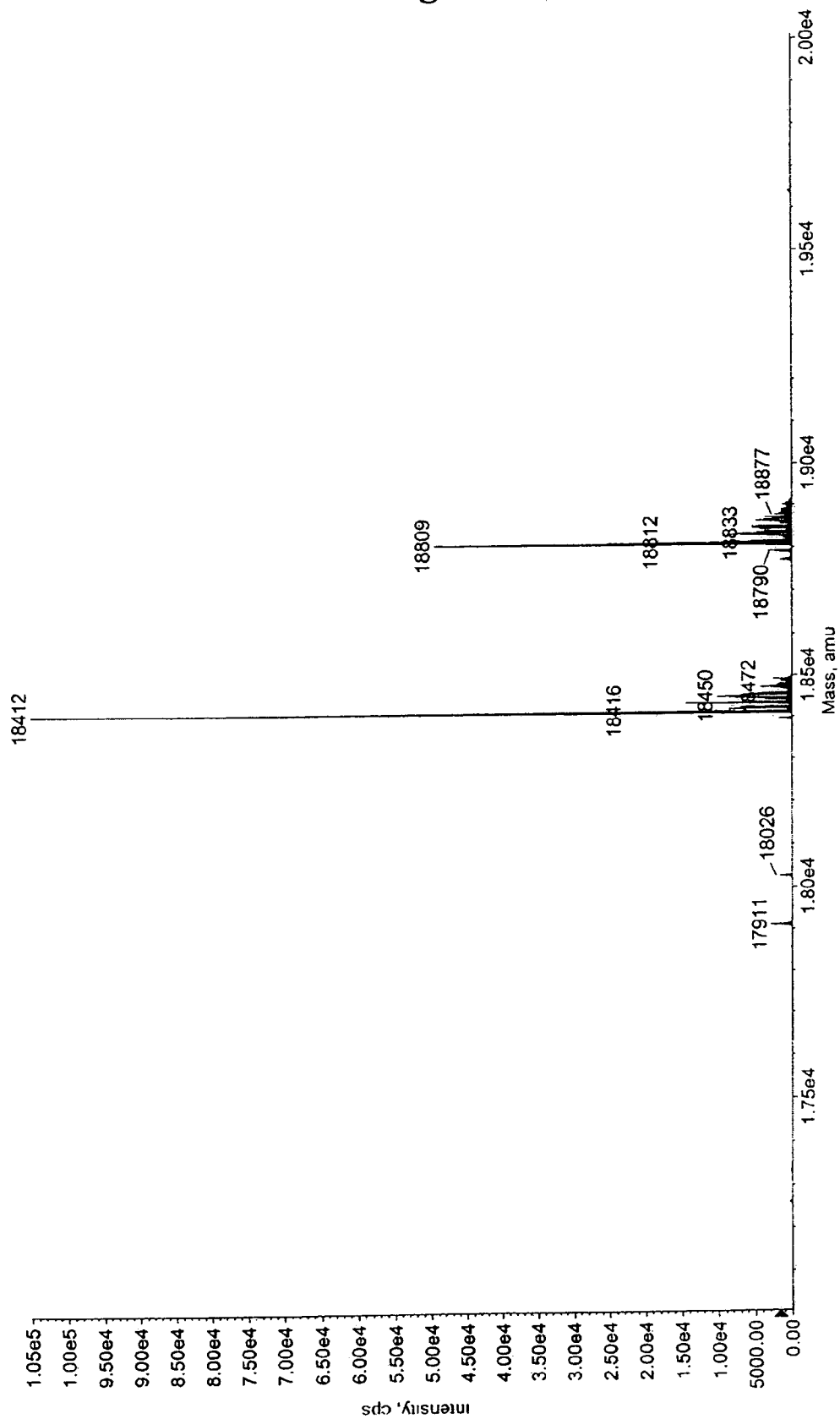
FIG. 26. Deconvoluted electrospray MS spectrum showing the expected masses of 18,414 and 18,809 for the reaction of Ellman's reagent with ARP E1.

The deconvoluted Electrospray MS spectrum (FIG. 26) has the two masses expected for the reaction of Ellman's reagent with the E1 protein. No other masses of any significance are present.

The secondary result of this analysis is that the drug substance produced by each of the batches (molecular weight of 18,414 Da) is highly likely to exist in the reduced form.

Protocol

Chemicals:

1. DTNB (5,5'-Dithio-bis-(2-nitrobenzoic acid)=Ellman's reagent), Pierce, Cat.#22582

2. Cys (Cysteine), Sigma, Cat.# C6852

3. DMSO (Dimethyl sulfoxide), Sigma, Cat.# D8418

4. Gu-HCl (Guanidine chloride), Fisher, Cat.#BP178-500

5. Tris (Trizma base), Sigma, Cat.#T1503

6. HCl (Hydrochloric acid), EMScience, Cat.#HX 0603-75

7. $CH_3COONH_4$ (Ammonium acetate), Baker, Cat.#0596-01

8. $H_2O$, Baker, HPLC reagent, Cat.# 4218-03

Stock Solutions:

1. Tris-HCl: 1M, pH 7.88

2. Ammonium acetate: 1M, pH 6.96

3. DTNB: 100 mM in DMSO 4. 10×PBS (used for Stage II)

5. Cys: 100 mM in PBS

Working Solutions:

1. Reaction buffer: 0.1M tris-HCl, pH 7.92-8.0

2. Dialysis buffer: 10 mM ammonium acetate pH 6.7

3. DTNB: 440 µM in 0.1M tris

4. Gu-HCl: 8M in 0.1M tris

5. Cys: 195.5 µM in PBS

6. PBS

7. Protein: E1-9, 1.8 mg/ml=195.5 µM in Cys

Preparation of Working Solutions:

All working solutions except Gu-HCl and protein were prepared from stock solutions (#1, 2, 3, 6) or by dissolving the solid reagent (#5) immediately before the experiment. Gu-HCl was prepared 1 week prior to the experiment and kept at room temperature. Protein was kept at −80° C. and was defrosted immediately before the experiment.

Immediately before the experiment all solutions were degassed in a dessicator on ice for 30 min, opened to air under nitrogen and brought to 22° C. (room temperature on that day) by 15 min incubation in 22° C. water bath for 15 min with occasional shaking.

Sample Treatment:

1. DTNB modification. 45 µl of test solutions (PBS, Cys, protein) were mixed with 225 µl of Gu-HCl and incubated at room temperature 15 min to denature the protein. 20 µl of DTNB solution was added on the plate reader and $OD_{414}$ was monitored for 1 hr with readings every 30 sec. The highest $OD_{414}$ obtained within 1 hr was used for calculating the concentration of the $TNB^2$-ion released with the use of $\delta_{414}$=14,047 (Methods in Enzymology, 1983, 91, 49-60). PBS $OD_{414}$ reading was subtracted from Cys and protein readings. In the control protein sample DTNB was substituted by 0.1M tris.

Results: Cys sample: 73% DTNB-modified.

Protein sample: 34% DTNB-modified.

2. Dialysis. After the reaction DTNB-modified and control protein samples were dialysed to remove Gu-HCl in separate beakers in 3×300 ml of 10 mM ammonium acetate for 3-10 hrs each.

3. Sample analysis. To determine the presence of modified protein both samples were analyzed by C8 RP-chromatography according to standard protocol. The number of modified Cys residues was estimated by determination of the molecular weight increase after DTNB modification (M-Scan, standard protocol). The minor component (probably, same as the minor component on C8 chromatogram (~16% of total by peak height) showed 2 modified residues (Mol. wt. increase=397 Da). The major component was oxidized to 18412 Da.

EXAMPLE 24

Disulfide Bond and ARP Activity

Directed point mutagenesis to change Cys residue into Ser residue was performed by using specific primers and PCR.

Mutations (Cys35→Ser in one mutant and Cys73→Ser+ Arg8→CTrp in the other one) were confirmed by sequencing. Conditioned media and bacterial extracts were analyzed by DC-assay. Both modifications resulted in about 10-fold decrease of the activity compared to non-modified ARP. Since Arg80 is in a non-conserved region usually occupied by a hydrophobic amino acid, change it to hydrophobic Trp is likely of low importance. This implies that both Cys residues in the ARP molecule are important for DC activity, possibly due to formation of a disulfide bond.

Figure 27:
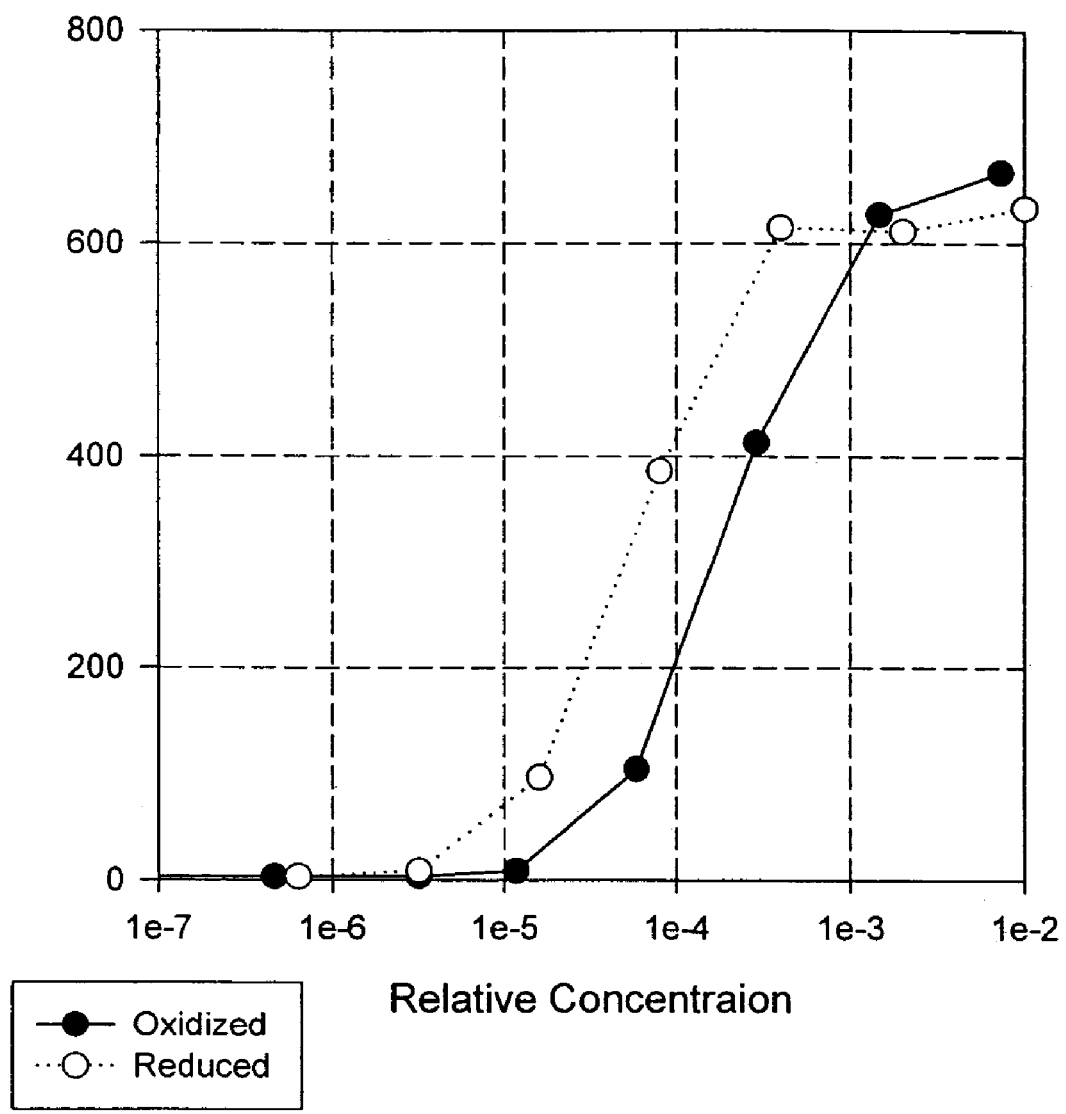
FIG. 27. Dose/response curves for both the oxidized and reduced forms of ARP. The curves are adjusted to constant protein concentration.

Both the oxidized and the reduced forms of ARP are active when added to the assay system. In an in vivo study, the reduced form was 2-5× more active than the oxidized form as shown in FIG. 27. In an in vitro study where an excess of either oxidized or reduced glutathione was added to the assay system, reduced glutathione lowered the responses in the DC assay. In both of these experiments however, it was not possible to determine the redox potential in the immediate environment of the cell so it is not possible to say which form is interacting directly with DC cells.

REFERENCES CITED AND EQUIVALENTS

All references cited herein are incorporated herein by reference in their entirety and for all purposes to the same extent as if each individual publication or patent or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims along with the full scope of equivalents to which such claims are entitled.

What is claimed is:

1. A purified polypeptide selected from the group consisting of:
   (a) a purified polypeptide which comprises SEQ ID NO: 3, 4, 6, or 7;
   (b) a purified polypeptide which comprises SEQ ID NOs: 3, 4, 5, 6, and 7;
   (c) a purified polypeptide which comprises an amino acid sequence which has at least 90% identity to SEQ ID NO: 29 as determined by a BLAST 2.0 algorithm set to default parameters; and
   (d) a purified polypeptide which comprises a variant of an amino acid sequence comprising SEQ ID NO: 3, 4, 5, 6 and 7, wherein said variant has only amino acid substitutions of similar polarity relative to SEQ ID NO:3, 4, 5, 6 and 7, respectively; and wherein said peptide of (a), (b), (c), or (d) stimulates release of interleukin 12 from dendritic cells, said dendritic cells having been isolated from a mammal within 10 hours of assaying said ability.

2. The purified polypeptide of claim 1, wherein the polypeptide comprises SEQ ID NO: 3, 4, 6 or 7, wherein said polypeptide has a molecular weight of 18 to 25 kD as assayed by sodium dodecyl sulfate-polyacrylamide gel electrophoresis, and an isoelectric point (pI) between 4.0 and 4.7.

3. The purified polypeptide of claim 1, wherein the polypeptide comprises SEQ ID NO: 3, 4, 5, 6 and 7, wherein said polypeptide has a molecular weight of 18 to 25 kD as assayed by sodium dodecyl sulfate-polyacrylamide gel electrophoresis, and an isoelectric point (pI) between 4.0 and 4.7.

4. A sterile pharmaceutical composition comprising a therapeutically effective amount of the polypeptide of claim 1 or a protein having at least 90% identity to any one of the proteins selected from the group consisting of SEQ ID NO: 28 or SEQ ID NO: 30 as determined by a BLAST 2.0 algorithm set to default parameters, and wherein said protein stimulates release of interleukin-12 from dendritic cells; and a pharmaceutical acceptable carrier.

5. A purified polypeptide comprising the protein of SEQ ID NO: 28.

6. The purified polypeptide of claim 5, wherein the protein consists of SEQ ID NO:28.

7. A pharmaceutical composition comprising the purified polypeptide of claim 6 and a pharmaceutically acceptable carrier.

8. The composition of claim 7, wherein the pharmaceutically acceptable carrier is sterile.

9. A purified polypeptide comprising the protein of SEQ ID NO: 30.

10. The purified polypeptide of claim 9, wherein the protein consists of SEQ ID NO:30.

11. A pharmaceutical composition comprising the purified polypeptide of claim 10 and a pharmaceutically acceptable carrier.

12. The composition of claim 11, wherein the pharmaceutically acceptable carrier is sterile.

13. The composition of claim 4, further comprising another protein, wherein the other protein is a serum albumin.

* * * * *